(12) United States Patent
Zhang et al.

(10) Patent No.: US 9,676,794 B2
(45) Date of Patent: *Jun. 13, 2017

(54) BENZODIAZEPINE DIMERS, CONJUGATES THEREOF, AND METHODS OF MAKING AND USING

(71) Applicant: BRISTOL-MYERS SQUIBB COMPANY, Princeton, NJ (US)

(72) Inventors: Yong Zhang, West Windsor, NJ (US); Ivar M. McDonald, East Haddam, CT (US); Naidu S. Chowdari, Sunnyvale, CA (US); Tram N. Huynh, Pennington, NJ (US); Robert M. Borzilleri, Carversville, PA (US); Sanjeev Gangwar, Foster City, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/351,843

(22) Filed: Nov. 15, 2016

(65) Prior Publication Data

US 2017/0073357 A1    Mar. 16, 2017

Related U.S. Application Data

(63) Continuation of application No. 14/994,296, filed on Jan. 13, 2016.

(60) Provisional application No. 62/103,157, filed on Jan. 14, 2015, provisional application No. 62/215,928, filed on Sep. 9, 2015.

(51) Int. Cl.
    *C07D 487/04* (2006.01)
    *C07D 519/00* (2006.01)

(52) U.S. Cl.
    CPC .................................. *C07D 519/00* (2013.01)

(58) Field of Classification Search
    CPC .......................... C07D 487/04; C07D 519/00
    See application file for complete search history.

(56) References Cited

U.S. PATENT DOCUMENTS

| | | |
|---|---|---|
| 7,049,311 B1 | 5/2006 | Thurston et al. |
| 7,244,724 B2 | 7/2007 | Liu et al. |
| 7,407,951 B2 | 8/2008 | Thurston et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,659,241 B2 | 2/2010 | Senter et al. |
| 7,741,319 B2 | 6/2010 | Howard et al. |
| 8,124,738 B2 | 2/2012 | Terret et al. |

(Continued)

FOREIGN PATENT DOCUMENTS

| | | |
|---|---|---|
| WO | WO 2013/041606 A1 | 3/2013 |
| WO | WO 2013/177481 A1 | 11/2013 |

(Continued)

OTHER PUBLICATIONS

Scott Jeffrey et al., *Bio Conjugate Chemistry*, "A Potent Anti-CD70 Antibody-Drug Conjugate Combining a Dimeric Pyrrolobenzodiazepine Drug with Site-Specific Conjugation", vol. 24: pp. 1256-1263, 2013.

(Continued)

*Primary Examiner* — Bruck Kifle
(74) *Attorney, Agent, or Firm* — Yuan Chao

(57) ABSTRACT

Benzodiazepine dimers having a structure represented by

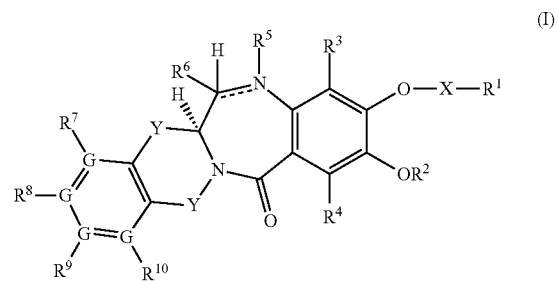

wherein $R^1$ is

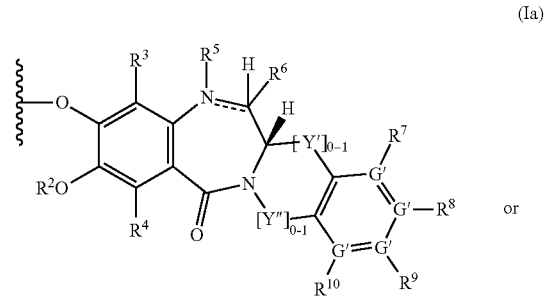

or

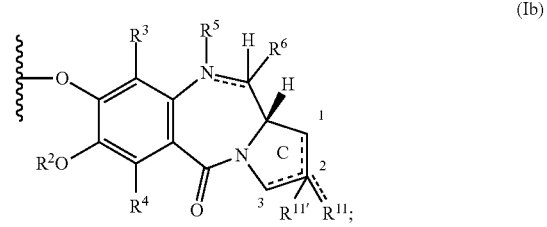

wherein the variables in formulae (I), (Ia), and (Ib) are as defined in the application. Such dimers are useful as anticancer agents, especially when used in an antibody-drug conjugate (ADC).

1 Claim, 26 Drawing Sheets

(56) References Cited

U.S. PATENT DOCUMENTS

| | | |
|---|---|---|
| 8,163,736 B2 | 4/2012 | Gauzy et al. |
| 8,268,970 B2 | 9/2012 | Terrett et al. |
| 8,383,118 B2 | 2/2013 | Vistica et al. |
| 8,404,678 B2 | 3/2013 | Bouchard et al. |
| 8,426,402 B2 | 4/2013 | Li et al. |
| 8,481,042 B2 | 7/2013 | Commercon et al. |
| 8,501,934 B2 | 8/2013 | Howard et al. |
| 8,592,576 B2 | 11/2013 | Howard et al. |
| 8,680,247 B2 | 3/2014 | Terrett et al. |
| 8,697,688 B2 | 4/2014 | Howard et al. |
| 8,765,740 B2 | 7/2014 | Li et al. |
| 2007/0191349 A1 | 8/2007 | Howard et al. |
| 2011/0256157 A1 | 10/2011 | Howard et al. |
| 2013/0028919 A1 | 1/2013 | Howard et al. |
| 2013/0137659 A1 | 5/2013 | Commercon et al. |
| 2013/0266595 A1 | 10/2013 | Elygare et al. |
| 2014/0120118 A1 | 5/2014 | Howard |
| 2014/0127239 A1 | 5/2014 | Howard |
| 2014/0234346 A1 | 8/2014 | Howard |
| 2014/0274907 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |

FOREIGN PATENT DOCUMENTS

| | | |
|---|---|---|
| WO | WO 2014/031566 A1 | 2/2014 |
| WO | WO 2014/080251 A1 | 3/2014 |
| WO | WO 2014/096365 A1 | 6/2014 |
| WO | WO 2014/096368 A1 | 6/2014 |
| WO | WO 2014/140174 A1 | 9/2014 |
| WO | WO 2014/140862 A2 | 9/2014 |
| WO | WO 2014/174111 A1 | 10/2014 |

OTHER PUBLICATIONS

Stephen J. Gregson, et al., *Bioorganic & Medicinal Chemistry Letters* "Synthesis of the First Example of a C2-C3/C20-C30-endo Unsaturated Pyrrolo[2,1-c][1,4]benzodiazepine Dimer",\ 11: pp. 2859-2862, 2011.

Kiran Kumar Kothakonda, et al., *Bioorganic & Medicinal Chemistry Letters*, "Synthesis of a novel tetrahydroisoquinolino[2,1-c][1,4]benzodiazepine ring system with DNA recognition potential", 14: pp. 4371-4373, 2014.

Stephen J. Gregson et al., *ChemComm*, "Synthesis of a novel C2/C2A-*exo* unsaturated pyrrolobenzodiazepine cross-linking agent with remarkable DNA binding affinity and cytotoxicity", pp. 797-798, 1999.

John A Hartley, *Expert Opinion Investig*. Drugs, "The development of pyrrolobenzodiazepines as antitumour agents", vol. 20: pp. 733-744. 2011.

John A. Hartley, et al., *Invest New Drugs*, "DNA Interstrand cross-linking and in vivo antitumor activity of the extended pyrrolo[2,1-c][1,4]benzodiazepine dimer SG2057", vol. 30: pp. 950-958, 2012.

D. Subhas Bose, et al. *J. Am. Chem. SOC*, "Rational Design of a Highly Efficient Irreversible DNA Interstrand Cross-Linking Agent Based on the Pyrrolobenzodiazepine Wing System", vol. 114: pp. 4939-4941, 1992.

David E. Thurston, et al., *J. Med. Chem*, "Effect of A-Ring Modifications on the DNA-Binding Behavior and Cytotoxicity of Pyrrolo[2,1-c][1,4]benzodiazepines", vol. 42: pp. 1951-1964, 1999.

Stephen J. Gregson et al., *J. Med. Chem*, "Design, Synthesis, and Evaluation of a Novel Pyrrolobenzodiazepine DNA-Interactive Agent with Highly Efficient Cross-Linking Ability and Potent Cytotoxicity", vol. 44: pp. 737-748, 2001.

Stephen J. Gregson et al., *J. Med. Chem*, "Linker Length Modulates DNA Cross-Linking Reactivity and Cytotoxic Potency of C8/C8¢ Ether-Linked C2-*exo*-Unsaturated Pyrrolo[2,1-c][1,4]benzodiazepine (PBD) Dimers", vol. 47: pp. 1161-1174, 2004.

Dyeison Antonow, et al., *J. Med. Chem*, "Structure-Activity Relationships of Monomeric C2-Aryl Pyrrolo[2,1-c][1,4]benzodiazepine (PBD) Antitumor Agents", vol. 53: pp. 2927-2941, 2010.

David E. Thurston, et al., *J. Org. Chem.*, "Synthesis of Sequence-Selective C8-Linked Pyrrolo[2,1-c][1,4]benzodiazepine DNA Interstrand Cross-Linking", vol. 61: pp. 8141-8147, 1996.

David Schrama et al., *Nature Reviews Drug Discovery*, "Antibody targeted drugs as cancer Therapeutics", vol. 5: pp. 147-159, 2006.

International Search Report and Written Opinion, for PCT Application No. PCT/US2016/013136, mailed Mar. 15, 2016.

23: one imine bond reduced
24: both imine bonds reduced

BENZODIAZEPINE DIMERS, CONJUGATES THEREOF, AND METHODS OF MAKING AND USING

CROSS-REFERENCE TO RELATED APPLICATIONS

This application is a continuation of U.S. application Ser. No. 14/994,296, filed Jan. 13, 2016; which claims the benefit under 35 U.S.C. §119(e) of U.S. Provisional Application Ser. No. 62/103,157, filed Jan. 14, 2015, and U.S. Provisional Application Ser. No. 62/215,928, filed Sep. 9, 2015; the disclosures of which are incorporated herein by reference.

BACKGROUND OF THE INVENTION

This invention relates to benzodiazepine dimers, dimer-linker compounds derived therefrom, and conjugates thereof, and methods for their preparation and use.

Several naturally occurring cytotoxic compounds having a benzodiazepine ring system are known. Reflecting the additional presence in the molecular scaffold of a five-member pyrrolidine ring fused to the diazepine ring, such compounds are commonly referred to as pyrrolobenzodiazepines, or PBDs. Examples include tomaymycin and anthramycin.

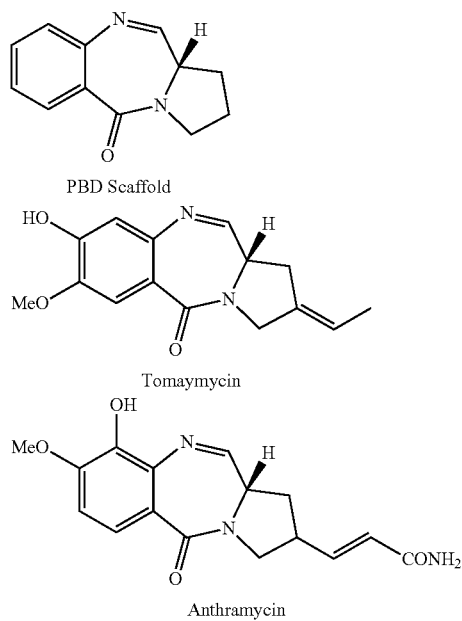

PBDs possess antibiotic and antitumor activity, the latter trait leading to interest in them as anticancer drugs. Mechanistically, PBDs bind to the minor groove of DNA in a sequence selective manner and, once bound, alkylate the DNA. The structure-activity relationship (SAR) of different substituents has been studied (Antonow et al. 2010; Thurston et al. 1999).

Additional studies have shown that PBD dimers show special promise as anticancer agents. The core structure of a typical PBD dimer can be represented by formula (A-1), where X is a bridging group connecting the two dimer halves.

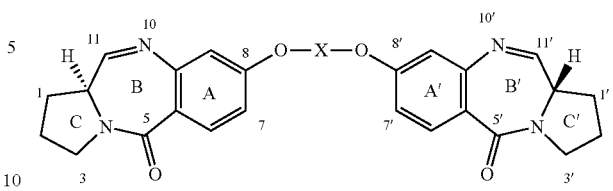

(A-1)

As with monomeric PBDs, the dimers are DNA minor groove binder-alkylators. Being bifunctional, alkylation by a dimer results in cross-linked DNA, making DNA repair more difficult. (DNA alkylation occurs via the imine group. PDBs having one of the imine groups reduced can still alkylate DNA, but cannot crosslink it. They are still biologically active, albeit generally less so, but their different pharmacokinetic profile may be preferable for some applications.) For a review on the evolution of PBDs as antitumor agents, from naturally occurring monomers to synthetic monomers to synthetic dimers, see Hartley 2011.

The SAR of PBD dimers has been explored via substituents on the A/A' and C/C' rings, unsaturation in the C/C' rings, the structure and length of the bridging group X, and the oxidation or reduction of the imine double bonds in rings B/B', and combinations of such features. See Bose et al. 1992, Gregson et al. 1999, Gregson et al. 2001a and 2001b, Gregson et al. 2004, Gregson et al. 2009, Hartley et al. 2012, Howard et al. 2007, Howard et al. 2009a. Howard et al. 2010, Howard et al. 2013a and 2013b, Liu et al. 2007, Thurston et al. 1996, Thurston et al. 2006, and Thurston et al. 2008. Most PBD dimers are joined via an 8/8' bridge as shown above, but a 7/7' bridge also has been disclosed (Howard et al. 2009b).

A type of anticancer agent that is generating strong interest is an antibody-drug conjugate (ADC, also referred to as an immunoconjugate). In an ADC, a therapeutic agent (also referred to as the drug, payload, or warhead) is covalently linked to an antibody whose antigen is expressed by a cancer cell (tumor associated antigen). The antibody, by binding to the antigen, delivers the ADC to the cancer site. There, cleavage of the covalent link or degradation of the antibody leads to the release of the therapeutic agent. Conversely, while the ADC is circulating in the blood system, the therapeutic agent is held inactive because of its covalent linkage to the antibody. Thus, the therapeutic agent used in an ADC can be much more potent (i.e., cytotoxic) than ordinary chemotherapy agents because of its localized release. For a review on ADCs, see Schrama et al. 2006.

PBD dimers have been proposed as the drug in an ADC. Attachment of the linker connecting to the antibody can be via a functional group located in a C/C' ring, the bridging group X, or by addition across the imine group in a B/B' ring. See Beau-Larvor et al. 2014, Bouchard et al. 2013, Commercon et al. 2013a and 2013b, Flygare et al. 2013, Gauzy et al. 2012, Howard 2104a-2014e, Howard et al. 2011, Howard et al. 2013c and 2013d, Howard et al. 2014a-2014h, Jeffrey et al. 2013, Jeffrey et al. 2014a and 2014b, and Zhao et al. 2014.

Another type of benzodiazepine dimer also has been proposed as a therapeutic agent for use in ADCs. Structurally, this type may be viewed as a PBD dimer further having a phenyl ring fused to each of C/C' rings, as shown in formulae (A-2) and (A-3). See Chari et al. 2013, Li et al. 2013, Fishkin et al. 2014, Li et al. 2014.

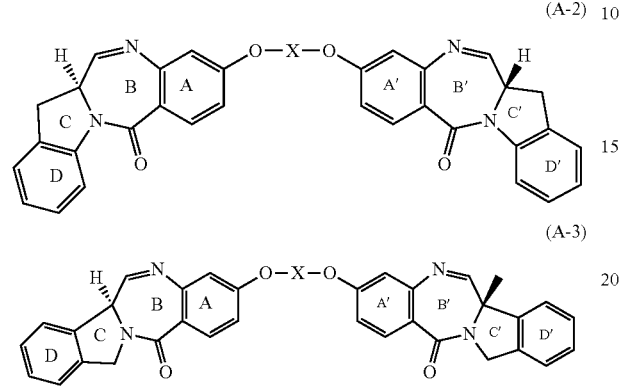

(A-2)

(A-3)

Benzodiazepine compounds having other ring systems, such as a tetrahydro-isoquinolino[2,1-c][1,4]benzodiazepine, also have been disclosed. Kothakonda et al. 2004.

Full citations for the documents cited herein by first author or inventor and year are listed at the end of this specification.

BRIEF SUMMARY OF THE INVENTION

This invention provides novel benzodiazepine dimers, preferably in which at least one of the benzodiazepine units has a tetrahydroisoquinoline (THIQ) ring system fused to a benzodiazepine ring system. Optionally, the imine bond in the benzodiazepine ring system can be reduced.

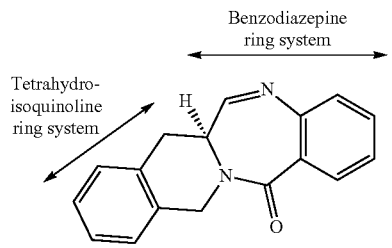 [SMILES: O=C1c2ccccc2N=C[C@@H]2Cc3ccccc3CN12]

Both units (halves) of the dimer can have a THIQ ring system ("THIQ-THIQ dimer" or "THIQ homodimer"), or one unit can have a THIQ ring system while the other unit has a different benzodiazepine ring system, such as a PBD ring system (generally, a "THIQ heterodimer" or, in this particular example, a "THIQ-PBD dimer"). In a THIQ-THIQ dimer the two units can be identical ("symmetric THIQ-THIQ dimer") or different ("asymmetric THIQ-THIQ dimer").

Thus, this invention provides a benzodiazepine dimer having a structure represented by formula (I):

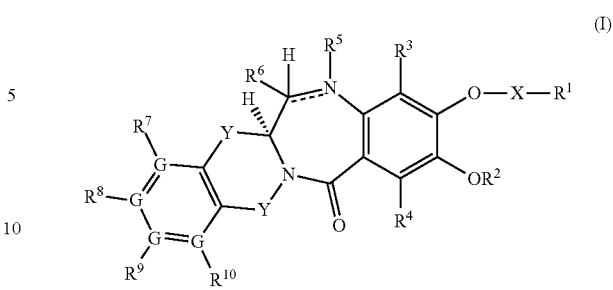

(I)

wherein $R^1$ is according to formula (Ia) or formula (Ib):

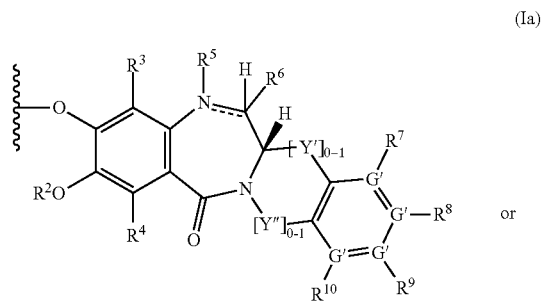

(Ia)

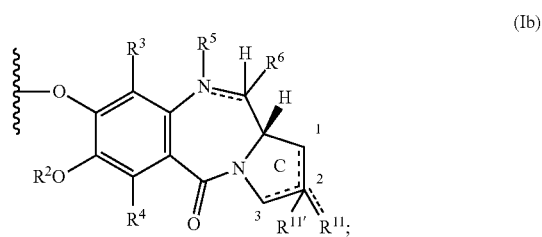

(Ib)

each G and G' is C or N, with the proviso that no more than two Gs or two G's are N;

each $R^2$ is independently H or $C_1$-$C_5$ alkyl;

each $R^3$ and $R^4$ is independently H, F, Cl, Br, OH, $C_1$-$C_3$ alkyl, O($C_1$-$C_3$ alkyl), cyano, $(CH_2)_{0-5}NH_2$, or $NO_2$;

each double line ═══ in a diazepine ring system independently represents a single bond or a double bond;

each $R^5$ is H if the double line ═══ to the N to which it is attached—i.e., with which it is associated—is a single bond and is absent if the double line is a double bond;

each $R^6$ is H, OH, $SO_3Na$, or $SO_3K$ if the double line ═══ to the C to which it is attached—i.e., with which it is associated—is a single bond and is absent if the double line is a double bond;

each $R^7$, $R^8$, $R^9$, and $R^{10}$ is independently H, $C_1$-$C_5$ alkyl, C≡C$(CH_2)_{1-5}X^2$, OH, O($C_1$-$C_5$ alkyl), cyano, $NO_2$, F, Cl, Br, $O(CH_2CH_2O)_{1-8}(C_{1-3}$ alkyl), $(CH_2)_{0-5}X^2$, $O(CH_2)_{2-5}X^2$, 3- to 7-membered cycloalkyl or heterocycloalkyl unsubstituted or substituted with $(CH_2)_{0-5}X^2$ or $O(CH_2)_{2-5}X^2$, 5- to 6-membered aryl or heteroaryl unsubstituted or substituted with $(CH_2)_{0-5}X^2$ or $O(CH_2)_{2-5}X^2$,

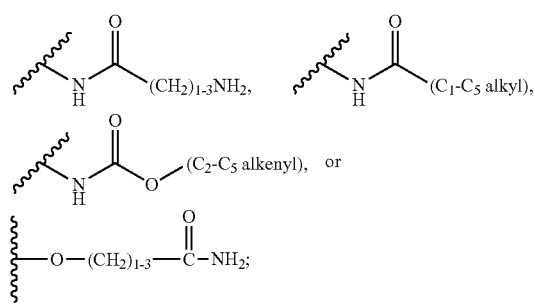

or where a $R^7$, $R^8$, $R^9$, or $R^{10}$ is attached to—i.e., is associated with—to a G or G' that is N, such $R^7$, $R^8$, $R^9$, or $R^{10}$ is absent;

the dotted lines in ring C of formula (Ib) indicate the optional presence of a C1-C2, C2-C3, or C2-$R^{11}$ double bond;

$R^{11}$ is H, =O, =$CH_2$, =CH($C_1$-$C_5$ alkyl), CH=CH $(CH_2)_{1-5}X^2$, C≡C$(CH_2)_{1-5}X^2$, $C_1$-$C_5$ alkyl, OH, O($C_1$-$C_5$ alkyl), cyano, $NO_2$, F, Cl, Br, O($CH_2CH_2O)_{1-8}$($C_{1-3}$ alkyl), $(CH_2)_{0-5}X^2$, 4- to 7-membered aryl, heteroaryl, cycloalkyl, or heterocycloalkyl unsubstituted or substituted with $(CH_2)_{0-5}X^2$, $O(CH_2)_{2-5}X^2$, 3- to 7-membered cycloalkyl or heterocycloalkyl unsubstituted or substituted with $(CH_2)_{0-5}X^2$ or $O(CH_2)_{2-5}X^2$, 5- to 6-membered aryl or heteroaryl unsubstituted or substituted with $(CH_2)_{0-5}X^2$ or $O(CH_2)_{2-5}X^2$;

$R^{11'}$ is absent if a C1-C2, C2-C3, or C2-$R^{11}$ double bond is present and otherwise is H;

X is

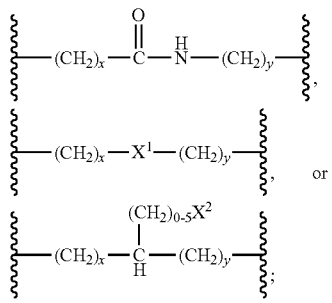

$X^1$ is $CH_2$, O, NH, $S(O)_{0-2}$, 3- to 7-membered cycloalkylene or heterocycloalkylene unsubstituted or substituted with $(CH_2)_{0-5}X^2$ or $O(CH_2)_{2-5}X^2$, 6-membered arylene unsubstituted or substituted with $(CH_2)_{0-5}X^2$ or $O(CH_2)_{2-5}X^2$, or 5-membered heteroarylene unsubstituted or substituted with $(CH_2)_{0-5}X^2$ or $O(CH_2)_{2-5}X^2$;

each $X^2$ is independently H, F, Cl, Br, OH, O($C_1$-$C_3$ alkyl), O($C_1$-$C_3$ alkylene), $CO_2H$, $N_3$, CN, $NO_2$, $CO_2$($C_1$-$C_3$ alkyl), $NH_2$, NH($C_1$-$C_5$ alkyl), N($C_1$-$C_5$ alkyl)$_2$, SH, CHO, N($CH_2CH_2)_2$N($C_1$-$C_3$ alkyl), $NHNH_2$, or C(=O)$NHNH_2$;

x and y are independently 1, 2, or 3;

each Y is independently $CH_2$, C=O, or $CHR^{12}$; wherein each $R^{12}$ is independently F, Cl, Br, or $C_1$-$C_3$ alkyl; and Y' and Y" are independently $CH_2$, C=O, or $CHR^{12}$; wherein each $R^{12}$ is independently F, Cl, Br, or $C_1$-$C_3$ alkyl, with the proviso that at least one of Y' and Y" is present (i.e., the associated subscript is 1);

or a pharmaceutically acceptable salt thereof.

In another embodiment, this invention provides a conjugate comprising a dimer of formula (I) covalently bonded to a targeting moiety that specifically or preferentially binds to a chemical entity on a target cell, which target cell preferably is a cancer cell. Preferably, the targeting moiety is an antibody—more preferably a monoclonal antibody; even more preferably a human monoclonal antibody—and the chemical entity is a tumor associated antigen. The tumor associated antigen can be one that is displayed on the surface of a cancer cell or one that is secreted by a cancer cell into the surrounding extracellular space. Preferably, the tumor associated antigen is one that is over-expressed by the cancer cell compared to normal cells or one that is expressed by cancer cells but not normal cells.

In another embodiment, there is provided a dimer according to formula (I) covalently bonded to a linker moiety having a reactive functional group, suitable for conjugation to a targeting moiety.

In another embodiment, there is provided a method for treating a cancer in a subject suffering from such cancer, comprising administering to the subject a therapeutically effective amount of a dimer of this invention or a conjugate thereof with a targeting moiety. In another embodiment, there is provided the use of a dimer of this invention or a conjugate thereof with a targeting moiety for the preparation of a medicament for the treatment of cancer in a subject suffering from such cancer. A dimer of this invention or a conjugate thereof with a targeting moiety can also be used to inhibit the proliferation, in vitro, ex vivo, or in vivo, of cancer cells. Especially, the cancer can be lung, gastric, ovarian, renal, or liver cancer.

BRIEF DESCRIPTION OF THE DRAWING(S)

FIGS. 1, 2, and 3 show schemes for the syntheses of various intermediates used in the preparation of dimers of this invention.

FIGS. 14 and 15 depict a scheme for the synthesis of intermediates used to make dimer-linker compounds referred to as "type (b)" hereinbelow, while

Figure 23:
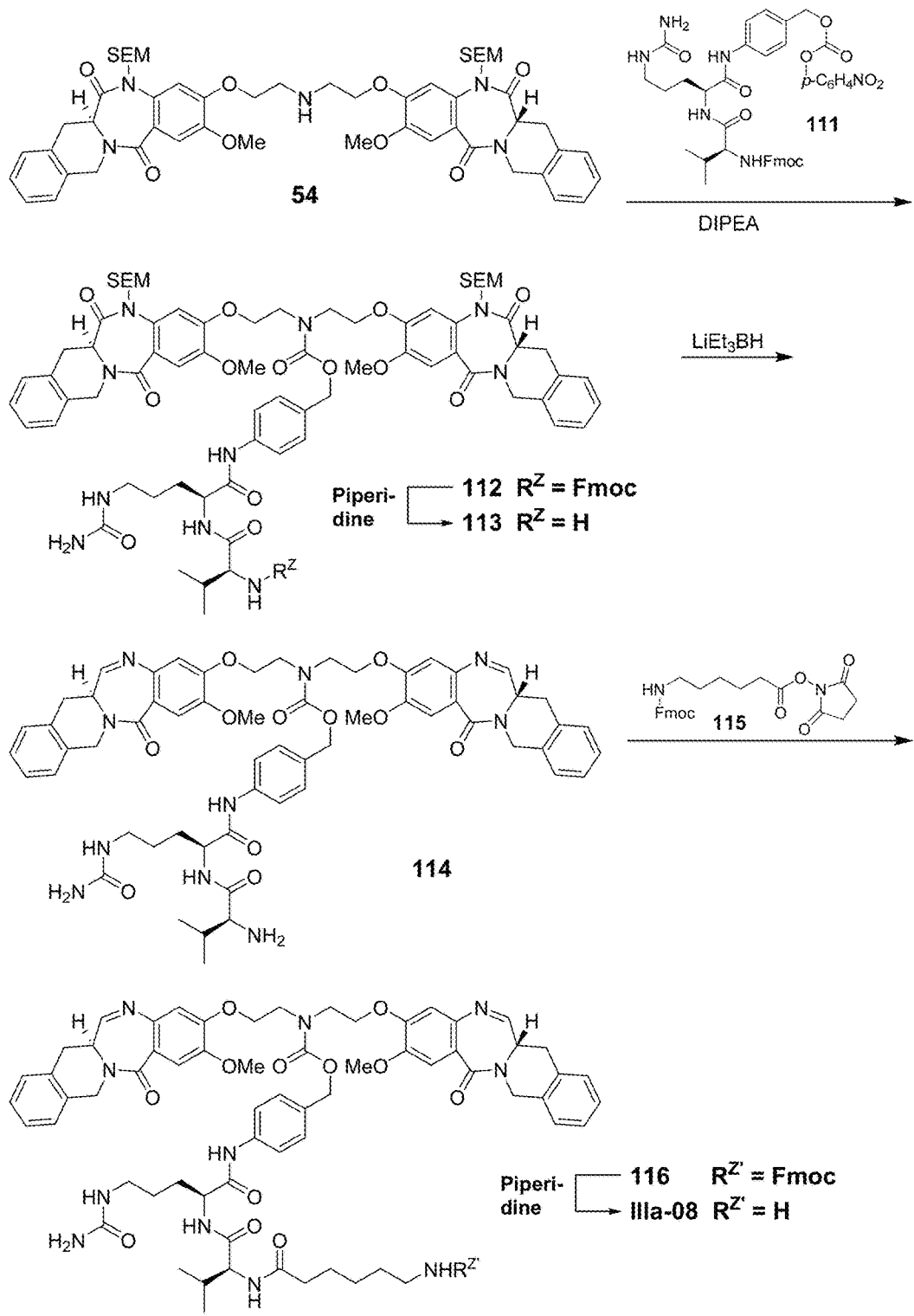

FIG. 23 relates to the synthesis of dimer-linker compounds having an alkylamino group, which can act as amine donors in a transglutaminase-mediated conjugation.

DETAILED DESCRIPTION OF THE INVENTION

Definitions

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5 \times 10^{-8}$ M or less, more preferably $1 \times 10^{-8}$ M or less, more preferably $6 \times 10^{-9}$ M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce inter-actions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., Cellular and Molecular Immunology, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cyclo-alkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexyl-phenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzo-furanyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzo-furanyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoro-methyl), hydroxyl, hydroxyalkyl (especially hydroxyethyl), cyano, nitro, alkoxy, —O(hydroxyalkyl), —O(haloalkyl) (especially —$OCF_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —$CO_2$H, —C(=O)NHOH, —C(=O)O (alkyl), —C(=O)O(hydroxyalkyl), —C(=O)$NH_2$, —C(=O)NH(alkyl), —C(=O)N(alkyl)$_2$, —OC(=O) (alkyl), —OC(=O)(hydroxyalkyl), —OC(=O)O(alkyl), —OC(=O)O(hydroxyalkyl), —OC(=O)$NH_2$, —OC(=O) NH(alkyl), —OC(=O)N(alkyl)$_2$, azido, —$NH_2$, —NH (alkyl), —N(alkyl)$_2$, —NH(aryl), —NH(hydroxyalkyl), —NHC(=O)(alkyl), —NHC(=O)H, —NHC(=O)$NH_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, C$_1$-C$_4$alkyoxy, O(C$_2$-C$_4$ alkylene)OH, and O(C$_2$-C$_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are C$_1$-C$_4$ alkyl, cyano, nitro, halo, and C$_1$-C$_4$alkoxy.

Where a range is stated, as in "C$_1$-C$_5$ alkyl" or "5 to 10%," such range includes the end points of the range, as in C$_1$ and C$_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use of stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include C$_1$-C$_5$ alkyl, C$_2$-C$_5$ alkenyl or C$_2$-C$_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line (~~~) transverse to a bond or an asterisk (*) at the end of the bond denotes a covalent attachment site. For instance, a statement that R is

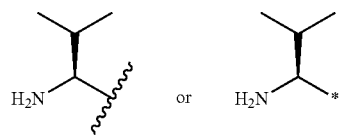

in the formula

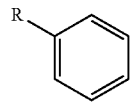

refers to

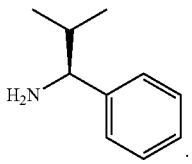

In the formulae of this specification, a bond traversing an aromatic ring between two carbons thereof means that the group attached to the bond may be located at any of the available positions of the aromatic ring. By way of illustration, the formula

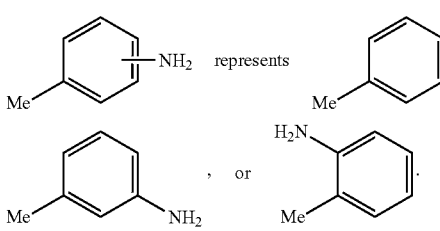

Dimers

In formulae (I), (Ia), and (Ib), preferably each $R^2$ is Me. More preferably, each $R^2$ is Me and each $R^3$, $R^4$, $R^7$, $R^8$, and $R^{10}$ is H (in respect of $R^7$, $R^8$, and $R^{10}$, where present).

In formulae (I) and (Ia), preferably each $R^7$, $R^8$, and $R^{10}$ is H and each $R^9$ is independently H, OH, OMe, $NH_2$, $NMe_2$, $O(CH_2CH_2O)_{1-8}Me$, $OCH_2CH_2OH$, or

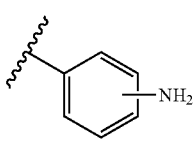

(especially the para-isomer).

In a preferred embodiment of formula (Ia), each G' is C, Y' and Y'' are both $CH_2$. In another preferred embodiment of formula (Ia), one G' is N, Y' is $CH_2$, and Y'' is absent (i.e., the associated subscript is 0).

Preferably, in formula (I), each $X^2$ is independently Me, $CO_2H$, $NH_2$, $NH(C_1$-$C_5$ alkyl), $N(C_1$-$C_5$ alkyl)$_2$, SH, CHO, $N(CH_2CH_2)_2N(C_1$-$C_3$ alkyl), $NHNH_2$, or $C(=O)NHNH_2$.

In formula (Ib), $R^{11}$ preferably is H, $=CH_2$, $CH=CHMe$, $=CHMe$, $C=CCH_2NH_2$,

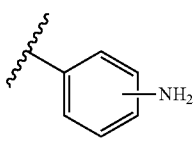

(especially the para-isomer), or

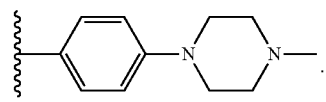 [SMILES: *c1ccc(N2CCN(C)CC2)cc1]

In formula (I), X preferably is

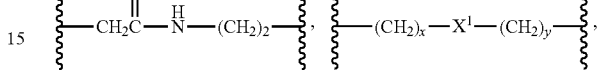

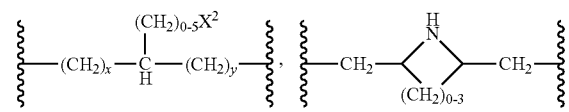

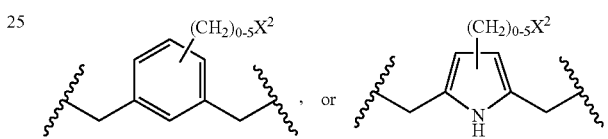

where $X^1$ is $CH_2$, O, or NH; $X^2$ is $CO_2H$, or $NH_2$; and the sum of x and y is 2 or 4.

More preferably, X is

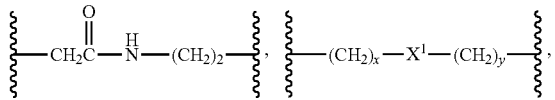

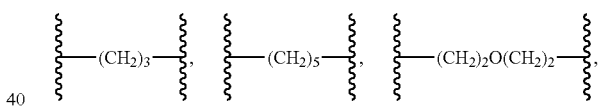

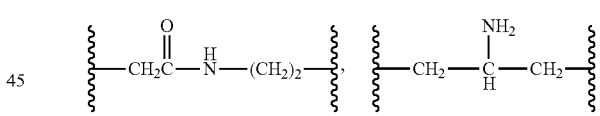

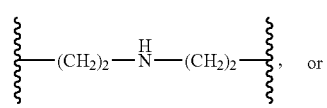

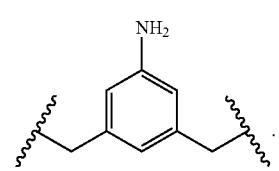

Preferably, where a formula includes two benzodiazepine ring systems each shown with a double line ====, at least one of such double lines is a double bond.

A dimer of this invention can be a THIQ-THIQ dimer; that is, in formula (I) $R^1$ is according to formula (Ia). Such a dimer can be represented by formula (IIa)

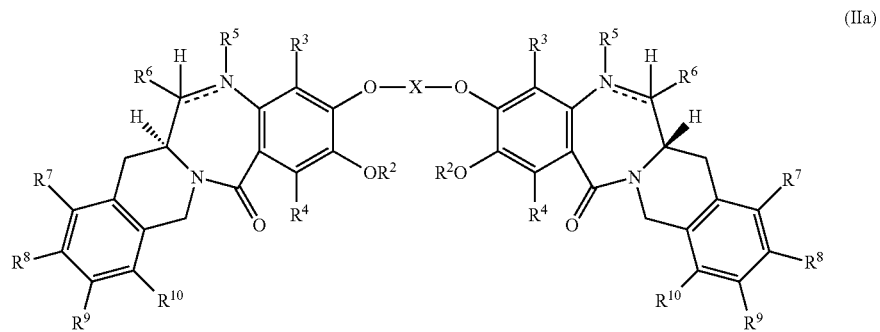

(IIa)

wherein
$R^2, R^3, R^4, R^5, R^6, R^7, R^8, R^9, R^{10}$, the double line ====, and X are as defined in the BRIEF SUMMARY OF THE INVENTION section hereinabove in respect of formula (I).

In a preferred embodiment according the formula (IIa), THIQ-THIQ dimers are represented by formula (IIa'),

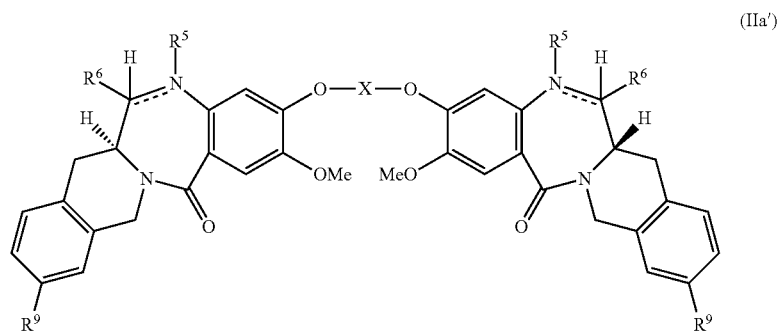

(IIa')

wherein
each $R^9$ is independently H, OH, OMe, $NH_2$, $NMe_2$, $O(CH_2CH_2O)_{1-8}Me$, $OCH_2CH_2OH$, or

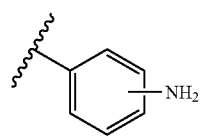

(especially the para-isomer); and

X is 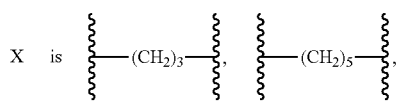

-continued

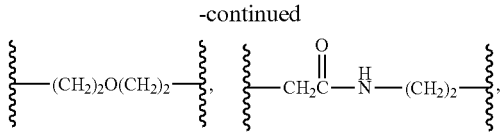

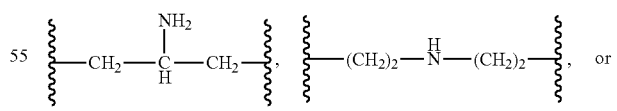

or

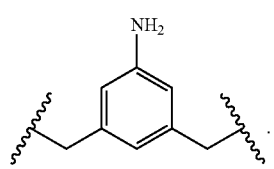

Specific examples of THIQ-THIQ dimers include:
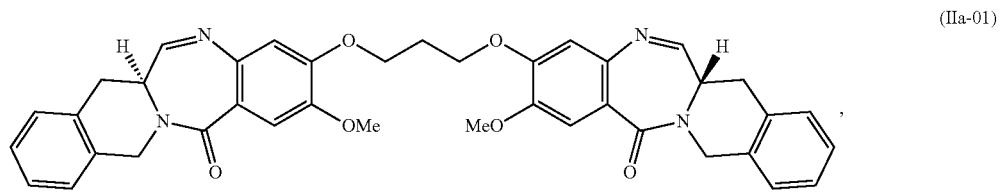
(IIa-01)
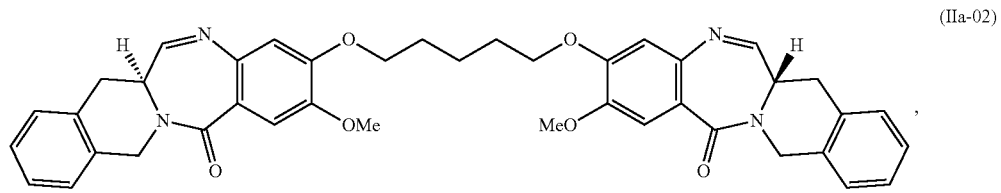
(IIa-02)
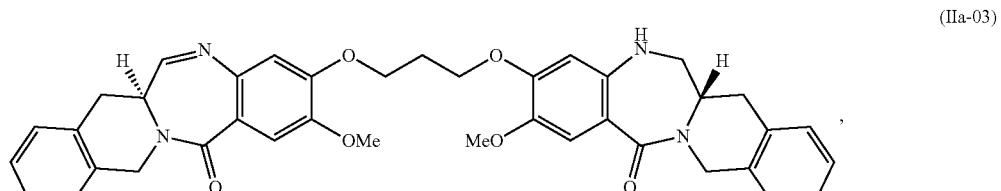
(IIa-03)
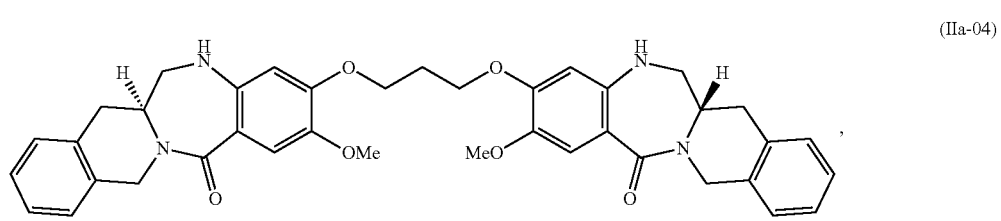
(IIa-04)
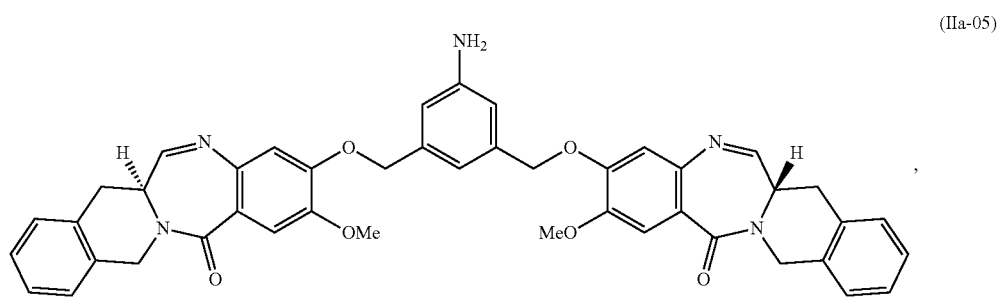
(IIa-05)
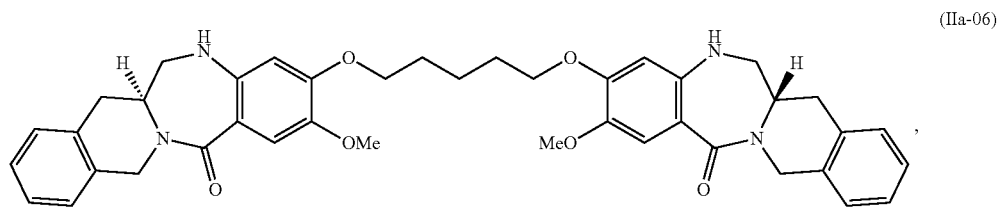
(IIa-06)
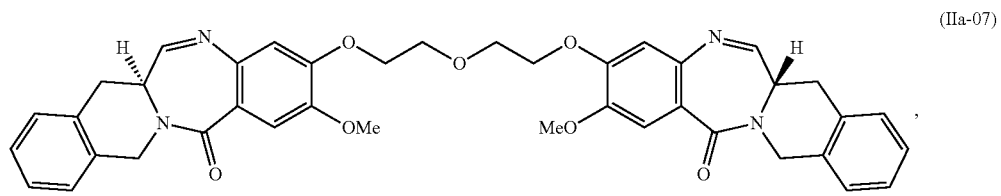
(IIa-07)

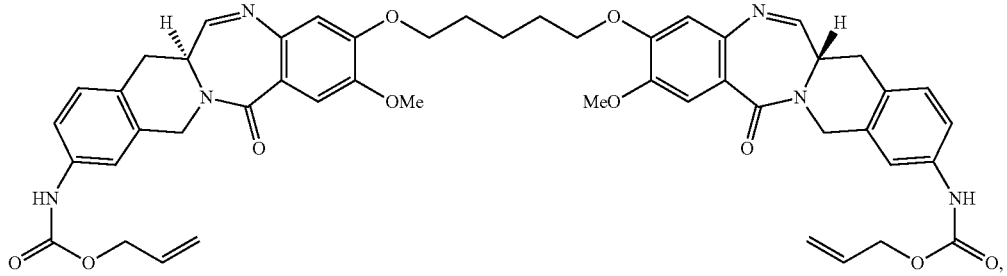
(IIa-08)
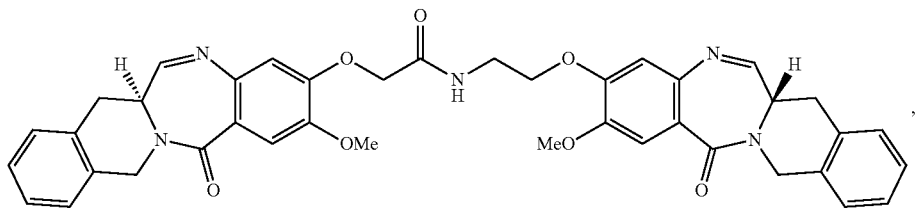
(IIa-09)
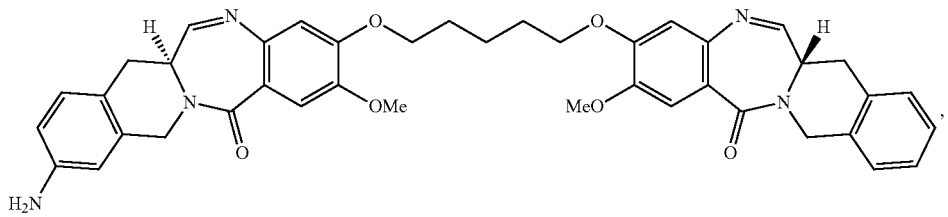
(IIa-10)
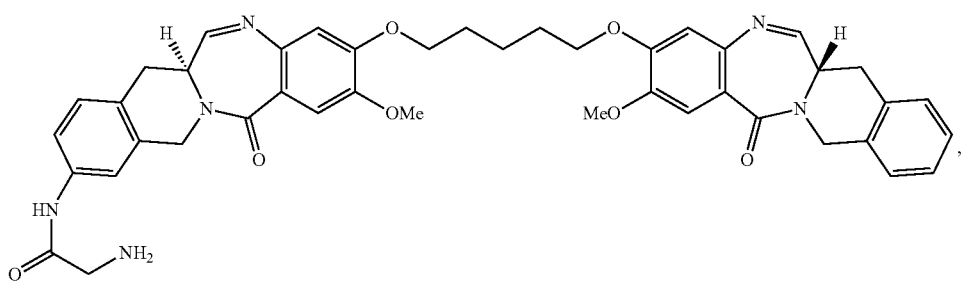
(IIa-11)
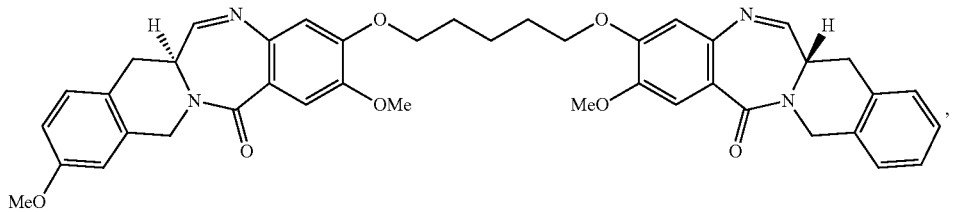
(IIa-12)
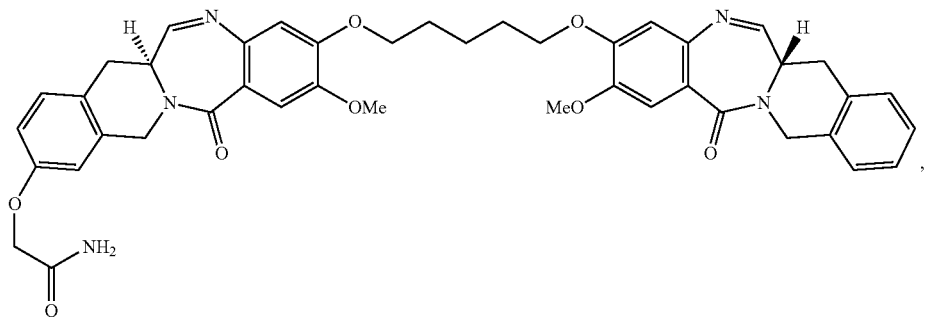
(IIa-13)

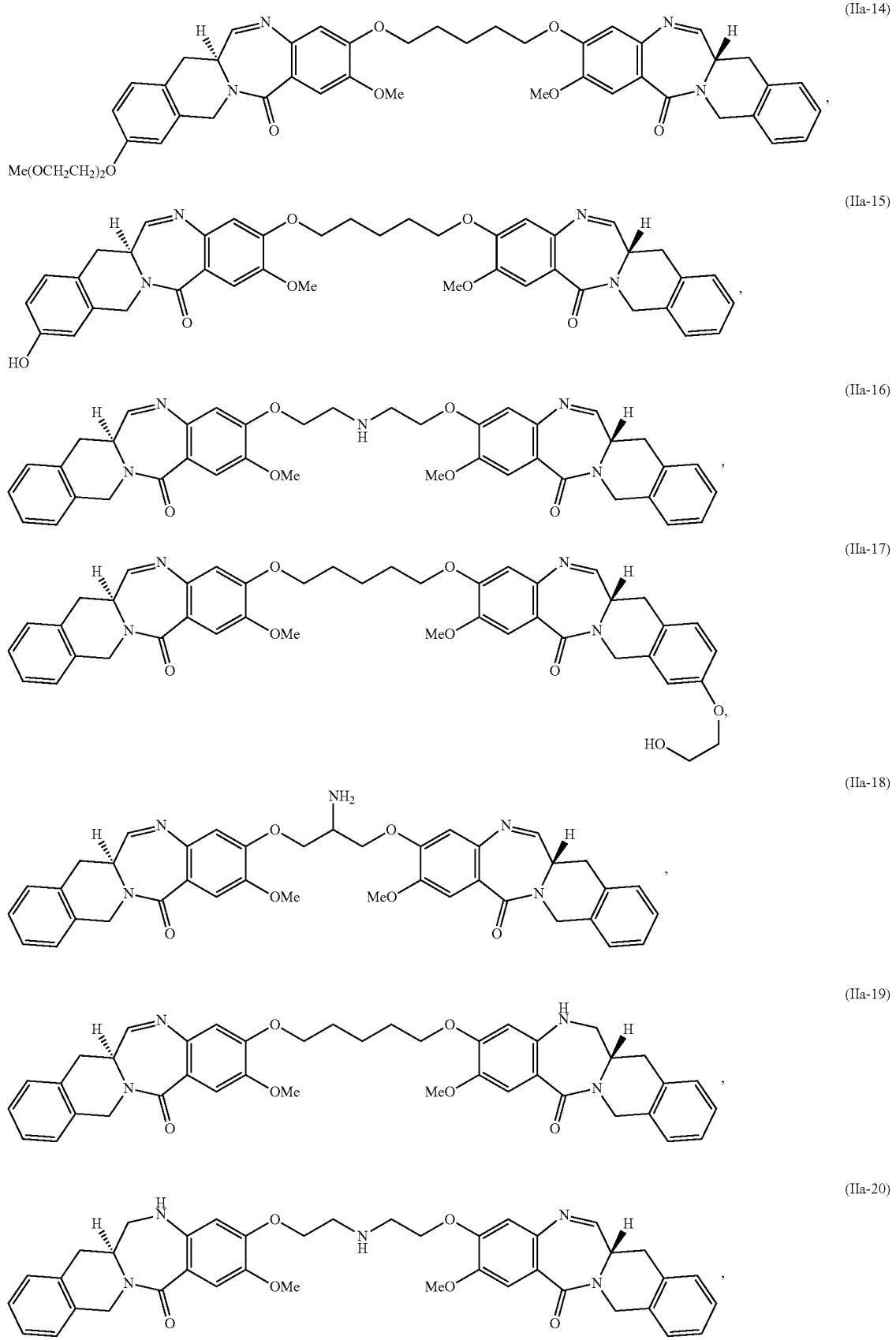

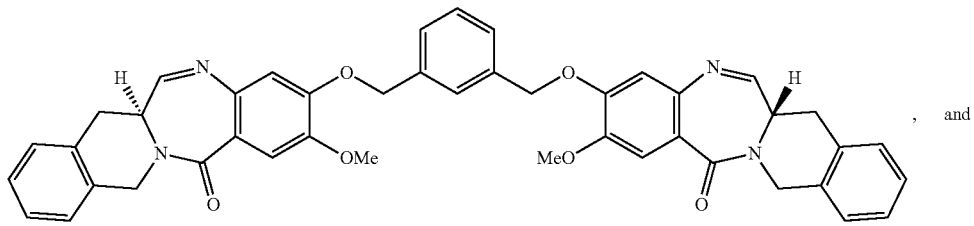

(IIa-21)

, and

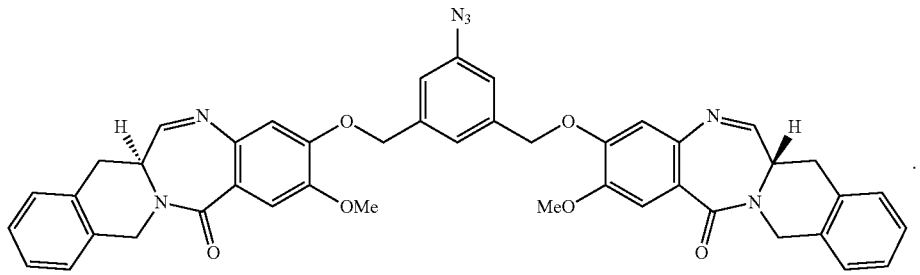

(IIa-22)

Especially preferred THIQ-THIQ dimers are (IIa-16) and (IIa-20).

In another embodiment, a dimer of this invention is a THIQ-PBD dimer; that is, in formula (I), $R^1$ is according to formula (Ib). Such a dimer can be represented by formula (IIb):

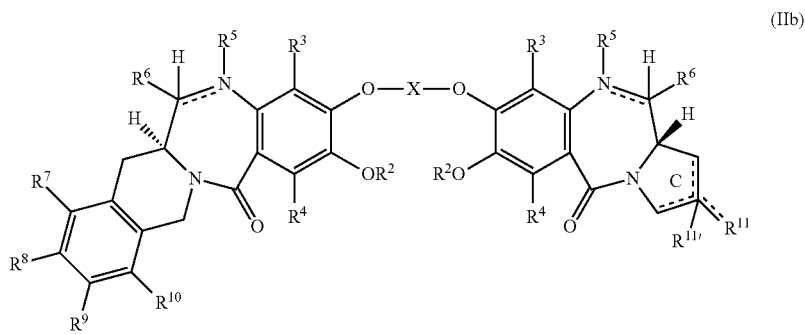

(IIb)

wherein $R^2, R^3, R^4, R^5, R^6, R^7, R^8, R^9, R^{10}, R^{11}, R^{11'}$, the double line ====, the dotted lines in ring C, and X are as defined in the BRIEF SUMMARY OF THE INVENTION section hereinabove in respect of formula (I).

A preferred THIQ-PBD dimer according to formula (IIb), is represented by formula (IIb'):

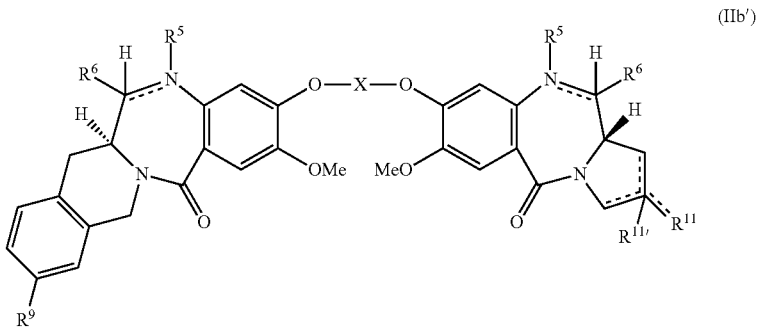

(IIb')

wherein
R$^9$ is H, OH, OMe, NH$_2$, NMe$_2$, O(CH$_2$CH$_2$O)$_{1-8}$Me, OCH$_2$CH$_2$OH, or
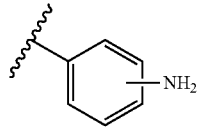
(especially the para-isomer);
R$^1$ is H, =CH$_2$, CH=CHMe, =CHMe, C≡CCH$_2$NH$_2$,
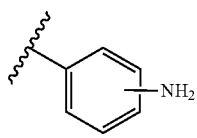
(especially the para-isomer), or
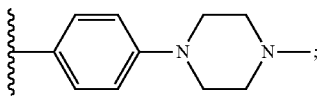
and
X is 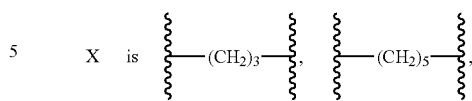
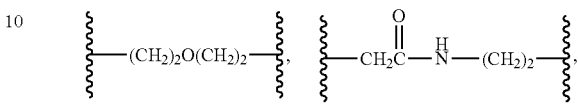
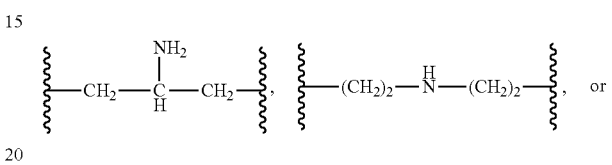
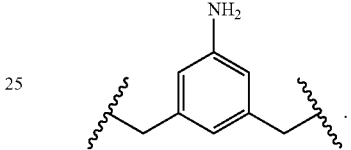
Specific examples of THIQ-PBD dimers include:
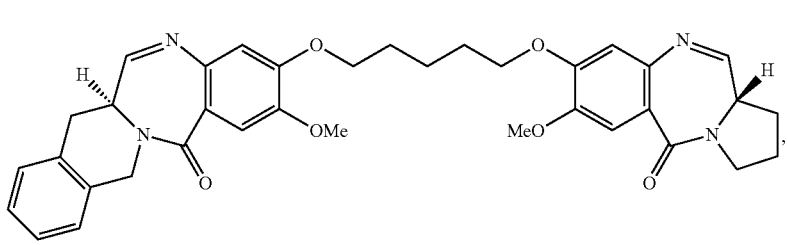
(IIb-01)
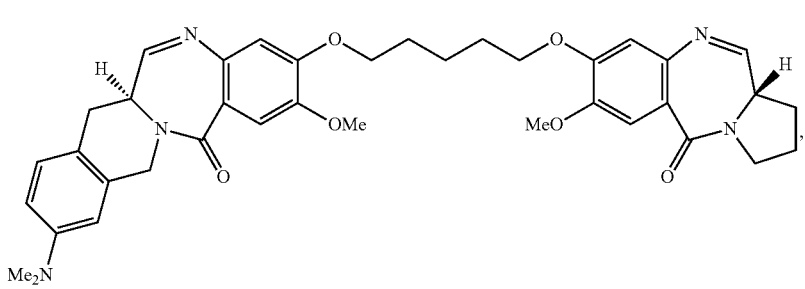
(IIb-02)
and
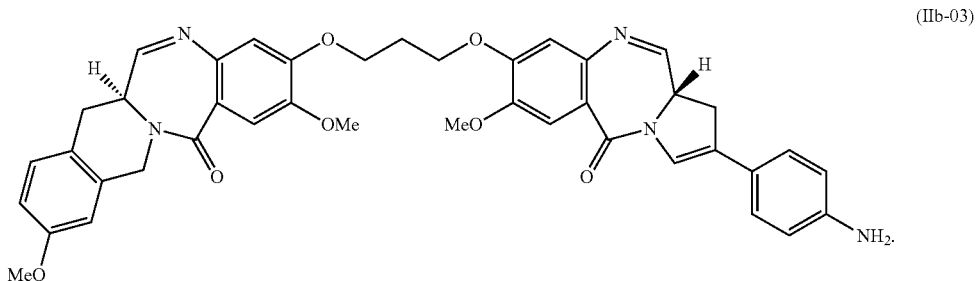
(IIb-03)

An especially preferred THIQ-PBD dimer is (IIb-03).

In another embodiment, a dimer of this invention comprises a benzodiazepine unit having a THIQ ring system and a benzodiazepine unit having an azaindoline (AZI) ring system ("THIQ-AZI dimer"). Such a dimer can be represented by formula (IIc):

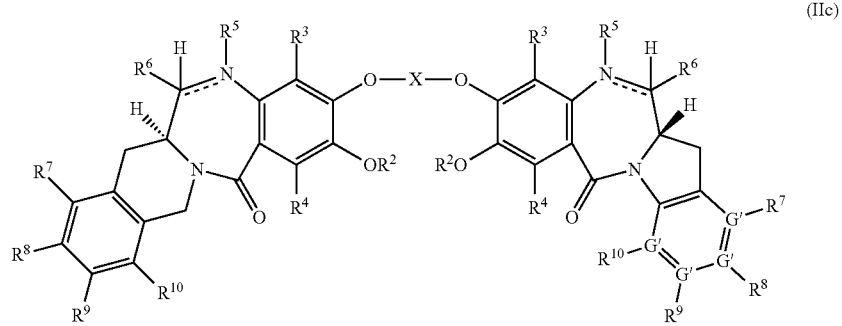

(IIc)

where
one G' is N and the others are C;
$R^2$, $R^3$, $R^4$, $R^5$, $R^6$, $R^7$, $R^8$, $R^9$, $R^{10}$, the double line ====, and X are as defined in the BRIEF SUMMARY OF THE INVENTION section hereinabove in respect of formula (I).

An example of a THIQ-AZI dimer is compound (IIc-01):

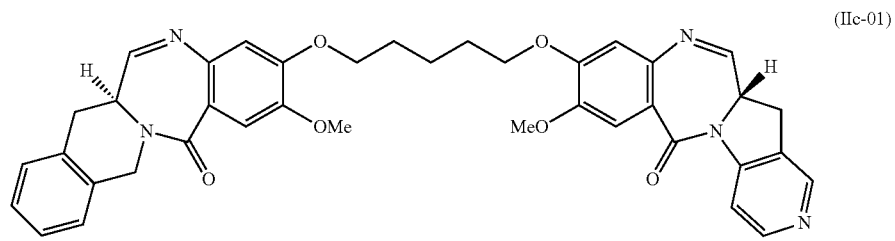 [SMILES: COc1cc2c(cc1OCCCCCOc1cc3c(cc1OC)C(=O)N1c4ccncc4C[C@H]1C=N3)N=C[C@@H]1Cc3ccccc3CN1C2=O]

(IIc-01)

Conjugates
General

Dimers of this invention can be used as therapeutic agents per se, but preferably are used as conjugates with a targeting moiety that specifically or preferentially binds to a chemical entity on a cancer cell. Preferably, the targeting moiety is an antibody or antigen binding portion thereof and the chemical entity is a tumor associated antigen.

Thus, another embodiment of this invention is a conjugate comprising dimer of this invention and a ligand, represented by formula (II)

(II)

where Z is a ligand, D is a dimer of this invention, and —$(X^D)_a C(X^Z)_b$— are collectively referred to as a "linker moiety" or "linker" because they link Z and D. Within the linker, C is a cleavable group designed to be cleaved at or near the site of intended biological action of dimer D; $X^D$ and $X^Z$ are referred to as spacer moieties (or "spacers") because they space apart D and C and C and Z, respectively; subscripts a, b, and c are independently 0 or 1 (that is, the presence of $X^D$, $X^Z$ and C are optional). Subscript m is 1, 2, 3, 4, 5, 6, 7, 8, 9, or 10 (preferably 1, 2, 3, or 4). D, $X^D$, C, $X^Z$ and Z are more fully described hereinbelow.

Ligand Z—for example an antibody—performs a targeting function. By binding to a target tissue or cell where its antigen or receptor is located, ligand Z directs the conjugate there. (When ligand Z is an antibody, the conjugate is sometimes referred to as antibody-drug conjugate (ADC) or an immunoconjugate. Preferably, the target tissue or cell is a cancer tissue or cell and the antigen or receptor is a tumor-associated antigen, that is, an antigen that is uniquely expressed by cancerous cells or is overexpressed by cancer cells, compared to non-cancerous cells. Cleavage of group C at the target tissue or cell releases dimer D to exert its cytotoxic effect locally. In some instances, the conjugate is internalized into a target cell by endocytosis and cleavage takes place within the target cell. In this manner, precise delivery of dimer D is achieved at the site of intended action, reducing the dosage needed. Also, dimer D is normally biologically inactive (or significantly less active) in its conjugated state, thereby reducing undesired toxicity against non-target tissue or cells. As anticancer drugs are often highly toxic to cells in general, this is an important consideration.

As reflected by the subscript m, each molecule of ligand Z can conjugate with more than one dimer D, depending on the number of sites ligand Z has available for conjugation and the experimental conditions employed. Those skilled in the art will appreciate that, while each individual molecule of ligand Z is conjugated to an integer number of dimers D, a preparation of the conjugate may analyze for a non-integer ratio of dimers D to ligand Z, reflecting a statistical average. This ratio is referred to as the substitution ratio (SR) or, synonymously, the drug-antibody ratio (DAR).

Ligand Z

Preferably, ligand Z is an antibody. For convenience and brevity and not by way of limitation, the detailed subsequent discussion herein about the conjugation of ligand Z is written in the context of its being an antibody, but those skilled in the art will understand that other types of ligand Z can be conjugated, mutatis mutandis. For example, conjugates with folic acid as the ligand can target cells having the folate receptor on their surfaces (Leamon et al., Cancer Res. 2008, 68 (23), 9839). For the same reason, the detailed discussion below is primarily written in terms of a 1:1 ratio of antibody Z to analog D (m=1).

Preferably, ligand Z is an antibody against a tumor associated antigen, allowing the selective targeting of cancer cells. Examples of such antigens include: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H4, also known as O8E; in particular antibodies 2A7, 1G11, and 2F9); Rao-Naik et al., U.S. Pat. No. 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Vistica et al., U.S. Pat. No. 8,383,118 B2 (2013, fucosyl-GM1, in particular antibodies 5B1, 5B1a, 7D4, 7E4, 13B8, and 18D5) Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA. in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Terrett et al., U.S. Pat. No. 8,680,247 B2 (2014; glypican-3; in particular antibodies 4A6, 11E7, and 16D10); Harkins et al., U.S. Pat. No. 7,335,748 B2 (2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference. Each of the aforementioned antibodies can be used in an ADC with d dimer of this invention.

Ligand Z can also be an antibody fragment or antibody mimetic, such as an affibody, a domain antibody (dAb), a nanobody, a unibody, a DARPin, an anticalin, a versabody, a duocalin, a lipocalin, or an avimer.

Any one of several different reactive groups on ligand Z can be a conjugation site, including ε-amino groups in lysine residues, pendant carbohydrate moieties, carboxylic acid groups, disulfide groups, and thiol groups. Each type of reactive group represents a trade-off, having some advantages and some disadvantages. For reviews on antibody reactive groups suitable for conjugation, see, e.g., Garnett, Adv. Drug Delivery Rev. 53 (2001), 171-216 and Dubowchik and Walker, Pharmacology & Therapeutics 83 (1999), 67-123, the disclosures of which are incorporated herein by reference.

In one embodiment, ligand Z is conjugated via a lysine ε-amino group. Most antibodies have multiple lysine ε-amino groups, which can be conjugated via amide, urea, thiourea, or carbamate bonds using techniques known in the art. However, it is difficult to control which and how many ε-amino groups react, leading to potential batch-to-batch variability in conjugate preparations. Also, conjugation may cause neutralization of a protonated ε-amino group important for maintaining the antibody's native conformation or may take place at a lysine near or at the antigen binding site, neither being a desirable occurrence.

In another embodiment, ligand Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with sodium cyanoborohydride. For additional disclosures on conjugation via carbohydrate side chains, see, e.g., Rodwell et al., Proc. Nat'l Acad. Sci. USA 83, 2632-2636 (1986); the disclosure of which is incorporated herein by reference. As with lysine ε-amino groups, there are concerns regarding reproducibility of the location of the conjugation site(s) and stoichiometry.

In yet another embodiment, ligand Z can be conjugated via a carboxylic acid group. In one embodiment, a terminal carboxylic acid group is functionalized to generate a carbohydrazide, which is then reacted with an aldehyde-bearing conjugation moiety. See Fisch et al., Bioconjugate Chemistry 1992, 3, 147-153.

In yet another embodiment, antibody Z can be conjugated via a disulfide group bridging a cysteine residue on antibody Z and a sulfur on the other portion of the conjugate. Some antibodies lack free thiol (sulfhydryl) groups but have disulfide groups, for example in the hinge region. In such case, free thiol groups can be generated by reduction of native disulfide groups. The thiol groups so generated can then be used for conjugation. See, e.g., Packard et al., Biochemistry 1986, 25, 3548-3552; King et al., Cancer Res. 54, 6176-6185 (1994); and Doronina et al., Nature Biotechnol. 21(7), 778-784 (2003); the disclosures of which are incorporated herein by reference. Again, there are concerns regarding conjugation site location and stoichiometry and the possible disruption of antibody native conformation.

A number of methods are known for introducing free thiol groups into antibodies without breaking native disulfide bonds, which methods can be practiced with a ligand Z of this invention. Depending on the method employed, it may be possible to introduce a predictable number of free sulfhydryls at predetermined locations. In one approach, mutated antibodies are prepared in which a cysteine is substituted for another amino acid. See, for example, Eigenbrot et al., U.S. Pat. No. 7,521,541 B2 (2009); Chilkoti et al., Bioconjugate Chem. 1994, 5, 504-507; Urnovitz et al., U.S. Pat. No. 4,698,420 (1987); Stimmel et al., J. Biol. Chem., 275 (39), 30445-30450 (2000); Bam et al., U.S. Pat. No. 7,311,902 B2 (2007); Kuan et al., J. Biol. Chem., 269 (10), 7610-7618 (1994); Poon et al., J. Biol. Chem., 270 (15), 8571-8577 (1995). In another approach, an extra cysteine is added to the C-terminus. See, e.g. Cumber et al., J. Immunol., 149, 120-126 (1992); King et al, Cancer Res., 54, 6176-6185 (1994); Li et al., *Bioconjugate Chem.*, 13, 985-995 (2002); Yang et al., *Protein Engineering*, 16, 761-770 (2003); and Olafson et al., *Protein Engineering Design & Selection*, 17, 21-27 (2004). A preferred method for introducing free cysteines is that taught by Liu et al., WO 2009/026274 A1, in which a cysteine bearing amino acid sequence is added to the C-terminus of the heavy chain of an antibody. This method introduces a known number of cysteine residues (one per heavy chain) at a known location away from the antigen binding site. The disclosures of the documents cited in this paragraph are all incorporated herein by reference.

In yet another embodiment, lysine ε-amino groups can be modified with reagents such as 2-iminothiolane or N-succinimidyl-3-(2-pyridyldithio)propionate (SPDP), converting an ε-amino group into a thiol or disulfide group—creating a cysteine surrogate, as it were. However, this method suffers from the same conjugation location and stoichiometry limitations associated with ε-amino groups proper.

Linker Components

As noted above, the linker portion of a conjugate of this invention comprises up to three elements: a cleavable group C and optional spacers $X^Z$ and $X^D$.

Cleavable group C is a group cleavable under physiological conditions, preferably selected such that it is relatively stable while the conjugate is in general circulation in the blood plasma, but is readily cleaved once the conjugate reaches its site of intended action, that is, near, at, or within the target cell. Preferably, the conjugate is internalized by a target cell upon binding of antibody Z to an antigen displayed on the surface of the target cell. Subsequently, cleavage of group C occurs in a vesicular body of the target cell (an early endosome, a late endosome, or, especially, a lysosome).

In one embodiment, group C is a pH sensitive group. The pH in blood plasma is slightly above neutral, while the pH inside a lysosome is acidic, circa 5. Thus, a group C whose cleavage is acid catalyzed will cleave at a rate several orders of magnitude faster inside a lysosome than in the blood plasma rate. Examples of suitable acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 102, 1048-1054 (1981) and Yang et al., *Proc. Natl Acad. Sci* (USA), 85, 1189-1193 (1988); the disclosures of which are incorporated herein by reference.

In another embodiment, group C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. For additional disclosures relating to disulfide cleavable groups in conjugates, see, e.g., Thorpe et al., *Cancer Res.* 48, 6396-6403 (1988); Santi et al., U.S. Pat. No. 7,541,530 B2 (2009); Ng et al., U.S. Pat. No. 6,989,452 B2 (2006); Ng et al., WO 2002/096910 A1; Boyd et al., U.S. Pat. No. 7,691,962 B2; and Sufi et al., US 2010/0145036 A1; the disclosures of which are incorporated herein by reference.

A preferred cleavable group is a peptide that is cleaved selectively by a protease inside the target cell, as opposed to by a protease in the serum. Typically, a cleavable peptide group comprises from 1 to 20 amino acids, preferably from 1 to 6 amino acids, more preferably from 1 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this context, the term "amino acid" also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an a-amino acid but functions in a manner similar to one. The amino acid can be of the "L" stereochemistry of the genetically encoded amino acids, as well as of the enantiomeric "D" stereochemistry.

Preferably, group C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of the target tissue, e.g., a protease released by nearby dying cells or a tumor-associated protease. Exemplary extracellular tumor-associated proteases are matrix metalloproteases (MMP), thimet oligopeptidase (TOP) and CD10.

For conjugates that are designed to be internalized by a cell, group C preferably comprises an amino acid sequence selected for cleavage by an endosomal or lysosomal protease, especially the latter. Non-limiting examples of such proteases include cathepsins B, C, D, H, L and S, especially cathepsin B. Cathepsin B preferentially cleaves peptides at a sequence -$AA^2$-$AA^1$- where $AA^1$ is a basic or strongly hydrogen bonding amino acid (such as lysine, arginine, or citrulline) and $AA^2$ is a hydrophobic amino acid (such as phenylalanine, valine, alanine, leucine, or isoleucine), for example Val-Cit (where Cit denotes citrulline) or Val-Lys. (Herein, amino acid sequences are written in the N-to-C direction, as in $H_2N$-$AA^2$-$AA^1$-$CO_2H$, unless the context clearly indicates otherwise.) Lys-Val-Ala, Asp-Val-Ala, Val-Ala, Lys-Val-Cit, and Asp-Val-Cit are also substrate peptide motifs for cathpsin B, although in some instances the cleavage rate may be slower. For additional information regarding cathepsin-cleavable groups, see Dubowchik et al., *Biorg. Med. Chem. Lett.* 8, 3341-3346 (1998); Dubowchik et al., *Bioorg. Med. Chem. Lett.*, 8 3347-3352 (1998); and Dubowchik et al., *Bioconjugate Chem.* 13, 855-869 (2002); the disclosures of which are incorporated by reference. Another enzyme that can be utilized for cleaving peptidyl linkers is legumain, a lysosomal cysteine protease that preferentially cleaves at Ala-Ala-Asn.

In one embodiment, Group C is a peptide comprising a two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to three amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu.

The preparation and design of cleavable groups C consisting of a single amino acid is disclosed in Chen et al., U.S. Pat. No. 8,664,407 B2 (2014), the disclosure of which is incorporated herein by reference.

Group C can also be a photocleavable one, for example a nitrobenzyl ether that is cleaved upon exposure to light.

Group C can be bonded directly to antibody Z or analog D; i.e. spacers $X^Z$ and $X^D$, as the case may be, can be absent. For example, if group C is a disulfide, one of the two sulfurs can be a cysteine residue or its surrogate on antibody Z. Or, group C can be a hydrazone bonded to an aldehyde on a carbohydrate side chain of the antibody. Or, group C can be a peptide bond formed with a lysine ε-amino group of antibody Z. In a preferred embodiment, dimer D is directly bonded to group C via a peptidyl bond to a carboxyl or amine group in dimer D.

When present, spacer $X^Z$ provides spatial separation between group C and antibody Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

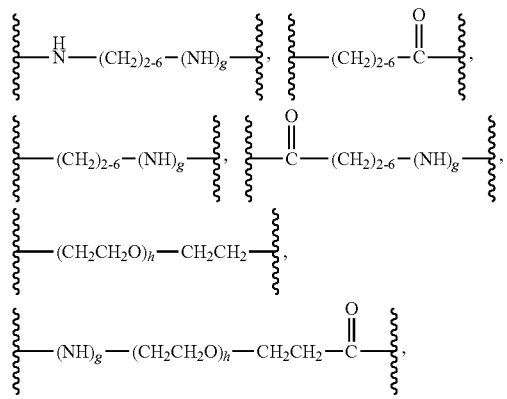

and combinations thereof, where the subscript g is 0 or 1 and the subscript h is 1 to 24, preferably 2 to 4. These segments can be combined, such as illustrated below:

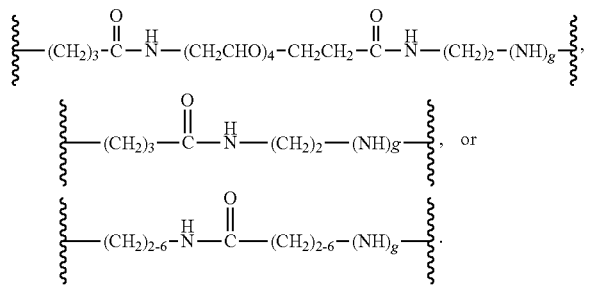

Spacer $X^D$, if present, provides spatial separation between group C and dimer D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, as described above in the context of spacer $X^Z$.

Spacers $X^Z$ and/or $X^D$, where present, preferably provide a linear separation of from 4 to 25 atoms, more preferably from 4 to 20 atoms, between Z and C or D and C, respectively.

The linker can perform other functions in addition to covalently linking the antibody and the drug. For instance, the linker can contain poly(ethylene glycol) (PEG) groups, which enhance solubility either during the performance the conjugation chemistry or in the final ADC product. Where a PEG group is present, it may be incorporated into either spacer $X^Z$ of $X^D$, or both. The number of repeat units in a PEG group can be from 2 to 20, preferably between 4 and 10.

Either spacer $X^Z$ or $X^D$, or both, can comprise a self-immolating moiety. A self-immolating moiety is a moiety that (1) is bonded to group C and either antibody Z or dimer D and (2) has a structure such that cleavage from group C initiates a reaction sequence resulting in the self-immolating moiety disbonding itself from antibody Z or dimer D, as the case may be. In other words, reaction at a site distal from antibody Z or dimer D (cleavage from group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof were to remain attached to dimer D, the biological activity of the latter may be impaired. The use of a self-immolating moiety is especially desirable where cleavable group C is a polypeptide, in which instance the self-immolating moiety typically is located adjacent thereto.

Exemplary self-immolating moieties (i)-(v) bonded to a hydroxyl or amino group on a partner molecule D are shown below:

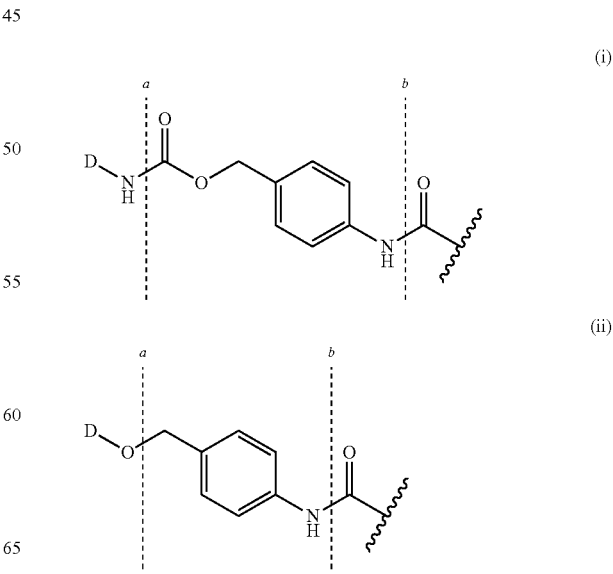

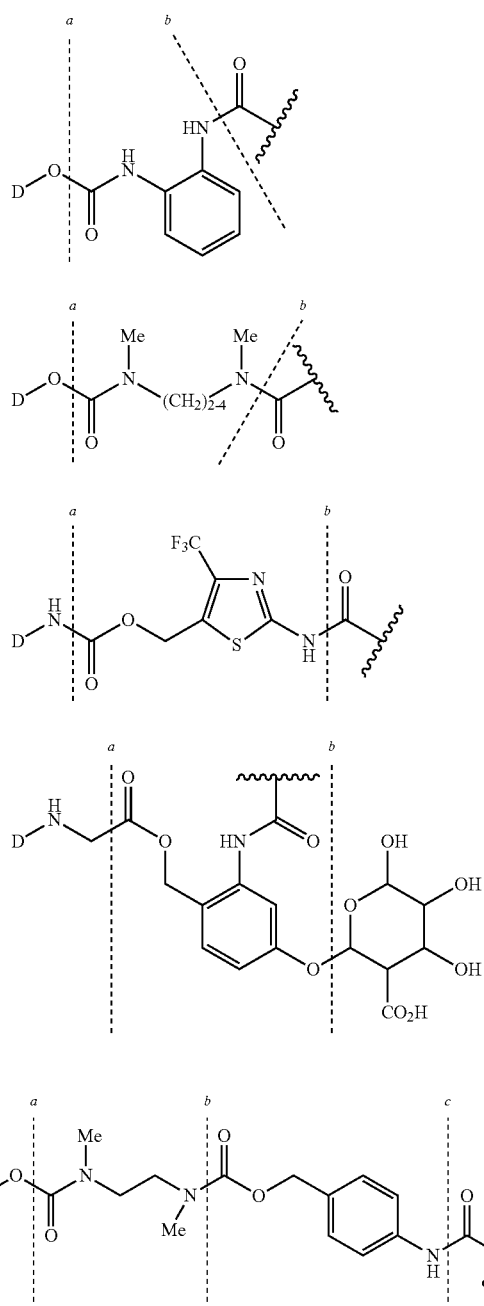

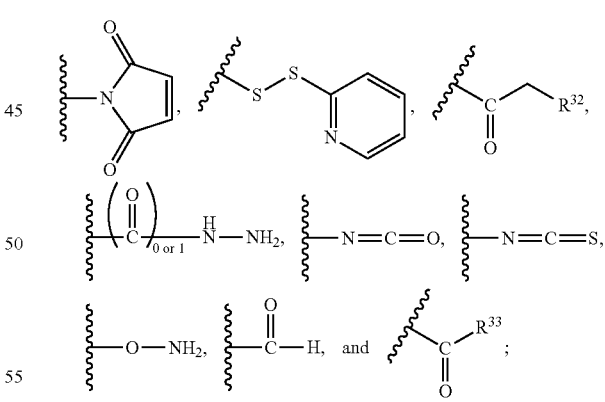

The self-immolating moiety is the structure between dotted lines a and b (or dotted lines b and c), with adjacent structural features shown to provide context. Self-immolating moieties (i) and (v) are bonded to a dimer D-NH$_2$ (i.e., dimer D is conjugated via an amino group), while self-immolating moieties (ii), (iii), and (iv) are bonded to a dimer D-OH (i.e., dimer D is conjugated via a hydroxyl or carboxyl group). Cleavage of the amide bond at dotted line b (e.g., by a peptidase) releases the amide nitrogen as an amine nitrogen, initiating a reaction sequence that results in the cleavage of the bond at dotted line a and the consequent release of D-OH or D-NH$_2$, as the case may be. Alternatively, the cleavage that triggers the self-immolating reaction can be by a different type of enzyme, for example by a β-glucuronidase, as in the instance of structure (vi). In some instances, self-immolating groups can be used in tandem, as shown by structure (vii). In such case, cleavage at dotted line c triggers self-immolation of the moiety between dotted lines b and c by a 1,6-elimination reaction, followed by self-immolation of the moiety between dotted lines a and b by a cyclization-elimination reaction. For additional disclosures regarding self-immolating moieties, see Carl et al., *J. Med. Chem.*, 24 (3), 479-480 (1981); Carl et al., WO 81/01145 (1981); Dubowchik et al., *Pharmacology & Therapeutics*, 83, 67-123 (1999); Firestone et al., U.S. Pat. No. 6,214,345 B1 (2001); Toki et al., *J. Org. Chem.* 67, 1866-1872 (2002); Doronina et al., *Nature Biotechnology* 21 (7), 778-784 (2003) (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; Jeffrey et al., U.S. Pat. No. 8,039,273; and Senter et al., US 2003/0096743 A1; the disclosures of which are incorporated by reference. A preferred self-immolating group is p-aminobenzyl oxycarbonyl (PABC) group, as shown in structure (i).

In another embodiment, an antibody targeting moiety and the dimer D are linked by a non-cleavable linker, i.e., element C is absent. Degradation of the antibody eventually reduces the linker to a small appended moiety that does not interfere with the biological activity of dimer D.

Conjugation Techniques

Conjugates of this invention preferably are made by first preparing a compound comprising an analog of this invention (represented by D in the formulae below) and linker $(X^D)_a(C)_c(X^Z)_b$ (where $X^D$, C, $X^Z$, a, b, and c are as defined for formula (II)) to form an analog-linker composition represented by formula (III):

$$D-(X^D)_a(C)_c(X^Z)_b-R^{31} \quad \text{(III)}$$

where $R^{31}$ is a functional group suitable for reacting with a complementary functional group on antibody Z to form the conjugate. Examples of suitable groups $R^{31}$ include amino, azide, cyclooctyne, where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties $D-(X^D)_aC(X^Z)_b-R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2 (2011); Sufi et al., US 2010/0145036 A1; and Chen et al., US 2010/0113476 A1; the disclosures of which are incorporated herein by reference.

Preferably reactive functional group —$R^{31}$ is —$NH_2$, —OH, —$CO_2H$, —SH, maleimido, cyclooctyne, azido (—$N_3$), hydroxylamino (—$ONH_2$) or N-hydroxysuccinimido. Especially preferred functional groups —$R^{31}$ are:

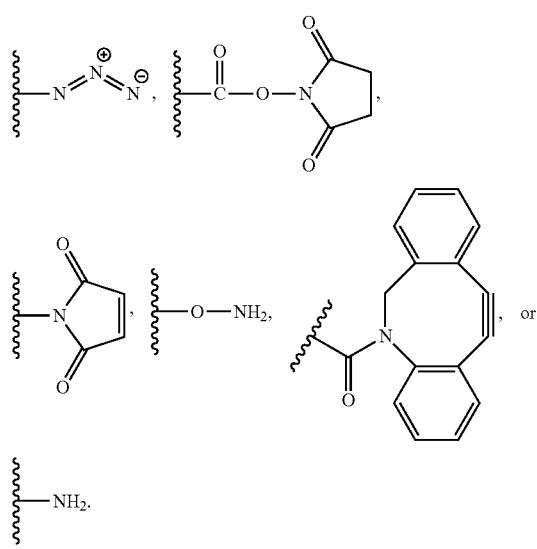

An —OH group can be esterified with a carboxy group on the antibody, for example, on an aspartic or glutamic acid side chain.

A —$CO_2H$ group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

Various techniques can be introducing an —SH group into an antibody. In a preferred one, an ε-amino group in the side chain of a lysine residue in the antibody is reacted with 2-iminothiolane to introduce a free thiol (—SH) group. The thiol group can react with a maleimide or other nucleophile acceptor group to effect conjugation:

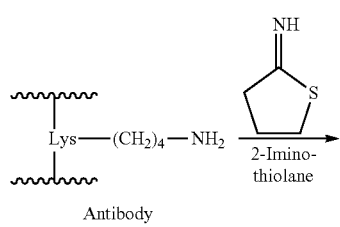

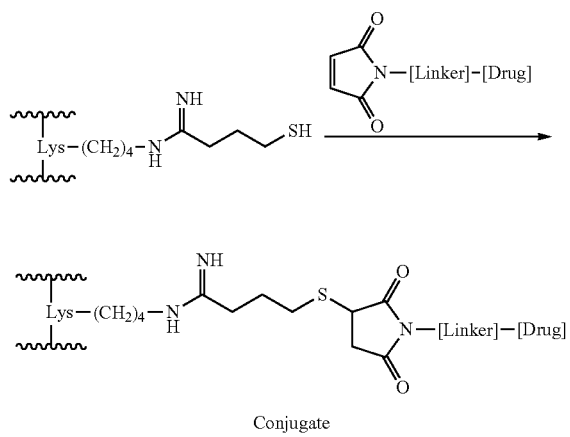

Conjugate

Typically, a thiolation level of two to three thiols per antibody is achieved. For a representative procedure, see Cong et al. 2014, the disclosure of which is incorporated herein by reference. Thus, in one embodiment, an antibody for conjugation to a dimer of this invention has one or more lysine residues (preferably two or three) modified by reaction with iminothiolane.

An —SH group can also be used for conjugation where the antibody has been modified to introduce a maleimide group thereto, in a Michael addition reaction that is the "mirror image" of that described above. Antibodies can be modified to have maleimide groups with N-succinimidyl 4-(maleimidomethyl)-cyclohexanecarboxylate (SMCC) or its sulfonated variant sulfo-SMCC, both reagents being available from Sigma-Aldrich.

An alternative conjugation technique employs copper-free "click chemistry," in which an azide group adds across the strained alkyne bond of a cyclooctyne to form an 1,2,3-triazole ring. See, e.g., Agard et al., *J. Amer. Chem. Soc.* 2004, 126, 15046; Best, *Biochemistry* 2009, 48, 6571, the disclosures of which are incorporated herein by reference. The azide can be located on the antibody and the cyclooctyne on the drug moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody (Ab):

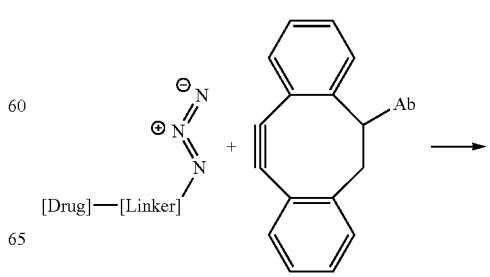

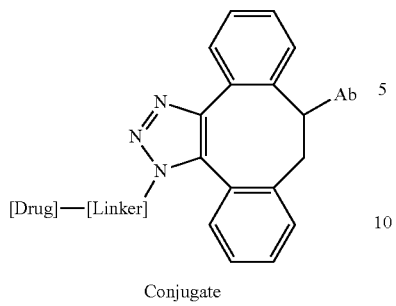

Conjugate

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenyalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., *Biotechnol. Bioeng.* 2009, 102 (2), 400-416. The foregoing disclosures are incorporated herein by reference. Thus, in one embodiment, an antibody that is used for making a conjugate with a dimer of this invention has one or more amino acids replaced by a non-natural amino acid, which preferably is p-acetylphenylalanine or p-azidophenylalanine, more preferably p-acetylphenylalanine.

Still another conjugation technique uses the enzyme transglutaminase (preferably bacterial transglutaminase or BTG), per Jeger et al., *Angew. Chem. Int. Ed.* 2010, 49, 9995. BTG forms an amide bond between the side chain carboxamide of a glutamine (the amine acceptor) and an alkyleneamino group (the amine donor), which can be, for example, the ε-amino group of a lysine or a 5-amino-n-pentyl group. In a typical conjugation reaction, the glutamine residue is located on the antibody, while the alkyleneamino group is located on the linker-drug moiety, as shown below:

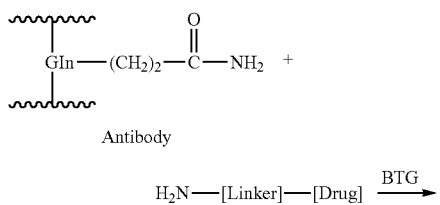

Antibody

H₂N—[Linker]—[Drug] $\xrightarrow{\text{BTG}}$

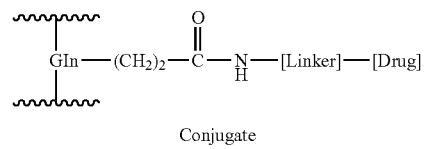

Conjugate

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297)—nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Further, it has been shown that an N297Q substitution in an antibody not only eliminates glycosylation, but also introduces a second glutamine residue (at position 297) that too is an amine acceptor. Thus, in one embodiment, an antibody that is conjugated to a dimer of this invention is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

Conjugation can also be effected using the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

Dimer-Linker Compounds

Generally, an ADC of a dimer of this invention comprises a linker attached to a functional group on the dimer, which linker is attached to the antibody. Reflecting the diversity of conjugation techniques available, the dimers of this invention can be elaborated into many different dimer-linker compounds suitable for conjugation to an antibody.

Generally, there are three different modes for attachment of the linker to a dimer of this invention, as illustrated in the figures below (with variables and optional substituents in the rings not shown for simplicity):

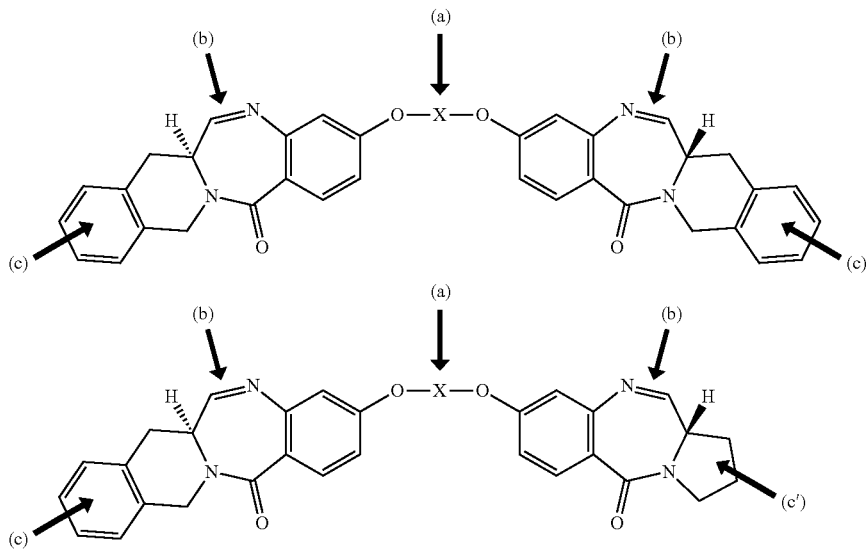

In type (a) dimer-linker compounds, a functional group for attachment of the linker is located in the bridge X between the two dimer halves. In type (b) dimer-linker compounds, the linker is attached as an addition product across an imine double bond. In types (c) and (c') dimer-linker compounds, a functional group for attachment of the linker is located at an "outside" ring of a THIQ, AZI, or PBD dimer unit.

In one embodiment, type (a) dimer-linker compound can be represented by the formula (IIIa):

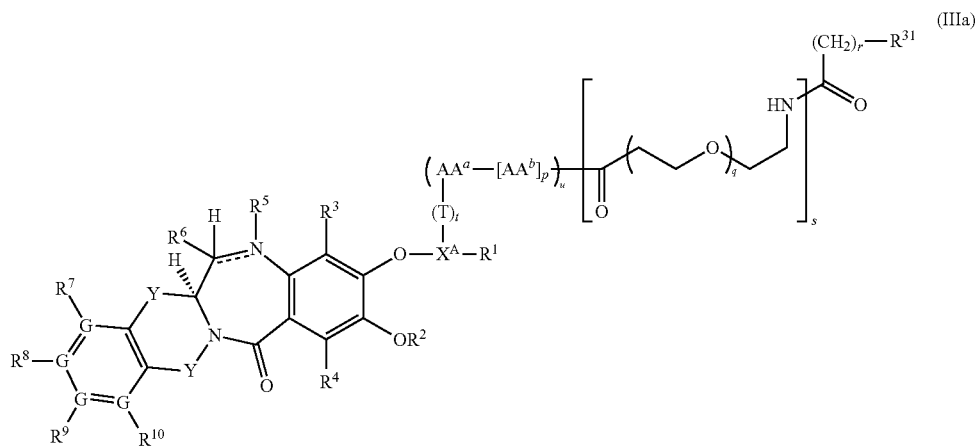

wherein

T is a self-immolating group;

t is 0 or 1;

$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

u is 0 or 1;

p is 1, 2, 3, or 4;

q is 1, 2, 3, 4, 5, 6, 7, 8, 9, 10, 11, or 12 (preferably 2, 3, 4, or 8);

r is 1, 2, 3, 4, or 5;

s is 0 or 1;

$R^{31}$ is 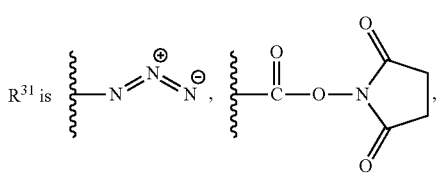

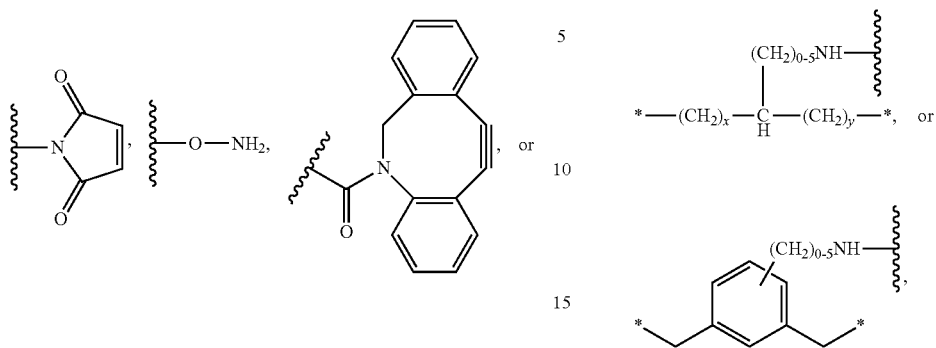

where each x and y is 1, 2, or 3 with the proviso that the sum of x and y is 2 or 4; the asterisks (*) indicate the positions of bonding of each $X^A$ to the adjacent O and $R^1$; and the wavy line indicates the position of bonding of each $X^A$ to T if T is present or to $AA^a$ if T is absent; and $R^1$, $R^2$, $R^3$, $R^4$, $R^5$, $R^6$, $R^7$, $R^8$, $R^9$, $R^{10}$, G, Y, and the double line ═══ are as defined in the BRIEF SUMMARY OF THE INVENTION section hereinabove in respect of formula (I).

In one preferred embodiment, u is 1 in formula (IIIa).

A preferred type (a) dimer-linker compound according to formula (IIIa) is represented by formula (IIIa'):

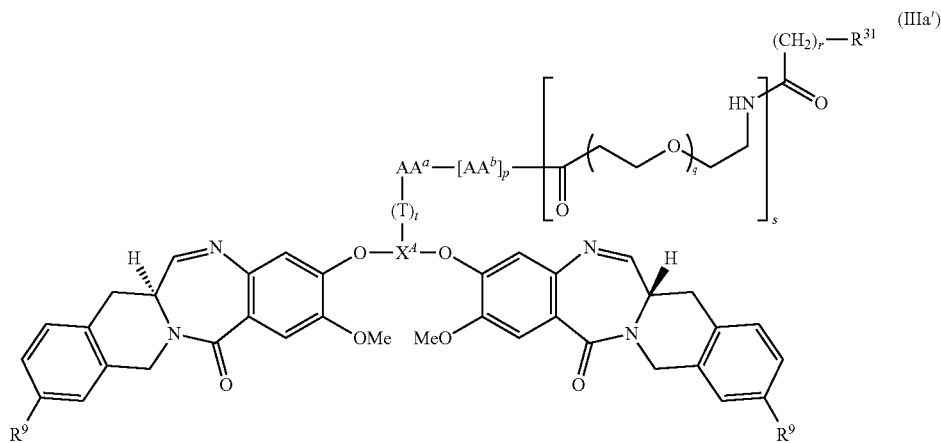

wherein each $R^9$ is independently H, $O(CH_2CH_2O)_{1-4}H$, $(CH_2CH_2O)_{1-4}(C_1-C_3\ alkyl)$, OH, Cl, F, or Br.
Preferably, in formulae (IIIa) and (IIIa'), $X^A$ is
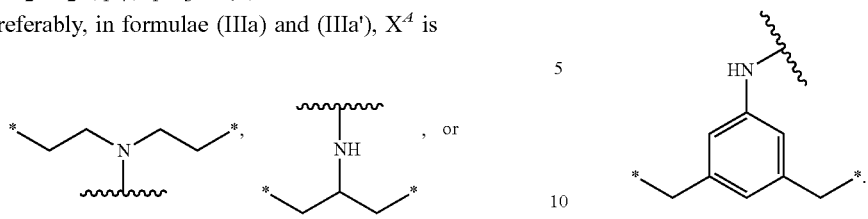
, or
Examples of type (a) dimer-linker compounds include:
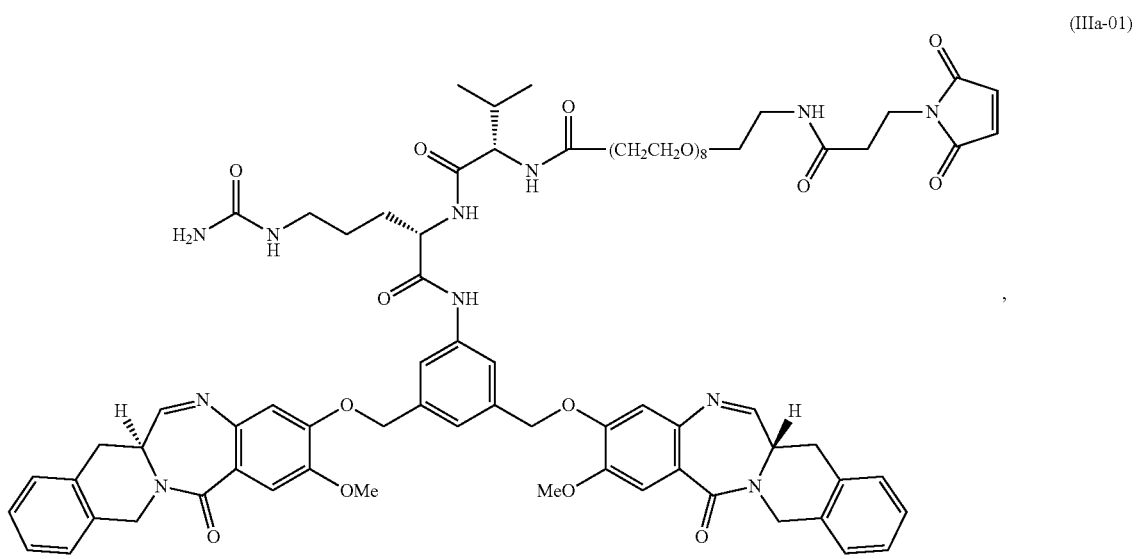
(IIIa-01)
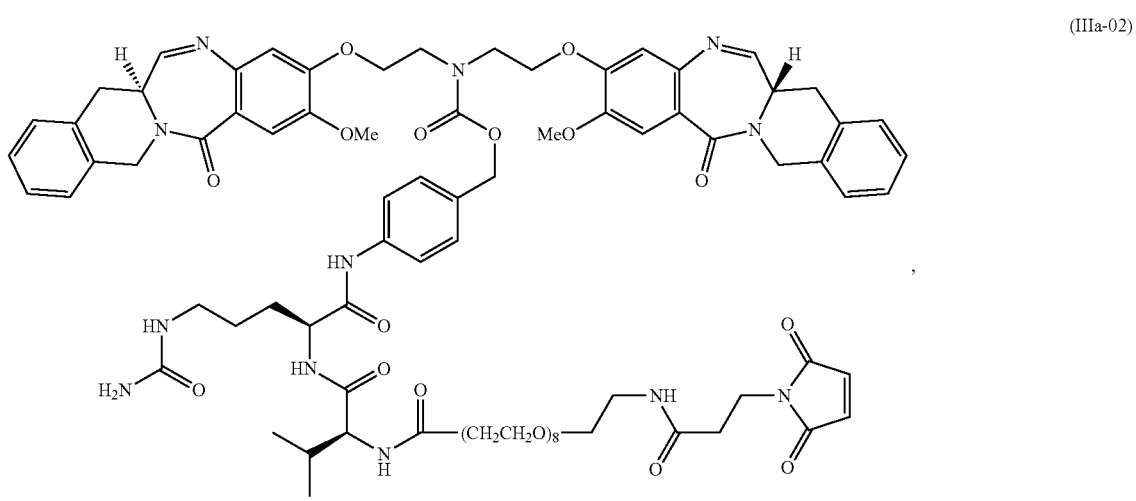
(IIIa-02)

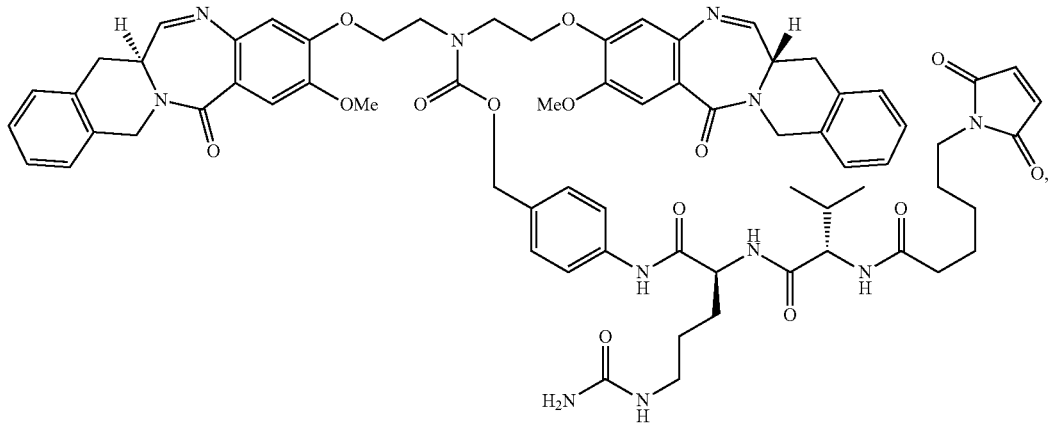
(IIIa-03)
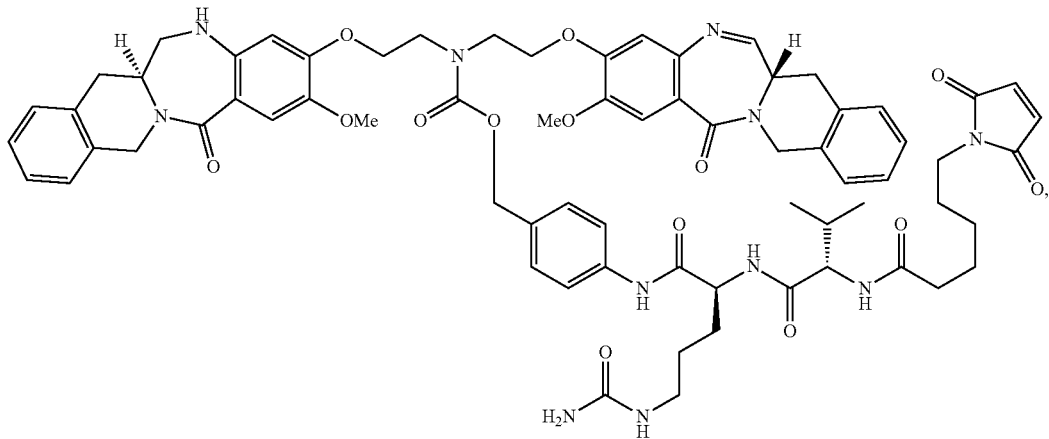
(IIIa-04)
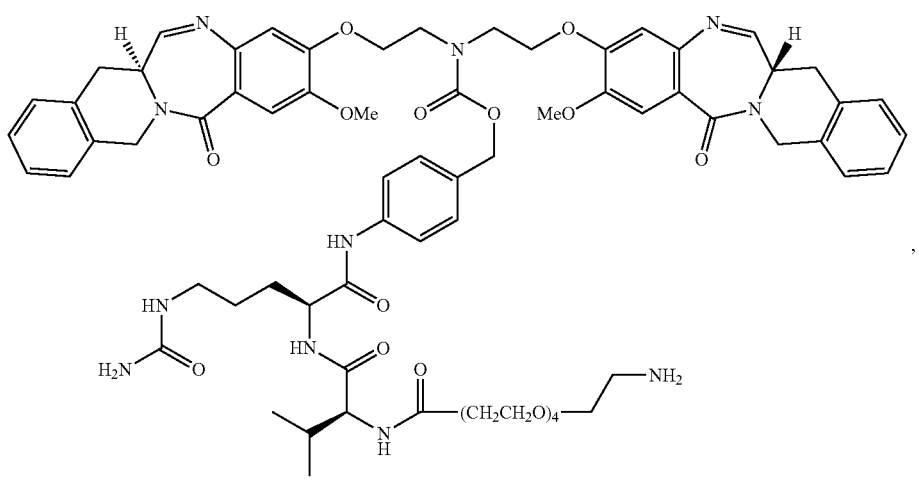
(IIIa-05)

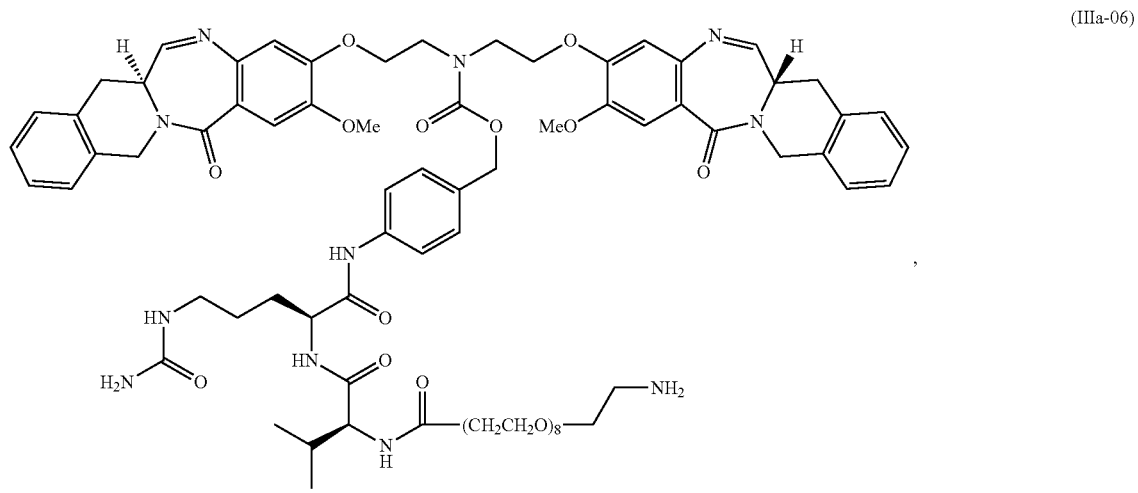
(IIIa-06)
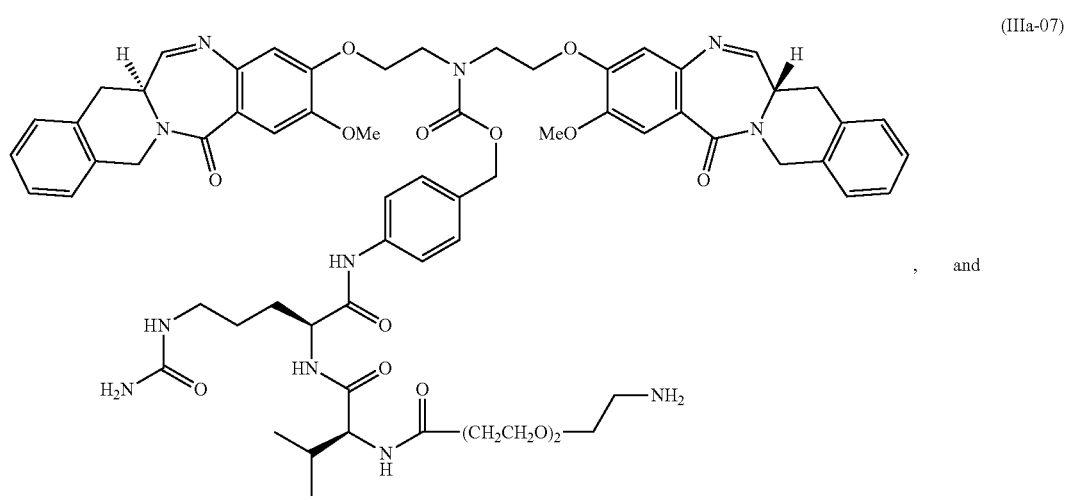
(IIIa-07) , and
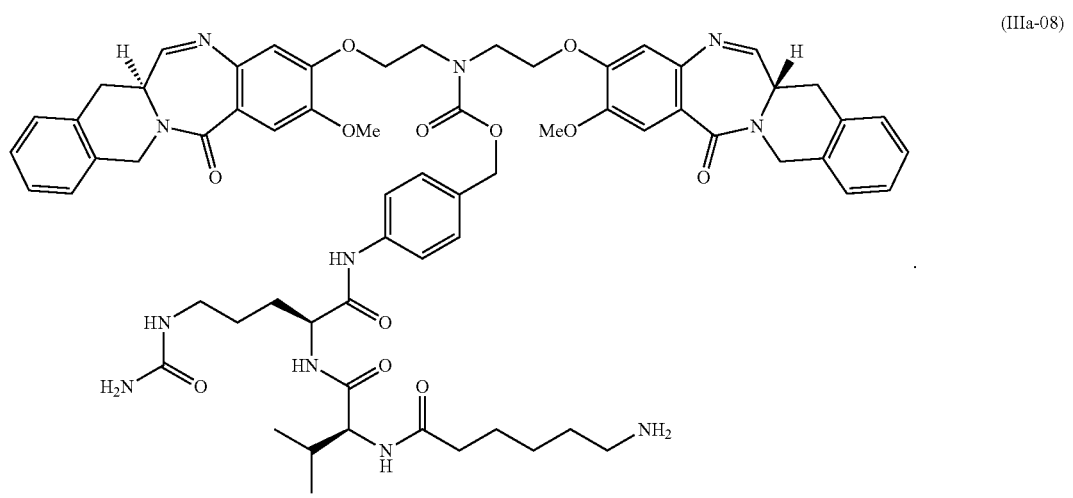
(IIIa-08)

A preferred subgenus of dimer-linkers is according to the formula below

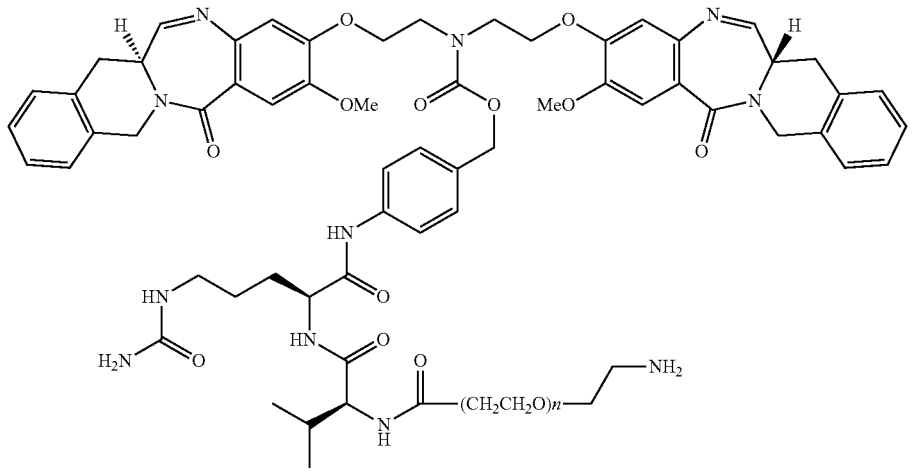

where the subscript n is 2, 3, 4, 5, 6, 7, 8, 9, 10, 11, or 12.

Especially preferred type (a) dimer linker compounds are (IIIa-03) and (IIIa-04).

In another embodiment, type (b) dimer-linker compounds can be represented by formula (IIIb):

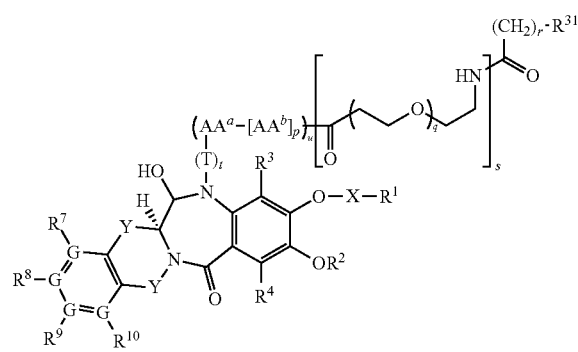

(IIIb)

wherein

T, t, $AA^a$, $AA^b$, u, p, q, s, r, and $R^{31}$ are as defined in respect of formula (IIIa); and $R^1$, $R^2$, $R^3$, $R^4$, $R^5$, $R^6$, $R^7$, $R^8$, $R^9$, $R^{10}$, X, Y, and G are as defined in the BRIEF SUMMARY OF THE INVENTION section hereinabove.

In one preferred embodiment, u is 1 in formula (IIIb).

A preferred type (b) dimer according to formula (IIIb) is represented by formula (IIIb')

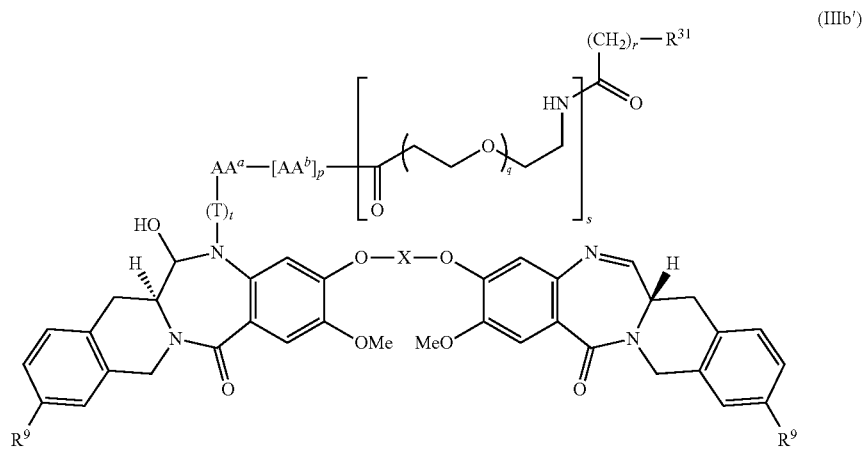

(IIIb')

wherein
each $R^9$ is independently H, $O(CH_2CH_2O)_{1-4}H$, $(CH_2CH_2O)_{1-4}(C_1-C_3\ alkyl)$, OH, Cl, F, or Br; and
X is 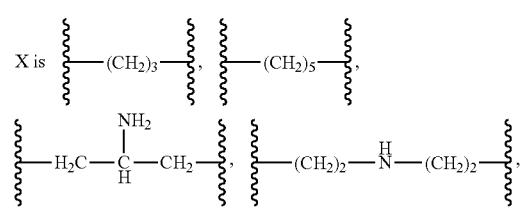 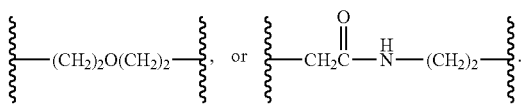
Examples of type (b) dimer-linker compounds include:
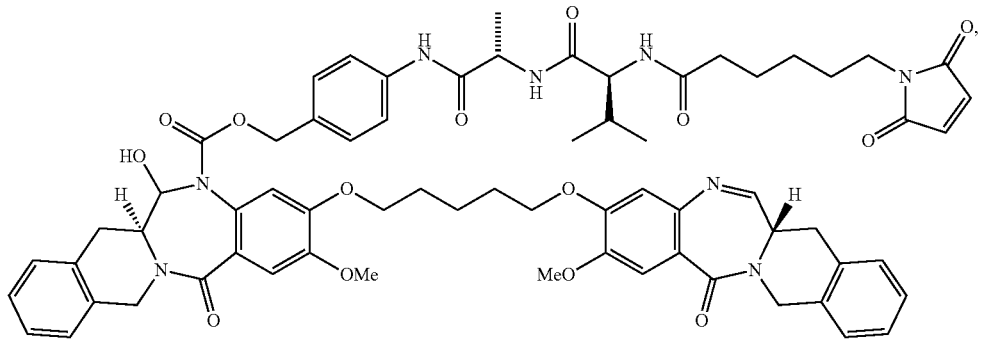
(IIIb-01)
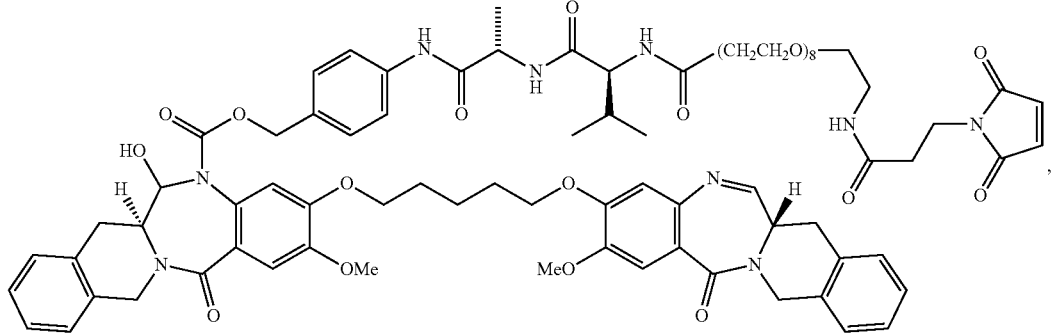
(IIIb-02)
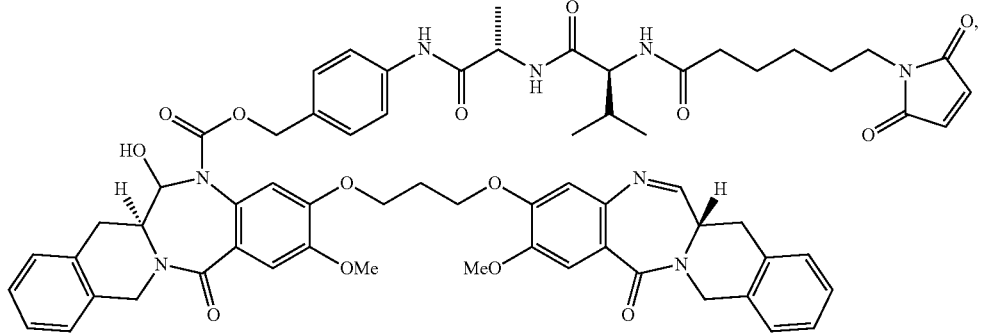
(IIIb-03)

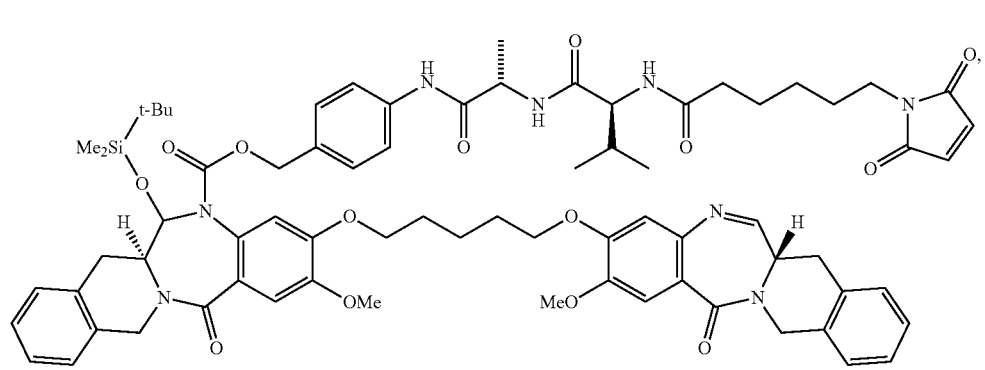
(IIIb-04)
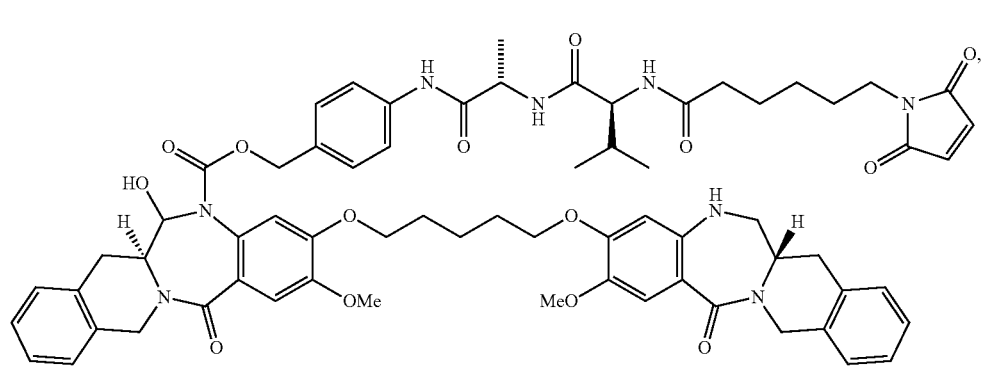
(IIIb-05)
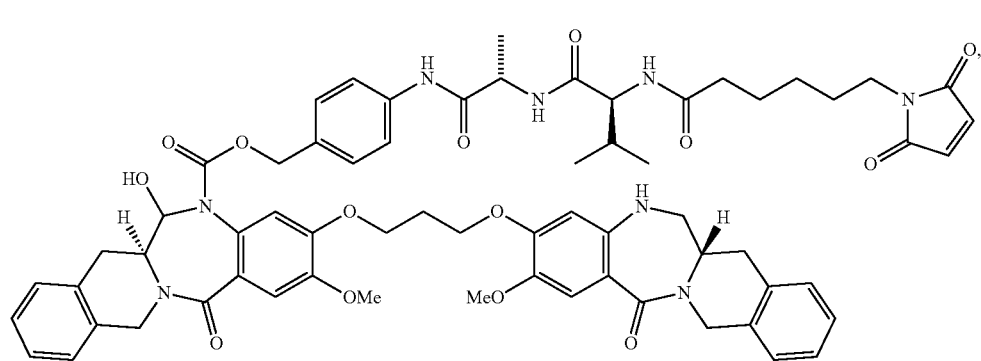
(IIIb-06)
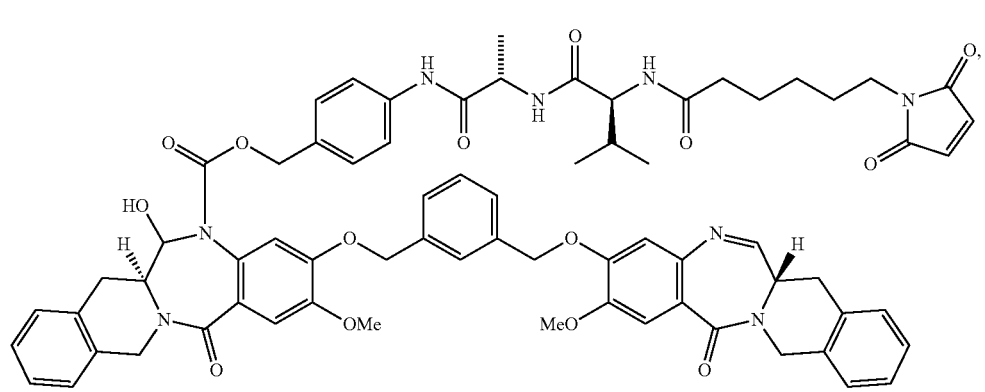
(IIIb-07)

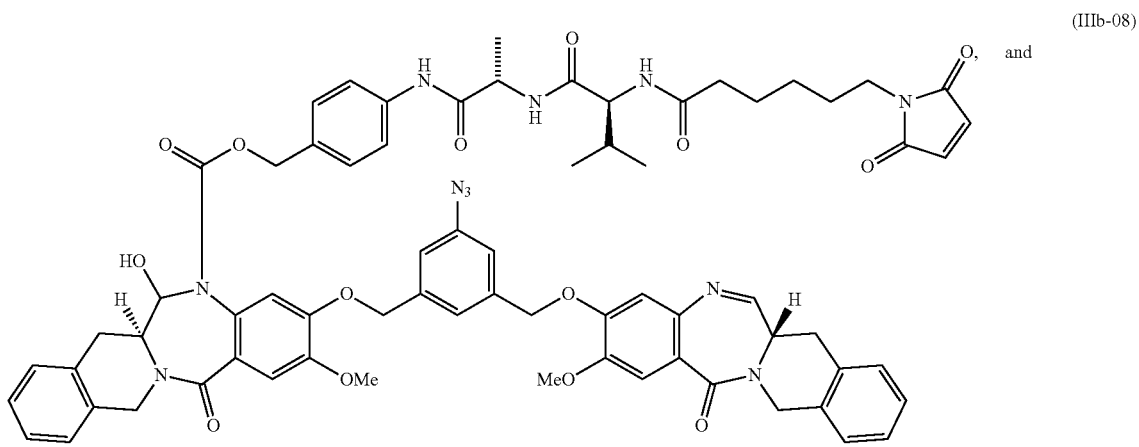

(IIIb-08)

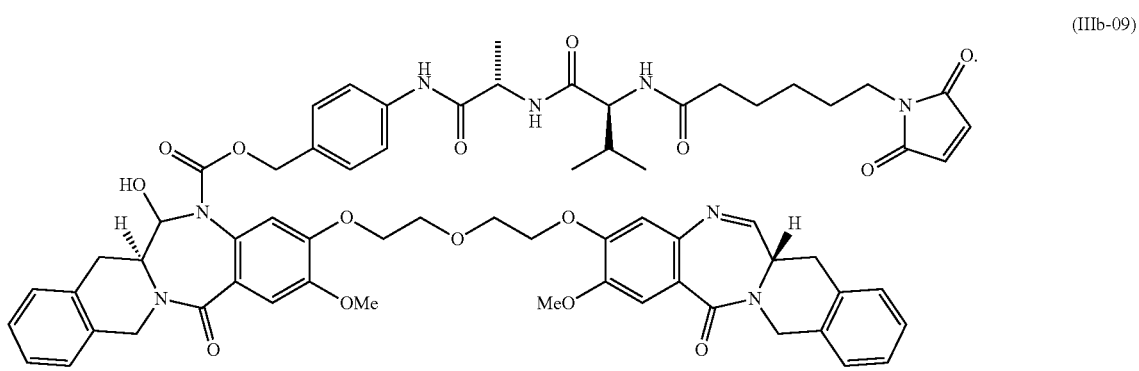

(IIIb-09)

In one embodiment, type (c) dimer-linker compounds can be represented by formula (IIIc):

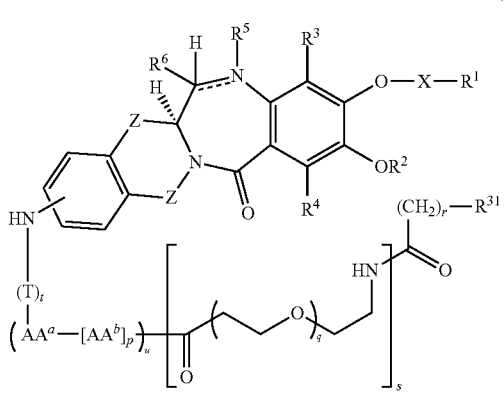

(IIIc)

wherein

T, t, $AA^a$, $AA^b$, u, p, q, s, r, and $R^{31}$ are as defined in respect of formula (IIIa); and $R^1$, $R^2$, $R^3$, $R^4$, $R^5$, $R^6$, Z, and the double line ══ are as defined in the BRIEF SUMMARY OF THE INVENTION section hereinabove.

In a preferred embodiment, u is 1 in formula (IIIc).

A preferred type (c) dimer-linker compound according to formula (IIIc) is represented by formula (IIIc'):

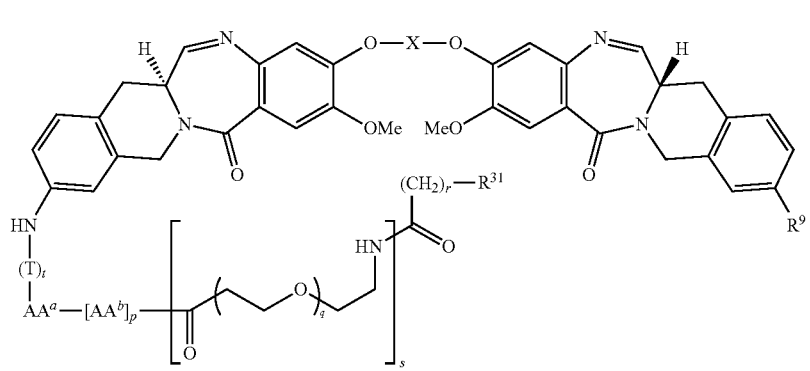
(IIIc')
wherein
R⁹ is H, $O(CH_2CH_2O)_{1-4}H$, $(CH_2CH_2O)_{1-4}(C_1$-$C_3$ alkyl), OH, Cl, F, or Br; and
X is 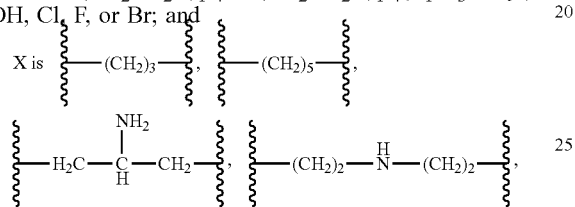
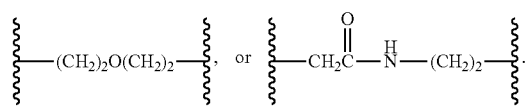
Examples of type (c) dimer-linker compounds include:
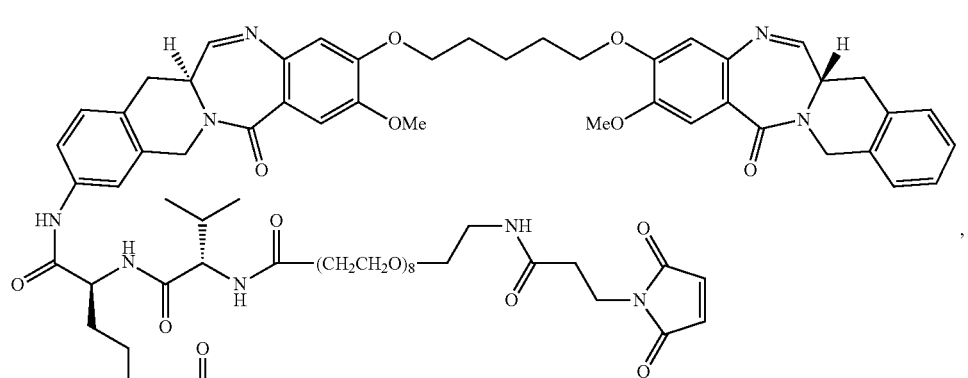
(IIIc-01)
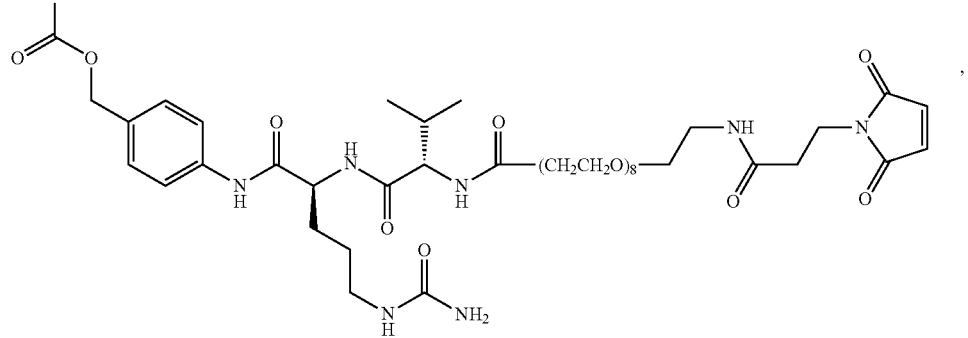
(IIIc-02)

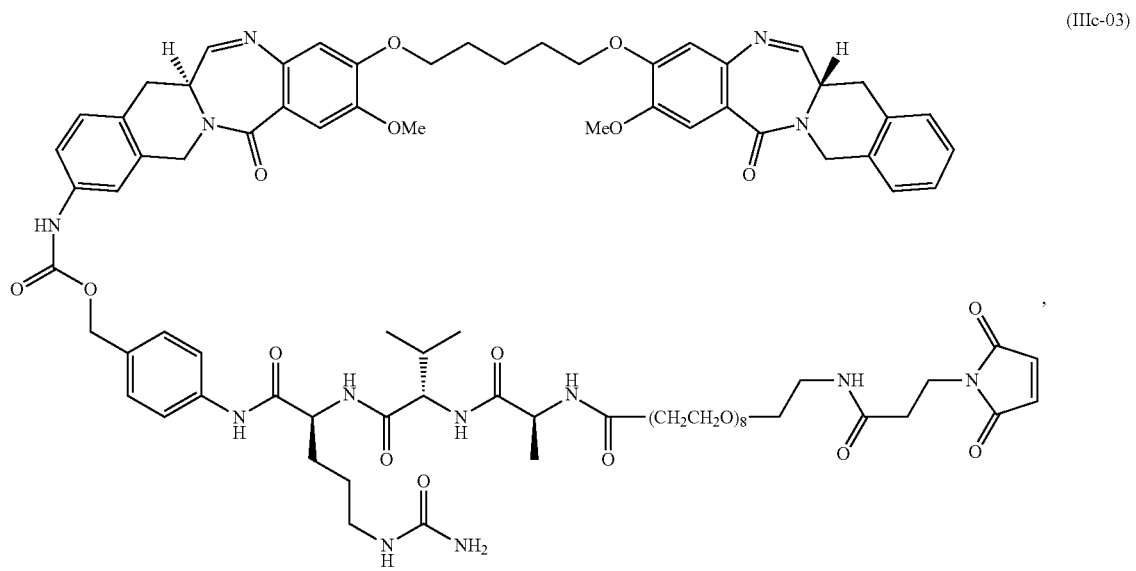
(IIIc-03)
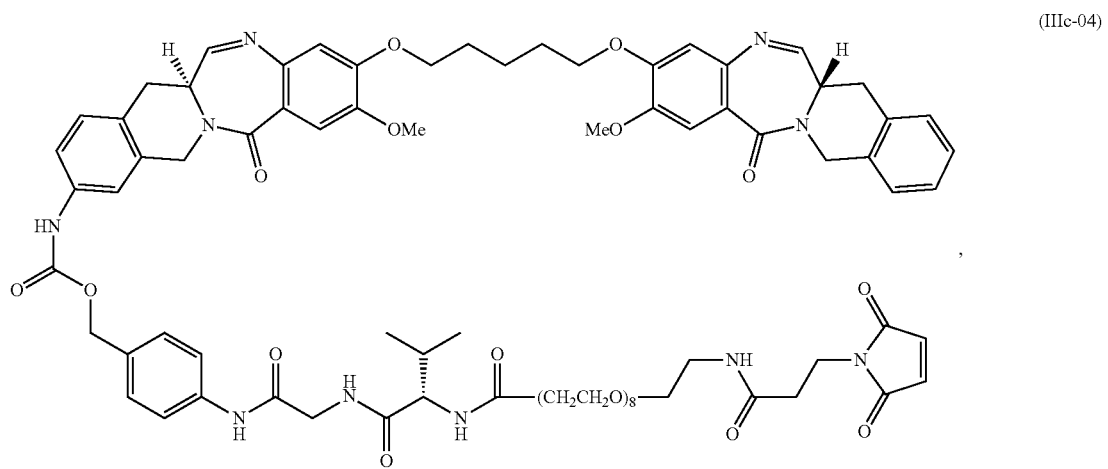
(IIIc-04)
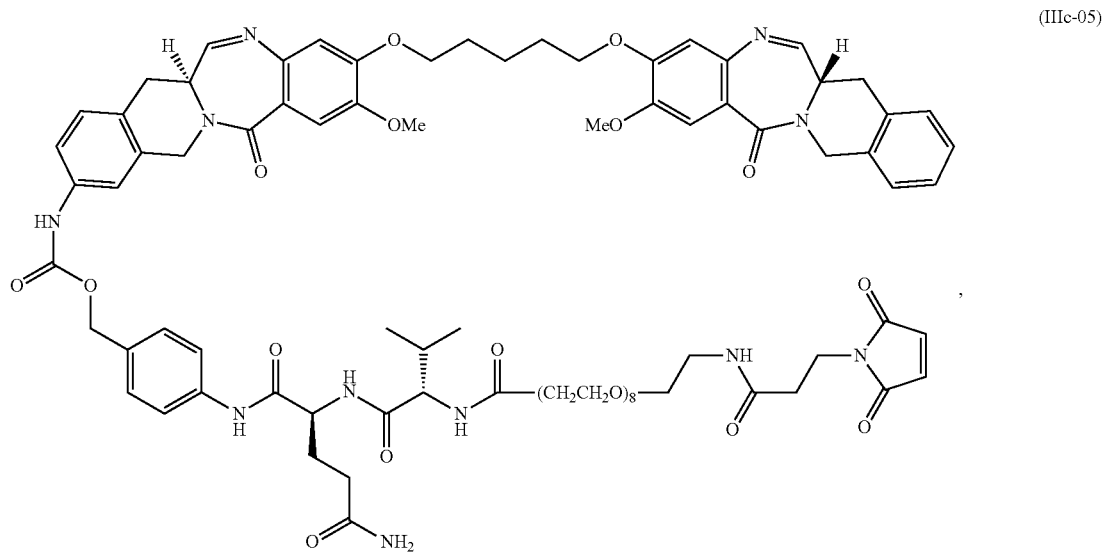
(IIIc-05)

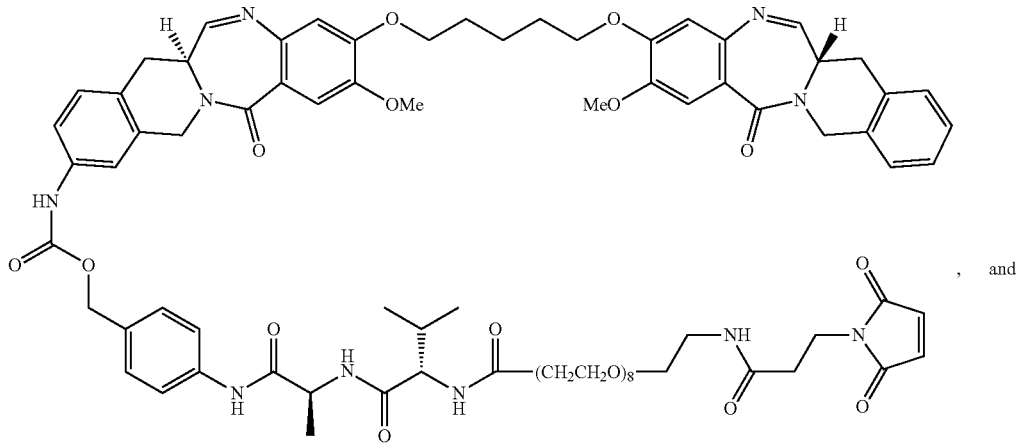
(IIIc-06)
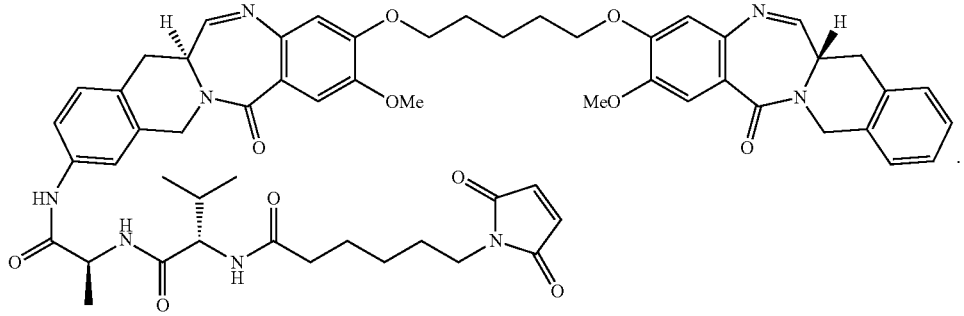
, and
(IIIc-07)
A preferred type (c') dimer-linker is represented by formula (IIIc"):
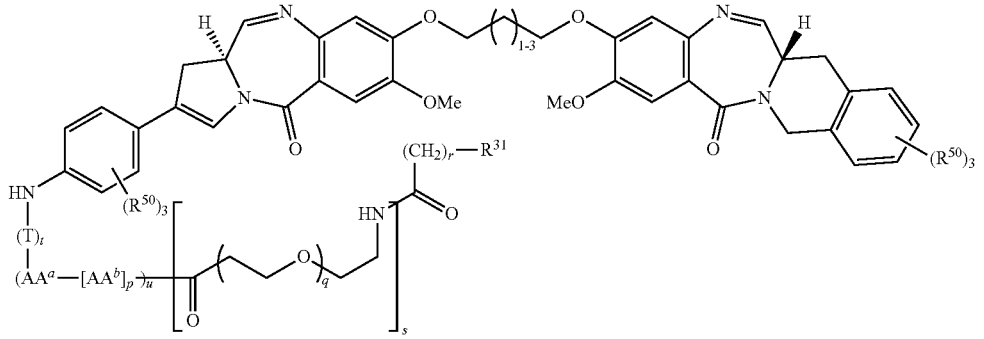
(IIIc")
wherein
T, t, $AA^a$, $AA^b$, u, p, q, s, r, and $R^{31}$ are as defined in respect of formula (IIIa); and
each $R^{50}$ is independently H, $O(C_1\text{-}C_3$ alkyl), $O(C_2\text{-}C_3$ alkylene), $O(C_2\text{-}C_3$ alkynyl), F, Cl, Br, or CN.

Preferably, in formula (IIIc"), the moiety

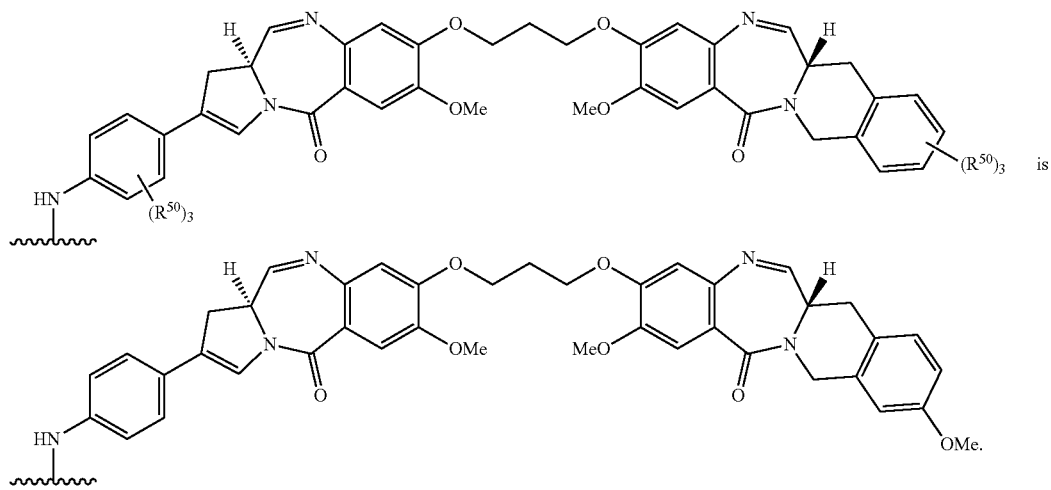

is

An example of a dimer-linker according to formula (IIIc") is:

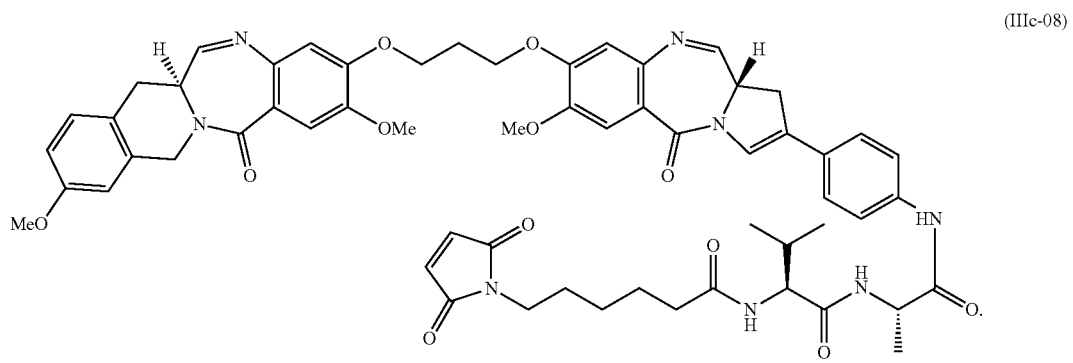 [SMILES: COc1ccc2c(c1)CN1C(=O)c3cc(OC)c(OCCCOc4cc5c(cc4OC)C(=O)N4C=C(c6ccc(NC(=O)[C@H](C)NC(=O)[C@@H](NC(=O)CCCCCN7C(=O)C=CC7=O)C(C)C)cc6)C[C@H]4C=N5)cc3N=C[C@@H]1C2]

(IIIc-08)

An especially preferred type (c)/(c') dimer-linker compound is (IIIc-08).

$R^{31}$ in formulae (IIIa), (IIIa'), (IIIb), (IIIb'), (IIIc), (IIIc') and (IIIc") is a reactive functional group capable of reacting with a complementary functional group on the antibody. to effect conjugation, as described above.

In formulae (IIIa), (IIIa'), (IIIb), (IIIb'), (IIIc), (IIIc'), and (IIIc"), $-AA^a-[AA^b]_p-$ represents a polypeptide whose length is determined by the value of p (dipeptide if p is 1, tetrapeptide if p is 3, etc.). $AA^a$ is at the carboxy terminus of the polypeptide and its carboxyl group forms a peptide (amide) bond with an amine nitrogen of the dimer. Conversely, the last $AA^b$ is at the amino terminus of the polypeptide and its a-amino group forms a peptide bond with

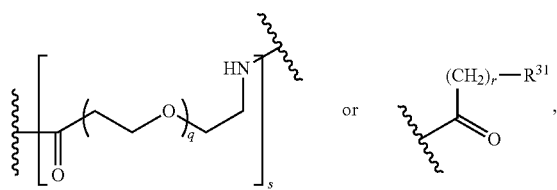

depending on whether s is 1 or 0, respectively. Preferred polypeptides $-AA^a-[AA^b]_p-$ are Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit, written in the conventional N-to-C direction, as in $H_2N$-Val-Cit-$CO_2H$). More preferably, the polypeptide is Val-Cit, Val-Lys, or Val-Ala. Preferably, a polypeptide $-AA^a-[AA^b]_p-$ is cleavable by an enzyme found inside the target (cancer) cell, for example a cathepsin and especially cathepsin B.

As indicated by the subscript t equals 0 or 1, a self-immolating group T is optionally present in dimer-linker compounds of formulae (IIIa), (IIIa'), (IIIb), (IIIb'), (IIIc), (IIIc') and (IIIc"). When present, the self-immolating group T preferably is a p-aminobenzyl oxycarbonyl (PABC) group, whose structure is shown below, with an asterisk (*) denoting the end of the PABC bonded to an amine nitrogen of the dimer and a wavy line ( ~~~~ ) denoting the end bonded to the polypeptide $-AA^a-[AA^b]_p-$.

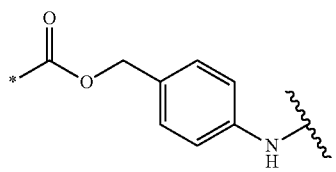 [SMILES: *Nc1ccc(COC(*)=O)cc1]

In a preferred embodiment, in formulae (IIIa), (IIIa'), (IIIb), (IIIb'), (IIIc), (IIIc') or (IIIc'') the group $R^{31}$ is

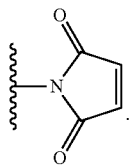

In another preferred embodiment, in formulae (IIIa), (IIIa'), (IIIb), (IIIb'), (IIIc), (IIIc') or (IIIc'') the group $R^{31}$ is

Preparation of Conjugates

This general procedure is based on introduction of free thiol groups into an antibody by reaction of lysine ε-amino groups with 2-iminothiolane, followed by reaction with a maleimide-containing drug-linker moiety, such as described above. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT (room temperature, circa 25° C.), the antibody is desalted into 50 mM HEPES, 5 mM Glycine, 2 mM DTPA, pH 5.5 using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about two to three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM HEPES, 5 mM glycine, 2 mM DTPA, pH 5.5)). The thiolated material is maintained on ice while the number of thiols introduced is quantitated as described above.

After verification of the number of thiols introduced, the drug (dimer)-linker moiety is added at a 2.5-fold molar excess per thiol. The conjugation reaction is allowed to proceed in conjugation buffer containing a final concentration of 25% propylene glycol and 5% trehalose. Commonly, the drug-linker stock solution is dissolved in 100% DMSO. The stock solution is added directly to the thiolated antibody.

The conjugation reaction mixture is incubated at RT for 2 h with gentle stirring. A 10-fold molar excess of N-ethyl maleimide (100 mM Stock in DMSO) is then added to the conjugation mixture and stirred for an additional hour to block any unreacted thiols.

The sample is then filtered via a 0.2µ filter The material is buffer exchanged via TFF VivaFlow 50 Sartorius 30 MWCO PES membrane into 10 mg/mL glycine, 20 mg/mL sorbitol, 15% acetonitrile pH 5.0 (5×TFF buffer exchange volume), to remove any unreacted drug. The final formulation is carried out by TFF into 20 mg/mL sorbitol, 10 mg/mL glycine, pH 5.0.

The following procedure can be used for transglutaminase mediated conjugation of dimer-linker compounds wherein the linker has an amine group that can act as an amine donor. The antibody can be one that has a transglutaminase-reactive glutamine, for example one with an N297A or N297Q substitution. Conjugation is carried out by recombinant bacterial transglutaminase with a molar ratio of antibody:enzyme of 5:1. The conjugation is carried out using standard protocols in 50 mM Tris buffer, pH 8.0, incubated overnight at 37° C. The resulting conjugate is purified on a Protein A column, pre-equilibriated with 50 mM Tris, pH 8.0. The conjugate is eluted with 0.1 M sodium citrate buffer, pH 3.5. The eluted fractions are neutralized with 1M Tris pH 9.0. The conjugated can be formulated in 20 mg/mL Sorbitol, 10 mg/mL Glycine, pH 5.0.

Those skilled in the art will understand that the above-described conditions and methodologies are exemplary and non-limiting and that other approaches for conjugation are known in the art and usable in the present invention.

Conjugates

In one embodiment, conjugates of this invention are derived from type (a) dimer-linker compounds and can be represented by the formula (IVa):

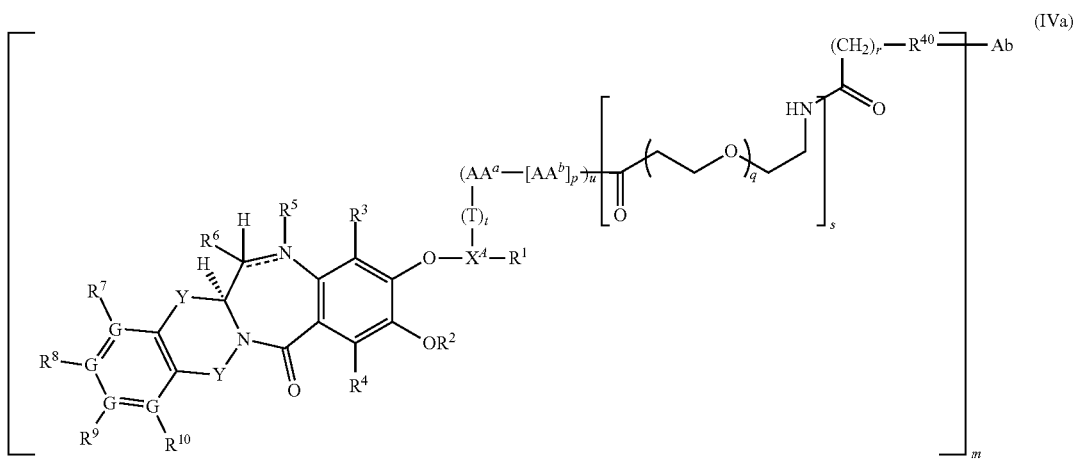

(IVa)

wherein
Ab is an antibody;

$R^{40}$ is 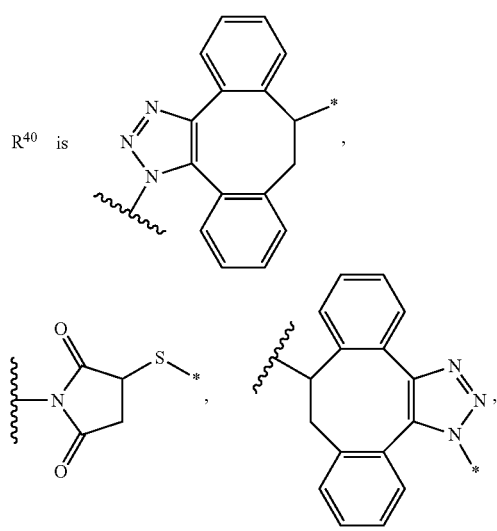,

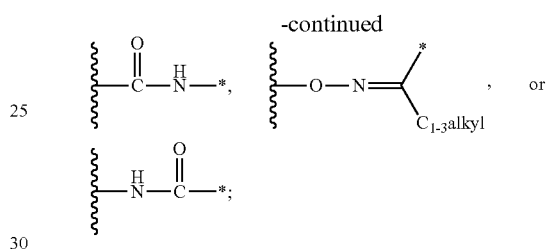

where the open valence of $R^{40}$ that is bonded to Ab is denoted by an asterisk (*) and the open valence of $R^{40}$ that is bonded to $(CH_2)_r$ is denoted by a wavy line ( ~~~~ );

m is 1, 2, 3, or 4;

T, t, $AA^a$, $AA^b$, u, p, q, s, r, and $X^A$ are as defined in respect of formula (IIIa); and $R^1$, $R^2$, $R^3$, $R^4$, $R^5$, $R^6$, $R^7$, $R^8$, $R^9$, $R^{10}$, Y, G, and the double line ==== are as defined in the BRIEF SUMMARY OF THE INVENTION section hereinabove.

In a preferred embodiment, u is 1 in formula (IVa).

A preferred conjugate according to formula (IVa) is represented by formula (IVa'):

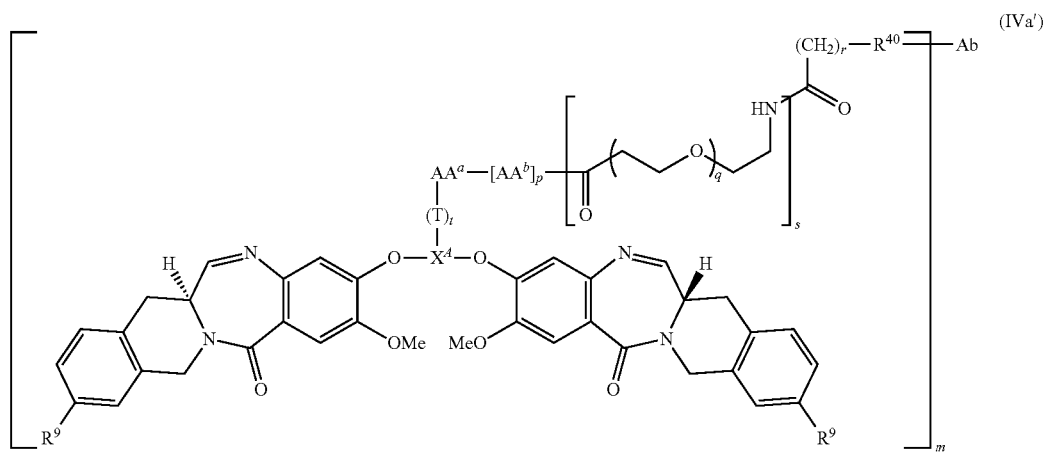

where
R⁹ is H, OH, OMe, $NH_2$, $NMe_2$, $O(CH_2CH_2O)_{1-8}Me$, $OCH_2CH_2OH$, or

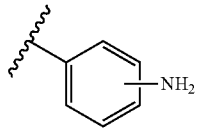

(especially the para-isomer); and
$X^A$ is

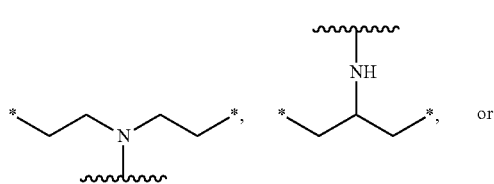

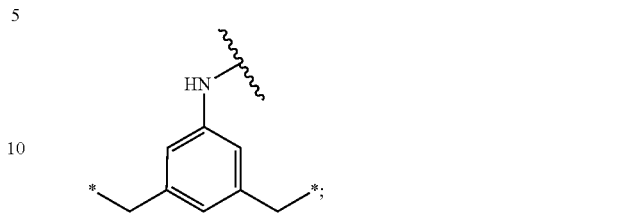

wherein the asterisks (*) indicate the positions of bonding of each $X^A$ to the adjacent O and $R^1$ and the wavy line indicates the position of bonding of each $X^A$ to T if T is present or to $AA^a$ if T is absent.

In another embodiment, conjugates of this invention are derived from type (b) dimer-linker compounds and can be represented by the formula (IVb):

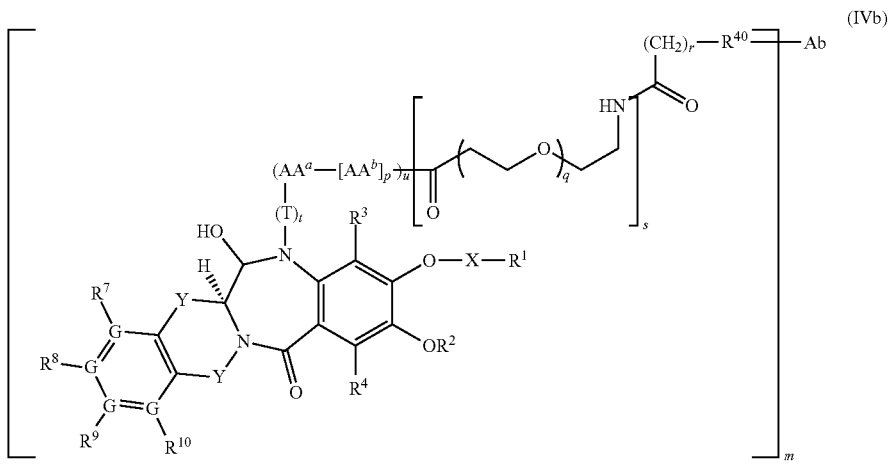

wherein
Ab, $R^{40}$, m, T, t, $AA^a$, $AA^b$, u, p, q, s, and r are as defined in respect of formula (IVa); and
$R^1$, $R^2$, $R^3$, $R^4$, $R^7$, $R^8$. $R^9$, $R^{10}$, Y, G, and X are as defined in the BRIEF SUMMARY OF THE INVENTION section hereinabove in respect of formula (I).

In a preferred embodiment, u is 1 in formula (IVb).

A preferred conjugate according to formula (IVb) is represented by formula (IVb'):

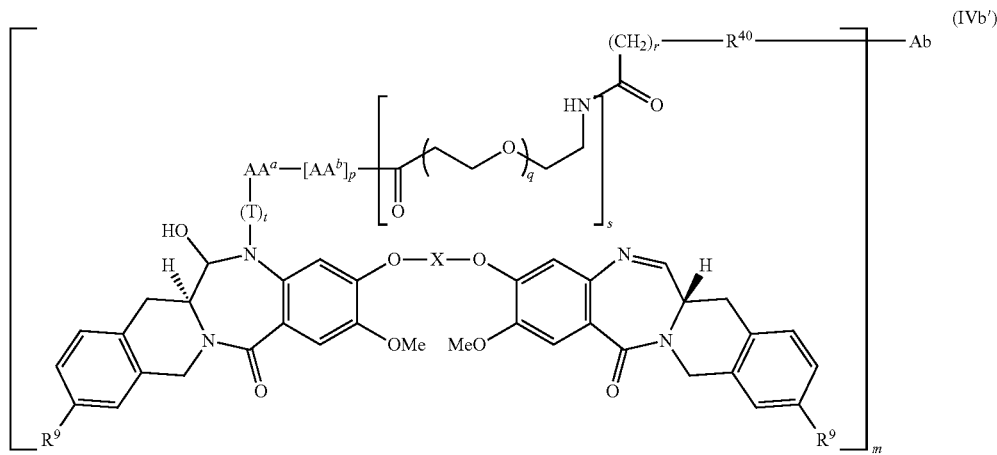

wherein
$R^9$ is H, OH, OMe, $NH_2$, $NMe_2$, $O(CH_2CH_2O)_{1-8}Me$, $OCH_2CH_2OH$, or

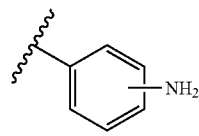

(especially the para-isomer); and

X is 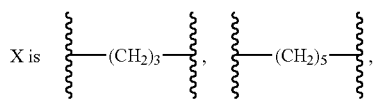

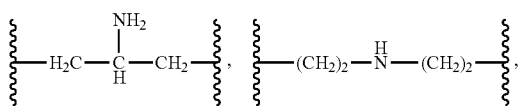

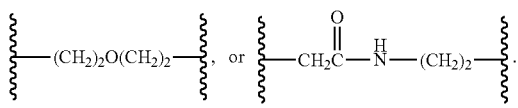

In another embodiment, conjugates of this invention are derived from type (c) dimer-linker compounds and can be represented by the formula (IVc):

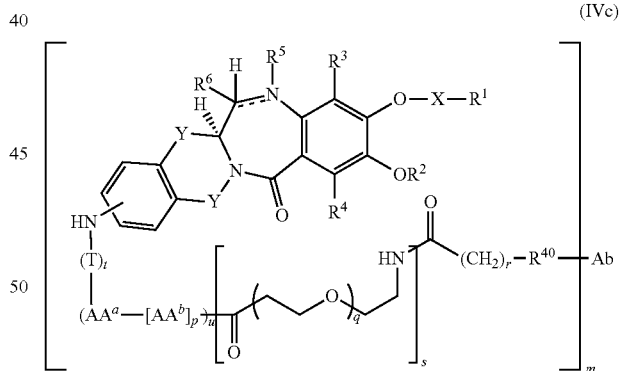

wherein
Ab, $R^{40}$, m, T, t, $AA^a$, $AA^b$, u, p, q, s, and r are as defined in respect of formula (IVa); and
$R^1$, $R^2$, $R^3$, $R^4$, $R^5$, $R^6$. Y, X, and the double line ═══ are as defined in the BRIEF SUMMARY OF THE INVENTION section hereinabove.

In a preferred embodiment, u is 1 in formula (IVc).

A preferred conjugate according to formula (IVc) is represented by formula (IVc'):

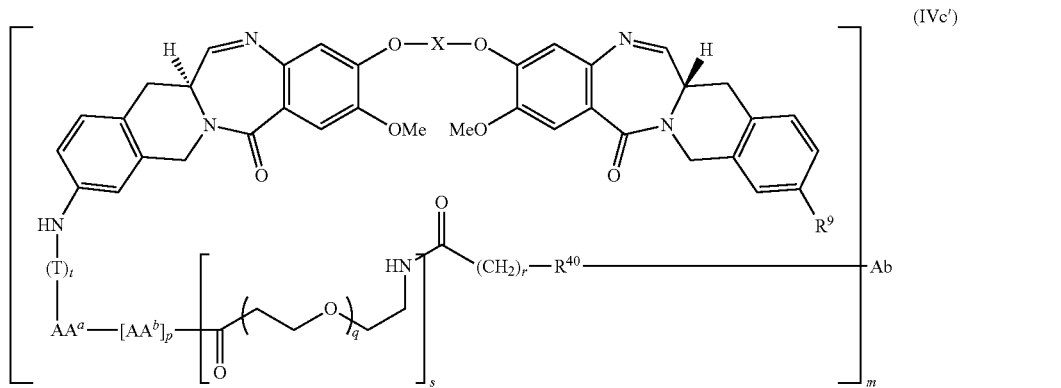

wherein
$R^9$ is H, OH, OMe, $NH_2$, $NMe_2$, $O(CH_2CH_2O)_{1-8}Me$, $OCH_2CH_2OH$, or

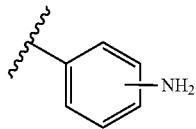

(especially the para-isomer); and
X is

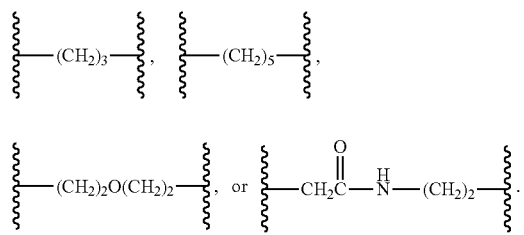

In another embodiment, a conjugate of this invention has a structure represented by formula (IVc″)

wherein Ab, $R^{40}$, m, T, t, $AA^a$, $AA^b$, u, p, q, s, and r are as defined in respect of formula (IVa); and each $R^{50}$ is independently H, $O(C_1\text{-}C_3$ alkyl), $O(C_2\text{-}C_3$ alkylene), $O(C_2\text{-}C_3$ alkynyl), F, Cl, Br, or CN.

The preferences stated hereinabove in respect of the dimer linkers of formulae (IIIa), (IIIa'), (IIIb), (IIIb'), (IIIc), (IIIc') and (IIIc″) for the polypeptide -$AA^a$-$[AA^b]_p$- and the self-immolating group T are also applicable to conjugates of formulae (IVa), (IVa'), (IVb), (IVb'), (IVc), (IVc') and (IVc″).

In formulae (IVa), (IVb), (IVc) and (IVc″), if the subscripts t and u are both 0, then the linker is of the non-cleavable type and relies on degradation of the antibody Ab to release the drug. The polyethylene glycol component optionally may be present (i.e., s is 1) if its presence is beneficial, for example by increasing the solubility of the drug-linker compound during conjugation and does not interfere with the biological activity of the drug.

Pharmaceutical Compositions

In another aspect, the present disclosure provides a pharmaceutical composition comprising a compound of the present invention, or of a conjugate thereof, formulated together with a pharmaceutically acceptable carrier or excipient. It may optionally contain one or more additional pharmaceutically active ingredients, such as an antibody or another drug. The pharmaceutical compositions can be

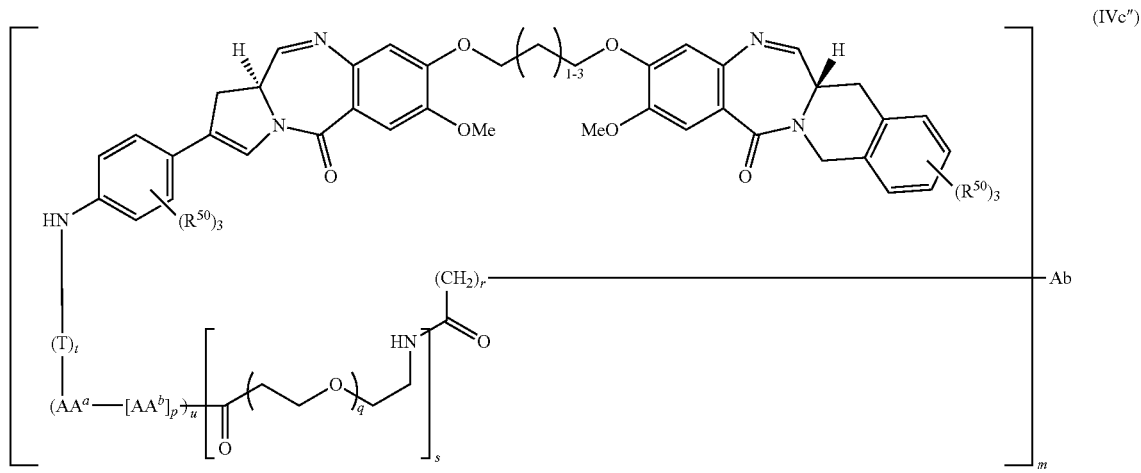

administered in a combination therapy with another therapeutic agent, especially another anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

Preferably, a pharmaceutical composition is suitable for intravenous, intra-muscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration. The compositions can also be provided in the form of lyophilates, for reconstitution in water prior to administration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg, or alternatively 0.1 to 5 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/mL and in some methods about 25-300 µg/mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal.

The pharmaceutical composition can be a controlled or sustained release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses

Compounds of this invention or their conjugates can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be renal, lung, gastric, or ovarian cancer.

Compounds of this invention or their conjugates can be administered in combination with other therapeutic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, β-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

EXAMPLES

The practice of this invention can be further understood by reference to the following examples, which are provided by way of illustration and not of limitation. The following general procedures are illustrative, with those skilled in the art understanding that alternative but equivalent methods can be used.

Some $^1$H-NMR spectra were run on Bruker 600, 500, or 400 MHz instruments and chemical shifts were reported in ppm ($\delta$) with reference to tetramethylsilane ($\delta$=0.0). Generally, evaporations were carried out under reduced pressure. These two LC/MS analysis methods are illustrative:

A Column: Waters BEH C18, 2.0×50 mm, 1.7-μm particles; Mobile Phase A: water with 0.05% TFA; Mobile Phase B: acetonitrile with 0.05% TFA; [2-98% in 1.5 min, with a 3 min run time]; Temperature: 40° C.; Flow: 0.8 mL/min. and a UV detector set at 220 or 254 nm.

B Column: PhenomenexLuna, 2.0×30 mm, 3-μm particles; Mobile Phase A: 10% acetonitrile/90% water with 0.1% TFA; Mobile Phase B: 90% acetonitrile/10% water with 0.1% TFA; [0-100% in 2 min, with a 4 min run time]; Temperature: 40° C.; Flow: 1.0 mL/min. and a UV detector set at 220 or 254 nm.

Example 1—Intermediate Compound 6

Figure 1:
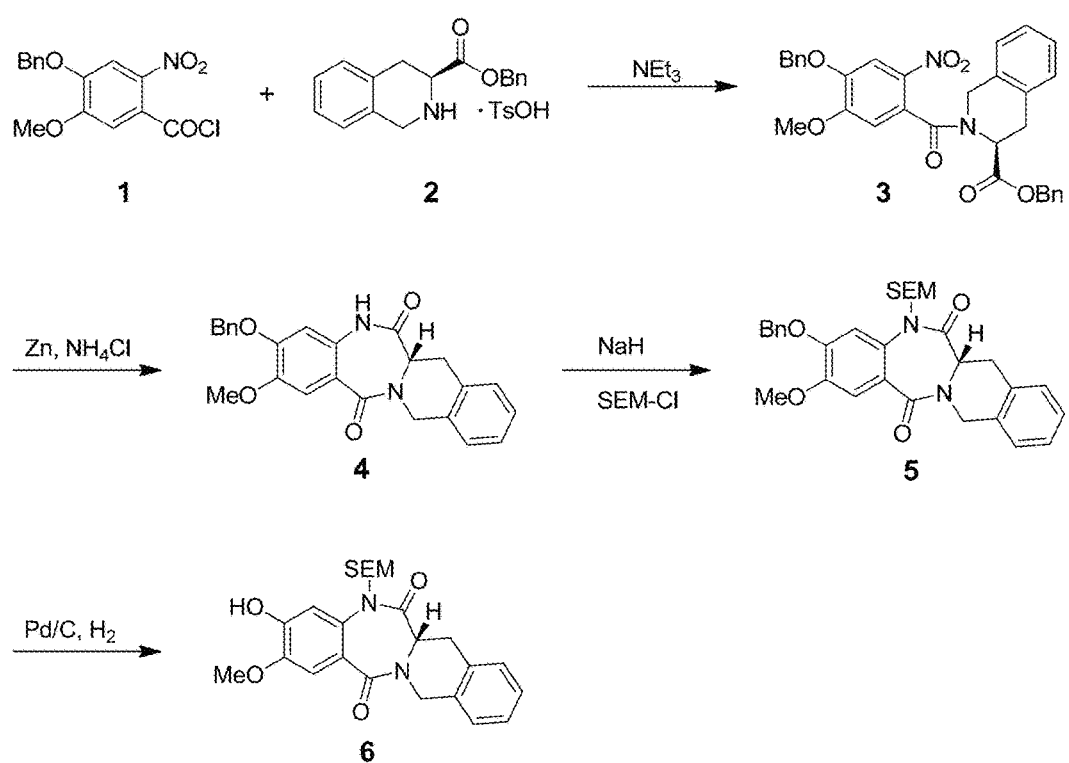

This example and FIG. 1 relate to the synthesis of intermediate compound 6, which is used for the preparation of dimers of this invention.

4-(Benzyloxy)-5-methoxy-2-nitrobenzoyl chloride 1 was prepared from the corresponding methyl ester as follows: To a solution of methyl 4-(benzyloxy)-5-methoxy-2-nitrobenzoate (Harve Chem, 15 g, 47.3 mmol) in tetrahydrofuran (THF, 350 mL) was added a solution of aq. NaOH (56.7 mL, 142 mmol, 2.5M). The reaction was stirred at 50° C. for 5 h. The reaction was cooled to room temperature (RT) and then concentrated in vacuo to remove the THF. The remaining aqueous layer was acidified with aq. HCl (6 N) to pH 2. The resulting yellow precipitate was filtered, washed with water, and dried under vacuum to give 4-(benzyloxy)-5-methoxy-2-nitrobenzoic acid (14.32 g, 100% yield). LCMS (M+H)=304.08. $^1$H NMR (400 MHz, METHANOL-d$_4$) δ 7.60 (s, 1H), 7.53-7.45 (m, 2H), 7.45-7.31 (m, 3H), 7.29 (s, 1H), 5.23 (s, 2H), 3.98 (s, 3H).

To a solution of the above nitrobenzoic acid (3.5 g, 11.54 mmol) in THF (150 mL) was added dropwise oxalyl chloride (1.212 mL, 13.85 mmol), followed by N,N-dimethylformamide (DMF, 50 uL). The resulting solution was stirred at RT for 2 h before it was concentrated in vacuo to give acid chloride 1 as a yellow solid.

Acid chloride 1 was dissolved in THF (35 mL) and added dropwise to a solution of (S)-benzyl 1,2,3,4-tetrahydroisoquinoline-3-carboxylate p-toluenesulfonic acid salt 2 (Accela, 5.58 g, 12.70 mmol) and triethylamine (4.83 mL, 34.6 mmol) in THF (80 mL) at 0° C. The reaction mixture was stirred at RT for 4 h before quenching with water and concentrated to remove the THF. The resulting mixture was extracted with EtOAc (3×). The combined organic layers were washed with sat. aq. NaHCO$_3$ and then brine and dried over Na$_2$SO$_4$ and concentrated in vacuo. The crude product mixture was purified using ISCO silica gel chromatography (80 g column, gradient from 0% to 100% EtOAc/dichloromethane (DCM) in 15 minutes) to give ester 3 (6.25 g, 98% yield). LCMS (M+H)=553. $^1$H NMR (400 MHz, CHLOROFORM-d) δ 7.95-7.72 (m, 1H), 7.57-7.35 (m, 5H), 7.34-7.0 (m, 8H), 7.14-6.98 (m, 1H), 6.94-6.69 (m, 1H), 5.39-5.19 (m, 2H), 5.19-5.08 (m, 1H), 4.99 (q, J=12.4 Hz, 1H), 4.75 (d, J=17.4 Hz, 1H), 4.65-4.40 (m, 2H), 4.28 (d, J=15.6 Hz, 1H), 3.86 (br. s., 3H), 3.71 (s, 1H), 3.50-3.18 (m, 1H).

A suspension of ester 3 (6.25 g, 11.31 mmol), zinc (4.44 g, 67.9 mmol), and NH$_4$Cl (7.26 g, 136 mmol) in MeOH (50 mL) was heated at 50° C. for 16 h. The reaction was cooled to RT and diluted with MeOH. The resulting mixture was filtered through a pad of CELITE™, washing successively with EtOAc, DCM and MeOH. The filtrates were combined and concentrated in vacuo. The crude product mixture was purified using ISCO silica gel chromatography (120 g column, gradient from 0% to 100% EtOAc/DCM in 15 minutes) to give dione 4 (4.5 g, 96% yield). LCMS (M+H)=415. $^1$H NMR (400 MHz, CHLOROFORM-d) δ 7.49-7.40 (m, 4H), 7.32 (br. s., 6H), 6.45 (s, 1H), 5.19 (s, 2H), 5.13 (d, J=15.4 Hz, 1H), 4.47 (d, J=15.2 Hz, 1H), 4.21 (t, J=6.7 Hz, 1H), 3.93 (s, 3H), 3.52 (dd, J=15.4, 7.0 Hz, 1H), 3.02 (dd, J=15.4, 6.4 Hz, 1H).

A solution of dione 4 (4.5 g, 10.86 mmol) in DMF (54.3 ml) was cooled to 0° C. before NaH (60% dispersion in mineral oil, 0.54 g, 13.57 mmol) was added batchwise. The resulting mixture was stirred for 30 min before (2-(chloromethoxy)ethyl)trimethylsilane (SEM-Cl, 2.31 ml, 13.03 mmol) was added. The reaction was warmed to RT and stirred for 1 h before quenching with water. The resulting mixture was extracted with EtOAc (3×). The combined organic layers were dried over $Na_2SO_4$ and concentrated in vacuo. The crude product mixture was purified using ISCO silica gel chromatography (80 g column, gradient from 0% to 50% EtOAc/DCM in 15 min) to give SEM-dione 5 (4.60 g, 78% yield). LCMS (M+H)=545. $^1$H NMR (400 MHz, CHLOROFORM-d) δ 7.59-7.41 (m, 2H), 7.40-7.21 (m, 9H), 5.43 (d, J=9.9 Hz, 1H), 5.21 (s, 2H), 5.14 (d, J=15.2 Hz, 1H), 4.50 (d, J=9.7 Hz, 1H), 4.41 (d, J=15.2 Hz, 1H), 4.33-4.16 (m, 1H), 4.13 (d, J=7.3 Hz, 1H), 3.92 (s, 3H), 3.82-3.46 (m, 3H), 3.06-2.84 (m, 1H), 1.26 (t, J=7.2 Hz, 1H), 0.97 (ddd, J=9.9, 6.8, 2.6 Hz, 2H), 0.10-0.01 (m, 9H).

A suspension of SEM-dione 5 (4.68 g, 8.59 mmol) and Pd/C (10%, 0.457 g) in EtOH (10 mL) was stirred under a balloon of H2 at RT for 3 h. The reaction was filtered through a CELITE™ pad, washed with EtOH, and concentrated in vacuo. The crude product mixture was purified using ISCO silica gel chromatography (120 g column, gradient from 0% to 100% EtOAc/DCM in 15 min) to give compound 6 (3.23 g, 83% yield). LCMS (M+H)=455. $^1$H NMR (400 MHz, CHLOROFORM-d) δ 7.40-7.21 (m, 5H), 5.97 (s, 1H), 5.46 (d, J=9.7 Hz, 1H), 5.18 (d, J=15.4 Hz, 1H), 4.72 (d, J=9.7 Hz, 1H), 4.58-4.24 (m, 2H), 3.95 (s, 3H), 3.83-3.44 (m, 3H), 3.14-2.88 (m, 1H), 0.99 (t, J=8.0 Hz, 2H), 0.14 (s, 9H).

Example 2—Intermediate Compound 13

Figure 2:
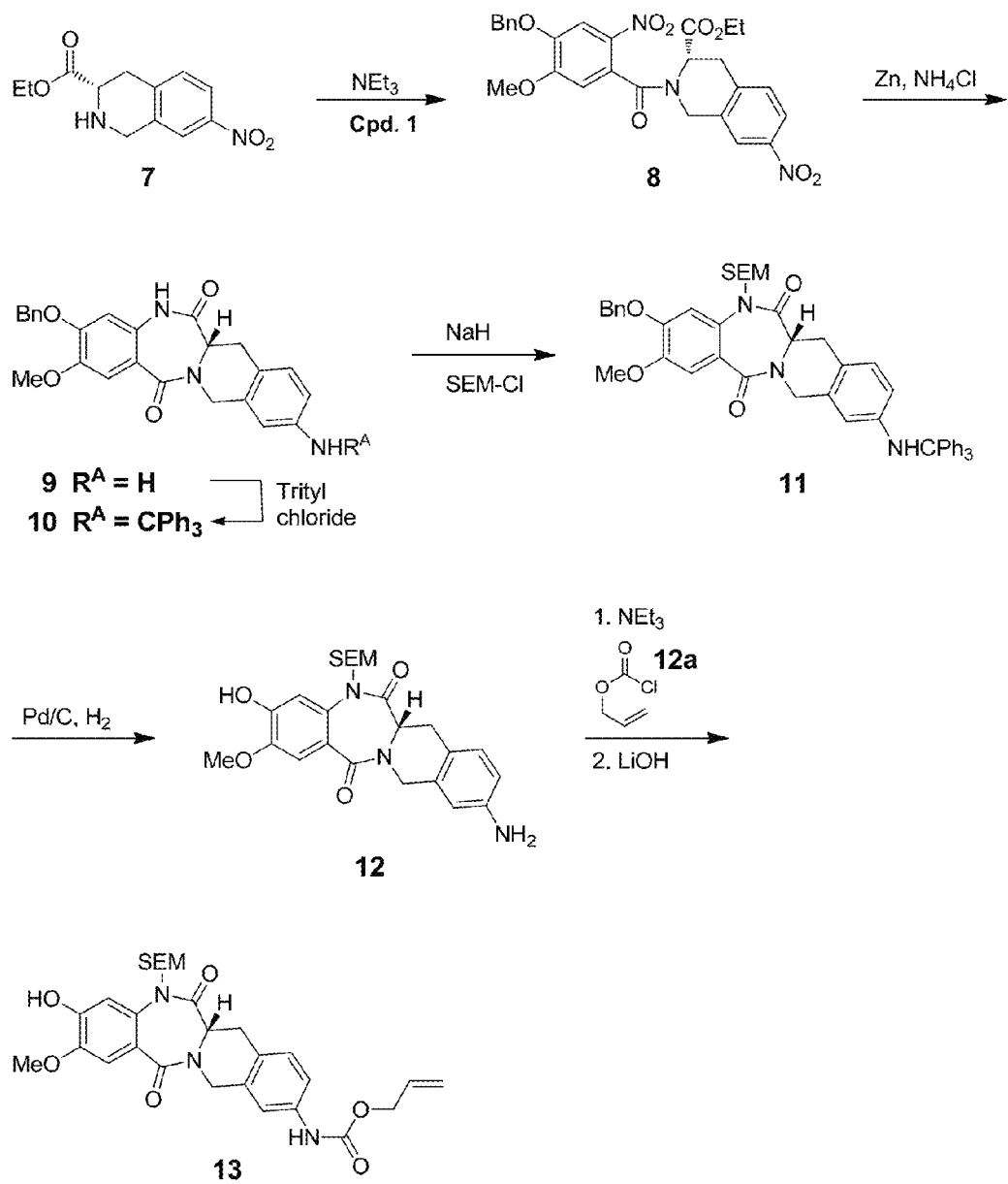

This example and FIG. 2 relate to the synthesis of intermediate compound 13, used in the preparation of dimers of this invention.

Acid chloride 1 was dissolved in THF (30 mL) and added dropwise to a solution of carboxylate 7 (Borzilleri et al., WO 2014/047024 A1 (2014), 1.6 g, 6.39 mmol) and $NEt_3$ (2.67 mL, 19.2 mmol) in THF (20 mL) at 0° C. The reaction solution was slowly warmed to RT and stirred for 30 min. The reaction was quenched with water and concentrated to remove THF. The resulting mixture was extracted with EtOAc (3×). The combined organic layers were washed with sat. aq. $NaHCO_3$, then brine, and dried over $Na_2SO_4$ and concentrated in vacuo. The crude product mixture was purified using ISCO silica gel chromatography (80 g column, gradient from 0% to 100% EtOAc/Hexane in 15 min) to give ethyl ester 8 (2.66 g, 78% yield). LCMS (M+H) =536.4.

A suspension of ethyl ester 8 (1.75 g, 3.55 mmol), zinc (1.394 g, 21.32 mmol), and $NH_4Cl$ (2.281 g, 42.6 mmol) in MeOH (10 mL) was heated at 50° C. overnight. The reaction mixture was filtered through a pad of CELITE™, washing with copious amount of 20% MeOH in DCM. The filtrate was concentrated to give amino-dione 9 as a white solid (1.25 g, 2.90 mmol, 82% yield). LCMS (M+H)=430.3 $^1$H NMR (400 MHz, DMSO-$d_6$) δ 10.26 (br. s., 1H), 7.53-7.31 (m, 6H), 7.24 (s, 1H), 6.92 (d, J=7.9 Hz, 1H), 6.78 (s, 1H), 6.50-6.41 (m, 2H), 5.07 (d, J=4.6 Hz, 2H), 5.00-4.88 (m, 2H), 4.84 (d, J=15.0 Hz, 1H), 4.09 (d, J=15.0 Hz, 1H), 4.01 (t, J=6.9 Hz, 1H), 3.75 (s, 3H), 3.12 (dd, J=15.3, 7.6 Hz, 1H), 2.78 (dd, J=15.2, 6.2 Hz, 1H).

To a solution of amino-dione 9 (1.6 g, 3.73 mmol) and trityl chloride (1.246 g, 4.47 mmol) in DCM (10 mL) was added $NEt_3$ (0.779 mL, 5.59 mmol). The reaction mixture was stirred at RT for 3 h and concentrated. The crude product mixture was purified using ISCO silica gel chromatography (80 g column, 0-50% EtOAc/Hexane) to give trityl-dione 10 as a white solid (2.2 g, 3.27 mmol, 88% yield). $^1$H NMR (400 MHz, CHLOROFORM-d) δ 8.01 (s, 1H), 7.50-7.12 (m, 22H), 6.77 (d, J=8.4 Hz, 1H), 6.47-6.34 (m, 2H), 6.16 (dd, J=8.1, 2.4 Hz, 1H), 5.02 (br. s., 1H), 4.91 (d, J=15.2 Hz, 1H), 4.18-4.09 (m, 2H), 4.05 (t, J=6.9 Hz, 1H), 3.92 (s, 3H), 3.28 (dd, J=15.4, 7.7 Hz, 1H), 2.75 (dd, J=15.4, 6.4 Hz, 1H).

To a solution of trityl-dione 10 (2.2 g, 3.27 mmol) in DMF (15 mL) at 0° C. was added NaH (60% dispersion in mineral oil, 0.236 g, 3.93 mmol). The mixture was stirred for 30 min before SEM-Cl (0.697 ml, 3.93 mmol) was added. The reaction mixture was stirred at 0° C. for 2 h before it was quenched with brine. The reaction mixture was extracted with EtOAc (3×). The combined organic layers were dried over $Na_2SO_4$ and concentrated in vacuo. The crude product mixture was purified using ISCO silica gel chromatography (40 g column, 0-50% EtOAc/Hexane) to give SEM-dione 11 (2.1 g, 2.62 mmol, 80% yield). LCMS (M-trityl)=560.4 $^1$H NMR (400 MHz, CHLOROFORM-d) δ 7.48-7.42 (m, 2H), 7.41-7.32 (m, 9H), 7.31-7.18 (m, 11H), 6.77 (d, J=8.1 Hz, 1H), 6.38 (d, J=2.2 Hz, 1H), 6.19 (dd, J=8.3, 2.3 Hz, 1H), 5.45 (d, J=9.7 Hz, 1H), 5.21 (s, 2H), 5.08-4.92 (m, 2H), 4.49 (d, J=9.7 Hz, 1H), 4.13-4.08 (m, 1H), 4.02 (d, J=15.2 Hz, 1H), 3.93 (s, 3H), 3.71 (td, J=9.6, 7.0 Hz, 1H), 3.61 (td, J=9.6, 7.2 Hz, 1H), 3.36 (dd, J=15.5, 8.3 Hz, 1H), 2.72 (dd, J=15.5, 6.5 Hz, 1H), 1.05-0.92 (m, 2H), 0.06 (s, 9H).

A suspension of SEM-dione 11 (950 mg, 1.18 mmol) and Pd/C (10%, 200 mg) in EtOAc (20 mL) was stirred under a balloon of $H_2$ for 2 days. The reaction mixture was filtered through a pad of CELITE™ and washed with EtOAc and then MeOH. The combined filtrates were concentrated and purified using ISCO silica gel chromatography (40 g column, 0-100% EtOAc/Hexane) to give compound 12 (510 mg, 1.08 mmol, 90% yield). LCMS (M+H)=470.2 $^1$H NMR (400 MHz, CHLOROFORM-d) δ 7.33 (s, 1H), 7.27 (s, 1H), 7.09 (d, J=8.6 Hz, 1H), 6.67-6.54 (m, 2H), 6.02 (s, 1H), 5.47 (d, J=9.7 Hz, 1H), 5.11 (d, J=15.2 Hz, 1H), 4.71 (d, J=9.7 Hz, 1H), 4.29 (d, J=15.2 Hz, 1H), 4.22 (dd, J=7.7, 6.5 Hz, 1H), 3.94 (s, 3H), 3.79-3.60 (m, 4H), 3.47 (dd, J=15.4, 7.7 Hz, 1H), 2.90 (dd, J=15.5, 6.4 Hz, 1H), 1.09-0.94 (m, 2H), 0.05 (s, 9H).

To a solution of compound 12 (500 mg, 1.065 mmol) in THF (3 mL) at 0° C. was added $NEt_3$ (0.742 mL, 5.32 mmol). Allyl chloroformate 12a (513 mg, 4.26 mmol) was added dropwise. The resulting solution was stirred at 0° C. for 2 h. The reaction was diluted with MeOH (5 mL) and aq. LiOH (2 mL, 2N) was added. The resulting mixture was stirred at RT for 16 h. The reaction was diluted with EtOAC and washed with brine. The organic layer was separated, dried over $Na_2SO_4$, and concentrated in vacuo. The crude product was purified by ISCO silica gel chromatography (24 g column, 0-10% MeOH/DCM) to give compound 13 as a white solid (440 mg, 0.795 mmol, 74.6% yield). LCMS (M+H)=554.2. $^1$H NMR (400 MHz, CHLOROFORM-d) δ

7.38-7.30 (m, 3H), 7.27-7.21 (m, 2H), 6.96 (s, 1H), 6.28 (s, 1H), 6.02-5.89 (m, 1H), 5.44 (d, J=9.8 Hz, 1H), 5.35 (dq, J=17.2, 1.5 Hz, 1H), 5.26 (dq, J=10.4, 1.3 Hz, 1H), 5.10 (d, J=15.4 Hz, 1H), 4.70 (d, J=9.8 Hz, 1H), 4.66 (d, J=5.1 Hz, 2H), 4.40 (d, J=15.4 Hz, 1H), 4.31-4.23 (m, 1H), 3.91 (s, 3H), 3.79-3.58 (m, 2H), 3.51 (dd, J=15.6, 7.3 Hz, 1H), 2.96 (dd, J=15.5, 6.4 Hz, 1H), 1.07-0.95 (m, 2H), 0.03 (s, 9H).

Example 3—Intermediate Compound 19

Figure 3:
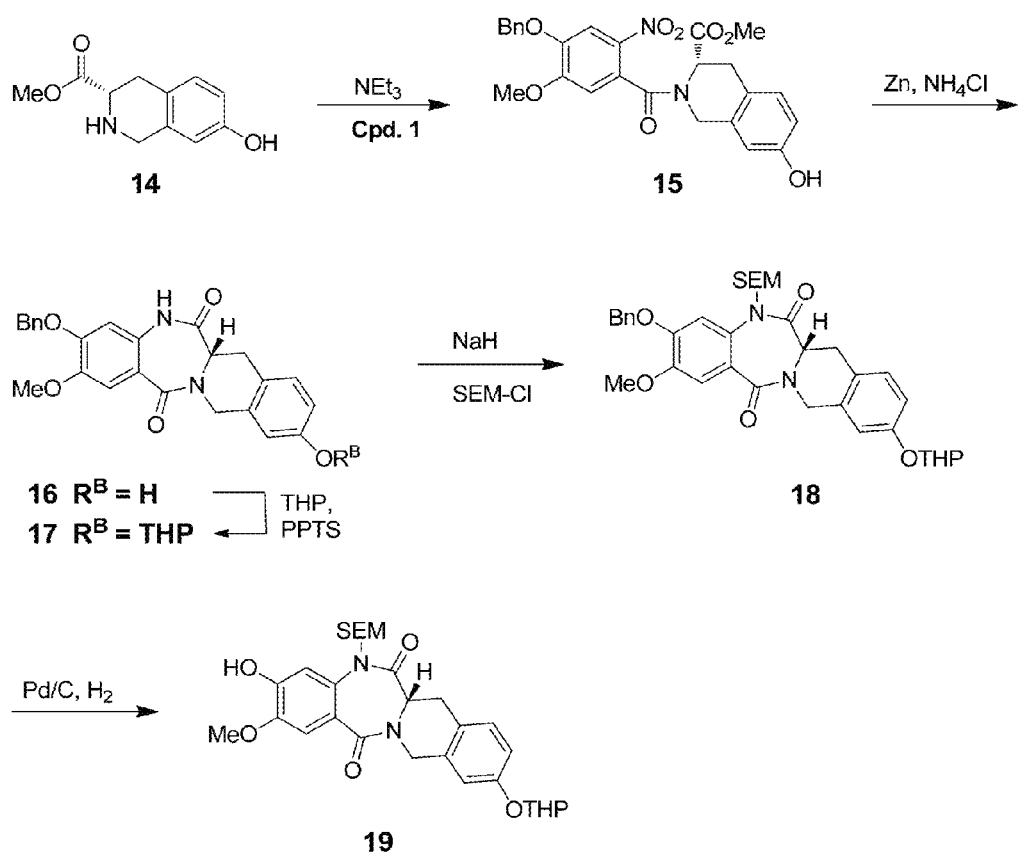

This example and FIG. 3 relate to the synthesis of compound 19, used as an intermediate for the synthesis of dimers of this invention.

Acid chloride 1 was dissolved in THF (30 mL) and added dropwise to a solution of carboxylate 14 (Buchstaller et al., US 2007/0191423 A1 (2007), 1.6 g, 5.21 mmol) and NEt$_3$ (2.9 mL, 20.8 mmol) in THF (20 mL) at 0° C. The reaction solution was stirred at 0° C. for 2 h before it was quenched with water. The resulting mixture was extracted with EtOAc (3×). The combined organic layers were washed with brine, and then dried over Na$_2$SO$_4$ and concentrated in vacuo. The resulting mixture was then taken up in MeOH (50 mL). Potassium carbonate (1 g) was added. The resulting suspension was stirred at RT for 1 h before it was filtered through a pad of CELITE™ and concentrated in vacuo. The crude product mixture was purified using ISCO silica gel chromatography (220 g column, gradient from 0% to 50% EtOAc/Hexane in 15 min) to give ester 15 (1.75 g g, 68% yield). LCMS (M+H)=493.1.

A suspension of ester 15 (1.75 g, 3.55 mmol), zinc (1.394 g, 21.32 mmol), and NH$_4$Cl (2.281 g, 42.6 mmol) in MeOH (10 mL) and heated at 50° C. overnight. The reaction mixture was then filtered through a pad of CELITE™, washing with 20% MeOH/DCM. The filtrate was concentrated to give compound 16 (1.25 g, 2.90 mmol, 82% yield). LCMS (M+H)=431.3. $^1$H NMR (400 MHz, DMSO-d$_6$) δ 10.25 (br. s., 1H), 9.26 (s, 1H), 7.53-7.32 (m, 5H), 7.24 (s, 1H), 7.07 (d, J=8.1 Hz, 1H), 6.79 (s, 1H), 6.71-6.60 (m, 2H), 5.08 (d, J=4.0 Hz, 2H), 4.83 (d, J=15.2 Hz, 1H), 4.22 (d, J=15.4 Hz, 1H), 4.08 (t, J=6.7 Hz, 1H), 3.76 (s, 3H), 3.16 (dd, J=15.4, 6.8 Hz, 1H), 2.85 (dd, J=15.1, 6.3 Hz, 1H).

To a solution of compound 16 (1.25 g, 2.90 mmol) in DCM (40 mL) was added pyridiniump-toluenesulfonate (PPTS, 0.073 g, 0.290 mmol) and tetrahydropyran (THP, 2.84 mL, 29.0 mmol). The reaction was stirred at RT overnight and was then quenched with sat. aq. NaHCO$_3$. The resulting mixture was extracted with DCM (3×). The combined organic layers were dried over Na$_2$SO$_4$ and concentrated in vacuo. The crude product mixture was purified using ISCO silica gel chromatography (40 g column 0-100% EtOAc/Hexane) to give compound 17 as a white solid (1.15 g, 2.235 mmol, 77% yield). LCMS (M+H)=515.3.

To a cooled solution of compound 17 (1.2 g, 2.332 mmol) in DMF (10 mL) was added NaH (60% dispersion in mineral oil, 0.168 g, 2.80 mmol). The mixture was stirred at 0° C. for 15 min and then warmed to RT and stirred for 10 min before it was cooled back to 0° C. SEM-Cl (0.496 mL, 2.80 mmol) was then added. The reaction was stirred at 0° C. for 30 min before it was allowed to warm to RT and stirred for 1 h. The reaction was then quenched with brine. The resulting mixture was extracted with EtOAc (3×). The combined organic layers were dried over Na$_2$SO$_4$ and concentrated in vacuo. The crude product mixture was purified using ISCO silica gel chromatography (40 g column, 0-50% EtOAc/Hexane) to give compound 18 (875 mg, 1.357 mmol, 58.2%). LCMS (M+H)=645.5. $^1$H NMR (400 MHz, CHLOROFORM-d) δ 7.48-7.41 (m, 2H), 7.39-7.28 (m, 4H), 7.24 (s, 1H), 7.19 (d, J=8.1 Hz, 1H), 7.02-6.92 (m, 2H), 5.51-5.32 (m, 2H), 5.20 (s, 2H), 5.12 (dd, J=15.3, 3.2 Hz, 1H), 4.50 (dd, J=9.8, 1.7 Hz, 1H), 4.33 (dd, J=15.3, 5.2 Hz, 1H), 4.22 (ddd, J=7.4, 6.5, 4.3 Hz, 1H), 3.91 (s, 4H), 3.76-3.56 (m, 3H), 3.47 (dd, J=15.4, 7.7 Hz, 1H), 2.92 (dd, J=15.4, 6.4 Hz, 1H), 2.03-1.92 (m, 1H), 1.88-1.81 (m, 2H), 1.74-1.57 (m, 3H), 0.97 (ddd, J=9.7, 6.8, 2.6 Hz, 2H), 0.09-0.01 (m, 9H).

A suspension of compound 18 (875 mg, 1.357 mmol) and Pd/C (10%, 87 mg) in EtOAc (10 mL) stirred under a balloon of H$_2$ for 2 h. The reaction mixture was then filtered through a pad of CELITE™ and concentrated in vacuo. The crude product mixture was purified using ISCO silica gel chromatography (40 g column, 0-100% EtOAc/Hexane) to give compound 19 as a white solid (485 mg, 0.874 mmol, 64.4% yield). LCMS (M+H)=555.1. $^1$H NMR (400 MHz, CHLOROFORM-d) δ 7.33 (d, J=0.7 Hz, 1H), 7.27 (s, 1H), 7.22 (d, J=8.1 Hz, 1H), 7.04-6.95 (m, 2H), 6.01 (s, 1H), 5.46 (d, J=9.7 Hz, 1H), 5.44-5.34 (m, 1H), 5.16 (dd, J=15.3, 2.6 Hz, 1H), 4.71 (dd, J=9.7, 1.8 Hz, 1H), 4.35 (dd, J=15.3, 4.5 Hz, 1H), 4.25 (ddd, J=7.7, 6.4, 4.0 Hz, 1H), 4.01-3.87 (m, 4H), 3.80-3.59 (m, 3H), 3.52 (dd, J=15.5, 7.8 Hz, 1H), 2.95 (dd, J=15.5, 6.4 Hz, 1H), 2.05-1.96 (m, 1H), 1.92-1.82 (m, 2H), 1.77-1.62 (m, 3H), 1.06-0.97 (m, 2H), 0.05 (s, 9H).

Example 4—Symmetric THIQ-THIQ Dimers

Figure 4A:
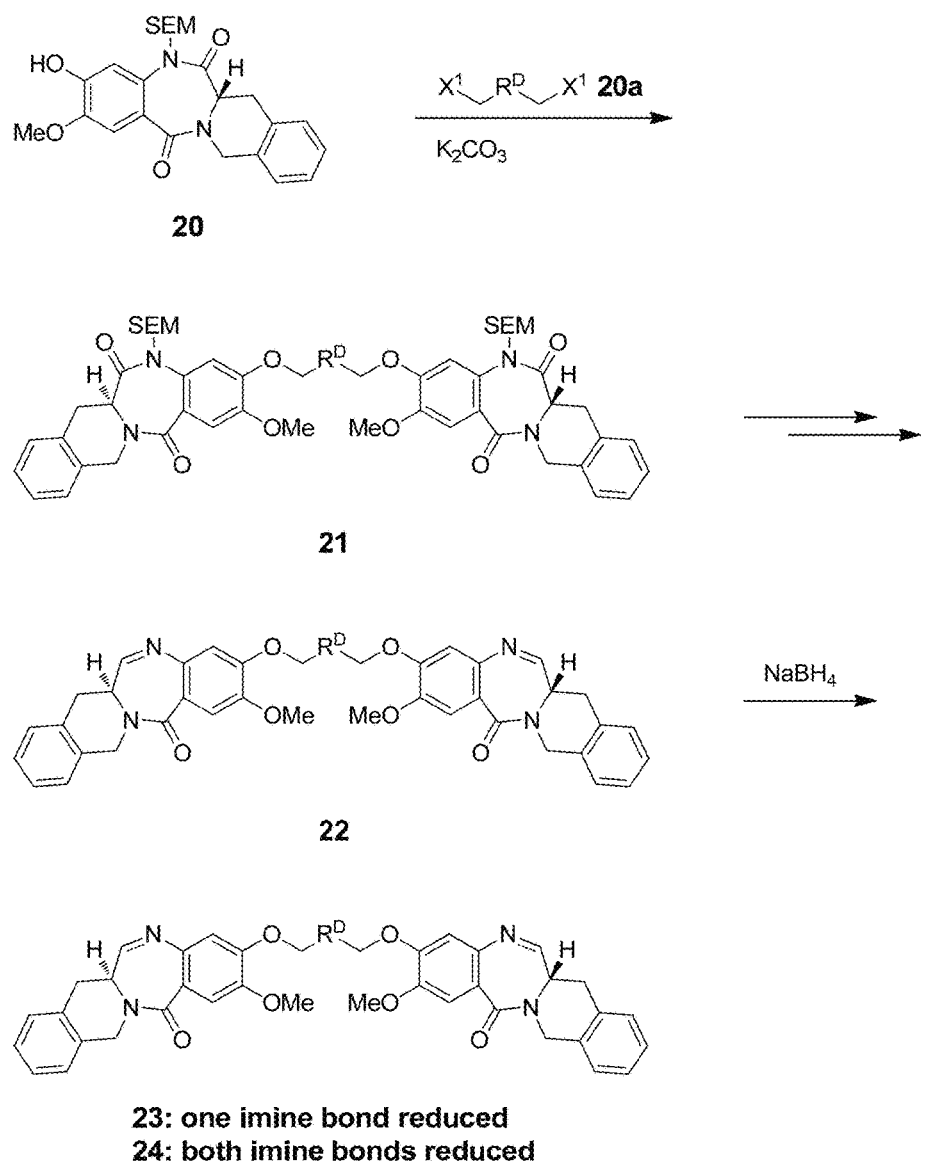
FIG. 4a shows a generic scheme for preparing of symmetric THIQ-THIQ dimers.

FIG. 4a shows a generic scheme for making symmetric THIQ-THIQ dimers The bridge connecting the two monomer halves derives from compound 20a.

The groups X$^5$ are leaving groups, such as I, Br, Cl, mesylate, and tosylate. The group Rx allows for structural variability in the bridge. Those skilled in the art will appreciate that, in certain instances, functional groups in Rx may need to be protected and de-protected as needed during the course of synthesis. Exemplary groups Rx include:

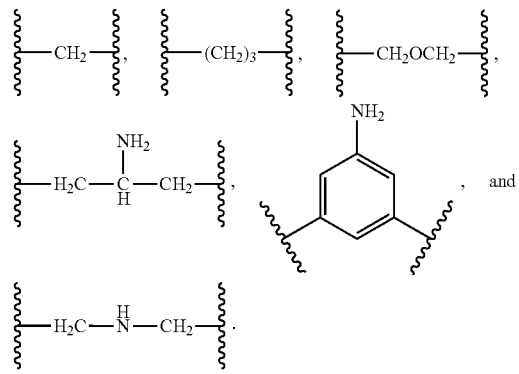

Although the scheme of FIG. 4a has general applicability, the aromatic ring in the THIQ rng system has been depicted as unsubstituted for the sake of simplicity. Those skilled in the art will understand that it can bear substituents as defined hereinabove.

Following the concept of FIG. 4a, compound (IIa-02) was synthesized as follows.

A suspension of compound 6 (50 mg, 0.11 mmol) and 1,5-diiodopentane (17.8 mg, 0.055 mmol) and K$_2$CO$_3$ (15.2 mg, 0.11 mmol) in DMF (1 mL) were stirred at RT for 14 h. The reaction mixture was then diluted with H$_2$O and extracted with EtOAc (3×). The combined organic layers were washed with brine, dried over Na$_2$SO$_4$, and concentrated in vacuo. The crude product mixture was purified using ISCO silica gel chromatography (12 g column, gradient from 0% to 10% MeOH/DCM in 15 minutes) to give compound 21 where each R$^9$ is H (22 mg, 21% yield). LCMS (M+H)=977.8.

To a solution of the product of the preceding reaction (22 mg, 0.023 mmol) in THF/EtOH (1:1, 1 mL) was added a solution of LiBH$_4$ in THF (2M, 116 μL, 0.232 mmol) at 0° C. The reaction was slowly warmed to RT and stirred for 15 min before it was quenched with brine. The resulting mixture was extracted with chloroform. The combined organic layers were washed with brine, dried over Na$_2$SO$_4$, and concentrated in vacuo. The crude product was then taken up in EtOH/chloroform (1:1, 2 mL). Silica gel (700 mg) was added, followed by water (0.6 mL). The resulting suspension was stirred at RT for 24 h and then filtered, washing with 10% MeOH/chloroform. The filtrate was concentrated and purified using reverse phase HPLC (Column: Phenomenex Luna C18 20×100 mm; Mobile Phase A: 10:90 acetonitrile:water with 0.1% trifluoroacetic acid (TFA); Mobile Phase B: 90:10 acetonitrile:water with 0.1% TFA acid; Gradient: 20-70% B over 15 minutes; Flow: 20 mL/min; Detection: UV at 220 nm) to give dimer (IIa-02) (7.5 mg, 9.86 μmol, 43.8% yield) LCMS M+H=685.2. $^1$H NMR (400 MHz, CHLOROFORM-d) δ 7.55 (s, 2H), 7.49 (d, J=5.3 Hz, 2H), 7.42-7.31 (m, 8H), 6.82 (s, 2H), 5.03 (d, J=15.6 Hz, 2H), 4.58 (d, J=15.4 Hz, 2H), 4.26-4.04 (m, 4H), 4.00-3.92 (m, 8H), 3.37-3.25 (m, 2H), 3.21-3.10 (m, 2H), 2.02-1.90 (m, 4H), 1.70 (d, J=7.3 Hz, 2H).

Following the general scheme of FIG. 4a, additional symmetric THIQ-THIQ dimers were synthesized:
(a) Dimer (IIa-01) from compound 6 and 1,3-dibromopropane: LCMS M+H=657.2. $^1$H NMR (400 MHz, CHLOROFORM-d) δ 7.55 (s, 2H), 7.49 (d, J=5.3 Hz, 2H), 7.42-7.30 (m, 8H), 6.87 (s, 2H), 5.03 (d, J=15.6 Hz, 2H), 4.58 (d, J=15.4 Hz, 2H), 4.31 (tdd, J=9.6, 6.1, 3.6 Hz, 4H), 3.95 (s, 6H), 3.94 (s, 2H), 3.37-3.24 (m, 2H), 3.21-3.10 (m, 2H), 2.44 (t, J=6.1 Hz, 2H).
(b) Dimer (IIa-07) from compound 6 and 1-iodo-2-(2-iodoethoxy)ethane: LCMS M+H=687.2. $^1$H NMR (400 MHz, CHLOROFORM-d) δ 7.55 (s, 2H), 7.49 (d, J=5.3 Hz, 2H), 7.40-7.31 (m, 8H), 6.86 (s, 2H), 5.02 (d, J=15.4 Hz, 2H), 4.58 (d, J=15.4 Hz, 2H), 4.36-4.18 (m, 4H), 4.07-4.00 (m, 4H), 3.97-3.92 (m, 8H), 3.35-3.24 (m, 2H), 3.22-3.12 (m, 2H).
(c) Dimer (IIa-08) from compound 13 and 1,5-diiodopentane: LCMS M+H=883.3. $^1$H NMR (400 MHz, CHLOROFORM-d) δ 7.55 (s, 2H), 7.49 (d, J=5.3 Hz, 2H), 7.44-7.33 (m, 6H), 6.81 (s, 2H), 6.69 (s, 2H), 6.00 (dd, J=17.1, 10.5 Hz, 2H), 5.40 (dd, J=17.3, 1.4 Hz, 2H), 5.30 (dd, J=10.5, 1.2 Hz, 2H), 5.01 (d, J=15.6 Hz, 2H), 4.71 (d, J=5.5 Hz, 4H), 4.53 (d, J=15.6 Hz, 2H), 3.96 (s, 6H), 3.31-3.19 (m, 2H), 3.17-3.06 (m, 2H), 1.97 (br. s., 4H), 1.75-1.66 (m, 2H).

Example 5—Compound (IIa-05)

Figure 4B:
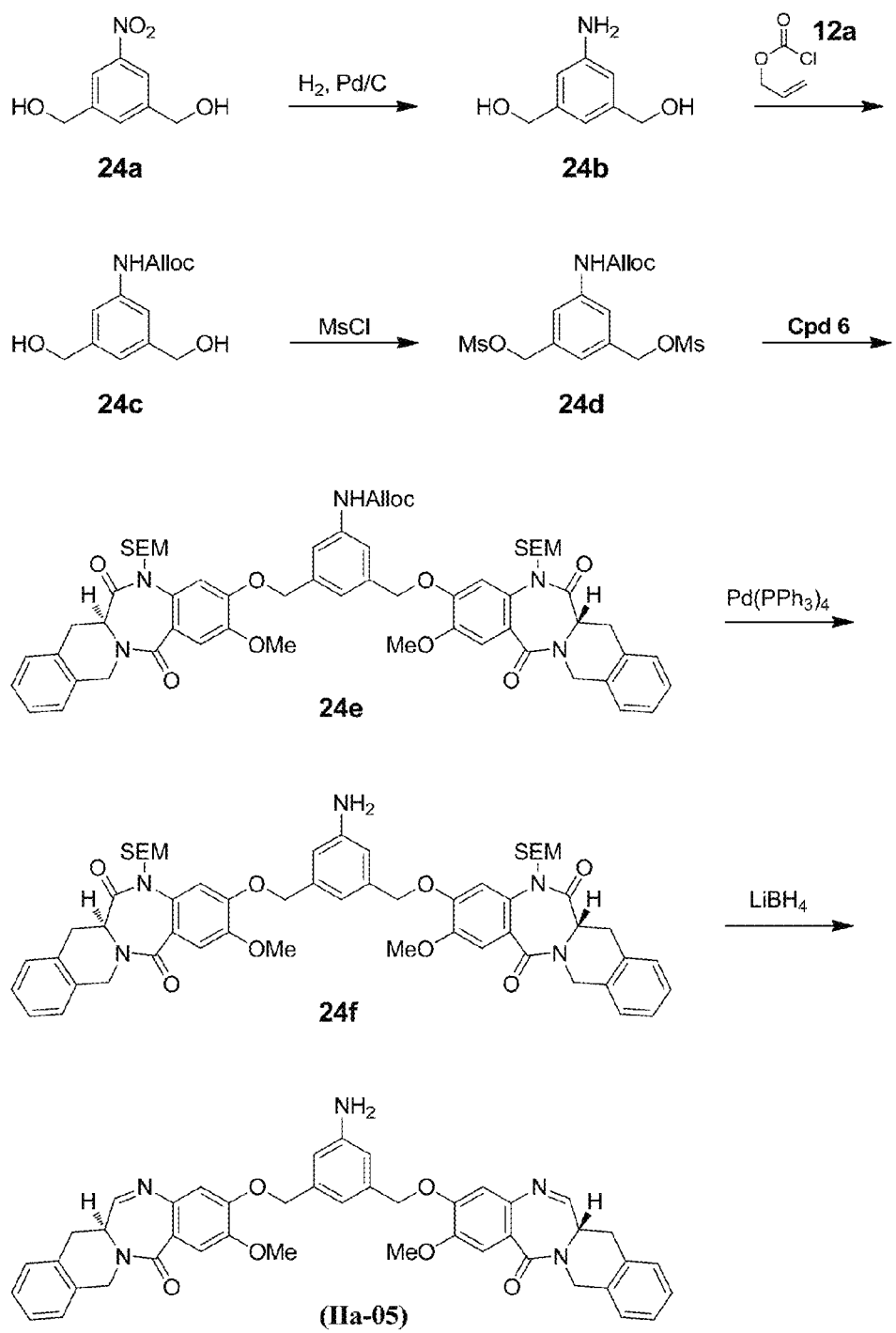
FIG. 4b shows the synthesis of a particular THIQ-THIQ dimer.

This example and FIG. 4b relate to the synthesis of compound (IIa-05) ((6aS,6a'S)-3,3'-(((5-amino-1,3-phenylene)bis(methylene))bis(oxy))bis(2-methoxy-6a,7-dihydrobenzo[5,6][1,4]diazepino[1,2-b]isoquinolin-14(12H)-one)), again following the general synthetic scheme of FIG. 4a, but entailing a protection-deprotection cycle as shown.

A suspension of 5-nitro-m-xylene-α,α-diol 24a (Aldrich, 1 g, 5.46 mmol) and Pd/C (291 mg, 0.273 mmol) in MeOH (50 mL) was stirred under a balloon of H$_2$ for 2 hours at RT. The reaction was filtered through CELITE™, and concentrated in vacuo. The crude 5-amino-1,3-phenylene)dimethanol 24b was used in the next step without further purification. LCMS (M+H)=154.

To a suspension of dimethanol 24b (600 mg, 3.92 mmol), K$_2$CO$_3$ (650 mg, 4.7 mmol) in THF (10 mL) at 0° C. was added allyl chloroformate 12a (0.5 mL, 4.7 mmol). The reaction mixture was stirred at 0° C. for 30 min before it was allowed to warm up to RT and stirred at RT for 3 h. The reaction was then quenched with water and extracted with EtOAc (2×). The organic layer was dried and concentrated in vacuo. The crude product was purified using ISCO silica gel chromatography (40 g column, gradient from 0% to 100% EtOAC/DCM in 15 min) to give allyl carbamate 24c (200 mg, 21.5% yield). LCMS (M+23)=261. $^1$H NMR (400 MHz, DMSO-d$_6$) δ 7.31 (s, 2H), 6.91 (s, 1H), 5.99 (ddt, J=17.2, 10.6, 5.4 Hz, 1H), 5.36 (dq, J=17.2, 1.6 Hz, 1H), 5.24 (dq, J=10.6, 1.4 Hz, 1H), 5.13 (t, J=5.7 Hz, 2H), 4.60 (dt, J=5.4, 1.3 Hz, 2H), 4.44 (d, J=5.5 Hz, 4H).

A suspension of the above allyl carbamate (462.5 mg, 1.949 mmol) and triethylamine (0.815 mL, 5.85 mmol) in DCM (20 mL) was cooled to −10° C. and treated with methanesulfonyl chloride (Ms-Cl, 0.395 mL, 5.07 mmol). The organic layer was washed with ice cold water, dried over Na$_2$SO$_4$ and concentrated in vacuo to give dimethanesulfonate 24d (750 mg, 95% yield). LCMS (M+H)=394. $^1$H NMR (400 MHz, CHLOROFORM-d) δ 7.52 (s, 2H), 7.15 (s, 1H), 7.04 (s, 1H), 6.09-5.87 (m, 1H), 5.39 (dd, J=17.2, 1.5 Hz, 1H), 5.29 (dd, J=10.3, 1.3 Hz, 1H), 5.21 (s, 4H), 4.69 (dt, J=5.7, 1.2 Hz, 2H), 3.02 (s, 6H).

A solution of dimethanesulfonate 24d (135 mg, 0.343 mmol) in dimethylsulfoxide (DMSO, 16 mL) was treated with compound 6 (312 mg, 0.686 mmol) and K$_2$CO$_3$ (142 mg, 1.029 mmol) at RT for 2 h. The reaction was quenched with water and extracted with EtOAc (3×). The mixture was dried and concentrated in vacuo. The crude product was purified by ISCO silica gel chromatography (40 g column, gradient from 0% to 100% EtOAc/Hexane in 15 min) to give carbamate 24e (250 mg, 66% yield). LCMS (M+1)=1110. $^1$H NMR (400 MHz, CHLOROFORM-d) δ 7.51 (s, 2H), 7.38-7.13 (m, 14H), 6.96-6.75 (m, 1H), 6.12-5.86 (m, 1H), 5.48 (d, J=10.1 Hz, 2H), 5.43-5.32 (m, 1H), 5.32-5.23 (m, 1H), 5.23-4.99 (m, 6H), 4.74-4.53 (m, 4H), 4.41 (d, J=15.2 Hz, 2H), 4.30 (d, J=0.9 Hz, 2H), 3.96-3.83 (m, 6H), 3.81-3.46 (m, 6H), 2.98 (s, 2H), 1.14-0.85 (m, 4H), 0.13-0.08 (m, 18H).

To a solution of carbamate 24e (200 mg, 0.180 mmol) in THF (5 mL) at 0° C. was added Pd(Ph$_3$P)$_4$ (8.33 mg, 7.20 μmol) and morpholine (0.038 mL, 0.432 mmol). The reaction was stirred at 0° C. for 2 hours. The reaction mixture was quenched with sat. aq. ammonium chloride (5 mL) and extracted with EtOAc (10 mL). The organic layer was washed with saturated aq. NaHCO$_3$, and then saturated aq. NaCl, dried over Na$_2$SO$_4$, filtered and concentrated. The crude product was purified using ISCO silica gel chromatography (40 g column, gradient from 0% to 10% Methanol/DCM in 15 minutes) to give compound 24f (160 mg, 87% yield). LCMS (M+1)=1026. $^1$H NMR (400 MHz, CHLOROFORM-d) δ 7.38-7.30 (m, 6H), 7.28 (d, J=5.1 Hz, 7H), 6.92-6.85 (m, 1H), 6.76 (d, J=1.1 Hz, 2H), 5.47 (d, J=10.1 Hz, 2H), 5.18 (d, J=15.2 Hz, 2H), 5.08 (d, J=8.6 Hz, 4H), 4.65 (d, J=10.1 Hz, 2H), 4.42 (d, J=15.4 Hz, 2H), 4.30 (d, J=0.9 Hz, 2H), 3.92 (s, 6H), 3.82-3.50 (m, 8H), 3.09-2.94 (m, 2H), 1.11-0.88 (m, 4H), 0.10-0.03 (m, 18H).

To a 0° C. solution of compound 24f (22 mg, 0.021 mmol) in THF (233 μL) and EtOH (233 μL) was added a solution of LiBH$_4$ (214 μL, 0.429 mmol, 2M in THF). The reaction was slowly warmed to RT and stirred at RT for 2 h. The reaction was quenched with water and extracted with chloroform 2×), then chloroform/MeOH (2×). The combined organic extracts were dried over Na$_2$SO$_4$ and concentrated in vacuo. The residue was dissolved in chloroform/EtOH/water (1:1:1, 2 mL), silica gel (0.7 g) was added, and the reaction was stirred for 3 days at RT. The reaction mixture was filtered through a CELITE™ plug, washing with chloroform, and the solution was concentrated. The residue was purified by reverse phase HPLC (Column: Phenomenex Luna C18 20×100 mm; Mobile Phase A: 10:90 acetonitrile:water with 0.1% TFA; Mobile Phase B: 90:10 acetonitrile:water with 0.1% TFA; Gradient: 20-80% B over 20 min; Flow: 20 mL/min; Detection: UV at 220 nm) to give dimer (IIa-05), isolated as a light yellow solid (8.1 mg, 46.3% yield). LCMS (M+1)=734. $^1$H NMR (400 MHz, CHLOROFORM-d) δ 7.57 (s, 1H), 7.47 (d, J=5.3 Hz, 1H), 7.43-7.30 (m, 4H), 6.99-6.79 (m, 1H), 6.73 (s, 1H), 5.40-4.90 (m, 4H), 4.59 (d, J=15.4 Hz, 1H), 4.17-3.85 (m, 4H), 3.39-3.05 (m, 2H).

Example 6—Reduction of Imine Double Bonds

This example describes the preparation of various THIQ-THIQ dimers with one or both imine bonds reduced.

In the first section of this example, the dimers prepared were (IIa-03) and (IIa-04).

To a solution of dimer (IIa-01) (6 mg, 9.14 μmol) in THF (0.7 mL) at 0° C. was added NaBH$_4$ (0.691 mg, 0.018 mmol). The resulting mixture was stirred for 40 min before it was quenched with water. The mixture was extracted with chloroform (3×). The organic layers were combined and concentrated in vacuo. Dimers (IIa-03) (LCMS (M+1): 659.1) and (IIa-04) (LCMS (M+1): 661.1) were separated by reverse phase HPLC (Column: Phenomenex Luna C18 20×100 mm; Mobile Phase A: 10:90 acetonitrile:water with 0.1% TFA; Mobile Phase B: 90:10 acetonitrile:water with 0.1% TFA; Gradient: 15-60% B over 20 minutes; Flow: 20 mL/min; Detection: UV at 220 nm).

In the next section of this example, (6aS,6a'S)-3,3'-(pentane-1,5-diylbis(oxy))bis(2-methoxy-5,6,6a,7-tetrahydrobenzo[5,6][1,4]diazepino[1,2-b]isoquinolin-14(12H)-one) (IIa-06) was prepared: To a solution of dimer (IIa-02) (28 mg, 0.041 mmol) in THF/MeOH (1:1, 1 mL) was added NaBH$_4$ (1.548 mg, 0.041 mmol). The reaction was stirred at RT for 2 h. A second batch of NaBH$_4$ (1.548 mg, 0.041 mmol) was added, and the reaction was stirred at RT overnight. The reaction was then quenched with water and extracted with DCM. The combined organic layers were concentrated and purified using reverse phase HPLC (Column: Phenomenex Luna C18 20×100 mm; Mobile Phase A: 10:90 acetonitrile:water with 0.1% TFA; Mobile Phase B: 90:10 acetonitrile:water with 0.1% TFA; Gradient: 20-80% B over 20 minutes; Flow: 20 mL/min; Detection: UV at 220 nm) to give compound (IIa-06) (4.2 mg, 5.49 μmol, 13.41% yield; LCMS (M+1): 689.2).

Example 7—Asymmetric THIQ-THIQ Dimers

Figure 5:
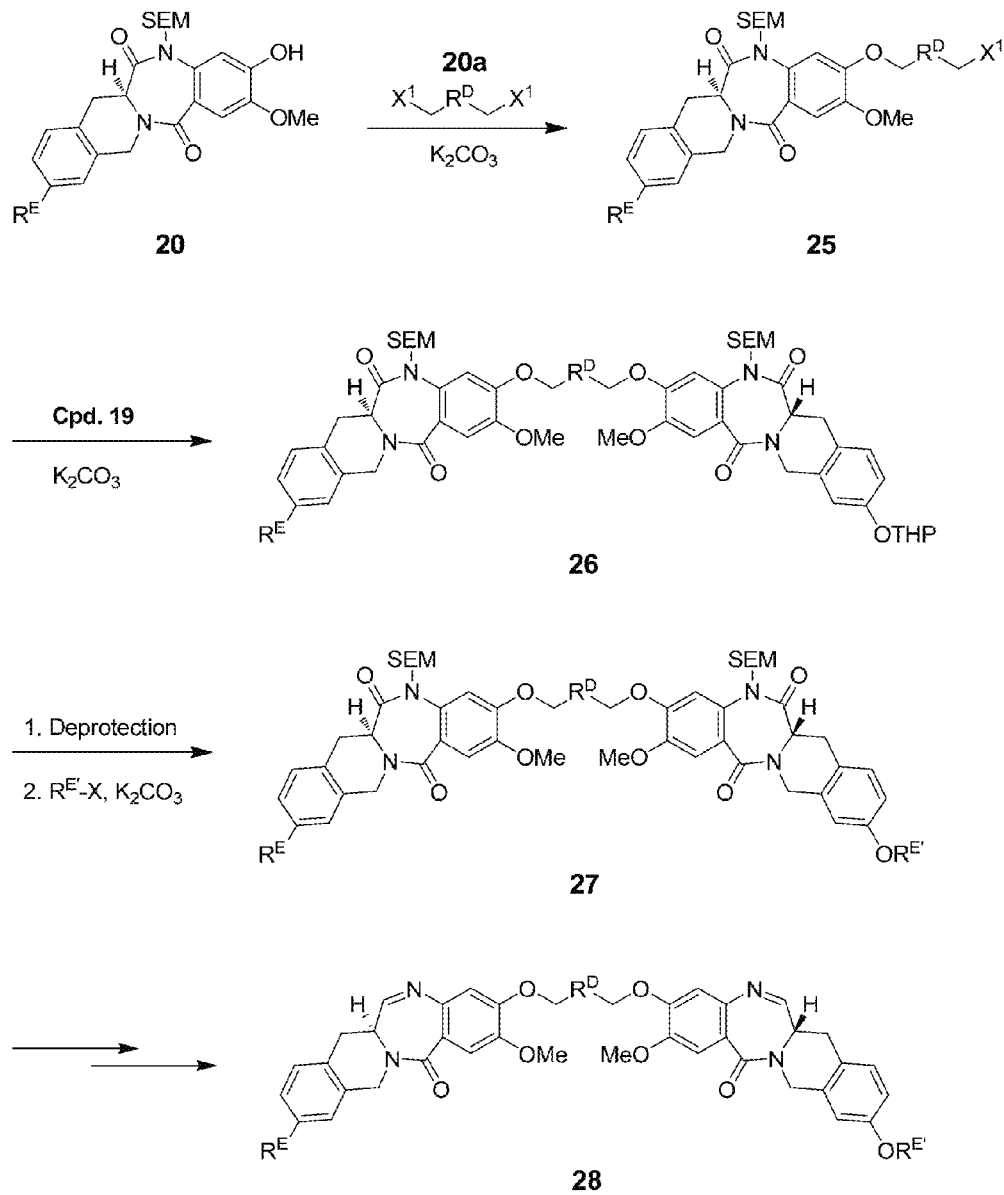
FIG. 5 shows a generic scheme for preparing asymmetric THIQ-THIQ dimers.

This example relates to the synthesis of asymmetric THIQ-THIQ dimers. FIG. 5 shows a general scheme for their synthesis. The groups $R^E$ and $R^{E'}$ in the figure can be various substituents as defined hereinabove.

The first section of this example relates to the synthesis of dimer (S)-10-hydroxy-2-methoxy-3-((5-(((S)-2-methoxy-14-oxo-6a,7,12,14-tetrahydrobenzo[5,6][1,4]diazepino[12-b]isoquinolin-3-yl)oxy)pentyl)oxy)-6a,7-dihydrobenzo[5,6][1,4]diazepino[12-b]isoquinolin-14(12H)-one (IIa-15), per the following reaction scheme:

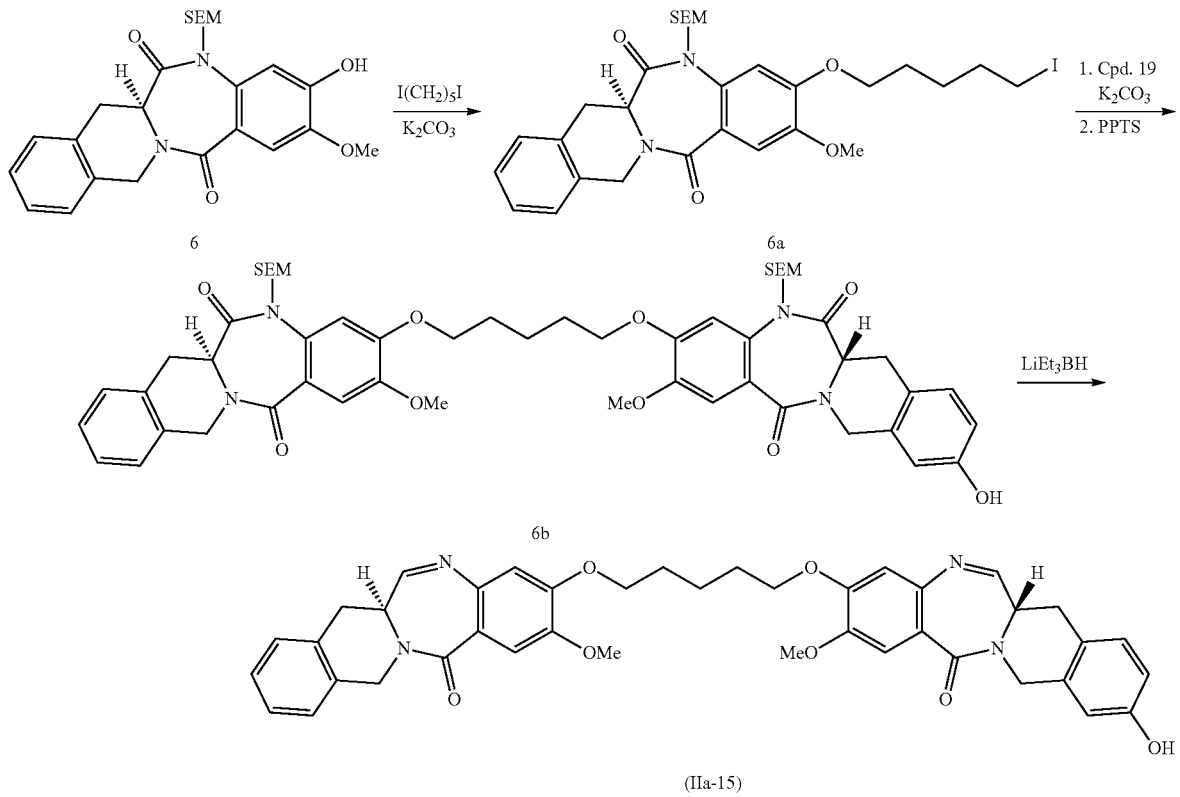

(IIa-15)

To a suspension of compound 6 (250 mg, 0.550 mmol) and $K_2CO_3$ (304 mg, 2.200 mmol) in DMSO (5 mL) was added 1,5-diiodopentane (891 mg, 2.75 mmol). The reaction was stirred at RT for 2 h before it was diluted with EtOAc and washed with brine. The organic layer was separated, dried over $Na_2SO_4$, and concentrated in vacuo. The crude product was purified using ISCO silica gel chromatography (12 g column, gradient 0-10% MeOH/DCM) to give compound 6a as a yellow oil (275 mg, 0.423 mmol, 77% yield). LCMS: (M+H)=651.2 $^1$H NMR (400 MHz, CHLOROFORM-d) δ 7.33-7.24 (m, 5H), 7.21 (s, 1H), 5.50 (d, J=9.9 Hz, 1H), 5.15 (d, J=15.4 Hz, 1H), 4.66 (d, J=9.9 Hz, 1H), 4.41 (d, J=15.4 Hz, 1H), 4.33-4.25 (m, 1H), 4.05 (d, J=8.6 Hz, 2H), 3.89 (s, 3H), 3.80 (td, J=9.6, 6.9 Hz, 1H), 3.72-3.62 (m, 1H), 3.56 (dd, J=15.5, 7.4 Hz, 1H), 3.22 (t, J=6.9 Hz, 2H), 3.00 (dd, J=15.6, 6.4 Hz, 1H), 1.98-1.80 (m, 4H), 1.67-1.54 (m, 2H), 0.98 (ddd, J=9.8, 6.7, 2.9 Hz, 2H), 0.04 (s, 9H).

To a solution of compound 6a (135 mg, 0.208 mmol) and compound 19 (110 mg, 0.198 mmol) in DMSO (3 mL) was added $K_2CO_3$ (82 mg, 0.595 mmol). The resulting suspension was stirred at RT for 5 h. The reaction was then diluted with EtOAc and washed with water. The organic layer was separated, dried over $Na_2SO_4$, and concentrated in vacuo. The residue was taken up in MeOH (10 mL). PPTS (~15 mg) was added, and the reaction was stirred at 40° C. for 1 h. The reaction was then concentrated and purified using ISCO silica gel chromatography (0-100% EtOAc/Hexane, 24 g column) to give compound 6b (141 mg, 0.142 mmol, 71.6% yield). LCMS (M+H)=993.7. $^1$H NMR (400 MHz, CHLOROFORM-d) δ 7.36-7.29 (m, 4H), 7.27-7.24 (m, 1H), 7.23-7.10 (m, 4H), 6.94 (d, J=2.2 Hz, 1H), 6.79 (dd, J=8.1, 2.4 Hz, 1H), 5.51 (t, J=9.6 Hz, 2H), 5.18 (dd, J=19.4, 15.2 Hz, 2H), 4.69 (dd, J=9.9, 7.5 Hz, 2H), 4.42 (d, J=15.4 Hz, 1H), 4.37-4.26 (m, 2H), 4.22 (dd, J=7.7, 6.6 Hz, 1H), 4.09-4.00 (m, 3H), 3.88 (d, J=2.6 Hz, 6H), 3.80 (dd, J=7.0, 4.6 Hz, 2H), 3.68 (dd, J=6.8, 5.1 Hz, 2H), 3.60-3.43 (m, 2H), 3.10-2.82 (m, 2H), 2.00-1.87 (m, 4H), 1.69 (br. s., 2H), 0.98 (td, J=6.6, 3.3 Hz, 4H), 0.10-0.02 (m, 18H).

To a solution of compound 6b (18 mg, 0.018 mmol) in THF (0.6 mL) at −78° C. was added a solution of lithium triethylborohydride (1 M in THF, 362 μL, 0.362 mmol). The reaction was stirred at −78° C. for 1h before it was quenched with water (1 mL). The reaction was then extracted with chloroform (3×). The combined organic layers were dried over $Na_2SO_4$, filtered, and concentrated in vacuo. The residue was then taken up in chloroform/EtOH (1:1, 2 mL). Silical gel (0.8 g) was added, followed by water (0.6 mL). The resulting suspension was stirred at RT for 1 day and then filtered, washing with 10% MeOH/chloroform. The filtrate was concentrated in vacuo and purified using reverse phase HPLC (Column: Phenomenex Luna C18 20×100 mm; Mobile Phase A: 10:90 acetonitrile:water with 0.1% trifluoroacetic acid; Mobile Phase B: 90:10 acetonitrile:water with 0.1% TFA; Gradient: 20-80% B over 20 minutes; Flow: 20 mL/min; Detection: UV at 220 nm) to give dimer (IIa-15) (4.8 mg, 6.16 μmol, 34.0% yield). LCMS (M+H)=701.2.

The synthesis of dimer (S)-2,10-dimethoxy-3-((5-(((S)-2-methoxy-14-oxo-6a,7,12,14-tetrahydrobenzo[5,6][1,4]diazepino[1,2-b]isoquinolin-3-yl)oxy)pentyl)oxy)-6a,7-dihydrobenzo[5,6][1,4]diazepine[1,2-b]isoquinolin-14(12H)-one (IIa-12) from compound 6b was performed as follows. Compound 6b was alkylated with iodomethane using $K_2CO_3$, to give the corresponding methoxy product. LCMS (M+H)=1007.6. Reduction with $LiEt_3BH$ generally following the procedure described above gave dimer (IIa-12). LCMS (M+H)=715.3 $^1$H NMR (400 MHz, CHLOROFORM-d) δ 7.55 (d, J=1.6 Hz, 2H), 7.50 (d, J=5.3 Hz, 2H), 7.41-7.30 (m, 5H), 6.94-6.86 (m, 2H), 6.81 (m, 1H), 5.01 (t, J=14.9 Hz, 2H), 4.67-4.47 (m, 2H), 4.24-4.01 (m, 5H), 3.96 (s, 6H), 3.86 (s, 3H), 3.34-3.02 (m, 4H), 2.02-1.88 (m, 4H).

Following the above procedures, mutatis mutandis, additional asymmetric THIQ-THIQ dimers were synthesized:

(a) (IIa-13): LCMS (M+H)=758.3. $^1$H NMR (400 MHz, CHLOROFORM-d) δ 7.55 (d, J=2.2 Hz, 2H), 7.49 (dd, J=5.3, 3.4 Hz, 2H), 7.42-7.33 (m, 5H), 6.95-6.89 (m, 2H), 6.86-6.77 (m, 2H), 6.54 (br. s., 1H), 5.57 (br. s., 1H), 5.02 (dd, J=15.5, 10.9 Hz, 2H), 4.62-4.56 (m., 2H), 4.20-4.02 (m, 6H), 3.96 (s, 3H), 3.96 (s, 3H), 3.90-3.84 (m, 3H), 3.31-3.05 (m, 5H), 1.96 (m, 4H).

(b) (IIa-14): LCMS (M+H)=803.3.

(c) (IIa-17): LCMS (M+H)=745.2.

Example 8—Dimers with Asymmetric Bridge

Figure 6:
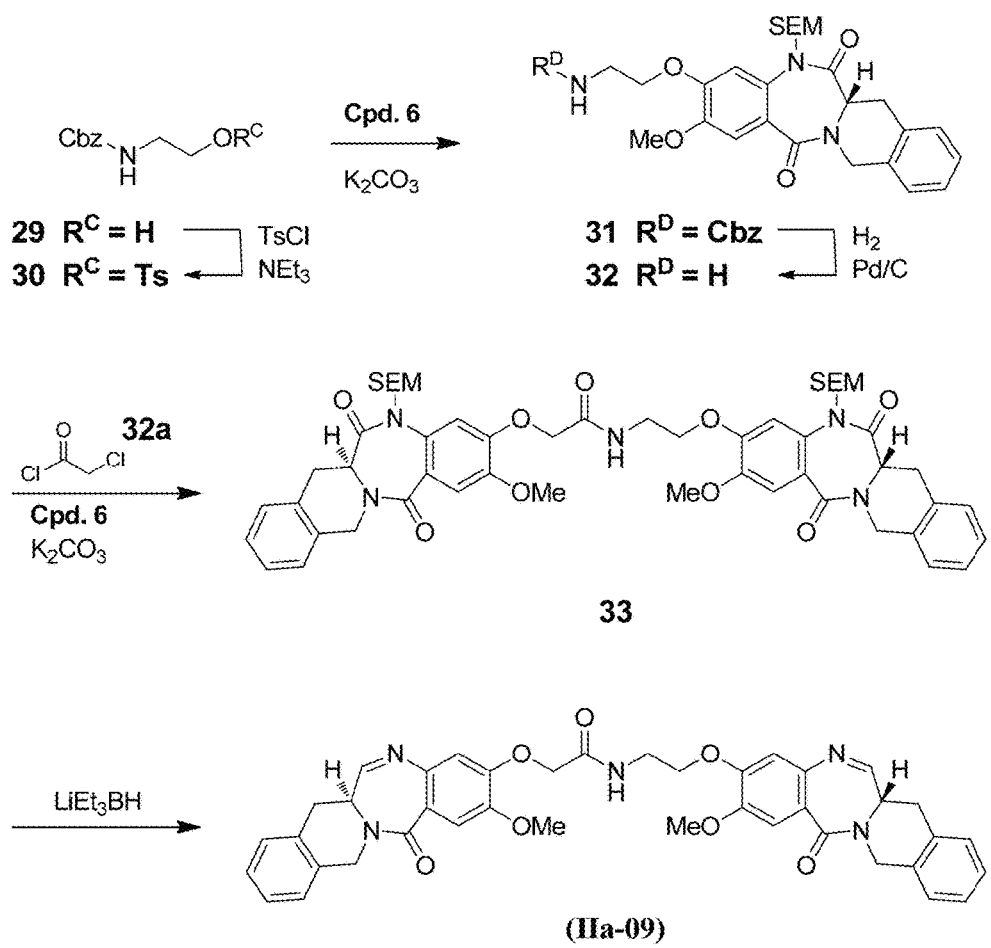
FIG. 6 shows a scheme for preparing a dimer of this invention where the bridge linking the two dimer halves is not bilaterally symmetric.

This example and FIG. 6 illustrate a synthetic strategy for making dimers in which the bridge linking the two dimer halves is not bilaterally symmetric. The specific illustration is with respect to dimer (IIa-09).

To a solution of benzyl (2-hydroxyethyl)carbamate 29 (Aldrich, 0.781 g, 4 mmol) and $NEt_3$ (1.115 mL, 8.00 mmol) were added p-toluenesulfonyl chloride (TsCl, 0.915 g, 4.80 mmol). The reaction was stirred at RT for 1 h. The reaction mixture was concentrated and purified using ISCO silica gel chromatography (0-100% EtOAC/HEx, 40 g column) to give the toluenesulfonate 30 (0.85 g, 2.43 mmol, 60.8% yield). LCMS (M+H)=350.

To a solution of compound 6 (160 mg, 0.352 mmol) and toluenesulfonate 30 (135 mg, 0.387 mmol) in DMF (3 mL) was added $K_2CO_3$ (97 mg, 0.704 mmol). The resulting suspension was stirred at RT for 2 h. The reaction was diluted with EtOAc and washed sequentially with aq. LiCl and brine. The organic layer was separated, dried over $Na_2SO_4$, and concentrated in vacuo. The crude material was purified using ISCO silical gel chromatography (0-10% MeOH/DCM, 24 g column) to give compound 31. LCMS (M+H)=632.3.

A suspension of compound 31 and 10% Pd/C (25 mg) in MeOH (8 mL) was stirred under a balloon of $H_2$ for 5 h. The reaction was then purged with $N_2$, filtered through a pad of CELITE™, and concentrated to give compound 32 (150 mg, 0.301 mmol, 86% yield). LCMS (M+H)=498 $^1$H NMR (500 MHz, CHLOROFORM-d) δ 7.65 (d, J=8.2 Hz, 1H), 7.38-7.23 (m, 4H), 7.21 (s, 1H), 7.07 (d, J=7.9 Hz, 1H), 6.90-6.64 (m, 3H), 5.41 (d, J=10.2 Hz, 1H), 5.14 (d, J=15.3 Hz, 1H), 4.76 (d, J=10.1 Hz, 1H), 4.44-4.33 (m, 2H), 4.32-4.17 (m, 3H), 3.80 (s, 3H), 3.72-3.50 (m, 4H), 3.39-3.30 (m, 2H), 3.05-2.93 (m, 1H), 0.98-0.87 (m, 2H), 0.00 (s, 9H).

To a solution of compound 32 (65 mg, 0.131 mmol) in DCM (2 mL) at 0° C. was added $NEt_3$ (0.055 mL, 0.39 mmol) and 2-chloroacetyl chloride 32a (22.13 mg, 0.196 mmol). The solution was stirred for 1 h and then diluted with DCM. The organic layer was washed with brine, dried over $Na_2SO_4$ and concentrated in vacuo. The residue was combined with compound 6 (59.4 mg, 0.131 mmol) and $K_2CO_3$ (4.2 mg, 0.392 mmol), and suspended in DMSO (1 mL). The resulting mixture was heated at 50° C. for 4 h. After cooling to RT, the reaction was diluted with EtOAc and washed with brine. The organic layer was separated, dried over $Na_2SO_4$, and concentrated in vacuo. The crude material was purified using ISCO silical gel chromatography (0-10% MeOH/DCM, 24 g column) to give acetamide 33 (95 mg, 0.096 mmol, 73.3% yield). LCMS (M+H)=992.5.

To a solution of acetamide 33 (40 mg, 0.040 mmol) in THF (0.6 mL) at −78 OC was added a solution of LiEt$_3$BH (0.4 mL, 1 M in THF). The reaction was then stirred at −78° C. for 1 h before it was quenched with water (1 mL). The reaction mixture was then extracted with chloroform (3×). The combined organic layers were dried over Na$_2$SO$_4$, filtered, and concentrated in vacuo. The residue was then taken up in chloroform/EtOH (1:1, 2 mL). Silica gel (0.8 g) was added, followed by water (0.6 mL). The resulting suspension was stirred at RT for 1 day and then filtered, washing with 10% MeOH/chloroform. The filtrate was concentrated in vacuo and purified using reverse phase HPLC (Column: Phenomenex Luna C18 20×100 mm; Mobile Phase A: 10:90 acetonitrile:water with 0.1% TFA; Mobile Phase B: 90:10 acetonitrile:water with 0.1% TFA; Gradient: 15-70% B over 15 minutes; Flow: 20 mL/min; Detection: UV at 220 nm) to give dimer (IIa-09) (11 mg, 0.014 mmol, 35.1% yield). LCMS (M+H)=700.2 $^1$H NMR (400 MHz, CHLOROFORM-d) δ 7.57 (d, J=9.5 Hz, 2H), 7.48 (dd, J=5.3, 0.9 Hz, 2H), 7.40-7.31 (m, 9H), 6.83 (d, J=4.0 Hz, 2H), 5.01 (d, J=15.6 Hz, 2H), 4.64-4.51 (m, 4H), 4.20 (td, J=9.4, 5.0 Hz, 2H), 3.96 (s, 3H), 3.95 (s, 3H), 3.91-3.82 (m, 4H), 3.34-3.23 (m, 2H), 3.20-3.11 (m, 2H).

Example 9—THIQ-PBD Dimers

The general scheme of FIG. 5 can be used to prepare THIQ-PBD dimers, with one of the two THIQ monomer units replaced by a PBD monomer unit. The THIQ monomer unit can be alkylated first and then the PBD monomer unit attached, or vice-versa.

Figure 7A:
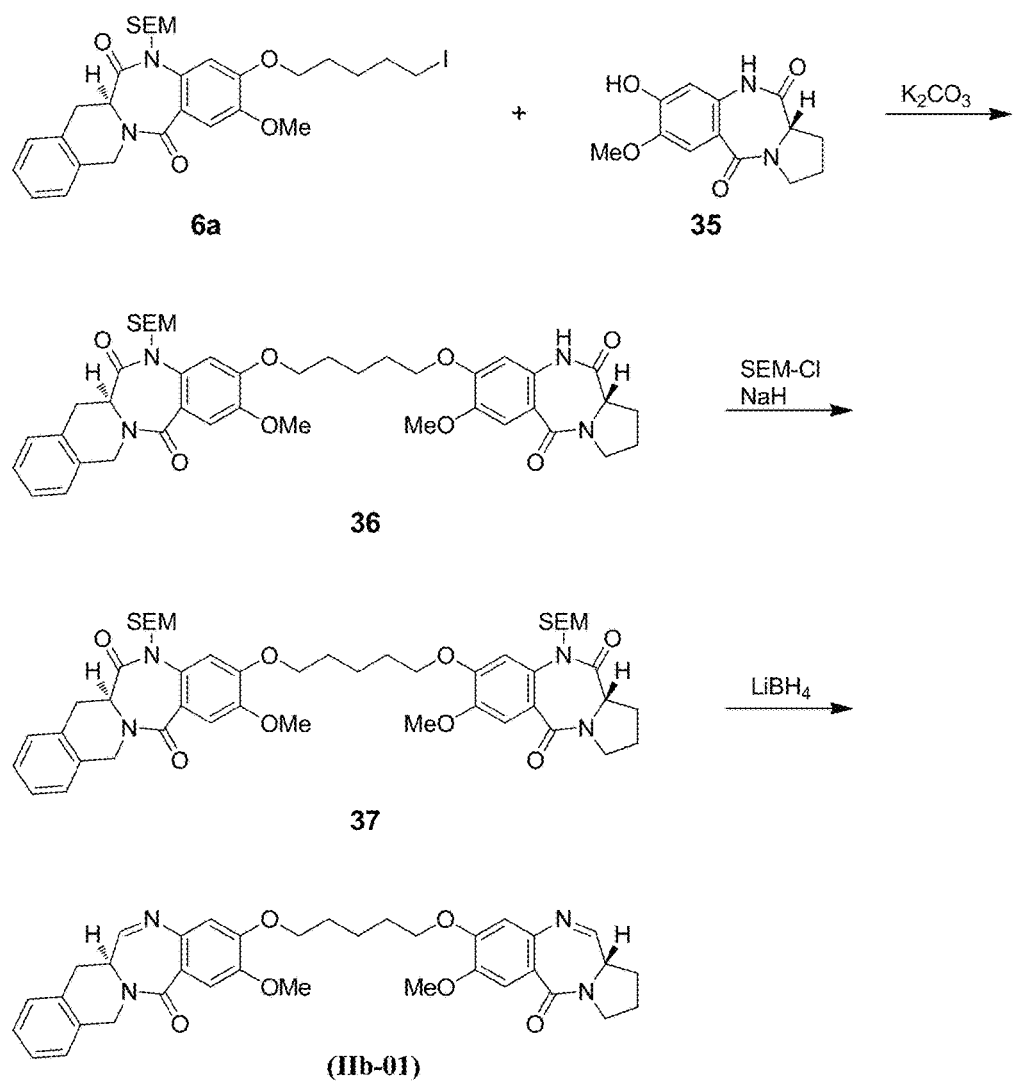
FIGS. 7a and 7b show schemes for the preparation of THIQ-PBD dimers.
Figure 7B:
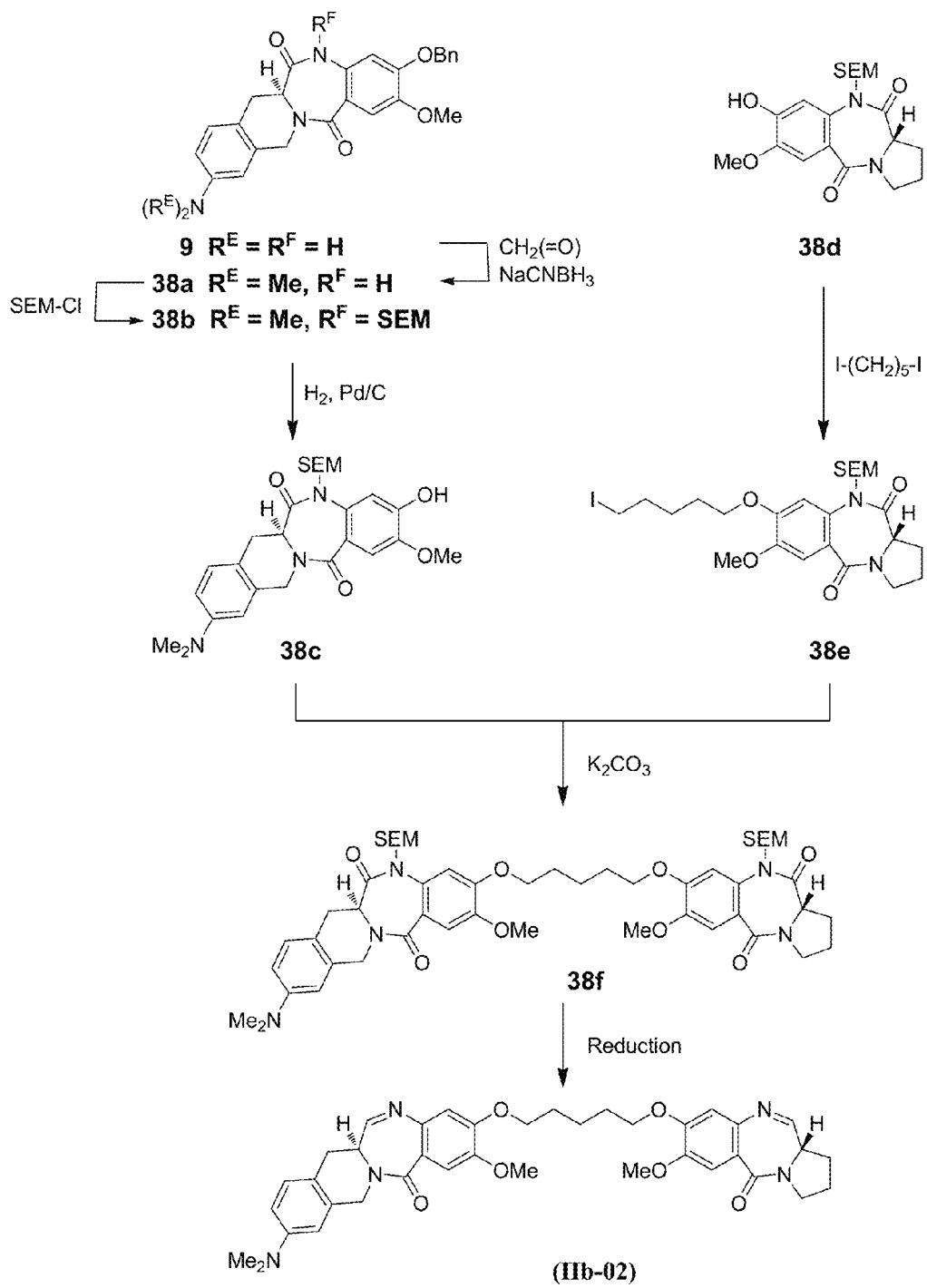

This example and FIGS. 7a and 7b illustrate the synthesis of THIQ-PBD dimers, with specific reference to dimers (IIb-01) and (IIb-02).

The preparation of dimer (IIb-01) is described first. The synthetic scheme is summarized in FIG. 7a and exemplifies the approach in which the THIQ is alkylated first.

A suspension of compound 6a (Example 7 above, 50 mg, 0.077 mmol), K$_2$CO$_3$ (31.9 mg, 0.231 mmol) and dione 35 (CAS Reg. No. 132391-70-9, Howard et al. 2014c, 40.3 mg, 0.154 mmol) in DMF (1.5 mL) was heated at 50° C. for 2 h. The reaction was cooled to RT and quenched with water. The resulting mixture was extracted with EtOAc (3×). The combined organic layers were washed with brine, dried over Na$_2$SO$_4$, and concentrated in vacuo. The crude material was purified using ISCO silica gel chromatography (24 g column, 0-10% MeOH/DCM) to give compound 36. LCMS (M+H)=785.4.

Compound 36 was dissolved in DMF (0.5 mL). The solution was cooled to 0° C. before NaH (60% dispersion in mineral oil, 3.07 mg, 0.077 mmol) and SEM-Cl (0.014 mL, 0.077 mmol) were added sequentially. The reaction was warmed to RT and stirred for 2 h. The reaction was then quenched with water, extracted with EtOAc, dried over Na$_2$SO$_4$, and concentrated in vacuo. Crude compound 37 was used in the next step without further purification (14 mg, 0.015 mmol, 20% yield). LCMS (M+H)=915.7.

To a solution of crude compound 37 (14 mg, 0.015 mmol) in THF/EtOH (1:1, 1 mL) at 0° C. was added a solution of LiBH$_4$ (101 μl, 0.202 mmol, 2 M in THF). The reaction was slowly warmed to RT and stirred for 15 min before it was quenched with brine. The resulting mixture was extracted with CHCl$_3$ (3×). The organic layer was separated, dried over Na$_2$SO$_4$, and concentrated in vacuo. The residue was then taken up in EtOH/chloroform (1:1, 2 mL). Silica gel (700 mg) was added, followed by water (0.6 mL). The resulting suspension was stirred at RT for 1 day and then filtered, washing with 10% MeOH/CHCl$_3$. The filtrate was concentrated and purified by reverse phase HPLC (Column: Phenomenex Luna C18 20×100 mm; Mobile Phase A: 10:90 CH$_3$CN:water with 0.1% TFA; Mobile Phase B: 90:10 acetonitrile:water with 0.1% TFA; Gradient: 15-60% B over 20 minutes; Flow: 20 mL/min; Detection: UV at 220 nm) to give (IIb-01) (0.92 mg, 1.330 μmol, 8.69% yield). LCMS (M+H)=623. $^1$H NMR (400 MHz, CHLOROFORM-d) δ 7.69 (d, J=4.4 Hz, 1H), 7.57-7.53 (m, 2H), 7.50 (d, J=5.1 Hz, 1H), 7.41-7.32 (m, 4H), 6.82 (d, J=1.5 Hz, 2H), 5.03 (d, J=15.6 Hz, 1H), 4.59 (d, J=15.6 Hz, 1H), 4.18-4.06 (m, 4H), 3.97 (s, 3H), 3.96 (s, 3H), 3.75 (d, J=7.3 Hz, 4H), 3.61 (dt, J=11.8, 7.8 Hz, 1H), 3.34-3.26 (m, 1H), 3.22-3.15 (m, 1H), 2.34 (br. s., 2H), 2.11-2.06 (m, 1H), 2.01-1.94 (m, 4H), 1.71-1.66 (m, 2H).

Turning now to the synthesis of dimer (IIb-02), the synthetic scheme is summarized in FIG. 7b. In this instance, it is the PBD monomer unit that is alkylated first and then coupled to the THIQ monomer unit.

To a solution of compound 9 (220 mg, 0.512 mmol) in MeOH (3 mL) and THF (3 mL) was added formaldehyde (37% aq. solution, 0.572 mL, 7.68 mmol) and a few drops of acetic acid. The solution was stirred at RT for 10 min before Na(CN)BH$_3$ (129 mg, 2.049 mmol) was added. The reaction was then stirred at RT for 2 h before it was concentrated in vacuo. The crude material was purified using ISCO silical gel chromatography (0-10% MeOH/DCM, 24 g column) to give compound 38a (230 mg, 0.503 mmol, 98% yield). LCMS (M+H)=458.

To a solution of compound 38a (230 mg, 0.503 mmol) in DMF (5 mL) at 0° C. was added NaH (60% dispersion in mineral oil, 25.1 mg, 0.628 mmol). The mixture was stirred for 15 min before SEM-Cl (0.111 mL, 0.628 mmol) was added. The reaction was slowly warmed to RT and stirred overnight. The reaction was then quenched with water and extracted with EtOAc (3×). The combined organic layers were dried over Na$_2$SO$_4$ and concentrated in vacuo. The crude material was purified using ISCO silica gel chromatography (0-10% MeOH/DCM) to give compound 38b. LCMS (M+H)=588.2.

Compound 38b was combined with 10% Pd/C (20 mg) and suspended in EtOH/EtOAc (1:1, 10 mL). The mixture was purged with N$_2$ and then stirred under a balloon of H$_2$ for 4 h. The reaction was then filtered through a pad of CELITE™ and concentrated in vacuo. The crude material was purified using ISCO silica gel chromategraphy (0-10% MeOH/DCM, 40 g column) to give compound 38c (190 mg, 0.382 mmol, 76% yield). LCMS (M+H)=498.2. $^1$H NMR (400 MHz, CHLOROFORM-d) δ 7.45 (s, 1H), 7.21 (s, 1H), 7.18-7.10 (m, 1H), 6.69 (m., 2H), 5.51 (d, J=9.9 Hz, 1H), 5.12 (d, J=15.2 Hz, 1H), 4.65 (d, J=10.1 Hz, 1H), 4.33 (d, J=15.2 Hz, 1H), 4.24 (d, J=0.4 Hz, 1H), 3.91 (s, 3H), 3.79 (s, 1H), 3.72-3.63 (m, 1H), 3.52-3.40 (m, 1H), 2.93 (s, 6H), 1.05-0.89 (m, 2H), 0.03 (s, 9H).

Compound 38d was prepared by generally following the procedures described above. LCMS (M+H)=393.4. $^1$H NMR (400 MHz, CHLOROFORM-d) δ 7.38 (s, 1H), 7.27 (s, 1H), 6.34 (s, 1H), 5.46 (d, J=9.8 Hz, 1H), 4.70 (d, J=9.8 Hz, 1H), 4.19-4.06 (m, 1H), 3.96 (s, 3H), 3.80-3.60 (m, 3H), 3.60-3.53 (m, 1H), 3.50 (d, J=2.9 Hz, 2H), 2.78-2.68 (m, 1H), 2.19-1.95 (m, 3H), 1.05-0.96 (m, 2H), 0.08-0.02 (m, 9H).

To a solution of compound 38d (1.2 g, 3.06 mmol) in DMF (10 mL) was added K$_2$CO$_3$ (1.268 g, 9.17 mmol) and 1,5-diiodopentane (5.94 g, 18.34 mmol). The reaction was stirred for 2 h before it was quenched with water. The resulting mixture was extracted with EtOAc (3×). The combined organic layers were washed with brine, dried over Na$_2$SO$_4$, and concentrated in vacuo. The crude product was purified using ISCO silica gel chromategraphy (24 g column, 0-10% MeOH/DCM) to give compound 38e (1.52 g, 2.58 mmol, 84% yield). LCMS (M+H)=589.1

To a solution of compound 38e (22.12 mg, 0.038 mmol) and compound 38c (17 mg, 0.034 mmol) in DMSO (1 mL) was added K$_2$CO$_3$ (9.44 mg, 0.068 mmol). The resulting mixture was stirred at RT for 14 h. The reaction was then diluted with EtOAc and washed sequentially with water and brine. The organic layer was separated, dried over Na$_2$SO$_4$, and concentrated in vacuo. The crude product was purified using ISCO silica gel chromatography (0-10% MeOH/DCM, 24 g column) to give compound 38f (27 mg, 0.028 mmol, 82% yield). LCMS (M+H)=958.3.

Compound 38f was converted to dimer (IIb-02) by reduction generally following the procedures described above. LCMS (M+H)=666.2. $^1$H NMR (400 MHz, CHLOROFORM-d) δ 7.68 (d, J=4.4 Hz, 1H), 7.54 (d, J=1.8 Hz, 2H), 7.52 (d, J=5.3 Hz, 1H), 7.23 (d, J=8.8 Hz, 1H), 6.82 (d, J=1.8 Hz, 2H), 6.73-6.65 (m, 2H), 4.97 (d, J=15.4 Hz, 1H), 4.53 (d, J=15.4 Hz, 1H), 4.29-4.03 (m, 4H), 3.96 (s, 3H), 3.92 (s, 3H), 3.84 (ddd, J=11.7, 7.1, 4.5 Hz, 1H), 3.78-3.72 (m, 1H), 3.66-3.56 (m, 1H), 3.28-3.17 (m, 1H), 3.06 (dd, J=15.4, 4.2 Hz, 1H), 3.01-2.95 (m, 6H), 2.34 (td, J=6.7, 3.0 Hz, 2H), 2.16-1.90 (m, 6H), 1.78-1.62 (m, 3H).

Example 10—THIQ-THIQ Dimers (IIa-10) and (IIa-11)

Figure 8:
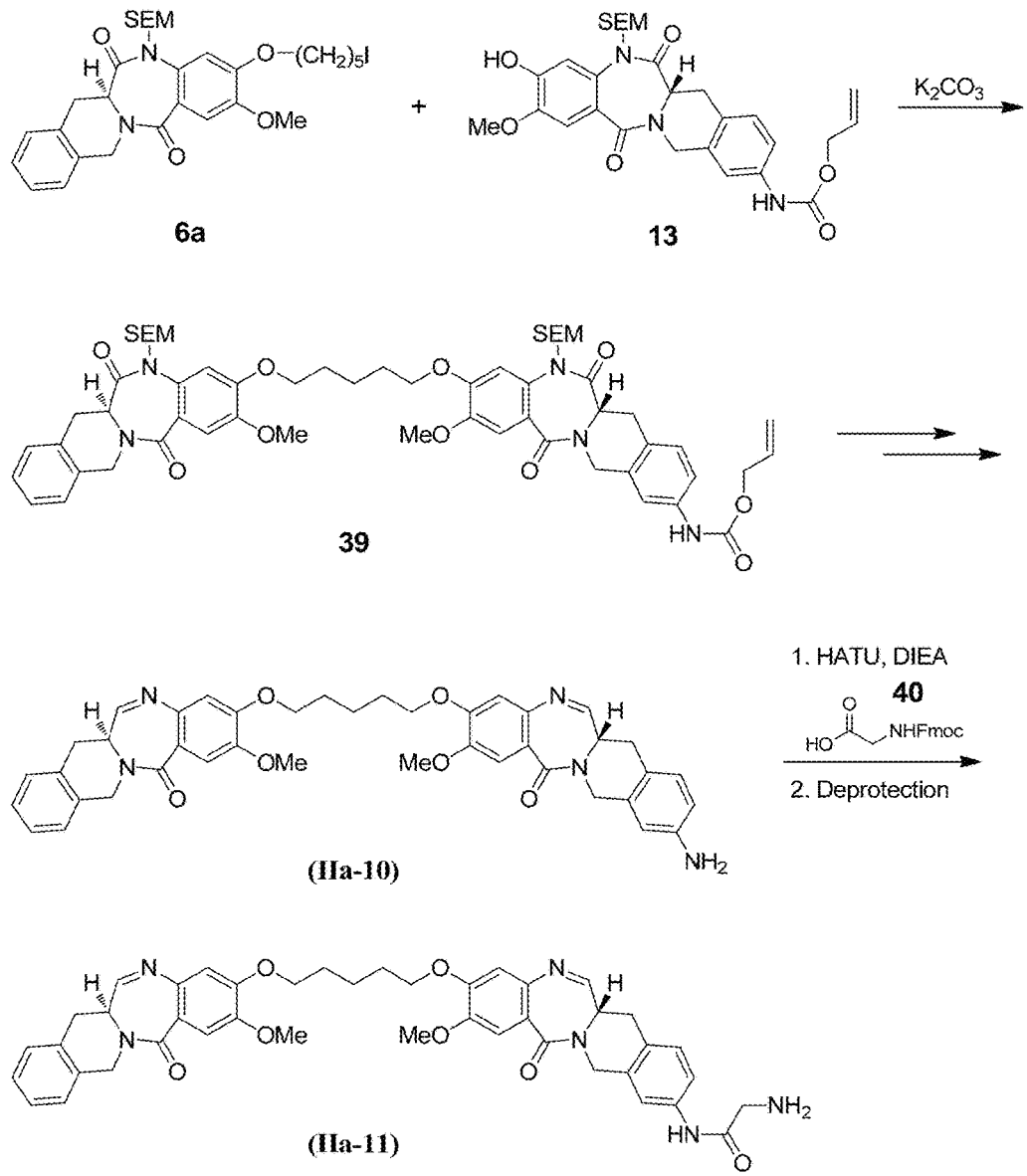
FIG. 8 shows a scheme for the preparation of additional asymmetric THIQ-THIQ dimers.

This example and FIG. 8 relate to the preparation of dimers (IIa-10) and (IIa-11).

To a solution of compound 6a (100 mg, 0.154 mmol) and compound 13 (68 mg, 0.123 mmol) in DMSO (3 mL) was added K$_2$CO$_3$ (50.9 mg, 0.368 mmol). The resulting suspension was stirred at RT for 5 h. The reaction was then diluted with EtOAc, washed with brine, dried over Na$_2$SO$_4$, and concentrated in vacuo. The crude material was purified using ISCO silica gel chromatography (0-10% MeOH/DCM, 12 g column) to give carbamate 39 (124 mg, 0.115 mmol, 94% yield). LCMS (M+H)=1076.3. $^1$H NMR (400 MHz, CHLOROFORM-d) δ 7.30 (d, J=0.9 Hz, 6H), 7.27-7.18 (m, 5H), 6.89 (s, 1H), 6.01-5.88 (m, 1H), 5.49 (dd, J=9.9, 4.0 Hz, 2H), 5.34 (dd, J=17.3, 1.4 Hz, 1H), 5.25 (dd, J=10.3, 1.1 Hz, 1H), 5.18-5.04 (m, 2H), 4.71-4.62 (m, 4H), 4.40 (d, J=15.4 Hz, 2H), 4.32-4.22 (m, 2H), 4.09-3.97 (m, 4H), 3.90-3.84 (m, 6H), 3.82-3.73 (m, 2H), 3.71-3.44 (m, 5H), 3.08-2.90 (m, 2H), 1.99-1.90 (m, 4H), 1.04-0.91 (m, 4H), 0.02 (s, 9H), 0.02 (s, 9H).

To a solution of carbamate 39 (124 mg, 0.115 mmol) in DCM (6 mL) at 0° C. was added morpholine (0.080 mL, 0.922 mmol). After the reaction was purged with N$_2$, Pd(Ph$_3$P)$_4$ (13.31 mg, 0.012 mmol) was added. The reaction was slowly warmed to RT and stirred under N$_2$ for 2 h. The reaction was then concentrated and purified using ISCO silica gel chromatography (0-10% MeOH/DCM) to give the corresponding aniline compound (90 mg, 0.091 mmol, 79% yield). LCMS (M+H)=992.5.

To a solution of the preceding aniline compound (89 mg, 0.090 mmol) in THF (3 mL) at −78° C. was added LiEt$_3$BH (1 M in THF, 0.448 mL, 0.448 mmol). The reaction was stirred at −78° C. for 1 h. The reaction then was quenched with water (1 mL) and extracted with chloroform (3×). The combined organic layers were dried over Na$_2$SO$_4$, filtered, and concentrated in vacuo. The residue was then taken up in chloroform/EtOH (1:1, 2 mL). Silica gel (0.7 g) was added, followed by water (0.6 mL). The resulting suspension was stirred at RT for 1 day and then filtered, washing with 10% MeOH/chloroform. The filtrate was concentrated and purified on HPLC (Column: Phenomenex Luna C18 20×100 mm; Mobile Phase A: 10:90 acetonitrile:water with 0.1% TFA; Mobile Phase B: 90:10 acetonitrile:water with 0.1% TFA; Gradient: 20-70% B over 20 minutes; Flow: 20 mL/min; Detection: UV at 220 nm) to give dimer (IIa-10) (19 mg, 0.024 mmol, 27.2% yield). LCMS (M+H)=700.2 $^1$H NMR (400 MHz, CHLOROFORM-d) δ 7.54 (d, J=2.4 Hz, 2H), 7.50 (t, J=4.7 Hz, 2H), 7.41-7.31 (m, 5H), 7.15 (d, J=8.6 Hz, 1H), 6.81 (d, J=1.8 Hz, 2H), 6.73-6.59 (m, 2H), 5.02 (d, J=15.6 Hz, 1H), 4.92 (d, J=15.4 Hz, 1H), 4.58 (d, J=15.6 Hz, 1H), 4.47 (d, J=15.4 Hz, 1H), 4.22-4.03 (m, 3H), 4.00-3.70 (m, 9H), 3.34-3.25 (m, 1H), 3.18 (dt, J=15.4, 4.2 Hz, 2H), 3.09-3.00 (m, 1H), 2.03-1.92 (m, 4H), 1.76-1.63 (m, 2H).

To a solution of dimer (IIa-10) (4.5 mg, 6.43 μmol), Fmoc-GLY-OH (ChemImpex, 3.82 mg, 0.013 mmol), and N,N,N',N'-tetramethyl-O-(7-azabenzotriazol-1-yl)uronium hexafluorophosphate (HATU, 4.89 mg, 0.013 mmol) in DMF (0.5 mL) was added N,N-diisopropylethylamine (DIEA, 3.37 μL, 0.019 mmol). The reaction was stirred at RT for 4 h before piperidine (100 uL) was added. The resulting mixture was stirred at RT for 1 h. The crude reaction mixture was then diluted with DMF, filtered, and purified on reverse phase HPLC (Column: Phenomenex Luna C18 20×100 mm; Mobile Phase A: 10:90 acetonitrile:water with 0.1% TFA; Mobile Phase B: 90:10 acetonitrile:water with 0.1% TFA; Gradient: 20-70% B over 20 minutes; Flow: 20 mL/min; Detection: UV at 220 nm) to give dimer (IIa-11) (0.94 mg, 1.180 μmol, 18.35% yield). LCMS (M+H)=757.2.

Example 11—THIQ-PBD Dimer (IIb-03)

Figure 9:
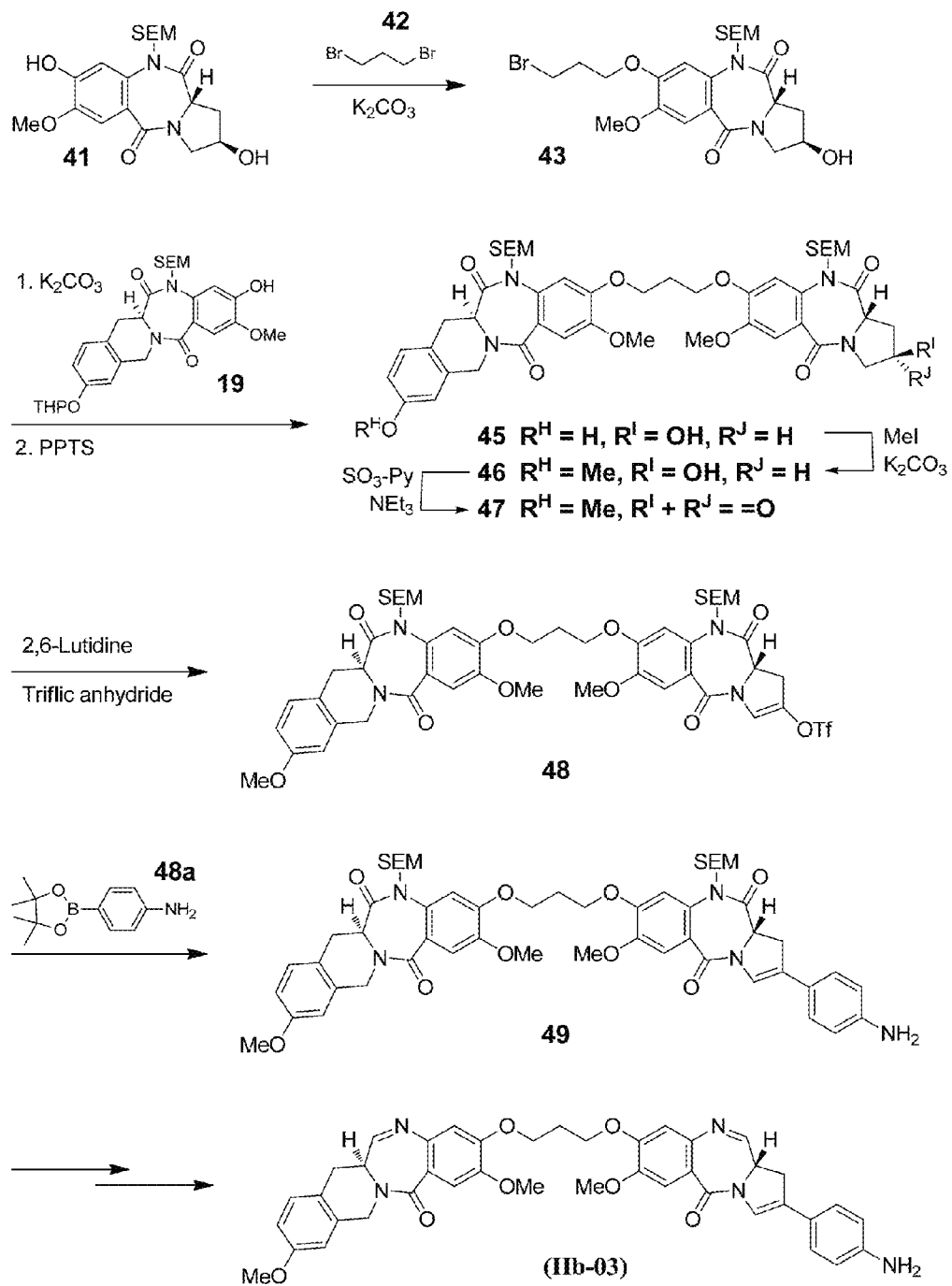
FIG. 9 shows a scheme for the preparation of another THIQ-PBD dimer.

This example and FIG. 9 relate to the preparation of the THIQ-PBD dimer (IIb-03).

Compound 41 was prepared generally following the procedures in the previous examples. LCMS (M+H)=409.1 $^1$H NMR (400 MHz, CHLOROFORM-d) δ 7.32 (s, 1H), 7.25 (s, 1H), 6.30 (s, 1H), 5.45 (d, J=9.7 Hz, 1H), 4.71 (d, J=9.8 Hz, 1H), 4.65 (br. s., 1H), 4.30 (dd, J=7.9, 5.9 Hz, 1H), 4.00-3.84 (m, 4H), 3.79-3.57 (m, 3H), 2.97 (dt, J=13.5, 5.5 Hz, 1H), 2.86 (br. s., 1H), 2.21-2.08 (m, 1H), 1.00 (t, J=8.4 Hz, 2H), 0.03 (s, 9H).

To a solution of dione 41 (500 mg, 1.224 mmol) in DMSO (3 mL) was added 1,3-dibromopropane 42 (1730 mg, 8.57 mmol) and K$_2$CO$_3$ (423 mg, 3.06 mmol). The reaction was stirred at RT for 3 h. The reaction was then quenched with water and extracted with EtOAc (3×). The combined organic layers were washed with brine, dried over Na$_2$SO$_4$, and concentrated in vacuo. The crude product was purified using ISCO silica gel chromatography (0-10% MeOH/DCM, 40 g column) to give bromopropoxy PBD 43 (540 mg, 0.918 mmmol, 75%) as a white foam. LCMS (M+H)=531.2.

To a solution of THIQ monomer 19 (100 mg, 0.180 mmol), prepared generally following the procedures of the preceding examples, and bromopropoxy PBD 43 (117 mg, 0.198 mmol) in DMSO (2 mL) was added K$_2$CO$_3$ (62.3 mg, 0.451 mmol). The mixture was stirred at RT for 16 h. The reaction was then diluted with EtOAc and washed sequentially with water and brine. The organic layer was separated, dried over Na$_2$SO$_4$, and concentrated. The resulting mixture was taken up in MeOH (10 mL), and PPTS (20 mg) was added. The reaction was stirred at 40° C. for 1 h. The reaction was the concentrated, taken up in EtOAc, washed with aq. NaHCO$_3$, and then brine. The organic layer was separated, dried over Na$_2$SO$_4$, and concentrated in vacuo. The crude product was purified using ISCO silical gel chromatography (0-20% EtOAc/Hexane, 24 g column) to give compound 45 (150 mg, 0.163 mmol, 91% yield). LCMS: (M+H)=919.3

To a solution of compound 45 (150 mg, 0.163 mmol) in DMSO (2 mL) was added K$_2$CO$_3$ (67.7 mg, 0.490 mmol) and iodomethane (46.3 mg, 0.326 mmol). The mixture was stirred at RT for 16 h. The reaction was then diluted with EtOAc and washed with water. The organic layer was dried over Na$_2$SO$_4$ and concentrated in vacuo. The crude product 46 was used in the next step without further purification. LCMS (M+H)=933.5.

To a 0° C. solution of crude 46 (150 mg, 0.161 mmol) in DCM (804 μL) and DMSO (804 μL) was added triethylamine (112 μl, 0.804 mmol) followed by sulfur trioxide pyridine complex (51.2 mg, 0.321 mmol). The reaction was allowed to warm to RT and stirred for 16 h. The reaction was then diluted with DCM (30 mL), washed sequentially with sat. aq. NH$_4$Cl (10 mL), H$_2$O (2×10 mL), and sat. aq. NaHCO$_3$ (10 mL). The organic layer was dried over Na$_2$SO$_4$, filtered, and concentrated in vacuo. The crude material was purified by ISCO silica gel flash chromatography (24 g column; gradient 0-100% EtOAc-CH$_2$C12) to provide ketone 47 (112 mg, 0.084 mmol, 52.4% yield). LCMS (M+H)=930.5.

To a solution of ketone 47 (112 mg, 0.120 mmol) in DCM (2 mL) was added 2,6-lutidine (0.028 mL, 0.241 mmol). The solution was then cooled to −78° C. Triflic anhydride (0.030 mL, 0.180 mmol) was then added dropwise. The reaction was slowly warmed to 0° C. and stirred for 2 h. The reaction was then quenched with brine and extracted with DCM. The organic layer was separated, dried over Na$_2$SO$_4$, and concentrated in vacuo. The crude product was purified using ISCO silica gel chromatography (0-10% MeOH/DCM, 24 g column) to give triflate 48 (81 mg, 0.076 mmol, 63.3% yield). LCMS (M+H)=1062.

To a vial with screw-cap top was added triflate 48 (81 mg, 0.076 mmol), 4-(4,4,5,5-tetramethyl-1,3,2-dioxaborolan-2-yl)aniline 48a (20.03 mg, 0.091 mmol) and [1,1'-bis(diphenylphosphino)ferrocene]dichloropalladium(II) (2.79 mg, 3.81 μmol). The vial was evacuated and backfilled with N$_2$. THF (2 mL) and a solution of aq. K$_3$PO$_4$ (1 M, 0.38 μl, 0.38 mmol) was added. The mixture was stirred under N$_2$ at 45° C. for 2 h. The reaction was diluted with EtOAc and washed with brine. The organic layer was separated, dried over Na$_2$SO$_4$, filtered, and concentrated in vacuo. The crude material was purified using ISCO silica gel flash chromatography (12 g column; linear gradient 0-100% EtOAc-Hex) to provide the compound 49 (53 mg, 0.053 mmol, 69.1% yield). LCMS (M+H)=1006.3. $^1$H NMR (400 MHz, CHLOROFORM-d) δ 7.41 (s, 1H), 7.33 (s, 1H), 7.29-7.20 (m, 6H), 6.91-6.80 (m, 2H), 6.68 (d, J=8.6 Hz, 2H), 5.51 (dd, J=11.9, 10.0 Hz, 2H), 5.13 (d, J=15.4 Hz, 1H), 4.75 (dd, J=16.8, 10.0 Hz, 2H), 4.60 (dd, J=10.6, 3.4 Hz, 1H), 4.39 (d, J=15.3 Hz, 1H), 4.33-4.21 (m, 5H), 3.93 (s, 3H), 3.89 (s, 3H), 3.82 (s, 3H), 3.80-3.74 (m, 3H), 3.69 (tdd, J=9.5, 7.2, 5.0 Hz, 2H), 3.51 (dd, J=15.5, 7.5 Hz, 1H), 3.12 (ddd, J=16.1, 10.6, 2.1 Hz, 1H), 3.03-2.87 (m, 1H), 2.44 (t, J=5.9 Hz, 2H), 1.03-0.92 (m, 4H), 0.04 (s, 9H), 0.03 (s, 9H).

To a solution of compound 49 (7 mg, 6.96 μmol) in THF (1 mL) at −78° C. was added dropwise a solution of lithium triethylborohydride (0.070 mL, 0.070 mmol, 1M in THF). The reaction was stirred at −78° C. for 1 h before it was quench with brine. The mixture was extracted with 10% MeOH/chloroform (3×). The combined organic layers were dried over Na$_2$SO$_4$, and concentrated in vacuo. The residue was taken up in THF/EtOH (1:1, 2 mL). Aqueous formic acid (0.05%, 1 mL) was added. The reaction was then stirred at RT for 2 h. The mixture was neutralized with aq. NaHCO$_3$ and extracted with chloroform (3×). The combined organic layers were concentrated and purified using ISCO silica gel flash chromatography (0-6% MeOH/DCM, 4 g column) to give dimer (IIb-03) (2.1 mg, 2.65 μmol, 38.1% yield). LCMS (M+H)=714.0.

Example 12—Dimers (IIa-16) and (IIa-18)

Figure 10:
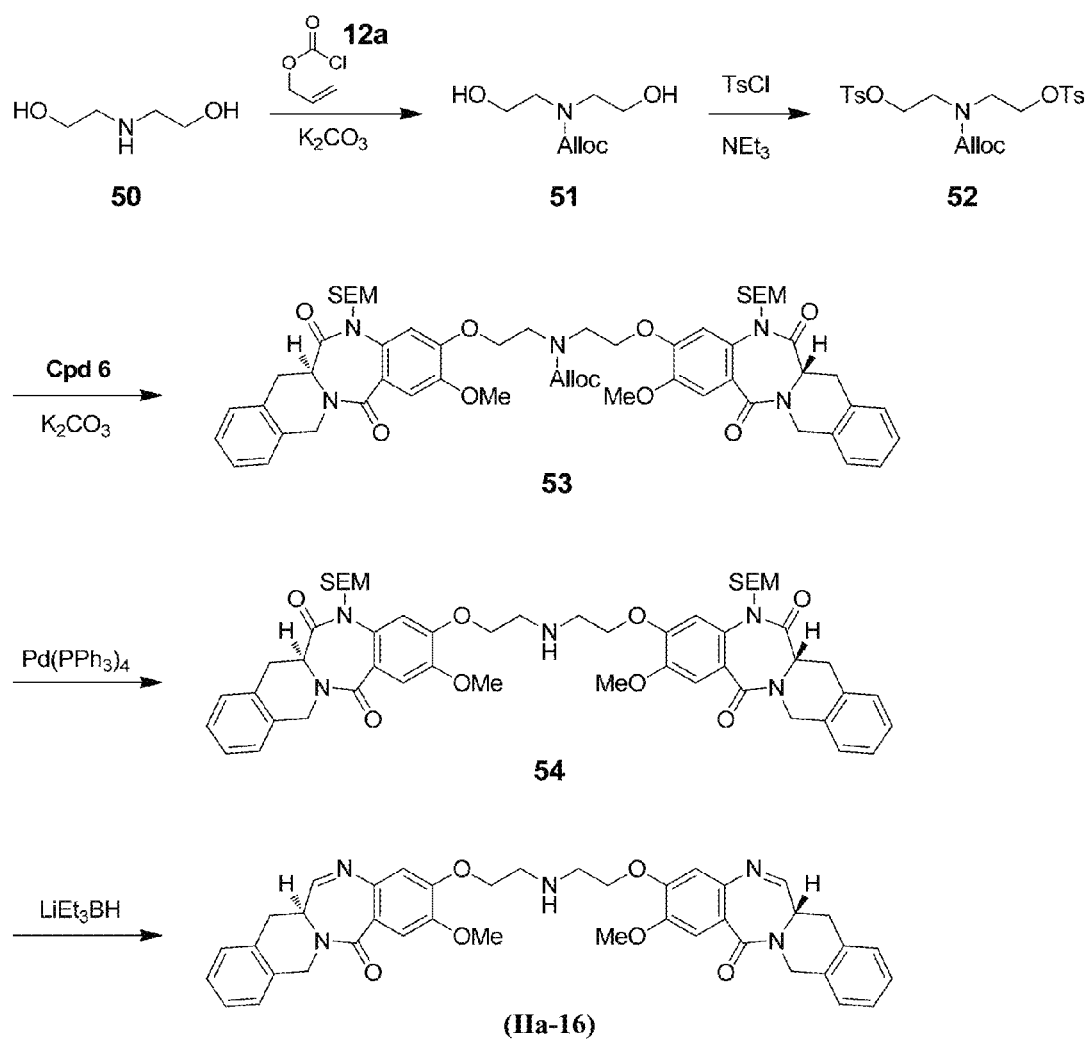
FIGS. 10 and 11 show schemes for the synthesis of dimers of this invention, where the bridge connecting the two dimer halves has an amine group, suitable for attachment of a linker group for the construction of an ADC.
Figure 11:
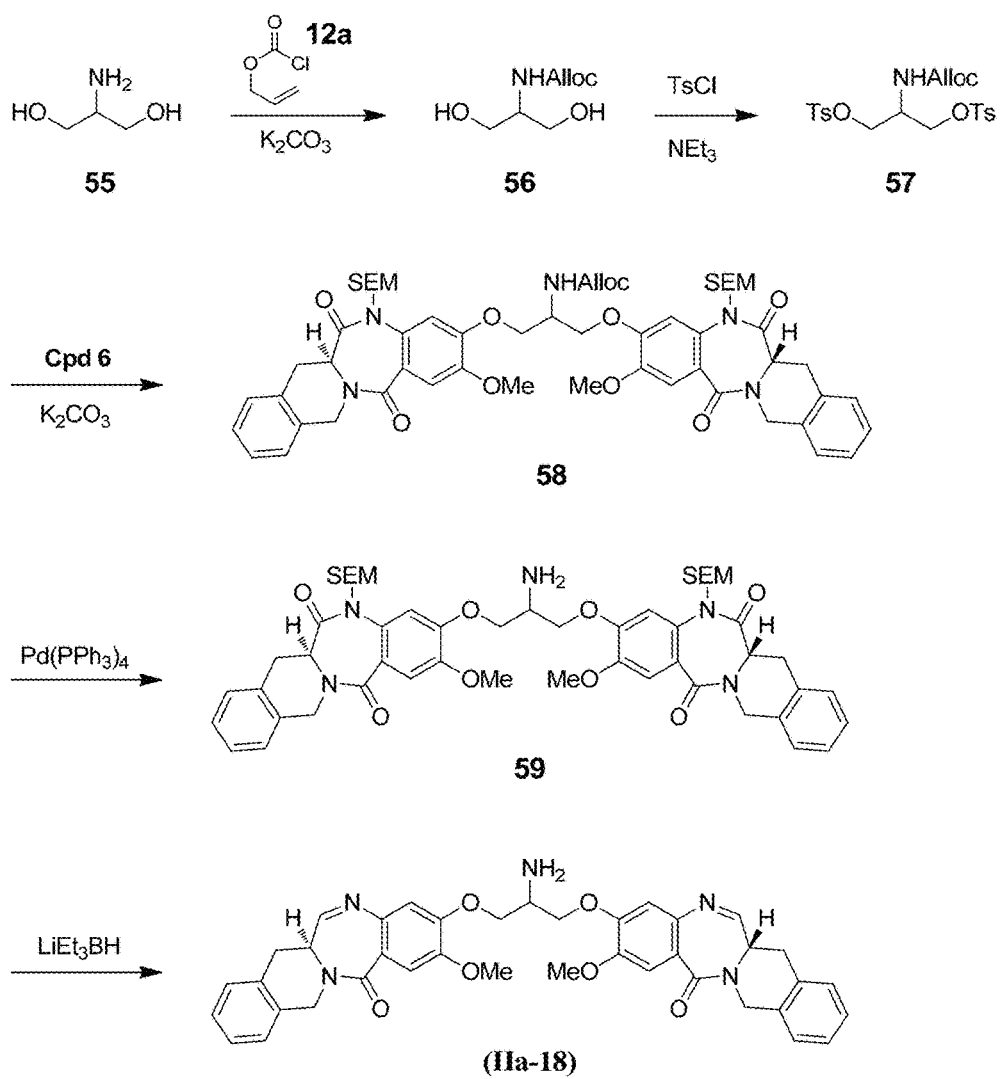

This example and FIGS. 10 and 11 relate to the synthesis of dimers having an amine group in the bridge connecting the two halves of the dimer, such amine group being a suitable functional group for attachment of a linker. (See type (a) dimer-linker compounds, discussed hereinabove.)

The scheme for the synthesis of dimer (IIa-16) ((6aS,6a'S)-3,3'-((azanediylbis(ethane-2,1-diyl))bis(oxy))bis(2-methoxy-6a,7-dihydrobenzo[5,6][1,4]diazepino[1,2-b]isoquinolin-14(12H)-one)) is shown in FIG. 10.

To a suspension of 2,2'-azanediyldiethanol 50 (5 g, 47.6 mmol, Fluka) and K$_2$CO$_3$ (6.57 g, 47.6 mmol) in acetonitrile (50 mL) at 0° C. was added allyl chloroformate 12a (5.07 mL, 47.6 mmol) and stirred at RT for 3 h. LCMS showed formation of product. The reaction mixture was cooled to 0° C., quenched with water (200 mL), and extracted with EtOAc (3×100 mL). The combined organic layers were washed with sat. NaHCO$_3$ (100 mL), water (100 mL), and brine (100 mL). The organic layer was dried over MgSO$_4$ and concentrated to afford carbamate 51 (2.55 g, 13.48 mmol, 28.3% yield) as light yellow oil. $^1$H NMR (400 MHz, CDCl$_3$) δ 5.94 (m, 1H), 5.32 (dd, J=17.6, 1.6 Hz, 1H), 5.24 (dd, J=10.4, 1.2 Hz, 1H), 4.62 (d, J=6.8 Hz, 2H), 3.84 (d, J=12.4 Hz, 2H), 3.52 (s, 2H), 2.86 (s, 2H). LCMS: [M+1] =190.1.

To a solution of carbamate 51 (600 mg, 3.17 mmol) and NEt$_3$ (1.768 mL, 12.68 mmol) in DCM (5 mL) at 0° C. was added TsCl (1814 mg, 9.51 mmol) in DCM (5 mL) and stirred at RT for 1 h. LCMS showed product formation. The reaction solution was concentrated and the crude product was purified on COMBIFLASH™ using 80 g silica column and 0-70% EtOAc/hexane over 25 min. 70% fraction provided compound 52 as a thick oil (54% yield). $^1$H NMR (400 MHz, CDCl$_3$) δ 7.78 (m, 4H), 7.38 (m, 4H), 5.82 (m, 1H), 5.22 (m, 2H), 4.48 (m, 2H), 4.13 (m, 4H), 3.52 (m, 4H), 2.47 (s, 6H). LCMS: [M+Na]=520.1.

A solution of compound 52 (39.8 mg, 0.080 mmol) and compound 6 (80 mg, 0.176 mmol) and K$_2$CO$_3$ (33.2 mg, 0.240 mmol) in DMSO (1.5 mL) was stirred at 50° C. for 19 h. LCMS showed a major peak corresponding to product. The reaction mixture was poured into water containing AcOH (0.027 mL, 0.480 mmol, 30 mL). Saturated brine (10 mL) was added and extracted with EtOAc (3×15 mL). The combined organic layers were concentrated and purified on ISCO COMBIFLASH™ 24 g column using 0-100% EtOAc/hexane over 30 min. 70% EtOAc/hexane fraction provided compound 53 (64% yield). LCMS (m+1)=1062.5.

To a solution of compound 53 (54 mg, 0.051 mmol) in THF (4 mL) was added morpholine (0.022 mL, 0.254 mmol) and Pd(Ph$_3$P)$_4$ (2.94 mg, 2.54 μmol) and stirred under nitrogen atmosphere at RT for 2 h. LCMS showed reaction was complete. The reaction mixture was concentrated and purified on ISCO COMBIFLASH™ 24 g column using 0-8% MeOH/DCM to afford compound 54 as white solid (64% yield). LCMS: (m+1)=978.5.

To a solution of compound 54 (35 mg, 0.036 mmol) in THF (4 mL) was added LiEt$_3$BH (0.179 mL, 0.179 mmol)

at −76° C. The solution was stirred for 1 h. LCMS showed that the reaction was complete. The reaction was quenched with cold water (20 mL) and the reaction mixture was extracted with CHCl$_3$ (3×10 mL). The resulting residue was treated with DCM/EtOH/water (1:2:1=4 mL) and silica gel (1 g) for 4 days. This mixture was filtered through a sintered glass funnel and the silica gel was washed with CHCl$_3$-MeOH (8:2, 100 mL). The filtrate was concentrated under high vacuum and purified on a 24 g silica gel column using MeOH/DCM. 20% MeOH/DCM fraction provided dimer (IIa-16) in 65% yield. LCMS: (m+1)=686.3.

Dimer (IIa-18) was analogously prepared, starting from 2-amino-propanol-1,3-diol 55 and proceeding through compounds 56, 57, 58, and 59.

Compound 56: light yellow oil, $^1$H NMR (400 MHz, CDCl$_3$) δ 5.94 (m, 1H), 5.50 (brs, 1H), 5.29 (m, 2H), 4.60 (d, J=7.2 Hz, 2H), 3.83 (m, 5H). LCMS (m+1)=176.

Compound 57: white solid, 1H NMR (400 MHz, CDCl$_3$) δ 7.78 (m, 4H), 7.38 (m, 4H), 5.88 (m, 1H), 5.25 (m, 2H), 5.02 (brs, 1H), 4.53 (d, J=5.6 Hz, 2H), 4.09 (m, 5H), 2.48 (s, 6H).

Compound 58: MS (m+1)=1048.

Compound 59: LCMS (m+1)=964.46.

Dimer (IIa-18): LCMS (m+1)=672.3.

Example 13—Type (a) Dimer-Linker (IIIa-01)

Figure 12:
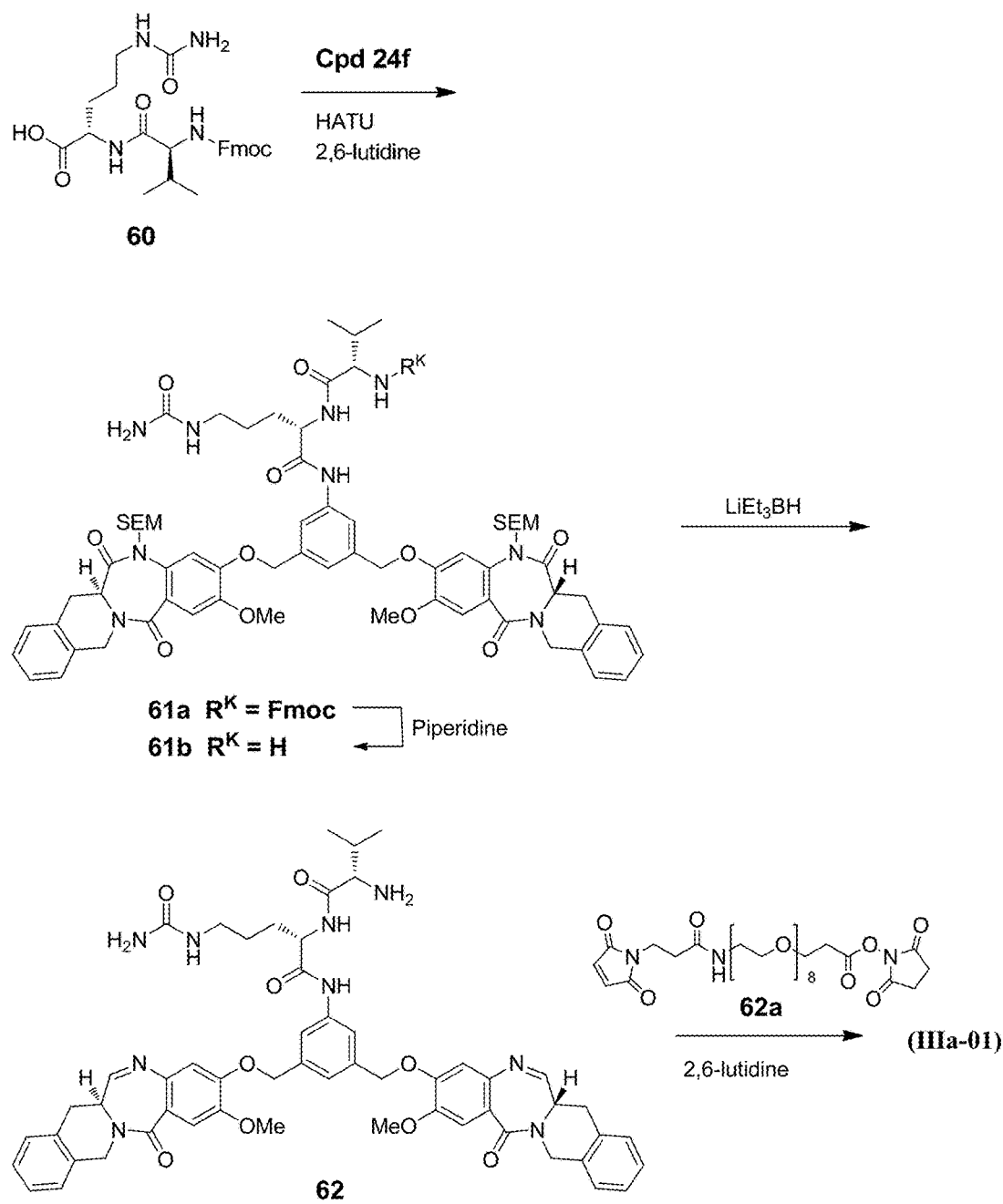
FIGS. 12 and 13 depict schemes for the synthesis of dimer-linker compounds referred to as "type (a)" hereinbelow.

This example and FIG. 12 describe the preparation of type (a) dimer-linker (IIIa-01).

To a 100 mL round-bottom flask was added Fmoc-Val-Cit 60 (Firestone et al., U.S. Pat. No. 6,214,345 B1 (2001), Example 56, 363 mg, 0.731 mmol), HATU (278 mg, 0.731 mmol), and DMF (20 mL). The resulting solution was stirred at 0° C. for 10 min before 2,6-lutidine (0.113 mL, 0.97 mmol) was added. The mixture was added to compound 24f (500 mg, 0.487 mmol). The reaction mixture was slowly warmed to RT and stirred for 5 h. The reaction was then quenched with 10% LiCl solution and extracted with EtOAc (3×). The combined organic layers were washed with 10% LiCl and then brine, before drying over Na$_2$SO$_4$ and concentrating in vacuo. The crude product mixture was purified using ISCO silica gel chromatography (40 g column, gradient from 0% to 10% MeOH/DCM in 15 minutes) to give compound 61a (520 mg, 71% yield). LCMS (M+1)=1504. $^1$H NMR (400 MHz, CHLOROFORM-d) δ 7.83-7.69 (m, 4H), 7.58 (br. s., 2H), 7.45-7.17 (m, 16H), 7.15-6.93 (m, 1H), 5.45 (d, J=10.1 Hz, 2H), 5.24-4.97 (m, 7H), 4.71 (d, J=9.7 Hz, 5H), 4.56-4.02 (m, 8H), 3.87 (s, 6H), 3.79-3.49 (m, 8H), 3.03 (d, J=6.4 Hz, 3H), 1.77 (s, 7H), 1.09-0.82 (m, 11H), 0.10-0.10 (m, 18H).

To a solution of compound 61a (580 mg, 0.385 mmol) in DMF (7.7 mL) was added piperidine (191 µl, 1.927 mmol). The reaction was stirred at RT for 1 h. The crude product mixture was then concentrated and purified using ISCO silica gel chromatography (40 g column, gradient from 0% to 10% MeOH/DCM in 15 minutes) to give compound 61b (318 mg, 64% yield). LCMS (M+1)=1282.

To a −78° C. solution of compound 61b (200 mg, 0.156 mmol) in THF (4 mL) was added a solution of LiEt$_3$BH (0.780 mL, 0.780 mmol) (1M in THF). The reaction was stirred at −78° C. for 2 h. The reaction was quenched with water and extracted with chloroform (2×), then chloroform/MeOH (2×). The combined organic extracts were dried and concentrated. The residue was then taken up in chloroform/EtOH/water (1:1:1, 4 mL) and silica gel (0.7 g) was added. The resulting suspension was stirred at RT for 3 days before it was filtered through a CELITE™ plug, washed with chloroform, and concentrated. The material was taken up in DMF, and purified by reverse phase HPLC to give compound 62 (57 mg, 36.9% yield). LCMS (M+H)=990 $^1$H NMR (400 MHz, CHLOROFORM-d) δ 7.62-7.50 (m, 2H), 7.50-7.25 (m, 12H), 6.88-6.68 (m, 1H), 5.33-4.67 (m, 6H), 4.66-4.29 (m, 3H), 4.02-3.69 (m, 6H), 3.47-2.84 (m, 6H), 2.46-1.74 (m, 2H), 1.59 (br. s., 4H), 1.09-0.74 (m, 6H).

To a solution of compound 62 (23 mg, 0.023 mmol) and compound 62a (available as MAL-dPEG8-NHS® ester from QuantaBio; 32 mg, 0.046 mmol) in DMSO (1.4 mL) was added 2,6-lutidine (5.41 µl, 0.046 mmol). The reaction was stirred at RT for 2 h. The crude product mixture was filtered and purified by reverse phase HPLC (Column: Luna C18 20×100 mm; Mobile Phase A: 10:90 acetonitrile:water with 0.1% TFA; Mobile Phase B: 90:10 acetonitrile:water with 0.1% trifluoroacetic acid; Gradient: 20-70% B over 17 minutes; Flow: 20 mL/min; Detection: UV at 220 nm). The fractions containing product were passed through a PL-HCO3 MP 500 mg cartridge (Agilent). The filtrate was collected by gravity, and the column washed with 4 mL of ACN. The combined filtrates were concentrated and lyophilized to give dimer-linker (IIIa-01) (3 mg, 35.8% yield). LCMS (M+1)=1564.

Example 14—Type (a) Dimer-Linker (IIIa-02)

Figure 13:
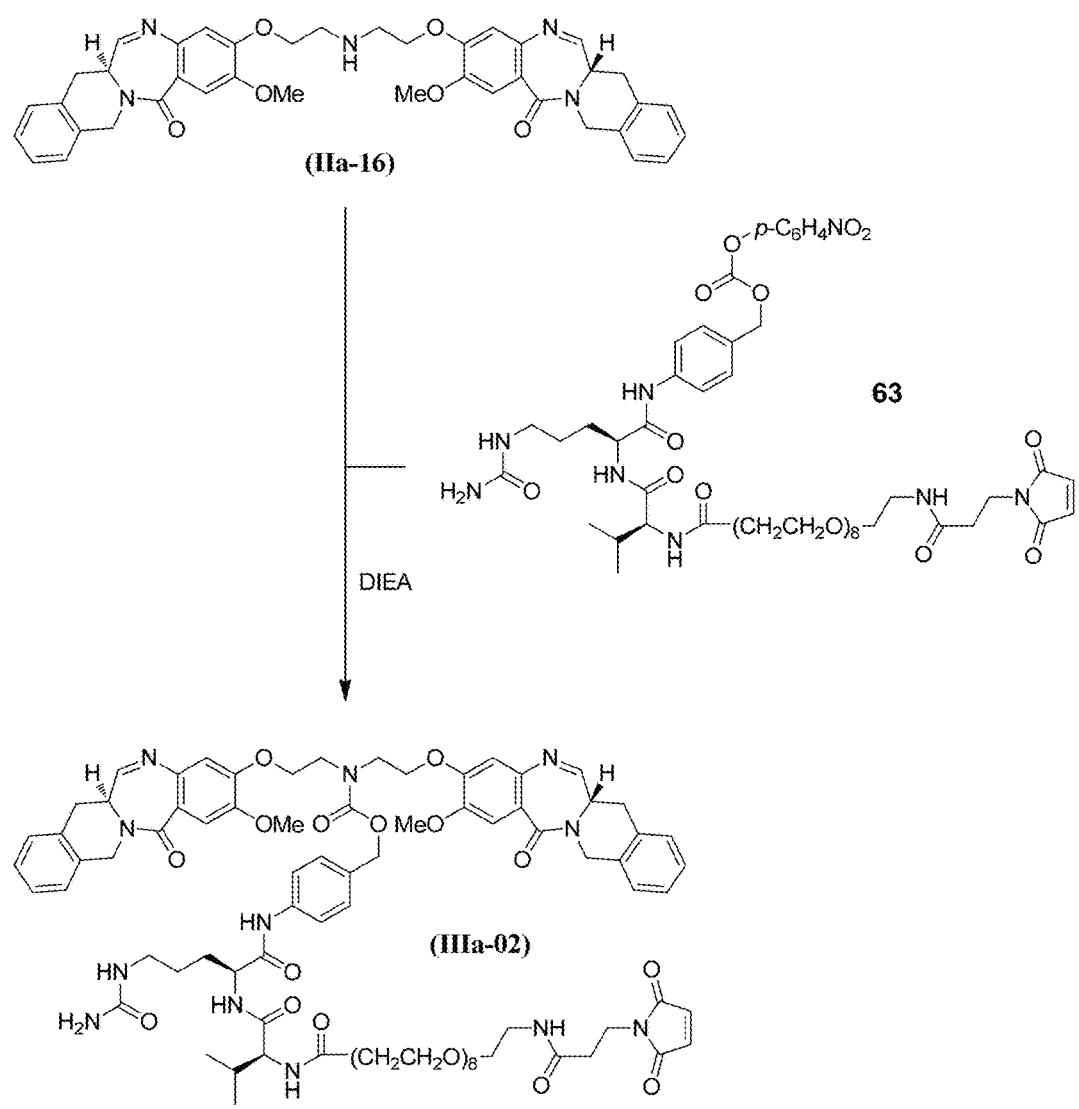

This example and FIG. 13 describe the preparation of type (a) dimer-linker (IIIa-02).

To a solution of carbonate 63 (3.92 mg, 3.50 µmol, preparation described hereinbelow) and dimer (IIa-16) (2 mg, 2.92 µmol) in DMSO (0.2 mL) was added DIEA (1.528 µL, 8.75 µmol). The reaction mixture was stirred at RT overnight. Purification by RHPLC using acetonitrile/water (0.05% formic acid) over 30 min yielded product-containing fractions, which were filtered through a basic resin (PL-HCO$_3$ MP-Resin 1.8 mmol/g; Agilent Part # PL3540-C603) and washed with acetonitrile (5 mL). Lyophilization gave dimer-linker (IIIa-02) as white solid in 52% yield. LCMS (m+1)=1666.

Those skilled in the art will appreciate that the procedures for making type (a) dimer linker compounds in this and the preceding example can be adapted for making other type (a) dimer linker compounds, mutatis mutandis.

Example 15—Type (b) Dimer-Linker Compounds

Figure 14:
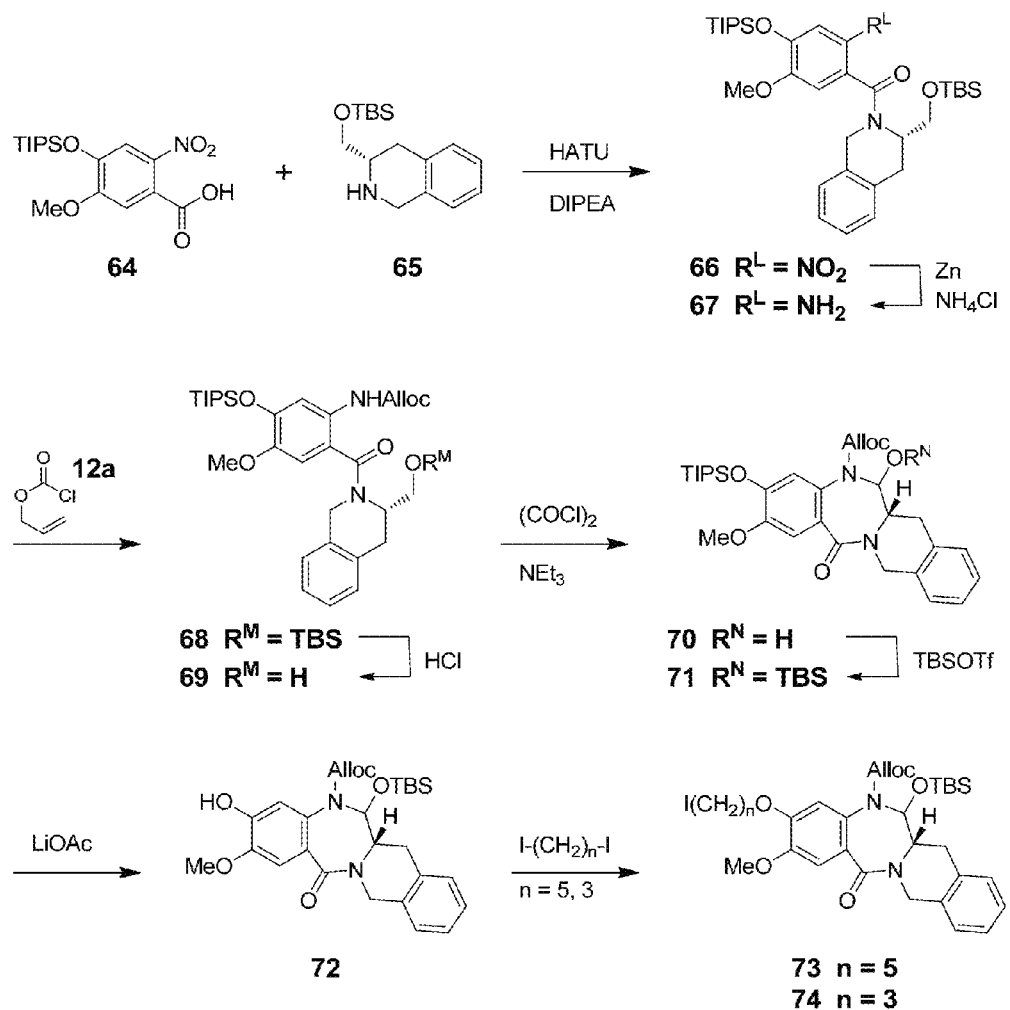
Figure 15:
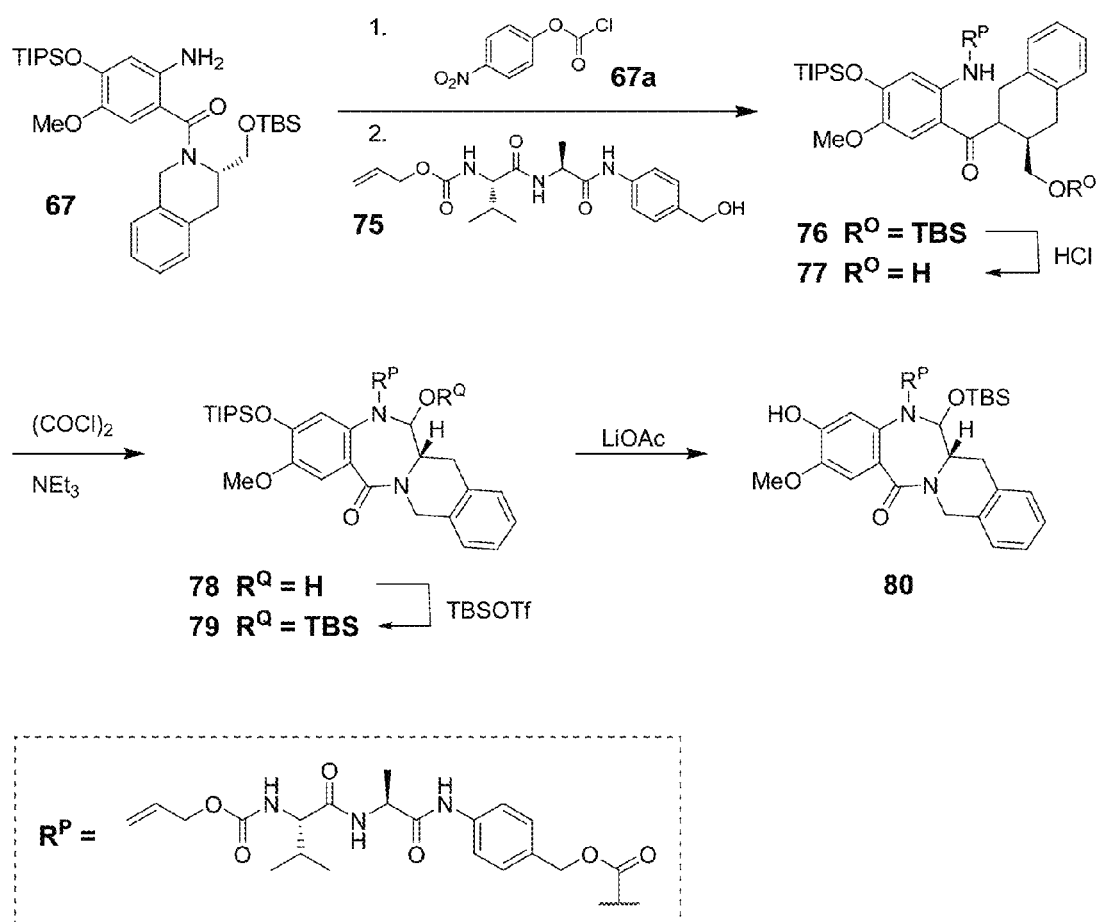
Figure 16:
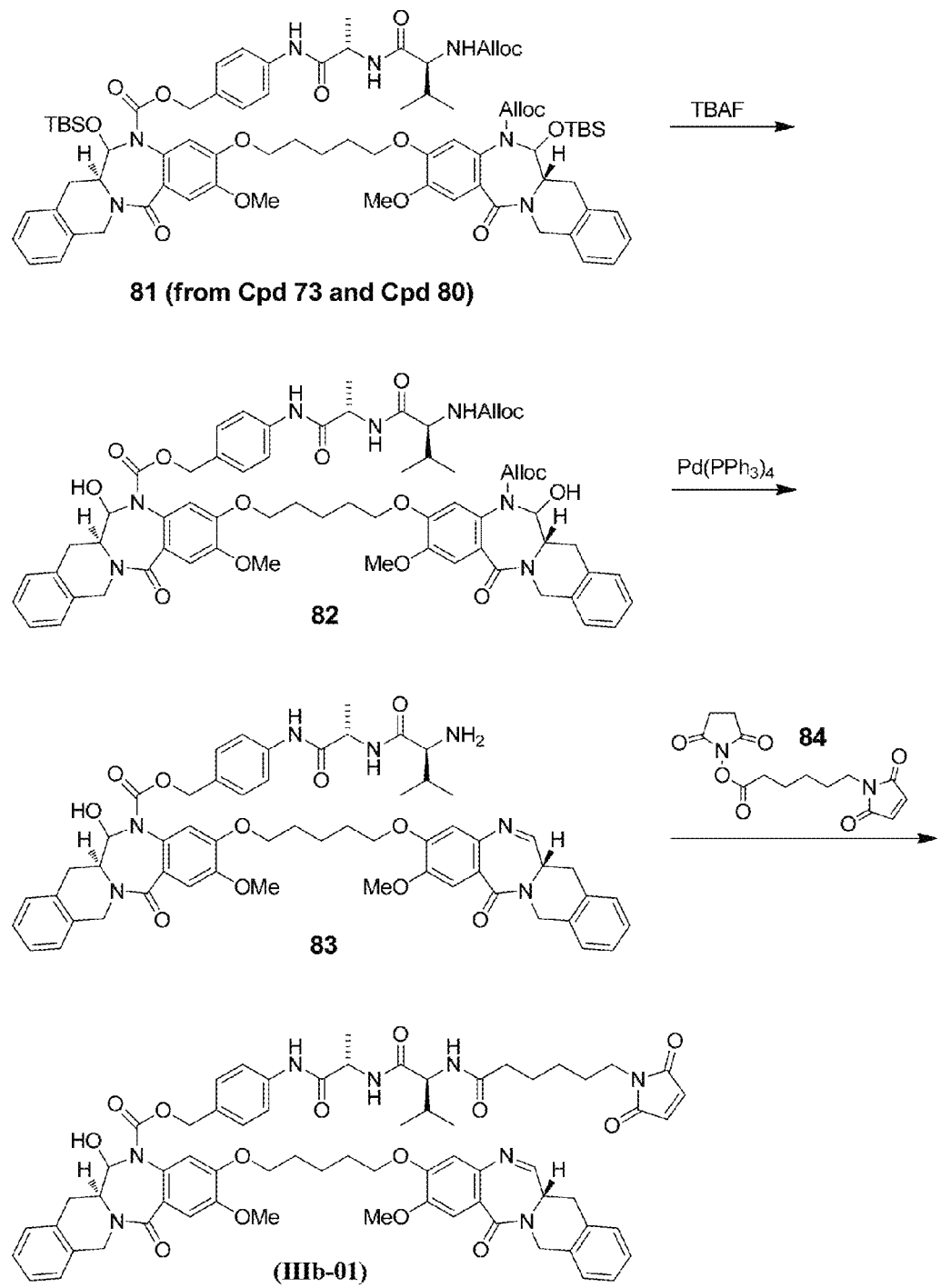
FIG. 16 depicts the synthesis of such a dimer-linker compound from the intermediates so made.

This example and FIGS. 14-16 relate to the preparation of compounds 73 and 74, used in the synthesis of type (b) dimer-linker compounds, and the preparation of such dimer-linker compounds from them.

A flask was charged with 5-methoxy-2-nitro-4-((triisopropylsilyl)oxy)benzoic acid 64 (CAS Reg. No. 1430738-03-6, 9.0 g, 24.36 mmol) and HATU (10.19 g, 26.8 mmol) in DCM (100 mL) at 0° C. The reaction mixture was stirred for 10 min and treated with DIEA (4.68 mL, 26.8 mmol) and isoquinoline 65 (CAS Reg. No. 215928-81-7, 7.43 g, 26.8 mmol). The reaction was maintained at 0° C. for 3 h and then stirred at RT for 24 h. The reaction mixture was poured into saturated NH$_4$Cl and DCM. The organic phase was collected and concentrated to a residue. The residue was further purified by silica gel chromategraphy (Biotage) eluting with 10%-30% EtOAc in hexanes. The product was collected and concentrated to afford amide 66 as a light tan oil (10.15 g, 66% yield). LCMS M+H=629.65.

A solution of amide 66 (10.1 g, 16.06 mmol) in MeOH (200 mL) was cooled to 0° C. and NH$_4$Cl (4.29 g, 80 mmol)

and zinc dust (5.25 g, 80 mmol) were added. The resulting green suspension was stirred at 0° C. for 45 min, then allowed to warm to RT overnight. The reaction mixture was filtered through a CELITE™ pad (washing with MeOH) and the filtrate was concentrated to a residue. The residue was taken up in DCM and loaded onto silica gel pad. This was flushed with 50% EtOAc and hexanes to afford aniline 67 (8.02 g, 83% yield). LCMS M+H=599.35.

Aniline 67 (2500 mg, 4.17 mmol) was dissolved in DCM (50 mL) and pyridine (0.878 mL, 10.85 mmol) was added. The mixture was cooled to −78° C. and allyl chloroformate 12a (0.579 mL, 5.43 mmol) was added. The reaction mixture was maintained at this temperature for 1 h and then allowed to warm to RT. The reaction mixture was poured into saturated NH$_4$Cl and DCM. The mixture was extracted with DCM and purified by silica gel chromatography (Biotage) eluting with 10%-50% EtOAc in hexanes to afford carbamate 68 (2.5 g, 88% yield). LCMS M+H=683.40.

Carbamate 68 (1.372 g, 2.009 mmol) was dissolved in MeOH (20 mL). 10% concentrated HCl in MeOH (2 mL, 6.58 mmol) was added. The mixture was aged for 20 min and quenched with NaHCO$_3$ (0.591 g, 7.03 mmol) in water. The mixture was diluted with water and extracted 4× with DCM. The combined organic phases were dried over Na$_2$SO$_4$, filtered, and evaporated. Purification by silica gel chromatography (Biotage) eluting with 10-50% EtOAc/Hexanes afforded alcohol 69 (963 mg, 84% yield). LCMS M+H=569.25.

Oxalyl chloride (2.0M, 1.450 mL, 2.90 mmol) was dissolved in DCM (30 mL) and then the mixture was cooled to −78° C. in a dry ice/acetone bath. To this was added DMSO (0.515 mL, 7.25 mmol, dissolved in ~2 mL DCM to prevent freezing during addition) and the temperature was maintained at −78° C. After 20 mins, alcohol 69 (1.65 g, 2.90 mmol) dissolved in DCM (10 mL) was added to the reaction. This was allowed to stir for an additional 30 min and followed by addition of NEt$_3$ (2.022 mL, 14.50 mmol). After 10 min the reaction was allowed to warm up to RT. This was quenched with saturated NH$_4$Cl and extracted with DCM (2×). The organic phases were combined, dried over Na$_2$SO$_4$, filtered and concentrated to residue. The residue was purified by silica gel chromatography (Biotage) eluting with 30%-100% EtOAc in hexanes. The product was collected and concentrated to afford aminal 70 as a white solid (1.51 g, 92% yield). LCMS M+H=567.30. $^1$H NMR (400 MHz, chloroform-d) δ 7.39-7.24 (m, 5H), 7.22 (s, 1H), 6.67 (s, 1H), 5.75 (dd, J=11.2, 5.6 Hz, 1H), 5.31 (dd, J=9.5, 4.0 Hz, 1H), 5.22-5.07 (m, 2H), 4.84 (d, J=15.8 Hz, 1H), 4.64-4.49 (m, 2H), 4.44 (d, J=5.3 Hz, 1H), 3.87 (s, 3H), 3.77-3.61 (m, 1H), 3.28-3.01 (m, 3H), 1.34-1.18 (m, 3H), 1.09 (dd, J=7.4, 2.6 Hz, 18H).

Aminal 70 (776 mg, 1.369 mmol) was dissolved in DCM (12 mL) and 2,6-lutidine (0.638 mL, 5.48 mmol) was added. The mixture was cooled on an ice bath and tertbutyldimethylsilyl trifluoromethanesulfonate (TBSOTf, 0.943 mL, 4.11 mmol) was added. The mixture was aged for 30 min, diluted with DCM, quenched with saturated NaHCO$_3$ solution, and extracted 2× with DCM. The combined organic phases were dried over Na$_2$SO$_4$, filtered, and evaporated to dryness. The residue was purified by silica gel chromatography (Biotage) eluting with 10-30% EtOAc/hexanes to afford silyl ether 71 (907.6 mg, 1.333 mmol, 97% yield) $^1$H-NMR showed the purified material was contaminated with ~0.25 equivalents 2,6-lutidine (~4 wt %), but was taken on without any further purification. LCMS M+H=681.25.

Silyl ether 71 (907 mg, 1.332 mmol) was dissolved in DMF (5 mL and water (0.1 ml). Lithium acetate (88 mg, 1.332 mmol) was added and the mixture was aged overnight. Most of the DMF was evaporated under a stream of nitrogen. The residue was diluted with EtOAc, washed 2× with 0.1M citric acid then once with brine. The organic phases were dried over Na$_2$SO$_4$, filtered, and evaporated to dryness. The residue was purified by silica gel chromatography (Biotage) eluting with 30-70% EtOAc/hexanes to afford phenol 72 (707.4 mg, 1.107 mmol, 83% yield) containing some EtOAc by $^1$H-NMR (approx. 1.3 equiv.; yield adjusted to account for EtOAc). LCMS M+H=525.10.

Phenol 72 (290 mg, 0.553 mmol) was dissolved in acetone (2800 μl) and cesium carbonate (180 mg, 0.553 mmol) and 1,5-diiodopentane (400 μL, 2.69 mmol) were added. The vial was sealed and heated to 60° C. overnight. After the reaction was allowed to proceed overnight, the solvent was evaporated, and the residue partitioned between EtOAc and water. The mixture was extracted twice, dried over Na$_2$SO$_4$, filtered, and evaporated to afford a crude residue that was purified by silica gel chromatography (Biotage) eluting with 10-50% EtOAc/hexanes to afford compound 73 (381 mg, 96% yield). LCMS M+H=721.10.

Compound 74 was similarly prepared from phenol 72 using 1,3-diiodopropane.

Turning now to the scheme of FIG. 15: Compound 67 (2.1 g, 3.51 mmol) was dissolved in DCM (30 mL) and pyridine (0.3 mL, 3.71 mmol) was added. The mixture was cooled to 0° C. 4-Nitrophenyl carbonochloridate 67a (0.707 g, 3.51 mmol) was added and the mixture aged for 7 min at the same temperature. A solution of compound 75 (CAS Reg. No. 1343407-91-9, 1.323 g, 3.51 mmol) and DIEA (0.750 mL, 4.29 mmol) in DMF (3 mL) was added. The mixture was placed on a rotary evaporator at RT to remove the DCM. After 20 min, the DMF was evaporated under a stream of nitrogen and then the residue was purified by silica gel chromatography (Biotage) eluting with 10-100% EtOAc in hexanes to afford compound 76 (1.579 g, 1.575 mmol, 44.9% yield). LCMS M+H=1002.50.

A solution of compound 76 (1.579 g, 1.575 mmol) in MeOH (14.4 ml) was treated with 10% concentrated HCl in MeOH (1.6 ml, 5.27 mmol). The mixture was aged 30 min, quenched with saturated NaHCO$_3$, and extracted with chloroform (3×). The combined organic phases were dried over Na$_2$SO$_4$, filtered and evaporated to leave a residue. The residue was combined with another batch of the same reaction (starting with 0.816 g of compound 76) for purification. The combined crude residues were purified by silica gel chromatography (Biotage) eluting with 20-100% EtOAc/Hexanes to afford carbamate 77 (1.7412 g, 1.961 mmol, 82% yield). LCMS M+H=888.30.

A solution of oxalyl chloride (2.0M, 1.00 mL, 2.000 mmol) in 10 mL DCM was cooled to −78° C. A solution of DMSO (0.348 mL, 4.90 mmol) in 5 mL DCM was added dropwise and the mixture aged at the same temperature for 10 min. A solution of carbamate 77 (1741.2 mg, 1.961 mmol) in 5 mL DCM was added dropwise and the mixture was again aged for 15 min. NEt$_3$ (1.366 mL, 9.80 mmol) was added dropwise; the mixture was aged at the same temperature for 5 min and then the cold bath was removed and the mixture was allowed to warm to RT. The mixture was quenched with NH$_4$Cl solution and extracted twice with DCM. The combined organic phases were washed with water and brine, dried over Na$_2$SO$_4$, filtered, and evaporated. The residue was purified by silica gel chromatography (Biotage) eluting with 50-80% EtOAc/Hexanes to afford compound 78 (1376.7 mg, 1.554 mmol, 79% yield). LCMS M+H=886.30.

Compound 78 (1045 mg, 1.179 mmol) was dissolved in DCM (10 ml) and 2,6-lutidine (0.549 ml, 4.72 mmol) was added. The mixture was cooled on an ice bath and TBSOTf (0.813 ml, 3.54 mmol) was added. After 1 h, the mixture was diluted with DCM, washed with saturated $NaHCO_3$ and brine, dried over $Na_2SO_4$, filtered and evaporated. The residue was purified by silica gel chromatography (Biotage) eluting 20-100% EtOAc/Hexanes. Some mixed fractions were obtained, which were repurified by silica gel chromatography (Biotage) eluting with 50% EtOAc/Hexanes (isocratic). The pure fractions were combined to afford compound 79 (676.9 mg, 0.677 mmol, 57.4% yield). LCMS M+H=1000.30.

A solution of compound 79 (676 mg, 0.676 mmol) in DMF (5 mL) and water (0.1 mL) was treated with lithium acetate (44.6 mg, 0.676 mmol). The mixture was aged overnight, and the solvent was evaporated under a stream of nitrogen. The residue was partitioned between EtOAc and 0.1M citric acid. The phases were separated and the organic phases were washed twice with 0.1M citric acid, once with brine and then dried over $Na_2SO_4$, filtered and evaporated. The residue was purified by silica gel chromatography (Biotage) eluting with 50-100% EtOAc/Hexanes to afford compound 80 (543.6 mg, 0.644 mmol, 95% yield). LCMS M+H=844.35.

Turning now to FIG. 16, it shows a scheme by which the previously made intermediate compounds 73 and 80 were used to make dimer-linker (IIIb-01).

A solution of compound 73 (326 mg, 0.452 mmol) and compound 80 (318 mg, 0.377 mmol) in acetone (1884 μl) was treated with cesium carbonate (123 mg, 0.377 mmol). The vial containing the mixture was sealed and warmed at 60° C. After allowing the reaction to procede overnight, the reaction mixture was diluted with EtOAc, washed with 0.1M citric acid and brine, dried over $Na_2SO_4$, filtered, and evaporated to residue. The residue was purified by silica gel chromatography (Biotage) eluting with 50-80% EtOAc/hexanes. This afforded compound 81 (338 mg, 0.235 mmol, 62.4% yield) contaminated with a closely-eluting impurity. The mixture was taken on to the next step without further purification (yield is uncorrected for purity). LCMS M+H=1436.65. HRMS found M+H=1436.6881, calculated=1436.6916. HRMS for closely-eluting impurity M+H=1378.6485.

To a solution of compound 81 (107 mg, 0.074 mmol, impure from the previous step) in THF (2 mL) was added tetrabutyl ammonium fluoride (TBAF, 1.0M, 0.16 mL, 0.160 mmol). The mixture was aged for 10 min, diluted with EtOAc, washed sequentially with water, saturated $NaHCO_3$ and brine and then dried over $Na_2SO_4$, filtered and evaporated. The crude residue was purified by silica gel chromatography (Biotage) eluting with 1-10% MeOH/DCM to afford compound 82 (71 mg, 0.059 mmol, 79% yield), contaminated with a closely eluting impurity (yield uncorrected for purity). LCMS M+Na=1230.25. HRMS found M+H=1208.5170, calculated=1208.5187. HRMS for closely-eluting impurity M+H=1150.4755.

A vial was charged with compound 82 (71 mg, 0.059 mmol, impure from previous step) and a 0.042 M solution of pyrrolidine in DCM (3.50 mL, 0.147 mmol) was added, followed by palladium tetrakistriphenylphosphine (4.07 mg, 3.53 μmol). The mixture was aged for 1 h, diluted with DCM, and washed with saturated $NH_4Cl$. The aqueous portion was re-extracted with DCM, the organic phases were combined, washed with brine, the brine layer was again re-extracted with DCM and the combined organic phases were dried over $Na_2SO_4$, filtered and evaporated. The residue was dissolved in DMF and purified by preparative HPLC over three injections (Sunfire C18 prep OBD column 19×100 mm, Solvent A=95% water, 5% ACN+0.1% TFA, solvent B=55% water, 95% ACN+0.1% TFA; gradient is 0-100% B over 10 min, with a hold to 12 min, fractions collected by UV at 254 nm). The purified fractions were passed through a $PL-HCO_3$-MP SPE 500 mg/6 mL cartridge to afford the product as a free base. The solution of the free base was evaporated to give compound 83 (30 mg, 0.029 mmol, 49.9% yield). LCMS M+H=1022.25.

A vial was charged with compound 83 (18.10 mg, 0.059 mmol) followed by 0.05M DIEA in DMF (0.8 ml, 0.040 mmol). This mixture was allowed to age overnight, and then was diluted with DMF (~0.4 mL) and purified by preparative HPLC (1 injection) (Sunfire C18 prep OBD column 19×100 mm, Solvent A=95% water, 5% ACN+0.1% TFA, solvent B=55% water, 95% ACN+0.1% TFA; gradient is 0-100% B over 10 min, with a hold to 12 min, fractions collected by UV at 254 nm). The purified fractions were passed through a $PL-HCO_3$-MP SPE 500 mg/6 mL cartridge to afford dime-linker (IIIb-01) (19.6 mg, 0.015 mmol, 52.2% yield) as a free base. LCMS M+H=1216. HRMS found M+H=1215.5387, calculated=1215.5397.

Analogously following the procedures described above, additional dimer-linker compounds were prepared:
(a) Compounds 74 and 80 were used to prepare dimer-linker (IIIb-03): LCMS M+H=1187.20. HRMS found M+H=1187.5087, calculated=1187.5084.
(b) Dimer-linkers (IIIb-01) and (IIIb-03) were reduced with sodium cyanoborohydride to yield dimer-linkers (IIIb-05) (LCMS (M+2H)/2=609.55. HRMS found M+H=1217.5561, calculated=1217.5554) and (IIIb-06) (LCMS M+H=1189. HRMS found M+H=1189.5268, calculated=1189.5241), respectively.
(c) Compound 83 was converted to dimer-linker (IIIb-02) by coupling with compound 62a: LCMS (M+2H)/2=799.25. HRMS found M+H=1596.7390, calculated=1596.7396.
(d) Compound 81 was converted to dimer-linker (IIIb-04) by reduction with palladium tetrakistriphenylphosphine and coupling with compound 84: LCMS M+H=1329. HRMS found M+H=1329.6247, calculated=1329.6262.

Those skilled in the art will appreciate that type (b) THIQ-PBD dimer-linker compounds can be made using a PBD equivalent of compound 73 or 74 or compound 80 and otherwise analogously following the procedures described hereinabove.

Example 16—Type (c) Dimer-Linkers

Compound 85, prepared by removal of the Alloc group from compound 39 (Example 10) was coupled with compound 60 and converted to compound 86 by analogously following the procedures described hereinabove.

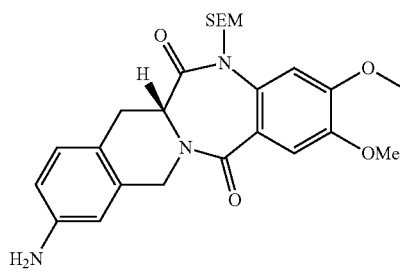

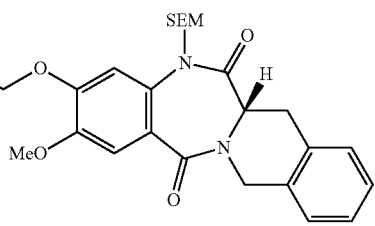

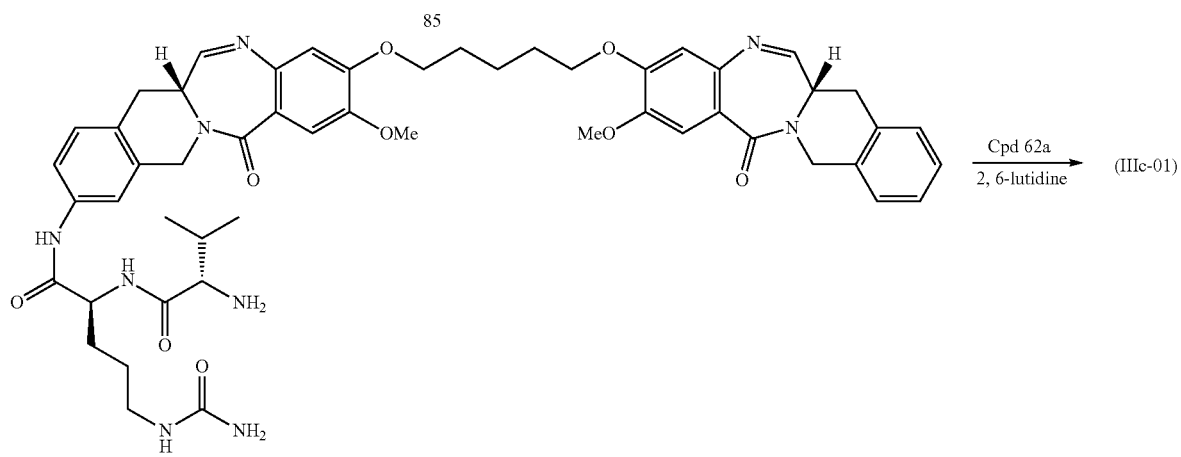

To a solution of compound 86 (9.6 mg, 10.04 μmol) and 2,6-dimethylpyridine (2.152 mg, 0.020 mmol) in DMSO (0.7 mL) was added a solution of MAL-dPEG®8-NHS ester (13.85 mg, 0.020 mmol) in DMSO (100 uL). The reaction was stirred at RT for 1 h. The solution was then diluted with acetonitrile, filtered, and purified using reverse phase HPLC (Column: Luna C18 20×100 mm; Mobile Phase A: 10:90 acetonitrile:water with 0.1% TFA; Mobile Phase B: 90:10 acetonitrile:water with 0.1% TFA; Gradient: 0-70% B over 15 minutes; Flow: 20 mL/min; Detection: UV at 220 nm). The fractions containing product were passed through a PL-HCO₃ MP 500 mg cartridge (Agilent). The filtrate was collected by gravity, and the column washed with 4 mL of ACN. The combined filtrates were concentrated and lyophilized to give the dimer-linker (IIIc-01) (9.4 mg, 5.53 μmol, 55.0% yield). LCMS (M+H)=1530.

Compound 87 (LCMS (M+2H)=435.9) was prepared from compound 85 by analogously following the procedures described hereinabove, mutatis mutandis.

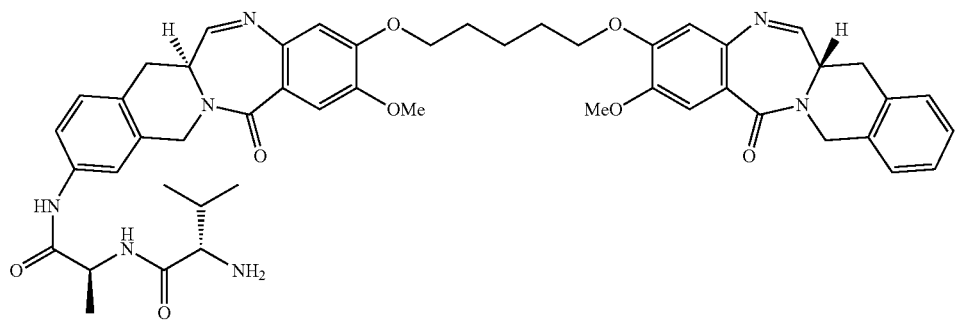

To a solution of compound 87 (5 mg, 5.75 μmol) and 2,5-dioxopyrrolidin-1-yl 6-(2,5-dioxo-2,5-dihydro-1H-pyrrol-1-yl)hexanoate (1.949 mg, 6.32 μmol) in DMSO (0.2 mL) was added 2,6-lutidine (1.339 μl, 0.011 mmol). The reaction was stirred at RT for 4 h. The reaction was then diluted with DMF (1 mL), filtered, and purified using reverse phase HPLC (Column: Luna C18 20×100 mm; Mobile Phase A: 10:90 acetonitrile:water with 0.1% TFA; Mobile Phase B: 90:10 acetonitrile:water with 0.1% TFA; Gradient: 20-80% B over 15 minutes; Flow: 20 mL/min; Detection: UV at 220 nm). The fractions containing product were passed through a PL-HCO₃ MP 500 mg cartridge (Agilent). The filtrate was collected by gravity, and the column washed with 4 mL of acetonitrile. The combined filtrates were concentrated and lyophilized to give dimer linker (IIIc-07) (1.8 mg, 1.524 μmol, 26.5% yield). LCMS (M+H)=1063.4.

Compound 88 was prepared from compound 49 by analogously following the procedures hereinabove. LCMS (M+H)=884.7

MeOH/DCM, 12 g column). Fractions containing the desired product was then concentrated to give a slightly yellow foam, which was taken up in H₂O/THF (2:1, 4 mL) and lyopholized to give dimer-linker (IIIc-08) (9.5 mg, 7.94 μmol, 30.5% yield). LCMS (M+H)=1077.8.

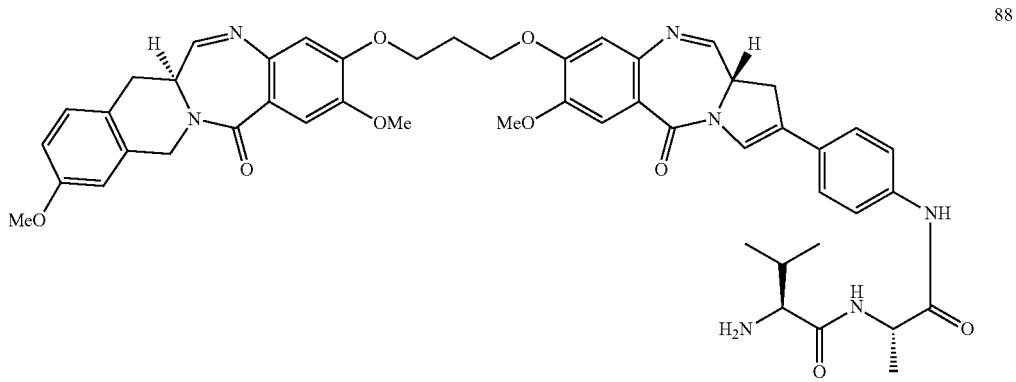 [SMILES: COc1ccc2c(c1)CN1C(=O)c3cc(OC)c(OCCCOc4cc5c(cc4OC)C(=O)N4C=C(c6ccc(NC(=O)[C@H](C)NC(=O)[C@@H](N)C(C)C)cc6)C[C@H]4C=N5)cc3N=C[C@@H]1C2]

88

To a solution of compound 84 (12.03 mg, 0.039 mmol) and compound 88 (23 mg, 0.026 mmol) in DMSO (0.2 mL) was added 2,6-lutidine (6.06 μl, 0.052 mmol). The reaction was stirred at RT for 5 h and then diluted with DCM and purified using ISCO silica gel chromatography (0-15%

Example 17—Type (c) Dimer-Linkers with Self-Immolating Group in the Linker

This example illustrates the preparation of dimer-linker compounds where the linker has a PABC self-immolating group, such as dimer-linker (IIIc-02). The linker moiety is assembled as shown below:

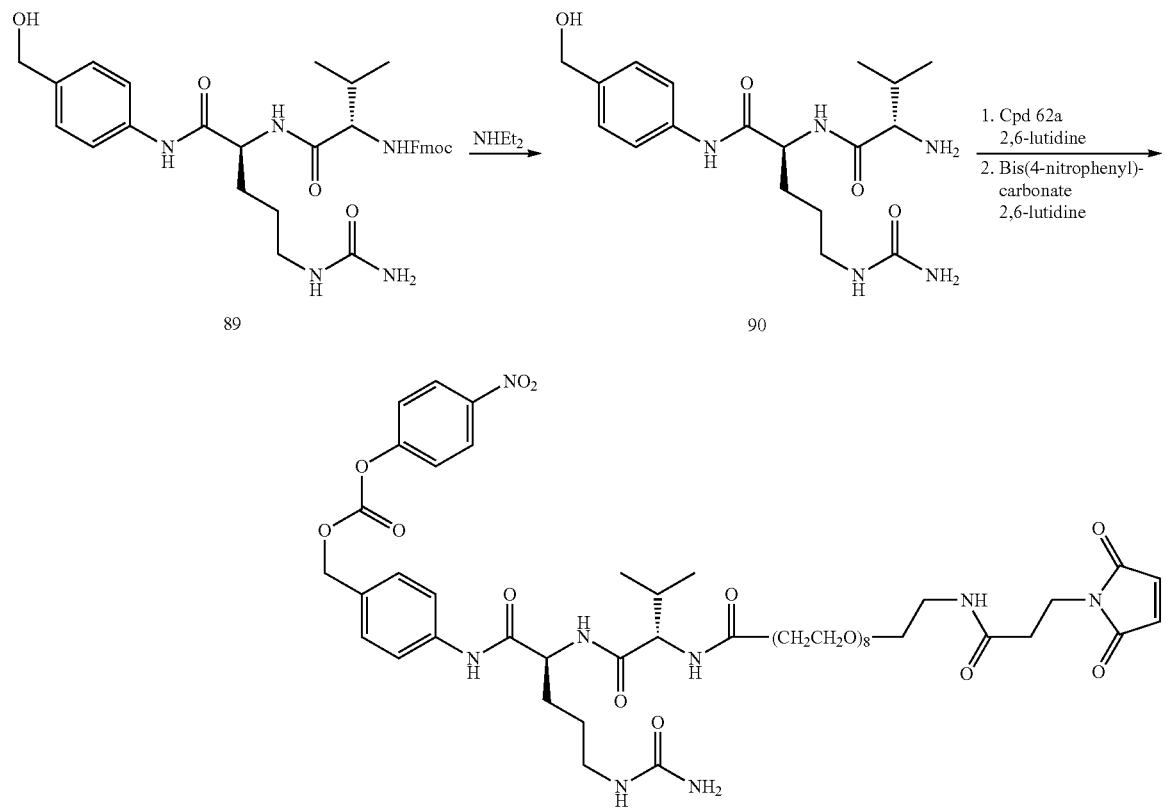

To a solution of compound 89 (Firestone et al. U.S. Pat. No. 6,124,345 B1 (2001), Example 57; 0.75 g, 1.246 mmol) in DMF (2 ml) and THF (8 mL) was added diethylamine (2.81 ml, 26.9 mmol). The reaction was stirred at RT for 1.5 h and concentrate. The crude product was triturated with DCM, filtered and dried under vaccume to give compound 90 as a white solid. LCMS (M+H)=380.2 $^1$H NMR (400 MHz, DMSO-d$_6$) δ 10.06 (s, 1H), 8.15 (d, J=7.3 Hz, 1H), 7.56 (d, J=8.5 Hz, 2H), 7.26 (d, J=8.3 Hz, 2H), 6.00 (t, J=5.4 Hz, 1H), 5.43 (s, 2H), 5.13 (t, J=5.3 Hz, 1H), 4.56-4.33 (m, 3H), 3.07-2.93 (m, 3H), 2.00-1.55 (m, 5H), 1.49-1.32 (m, 2H), 0.90 (d, J=6.8 Hz, 3H), 0.80 (d, J=6.8 Hz, 3H).

To a solution of compound 90 (79 mg, 0.209 mmol) in DMSO (2 mL) was added a solution of MAL-dPEG®8-NHS ester (120 mg, 0.174 mmol) in DMSO (1 mL), followed by 2,6-lutidine (37.3 mg, 0.348 mmol). The reaction was stirred at RT for 3 h. A solution of bis(4-nitrophenyl) carbonate (63.5 mg, 0.209 mmol) in DMF (2 mL) was added, followed by 2,6-lutidine (37.3 mg, 0.348 mmol). The reaction was then stirred at RT for 12 h. DIPEA (0.061 mL, 0.348 mmol) was then added, and the reaction was stirred at RT for 3 h. The crude product mixture was diluted with DMF, filtered, and purified using reverse phase HPLC (Column: Phenomenex Luna C18 20×100 mm; Mobile Phase A: 10:90 acetonitrile:water with 0.1% TFA; Mobile Phase B: 90:10 acetonitrile:water with 0.1% TFA; Gradient: 0-70% B over 15 minutes; Flow: 20 mL/min; Detection: UV at 220 nm) to give compound 63 (40 mg, 0.036 mmol, 20.54% yield). LCMS (M+H)=1119.5.

To compound (IIa-10) (3.5 mg, 5.00 μmol) was added a solution of compound 91 (5.60 mg, 5.00 μmol) in DMSO (0.16 mL), followed by DIPEA (2.62 μL, 0.015 mmol), and HOAt (0.6 mg, 5.00 μmol). The reaction was stirred at RT for 24 h and diluted with DMF, filtered, and purified using reverse phase HPLC (Column: Phenomenex Luna C18 20×100 mm; Mobile Phase A: 10:90 acetonitrile:water with 0.1% TFA; Mobile Phase B: 90:10 acetonitrile:water with 0.1% TFA; Gradient: 20-80% B over 15 minutes; Flow: 20 mL/min; Detection: UV at 220 nm) to give dimer-linker (IIIc-02) (2.1 mg, 1.188 μmol, 23.74% yield) as a white solid. LCMS (M+H)=1679.6.

Analogously following the procedures above, additional dimer-linker compounds having a self-immolating group were prepared:
(IIIc-03) LCMS (M+2H)/2=876.1.
(IIIc-04) LCMS (M+2H)/2=790.5.
(IIIc-05) LCMS (M+H)=1650.9.
(IIIc-06) LCMS (M+H)=1593.9.

Those skilled in the art will appreciate that other dimer-linker compounds, type (c) or otherwise, having PABC self-immolating groups or other can be analogously prepared, mutatis mutandis.

Example 18—THIQ-AZI Dimers

Figure 17:
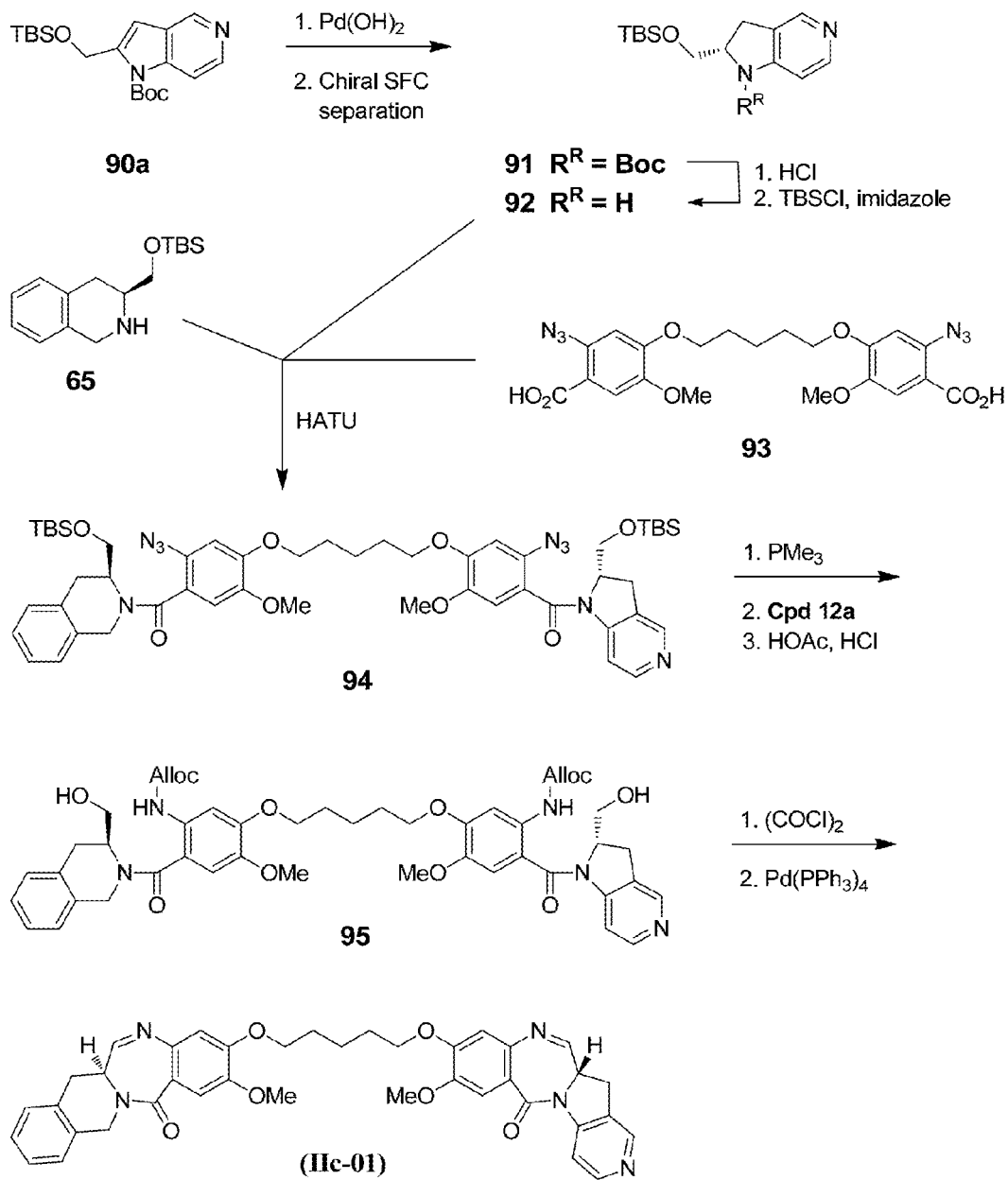
FIG. 17 shows a scheme for the preparation of a dimer of the type referred to as a THIQ-AZI dimer hereinbelow.

This example and FIG. 17 relate to the preparation of THIQ-AZI dimers, in particular dimer (IIc-01).

A Parr bottle was charged with compound 90a (CAS Reg. No. 1210045-50-3, 3.0 g, 8.27 mmol) and palladium hydroxide on carbon (20%, 50% wet; 1.0 g, 0.712 mmol) suspended in ethanol (60 mL) and acetic acid (10 mL). This was placed on the Parr apparatus and charged with 55 psi hydrogen. After shaking overnight, the reaction mixture was filtered through CELITE™ and the filtrate was concentrated to leave a residue. The residue was diluted with EtOAc and washed with saturated NaHCO$_3$. The residue was purified by silica gel chromatography (Biotage) eluting with 20%-50% EtOAC in hexanes to afford the racemic product (2.49 g, 83% yield) as a clear oil. LCMS (M+H)=365.55. $^1$H NMR (400 MHz, CHLOROFORM-d) δ 8.44-8.16 (m, 2H), 7.79-7.42 (m, 1H), 4.48 (br. s., 1H), 3.74 (d, J=6.5 Hz, 2H), 3.36-3.18 (m, 1H), 3.18-3.00 (m, 1H), 1.65-1.49 (m, 9H), 0.75 (s, 9H), 0.11-0.23 (m, 6H). This racemate was further purified by chiral SFC chromatography (Lux Cellulose-2 21.2×250 mm, 5 uM column, eluting with 30% acetonitrile in C02 at 140 bar and 35° C.) to afford two peaks. The second to elute peak ((−) isomer) was collected to afford azaindoline 91 as a colorless oil (1.01 g, 34% yield overall).

A vial was charged with azaindoline 91 (850 mg, 2.332 mmol) in MeOH (4 mL). To this was added 4M HCl in dioxane (8.5 ml, 34.0 mmol). The reaction was stirred at RT overnight. The reaction mixture was concentrated to a residue and then taken up in MeOH and ether. This was concentrated again (2×) to afford the deprotected residue. This residue was charged into a flask along with acetonitrile (1 mL). To this was added tert-butyldimethylsilyl chloride (TBS-Cl, 446 mg, 2.96 mmol) and imidazole (671 mg, 9.86 mmol) and the reaction was stirred at RT for 2 h. The reaction mixture was diluted with DCM and washed with saturated NH$_4$Cl. The organic phase was washed twice and then concentrated to a residue. The residue was purified by silica gel chromatography (Biotage) eluting with 5% (10% NH$_4$OH/MeOH) in chloroform. The product was collected and concentrated to compound 92 as a clear oil. $^1$H NMR (400 MHz, DMSO-d$_6$) δ 8.00-7.84 (m, 2H), 6.77 (br. s., 1H), 6.40 (d, J=5.8 Hz, 1H), 3.95 (dd, J=9.9, 5.1 Hz, 1H), 3.54 (d, J=5.8 Hz, 2H), 3.05 (dd, J=16.2, 9.9 Hz, 1H), 2.77-2.59 (m, 1H), 0.83 (s, 9H), 0.03 (d, J=7.5 Hz, 6H).

A vial was charged with compound 93 (CAS Reg. No. 313644-41-6, 420 mg, 0.863 mmol) in 5 mL DMF. To this was added HATU (821 mg, 2.159 mmol). After aging for 30 min, a solution of compound 65 (252 mg, 0.907 mmol) and compound 92 (240 mg, 0.907 mmol) and DIPEA (0.754 mL, 4.32 mmol) in 2 mL DMF was added. After aging an additional hour, the mixture was transferred to a flask containing ~100 mL water, and the mixture was acidified with 1N HCl. The resultant solids were collected by filtration and washed with water. The wet solids were collected, dissolved in DCM, dried over Na$_2$SO$_4$, filtered, and evaporated. The crude residue was purified by silica gel chromatography (Biotage) eluting with 0-10% MeOH/DCM to afford three products. The middle-eluting peak was heterodimeric amide 94 (353.1 mg, 0.356 mmol, 41.2% yield). LCMS (M+H)=992.30.

Amide 94 (200 mg, 0.202 mmol) was dissolved in THF (2 mL). To this was added water (200 μl, 11.10 mmol) and P(Me)$_3$ (605 μL, 0.605 mmol). After aging ~30 min, the solvent was evaporated and the sample was azeotroped with toluene. The residue was dissolved in DCM (10 mL). Pyridine (0.08 mL, 1.00 mmol) was added and the mixture was cooled to −78° C. Allyl chloroformate 12a (64.5 μL, 0.605 mmol) was added and the mixture was stirred at the same temperature for 30 min and then allowed to warm to RT. The mixture was quenched with NH$_4$Cl, extracted twice with DCM, dried over Na$_2$SO$_4$, filtered and evaporated. The residue was again dissolved in 7:1:1:2 AcOH/THF/MeOH/water (3 mL total) and stirred overnight. Because the deprotection was sluggish, after stirring overnight, 0.5 ml 10% HCl in MeOH was added, resulting in complete deprotection after an additional 30 minutes. The reaction mixture was carefully transferred into saturated NaHCO$_3$ to neutralize it. The mixture was extracted thrice with DCM, dried over Na$_2$SO$_4$, filtered and evaporated. The crude reside was purified by silica gel chromatography (Biotage), eluting with 3-6% (10% NH₄OH/MeOH) in chloroform. The main peak was collected to afford compound 95 (95.7 mg, 0.109 mmol, 54.0% yield). LCMS (M+H)=880.15.

A flask was charged with DMSO (0.018 mL, 0.256 mmol) in 0.5 mL DCM and cooled to −78° C. Oxalyl chloride (0.061 mL, 0.123 mmol) was added dropwise. The reaction mixture was aged 10 minutes at the same temperature, at which point a solution of compound 95 (45 mg, 0.051 mmol) in 0.5 mL DCM was added dropwise. After aging again for 30 minutes, triethylamine (0.071 mL, 0.511 mmol) was added dropwise. After stirring 30 min at −78° C., the coldbath was removed and the reaction mixture was allowed to warm to ambient temperature. The mixture was quenched with saturated NH₄Cl and extracted thrice with DCM. The extracts were washed thrice with NH₄Cl, once with brine, dried over Na₂SO₄, filtered and evaporated. The crude residue was dissolved in DCM (3 mL) and pyrrolidine (0.017 mL, 0.201 mmol) and palladium tetrakis triphenylphosphine (2.90 mg, 2.51 μmol) were added. The mixture was aged for 1 hour, washed with NH₄Cl and then brine, dried over Na₂SO₄, filtered, and evaporated to a residue. The residue was purified by prep-HPLC (sunfire ACN/water 0.1% TFA) with sodium NaHCO₃ solution placed in the tubes before the run to immediately neutralize the samples. The main peak was collected to afford the expected product by evaporating excess solvent and then extracting with DCM. The product was repurified by biotage DCM/MeOH 3-6% step gradient (1% increase each time). The main peak was collected, azeotroped many times with chloroform to remove methanol and afford THIQ-AZI dimer (IIc-01) (7 mg, 8.34 μmol, 16.60% yield). LCMS (M+H)=672.15.

Example 19—Dimer-linker (IIIa-03)

To a solution of compound 96 (Senter et al. 2010; 10 mg, 0.014 mmol) and dimer IIa-16 (13.01 mg, 0.019 mmol) in DMSO (0.5 mL) was added Hunig's Base (7.10 μL, 0.041 mmol) and stirred at RT overnight. This was purified on Shimadzu R-HPLC using XBridge prep C18, 5 m column and 5-55% acetonitrile/water (0.05% formic acid) over 30 min.

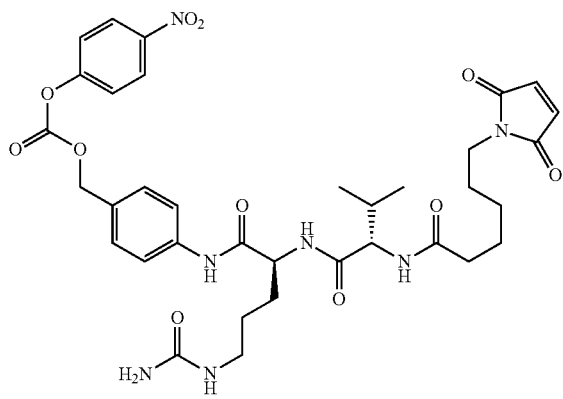

96

A fraction collected at 24 min provided dimer-linker IIIa-03 (5.6 mg, 4.36 μmol, 32.2% yield). The fractions with correct mass were filtered through a basic resin (PL-HCO₃ MP-Resin 1.8 mmol/g; Agilent Part # PL3540-#603) and washed with acetonitrile (5 mL) prior to lyophilization. MS (m+1)=1284.

Example 20—Dimer IIa-20 and Dimer-Linker IIIa-04

Figure 18A:
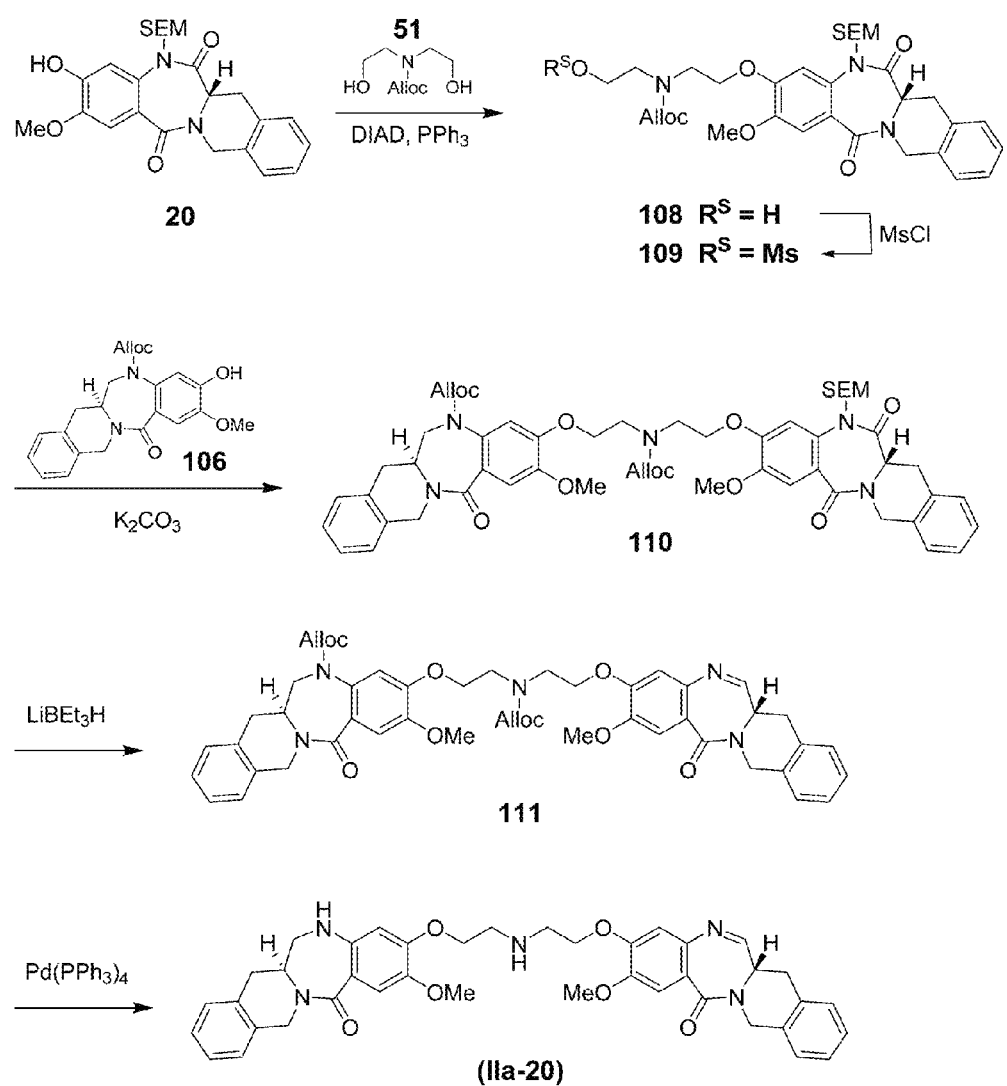
FIGS. 18a and 18b show, in combination, the synthesis of a dimer suitable for making type (a) dimer-linker compounds and a dimer-linker made therefrom.
Figure 18B:
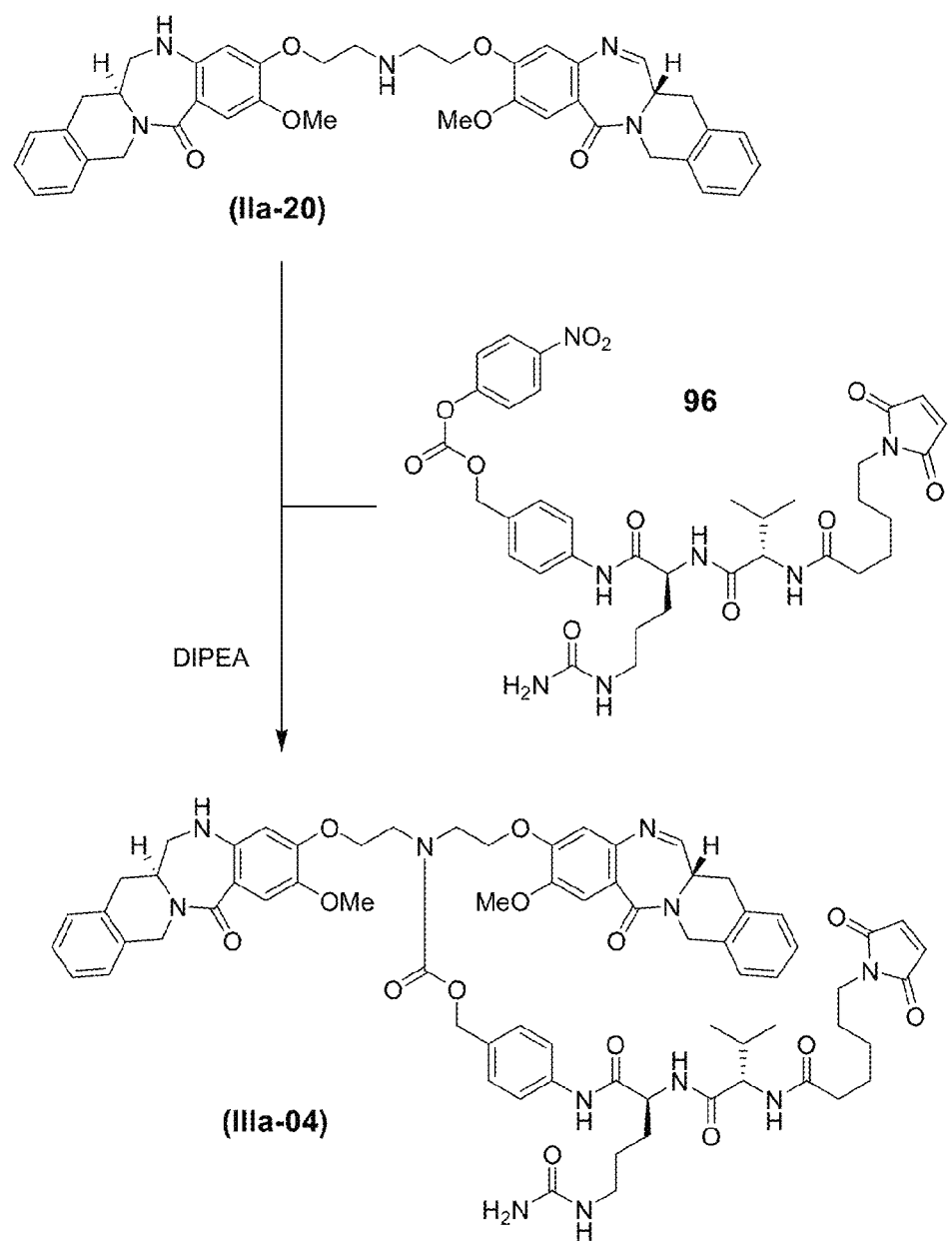

This example and FIGS. 18a and 18b relate to the synthesis of dimer (IIa-20) and dimer-linker (IIIa-04).

To a solution of triphenylphosphine (1.385 g, 5.28 mmol), compound 20 (2 g, 4.40 mmol) and compound 51 (1.165 g, 6.16 mmol) in THF (10 mL) was added diisopropyl azodicarboxylate (DIAD, 1.026 mL, 5.28 mmol) dropwise at 0° C. After stirring at RT overnight. Concentration and purification on an ISCO COMBIFLASH™ 120 g column using 0-100% EtOAc/hexane eluent provided alcohol 108 (1.28 g, 2.045 mmol, 46.5% yield) as white solid. MS (m+Na)=648.2. ¹H NMR (400 MHz, CDCl₃) δ 7.48 (m, 3H), 7.33 (m, 2H), 7.22 (m, 1H), 5.93 (m, 1H), 5.50 (t, J=10.0 Hz, 1H), 5.31 (d, J=16.0 Hz, 1H), 5.22 (dd, J=10.8, 1.6 Hz, 1H), 5.17 (d, J=15.2 Hz, 1H), 4.70 (t, J=11.2 Hz, 1H), 4.63 (m, 2H), 4.43 (m, 1H), 4.30 (m, 2H), 4.22 (m, 1H), 3.97 (m, 1H), 3.90 (s, 3H), 3.79 (m, 4H), 3.57 (m, 4H), 3.01 (dd, J=15.2, 2.0 Hz, 1H), 2.07 (m, 2H), 1.88 (m, 2H), 0.997 (m, 2H), 0.06 (s, 9H).

A suspension of alcohol 108 (0.64 g, 1.023 mmol) and triethylamine (TEA, 0.214 mL, 1.534 mmol) in DCM (10 mL) was cooled to 0° C. and treated with methanesulfonyl chloride (MsCl, 0.104 mL, 1.330 mmol). After stirring for 60 min at 0° C., LCMS showed 50% conversion to product. More TEA (0.214 mL, 1.534 mmol) and MsCl (0.104 mL, 1.330 mmol) was added and stirring was continued for 1 h to get complete conversion. The reaction was quenched with ice cold water (30 mL), extracted with DCM (2×30 mL), and washed with ice cold water (30 ml). The organic layer was dried over MgSO₄ and concentrated in a rotary evaporator to mesylate 109 (0.713 g, 1.012 mmol, 99% yield). MS (m+1)=704.2.

To a solution of compound 106 (336 mg, 0.852 mmol) and mesylate 109 (500 mg, 0.710 mmol) in DMSO (2 mL) was added K₂CO₃ (196 mg, 1.421 mmol). The reaction mixture was stirred at 50° C. overnight. The reaction mixture was diluted with EtOAc (50 mL) and water (50 mL). The aqueous layer was extracted with EtOAc (2×50 mL). The combined organic layers were concentrated and purified on ISCO COMBIFLASH™ 80 g column using 0-100% EtOAc/hexane elution gradient over 45 min provided compound 110 (180 mg, 0.180 mmol, 25.3% yield). MS (m+1)=1003.3

To a solution of compound 110 (180 mg, 0.180 mmol) in THF (4 mL) was added lithium triethylborohydride (SUPER HYDRIDE™, 0.898 mL, 0.898 mmol) at −76° C. The reaction mixture was stirred for 1 h. The reaction was quenched with cold water (1 mL) and extracted with DCM (3×10 mL). The organic layer was concentrated and treated with DCM/EtOH/water (1:2:1=4 mL) and silica gel (1 g) for 2 days. This mixture was filtered through a sintered funnel and the silica gel was washed with DCM-MeOH (8:2, 50 mL). The filtrate was concentrated under high vacuum and purified on 40 g silica gel column using MeOH/DCM eluent over 15 min. The 10% MeOH/DCM fraction at 9 min provided compound 111 (151 mg, 0.143 mmol, 80% yield) as white solid. MS (m+1)=856.3.

To a solution of compound 111 (151 mg, 0.176 mmol) in DCM (3 mL) was added Pd(PPh₃)₄ (10.19 mg, 8.82 μmol) and pyrrolidine (0.058 mL, 0.706 mmol). The reaction mixture was stirred under nitrogen at RT. Concentration and purification on an ISCO 24 g silica gel column using 0-20% MeOH/DCM provided dimer (IIa-20) (42 mg, 0.058 mmol, 32.9% yield) as white solid. MS (m+1)=688.2. ¹H NMR (400 MHz, CDCl₃) δ 7.55 (s, 1H), 7.48 (d, J=5.2 Hz, 1H), 7.41 (s, 1H), 7.25-7.40 (m, 9H), 7.21 (m, 1H), 6.85 (s, 1H), 6.27 (s, 1H), 5.03 (d, J=15.6 Hz, 1H), 4.83 (q, J=15.6 Hz, 2H), 4.57 (d, J=15.2, 1H), 4.30 (m, 2H), 4.21 (t, J=5.2 Hz, 2H), 4.13 (m, 1H), 3.94 (s, 3H), 3.84 (s, 3H), 3.51 (s, 1H), 3.46 (dd, J=10.8, 2.0 Hz, 1H), 3.20-3.30 (m, 6H), 3.12 (dd, J=15.2, 6.0 Hz, 2H), 2.83 (dd, J=15.2, 5.6 Hz, 2H).

To a solution of p-nitrophenyl carbonate 96 (20 mg, 0.027 mmol) and dimer (IIa-20) (22.37 mg, 0.033 mmol) in DMSO (1 mL) was added DIPEA (0.014 mL, 0.081 mmol). The reaction mixture was stirred at RT overnight. The reaction product was purified by R-HPLC using an XBridge prep OBD C18, 5 m column (30×250 mm) and 5-55% acetonitrile/water (0.05% formic acid) over 40 min (4 injections). A fraction collected at 31.8 min was filtered through a basic resin (PL-HCO$_3$ MP-Resin 1.8 mmol/g; Agilent Part #PL3540-#603) and washed with acetonitrile (5 mL). Lyophilization provided dimer-linker (IIIa-04) (8 mg, 5.91 μmol, 21.79% yield) as white solid. MS (m+1)=1286.5.

Example 21—Dimer IIa-21

Figure 19:
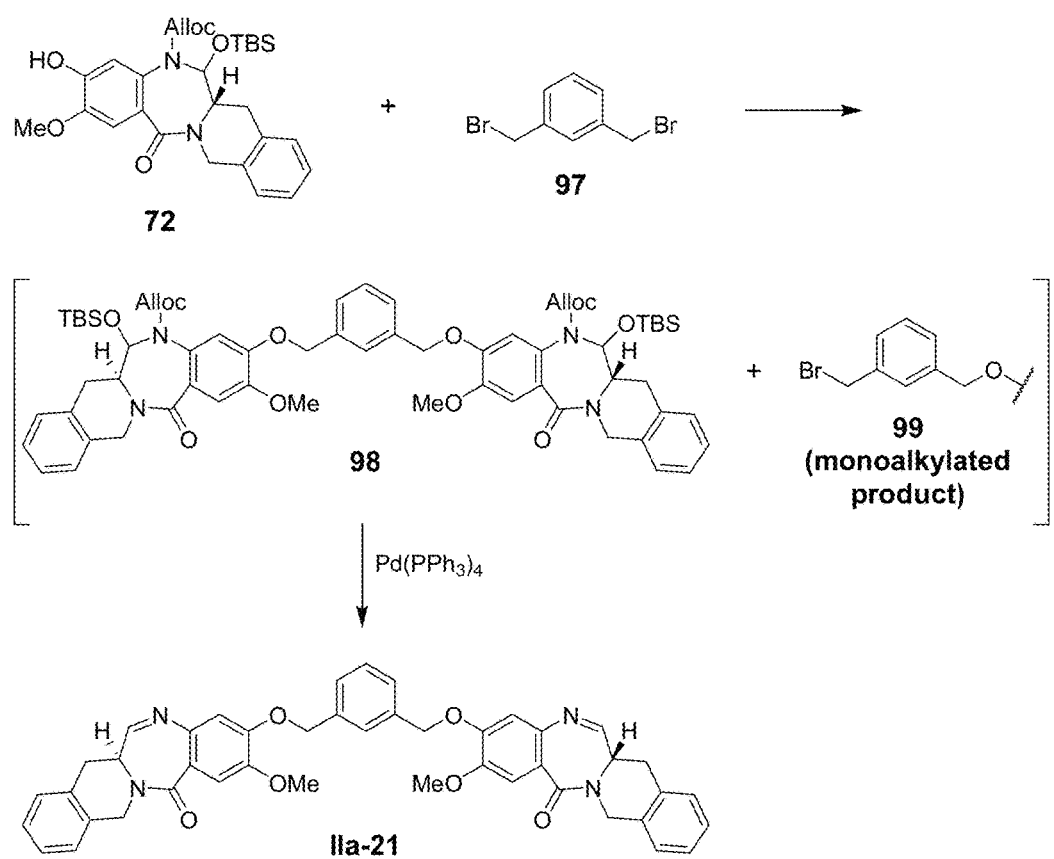
FIGS. 19 and 20 show schemes for the synthesis of additional THIQ-THIQ dimers.

This example and FIG. 19 relate to the synthesis of dimer (IIa-21).

A suspension of phenol 72 (68 mg, 0.13 mmol), 1,3-bis(bromomethyl)benzene 97 (17 mg, 0.065 mmol) and Cs$_2$CO$_3$ (42 mg, 0.13 mmol) in acetone (0.4 ml) was warmed to 40° C. for 1 h. The mixture was quenched with 0.1 M citric acid and extracted thrice with EtOAc. The combined organics were washed with brine and dried over Na$_2$SO$_4$, filtered and evaporated. The mixture was purified by silica gel chromatography, eluting with a gradient from 30-80% EtOAc in hexanes to afford two compounds. The first to elute was monoalkylated compound 99 (15.6 mg, 17% yield). LCMS M+H=707.10. The second to elute was dimer 98 (13.5 mg, 18% yield). LCMS M+H=1151.20.

Dimer 98 (13.5 mg, 0.012 mmol) was dissolved in a solution of pyrrolidine in DCM (0.042 M, 0.7 ml, 0.029 mmol) and Pd(PPh$_3$)$_4$ (2.0 mg, 1.7 μmol) was added. The mixture was stirred for 30 min ands partitioned between DCM and saturated NH$_4$Cl. The phases were separated and the aqueous fraction was extracted twice more with DCM. The combined organics were dried over Na$_2$SO$_4$, filtered and evaporated to a residue, which was then purified by preparative HPLC (Sunfire C18 prep OBD column 19×100 mm, Solvent A=95% water, 5% Acetonitrile+0.1% TFA; Solvent B=5% water, 95% Acetonitrile+0.1% TFA. Gradient of 0-100% over 10 min. The sample was divided into two equal injections. The fractions containing product were combined and passed through a PL-HCO$_3$-MP SPE 500 mg/6 mL cartridge, eluting with acetonitrile to afford a solution of the product as a free base. The bulk of the organic solvent was removed by rotary evaporation and water was removed by lyophilization to afford dimer (IIa-21) as a white powder (5.18 mg, 58% yield). LCMS M+H=719.10. HRMS found: M+H=719.2851, calc'd: 719.2864.

Example 22—Dimer IIa-22

Figure 20:
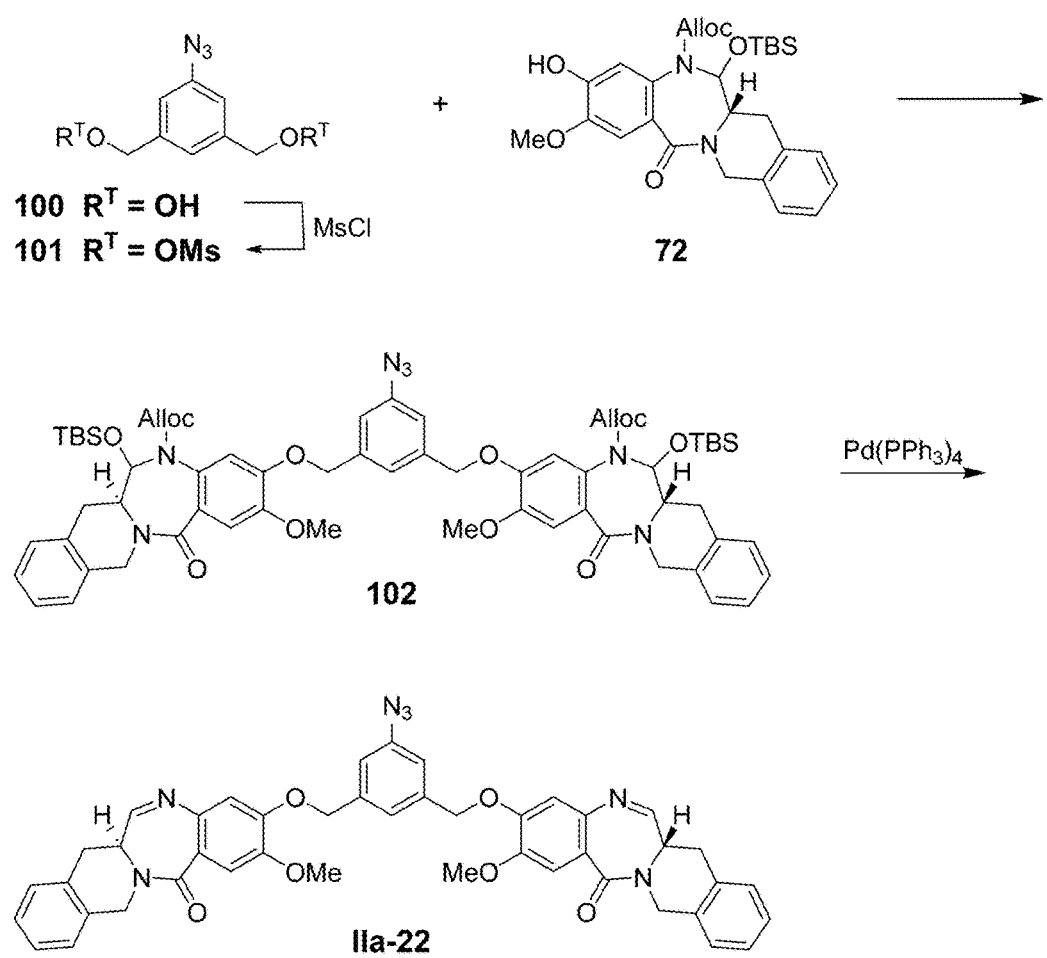

This example and FIG. 20 relate to the preparation of dimer (IIa-22).

A suspension of diol 100 (0.25 g, 1.40 mmol, prepared per J. Med. Chem. 2011, 4350) and NEt$_3$ (0.58 mL, 4.19 mmol) in DCM (5 mL) was cooled on an ice-water bath and treated with MsCl (0.25 mL, 3.2 mmol). The reaction mixture was stirred at the same temperature for 2 h, then quenched by the addition of water. The layers of the biphasic mixture were separated and the aqueous phase was extracted again with a portion of DCM. The combined organic phases were washed with cold dilute HCl (0.05N) followed by brine, and then dried over Na$_2$SO$_4$. Evaporation of the solvent afforded mesylate 101 as a white solid, which was used without further purification (0.425 g, 91% yield)$^1$H NMR (400 MHz, CHLOROFORM-d) δ 7.25 (s, 1H), 7.11 (s, 2H), 5.29-5.18 (m, 4H), 3.05 (s, 6H).

A suspension of phenol 72 (94 mg, 0.18 mmol), mesylate 101 (30 mg, 0.089 mmol) and Cs$_2$CO$_3$ (73 mg, 0.22 mmol) in acetone (0.4 ml) was warmed to 40° C. for 1 h. The mixture was quenched with 0.1 M citric acid and extracted thrice with EtOAc. The combined organic phases were washed with brine and dried over Na$_2$SO$_4$, filtered and evaporated. The mixture was purified by silica gel chromatography, eluting with a gradient from 30-80% EtOAc in hexanes to afford dimer 102 (82.6 mg, 77% yield). LCMS M+H=1192.15.

Dimer 102 (41.3 mg, 0.035 mmol) was deprotected according to the method for dimer (IIa-21) to afford dimer (IIa-22) as as a white powder (7.08 mg, 26% yield). LCMS M+H=760.10. HRMS found: M+H=760.2872, calc'd: 760.2878.

Example 23—Dimer-Linkers IIIb-07 and IIIb-08

Figure 21:
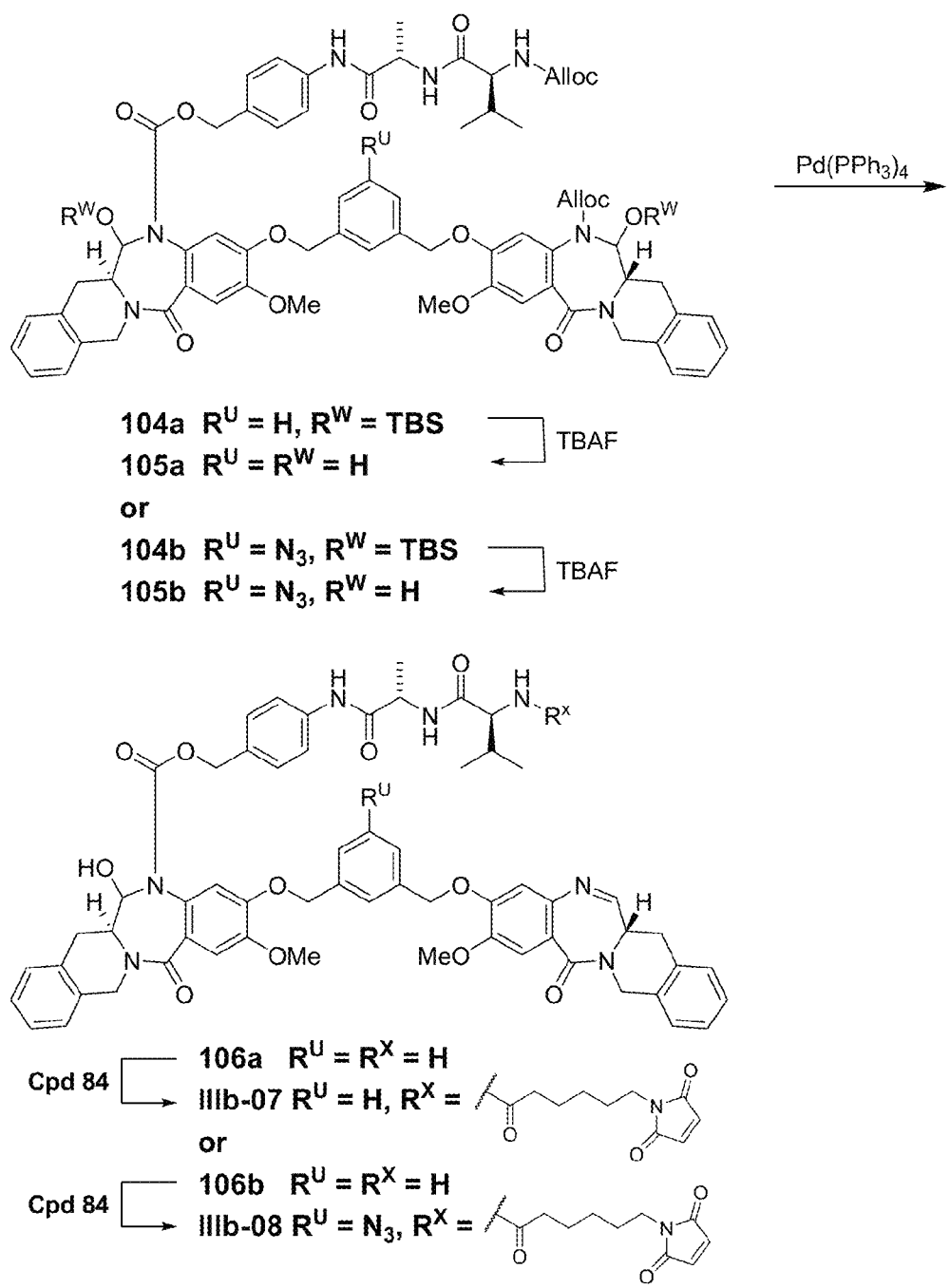
FIGS. 21 and 22 show schemes for the synthesis of additional "type (b)" dimer-linker compounds.

This example and FIG. 21 relate to the preparation of dimer linkers (IIIb-07) and (IIIb-08).

Compound 104a was prepared from phenol 80 and monoalkylated compound 99 as follows. Phenol 80 (18.6 mg, 0.022 mmol), compound 99 (15.6 mg, 0.022 mmol) and Cs$_2$CO$_3$ (7.18 mg, 0.022 mmol) were suspended in acetone (0.11 mL) and warmed to 40° C. for 1.5 h. The mixture was diluted with EtOAc and washed with 0.1M citric acid. The organic phases were dried over Na$_2$SO$_4$, filtered and evaporated to dryness. The crude material was purified by silica gel chromatography, eluting with 30-100% EtOAc in hexanes to afford the product 104a (23.3 mg, 72% yield). LCMS M+H=1472.20.

Dimer 104a (23.3 mg, 0.016 mmol) was dissolved in THF (0.4 mL) and a solution of TBAF in THF (0.035 mL, 1.0 M, 0.035 mmol) was added. The mixture was stirred for 0.5 h, and partitioned between EtOAc and saturated NH$_4$Cl, the phases separated and the aqueous fraction extracted twice more with DCM. The combined organic phases were dried over Na$_2$SO$_4$, filtered and evaporated to a residue, which was then purified by silica gel chromatography, eluting with a gradient from 0-10% MeOH in DCM to afford compound 105a (16.4 mg, 83% yield). LCMS M+Na=1265.25.

Dimer 105a (16.4 mg, 0.013 mmol) was dissolved in a solution of pyrrolidine in DCM (0.042 M, 0.8 ml, 0.033 mmol) and Pd(PPh$_3$)$_4$ (1.2 mg, 1.04 μmol) was added. The mixture was stirred for 1 h, partitioned between DCM and saturated NH$_4$Cl, the phases separated and the aqueous fraction extracted twice more with DCM. The combined organic phases were dried over Na$_2$SO$_4$, filtered and evaporated to a residue to obtain amine 106a, which was used without further purification (quantitative yield assumed).

Amine 106a (13.7 mg, 0.13 mmol) was dissolved in a solution of DIPEA in DMF (0.05 M, 0.31 mL, 0.016 mmol) and compound 84 (8 mg, 0.026 mmol) was added. The mixture was stirred for 20 hours, at which point it was diluted with DMF and purified by preparative HPLC (Sunfire C18 prep OBD column 19×100 mm, Solvent A=95% water, 5% Acetonitrile+0.1% TFA; Solvent B=5% water, 95% Acetonitrile+0.1% TFA. Gradient of 0-100% over 10 min. The fractions containing product were combined and passed through a PL-HCO$_3$-MP SPE 500 mg/6 mL cartridge, eluting with acetonitrile to afford a solution of the product as a free base. The bulk of the organic solvent was removed by rotary evaporation and water was removed by lyophilization to afford dimer-linker (IIIb-07) as a white powder (7.10 mg, 42% yield). LCMS M+H=1249.35. HRMS found: M+H=1249.5221, calc'd: 1249.5241.

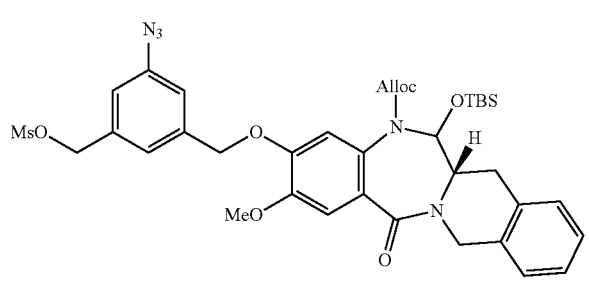

Bis-mesylate 101 (100 mg, 0.191 mmol) was reacted with compound 72, in an manner analogous to that described for the synthesis of compound 99, to afford monomesylate 103 (74.6 mg, 51% yield). LCMS M+H=764.10.

Mono-mesylate 103 (46.8 mg, 0.061 mmol) was reacted with compound 80 in an manner analogous to that described for the synthesis of compound 104a, to afford compound 104b (68.8 mg, 74% yield). LCMS M+H=1511.95.

Compound 104b (68.8 mg, 0.046 mmol) was deprotected in an manner analogous to that described for the synthesis of compound 105a, to afford compound 105b (51.4 mg, 88% yield).

Compound 105b (51.4 mg, 0.040 mmol) was deprotected in an manner analogous to that described for the synthesis of compound 106a, to afford amine 106b (44 mg, 100% yield, used crude in next step).

Amine 106b (46.8 mg, 0.061 mmol) was reacted with compound 84 in an manner analogous to that described for the synthesis of dimer-linker (IIIb-07) to afford dimer-linker (IIIb-08) (13.5 mg, 25% yield). HRMS found: M+H=1290.5245, calc'd: 1290.5255.

Example 24—Dimer-Linker IIIb-04

Figure 22:
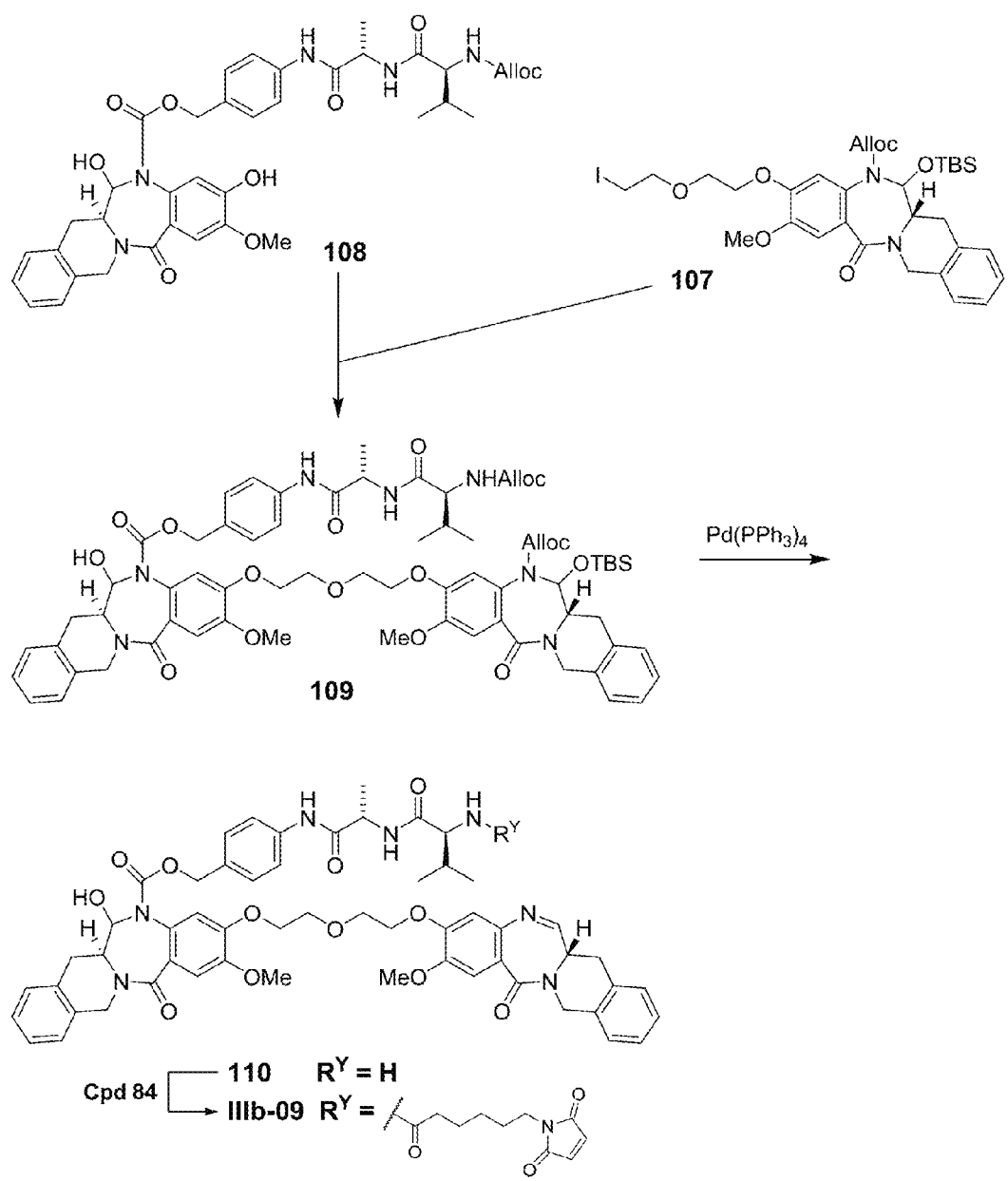

This example and FIG. 22 relate to the synthesis of dimer-linker (IIIb-09).

Bis-iodoethyl ether (46 mg, 0.088 mmol) was reacted with compound 72, in an manner analogous to that described for the synthesis of compound 99, to afford compound 107 (29 mg, 46% yield). LCMS M+H=723.20.

Silyl ether 78 (431 mg, 0.486 mmol) was dissolved in DMF (2.0 ml) and water (0.04 ml) and treated with lithium acetate (32 mg, 0.486 mmol). The mixture was warmed to 40° C. for 2.5 h and stirred at RT an additional hour, then the solvent was removed under a stream of nitrogen (over 3 days). The residue was treated with 0.1 M citric acid and extracted thrice with EtOAc. The combined organic phases were dried over $Na_2SO_4$, filtered and evaporated. The mixture was purified by silica gel chromatography, eluting with a gradient from 0-10% MeOH in DCM to afford phenol 108 (297 mg, 84% yield). LCMS M+H=730.40.

Mono-iodo compound 107 (29 mg, 0.04 mmol) was reacted with phenol 108 in an manner analogous to that described for the synthesis of compound 104a, to afford compound 109 (18.8 mg, 35% yield). LCMS M+Na=1347.15.

Compound 109 (18.8 mg, 0.014 mmol) was deprotected in an manner analogous to that described for the synthesis of compound 106a, to afford amine 110 (13 mg, 100% yield, used crude in next step).

Amine 110 (14 mg, 0.014 mmol) was reacted with compound 84 in an manner analogous to that described for the synthesis of dimer-linker (IIIb-07), to afford dimer-linker (IIIb-09) (8.6 mg, 53% yield). LCMS M+Na=1239.75.

Example 25—Dimer-Linkers IIIa-05, -06, -07, and -08

This example and FIG. 23 relate to the preparation of dimer-linkers IIIa-05, IIIa-06, IIIa-07, and IIIa-08. These dimer-linkers have an alkylamino group in the linker component and can serve as amine donors in a transglutaminase mediated conjugation to make an ADC.

To a solution of compound 54 (850 mg, 0.869 mmol) and compound 111 (CAS Reg. No. 863971-53-3, 666 mg, 0.869 mmol) in NMP (7 mL) was added DIPEA (0.228 mL, 1.303 mmol). The solution was stirred at RT overnight. LCMS showed product formation. The crude reaction was directly subjected to COMBIFLASH™ chromatography on an 120 g silical gel column, eluting with MeOH/DCM over 45 min. The fractions at 18 min provided compound 112 (0.8 g, 57% yield) as white solid. MS (m+1)=1605.6.

To a solution of compound 112 (0.7 g, 0.436 mmol) in THF (5 mL) was added piperidine (0.5 ml, 5.05 mmol). The solution was stirred at RT for 30 min. LCMS showed the reaction was complete. Concentration and purification on an 80 g COMBIFLASH™ silica gel column using MeOH/DCM over 40 min afforded a 30% MeOH/DCM fraction at 19-23 min, which yielded compound 113 (0.475 g, 0.343 mmol, 79% yield) as white solid. MS (m+1)=1383.6. $^1$H NMR (400 MHz, DMSO-$d_6$) δ 10.11 (s, 2H), 8.13 (s, 2H), 7.57 (d, J=8.4 Hz, 2H), 7.23 (m, 14H), 5.96 (t, J=5.6 Hz, 2H), 5.76 (s, 1H). 5.39 (s, 4H), 5.26 (t, J=6.0 Hz, 4H), 5.08 (dd, J=22.0, 10.4 Hz, 4H), 5.01 (s, 2H), 4.92 (d, J=15.6 Hz, 4H), 4.47 (m, 2H), 4.31 (m, 5H), 4.21 (m, 5H), 4.10 (q, J=5.2 Hz, 2H), 3.76 (m, 10H), 3.18 (d, J=5.2 Hz, 2H), 3.03 (m, 6H), 2.68 (m, 2H), 2.34 (m, 2H), 1.93 (m, 3H), 1.50-1.70 (m, 6H), 1.39 (m, 5H), 0.88 (d, J=6.8 Hz, 3H), 0.78 (d, J=6.8 Hz, 3H), 0.74 (m, 9H), 0.09, 0.10 (m, 9H).

To a solution of compound 113 (975 mg, 0.705 mmol) in THF (10 mL) at −76° C. was added $LiEt_3BH$ (SUPERHYDRIDE™, 3.52 mL, 3.52 mmol). The solution was stirred for 1 h. LCMS showed the reaction was complete. The reaction was quenched with cold water (1 mL) and concentrated. The resulting residue was treated with DCM/EtOH/water (1:2:1=8 mL) and silica gel (1 g) for 3 days. This mixture was filtered through a sintered funnel and the silica gel was washed with DCM-MeOH (8:2, 100 mL). The filtrate was concentrated under high vacuum and purified on a 24 g silica gel column using MeOH/DCM over 15 min. The 20% MeOH/DCM fraction provided compound 114 (422 mg, 0.387 mmol, 54.9% yield) as white solid. MS (m+1)=1091.6.

To a solution of compound 114 (67 mg, 0.061 mmol) and N-hydroxysuccinimide ester 115 (30.4 mg, 0.068 mmol) in DMF (1 mL) was added 2,6-lutidine (0.014 mL, 0.123 mmol). The reaction mixture was stirred at RT for 2 h. LCMS showed almost complete conversion to product 116. Piperidine (0.1 mL, 1.010 mmol) was added and the reaction mixture was stirred at RT for 1 h. The reaction mixture was injected onto an ISCO 150 g C18 column and eluted with water/acetonitrile (0.05% formic acid) over 30 min. The 34% water/acetonitrile fraction at 27 min was filtered through a basic resin (PL-HCO$_3$ MP-Resin 1.8 mmol/g; Agilent Part # PL3540-#603) and washed with acetonitrile (5 mL). Lyophilization provided dimer-linker IIIa-08 (27.5 mg, 0.020 mmol, 33.1% yield) as a white solid. MS (m+1)=1204.6.

Dimer-linkers IIIa-05 (MS (m+1)=1338.5), IIIa-06 (MS (m+1)=1514.06), and IIIa-07 (MS (m+1)=1250.2) were analogously prepared from compound 114, using the corresponding N-hydroxysuccinimide esters.

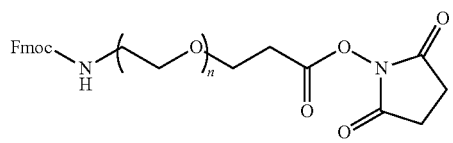

CAS Reg. No. 1807534-85-5, n=2
CAS Reg. No. 1314378-14-7, n=4
CAS Reg. No. 1334170-03-4, n=8

Example 26—Biological Activity of Dimers

The cytotoxic activity of dimers of this invention was tested against H226 lung cancer, 786-O renal cancer, N87 gastric cancer, and/or OVCAR3 ovarian cancer cell lines. The ability of dimers to inhibit cell proliferation can be measured by either an ATP luminescence assay or an MTS cell proliferation assay. Generally, these two methods yield comparable results.

This is a general procedure for an ATP luminescence assay: Cells are seeded at 1×103 cells/well in 96-well plates for 3 h for ATP CellTiterGlo™ assays, respectively. Serial dilutions (1:3) of compounds are added to the wells. Plates are allowed to incubate for 72 h. A CellTiterGlo™ cell viability kit from Promega is used to measure ATP content of cells treated with test compounds following manufacturer's instruction. A decrease in the ATP content is a measure of decrease in cellular viability. The EC$_{50}$ value—the concentration at which an agent reduces cell viability by 50% of the maximum effect—can be calculated using PRISM™ software, version 5.0 (GraphPad Software, La Jolla, Calif., USA).

The MTS cell proliferation assay was performed as follows: CellTiter 96 Aqueous Non-Radioactive Cell proliferation Kit from Promega (Madison, Wis.) is used to determine the number of viable cells in cell proliferation assay. Tumor cells are plated at certain seeding densities in sterile 384-well black clear bottom Matrix plates at 40 µL per well and incubated overnight at 37° C. in 5% CO$_2$ before assaying. On the next day, one set of cell plates (10 plates) is used to determine time zero cell density, and 3-(4,5-dimethylthiazol-2-yl)-5-(3-carboxymethoxyphenyl)-2-(4-sulfophenyl)-2H-tetrazolium is added at 4 µL/well into 10 plates followed by incubation at 37° C. in 5% CO$_2$ for three hours. This tetrazolium reagent is bioreduced by liver cells to form a formazan product which is soluble in aqueous solution. Absorbance at 490 nm is measured on an Envision reader (Perkin Elmer, Boston, Mass.). On the same day, compounds are added into remaining cell plates (T72 plates) and incubated at 37° C. in 5% CO$_2$. After 72 hours, 4 L MTS reagents are then added into those cell plates. The plates are further incubated at 37° C. in 5% CO$_2$ for three hours and the absorbance values at A490 were measured on an Envision reader.

Results are presented in Table IA:

TABLE IA

Biologic Activity of Dimers

| Dimer | Cancer Cell Line: EC$_{50}$ (pM) | | |
|---|---|---|---|
| | H226 | N87 | OVCAR3 |
| IIa-01 | — | 16 | 150 |
| IIa-02 | 46-180 | 49-150 | 77-120 |
| IIa-03 | 410 | 460 | 180 |
| IIa-04 | 8000 | 5700 | 2600 |
| IIa-05 | 150 | 150 | 90 |
| IIa-10 | 20 | 30 | 20 |
| IIa-16 | 188 | — | — |
| IIa-18 | 3200 | — | — |
| IIa-20 | — | 1.3 | — |
| IIa-21 | — | 0.02 | — |
| IIa-22 | — | 0.05 | — |
| IIb-01 | 440 | 330 | 220 |
| IIb-03 | 150 | 110 | 330 |
| IIc-01 | — | 0.28 | — |

Additional results, testing against DMS 79 and H187 small-cell lung cancer cell lines, are presented in Table IB.

TABLE IB

Biologic Activity of Dimers

| Dimer | Cancer Cell Line: IC$_{50}$ (nM) | |
|---|---|---|
| | DMS 79 | H187 |
| IIb-03 | 0.003 | 0.002 |
| IIa-16 | 0.006 | 0.005 |

Example 27—Biological Activity of Conjugates

Dimer-linker compounds were conjugated to several antibodies, following the general procedure described hereinabove: antibody 4A6 (anti-glypican 3 antibody; Terrett et al., U.S. Pat. No. 8,680,247 B2 (2014)); antibody 1F4 (anti-CD70 antibody; Coccia et al., US 2010/0150950 A1 (2010)); and antibody 6A4 (anti-mesothelin antibody; Terrett et al., U.S. Pat. No. 8,268,970 B2 (2012)). The CDR sequences and other sequence and structural information of these antibodies is disclosed in the aforecited references and such information is incorporated herein by reference.

Tests were conducted against N87 gastric cancer cells and Hep 3B liver cancer cells. Activity was measured using a $^3$H thymidine assay (Cong et al. 2014). N87 cells express mesothelin but not CD70 or glypican-3. Hep 3B cells express glypican-3 but not mesothelin.

Results are provided in Table IIA and IIB. Comparative data is also provided for conjugates of a PBD-PBD dimer-linker, compound A:

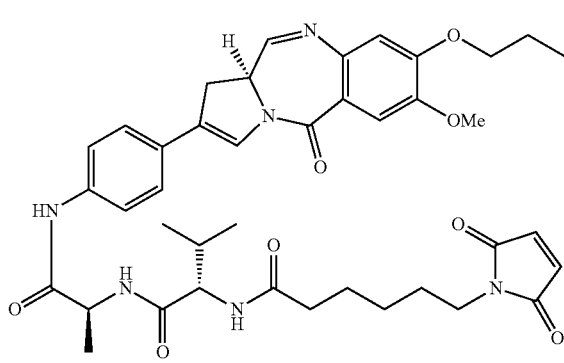
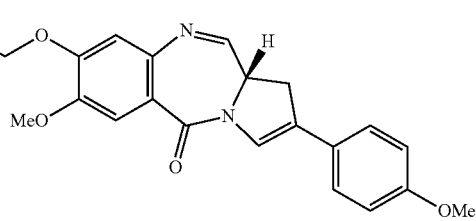

A

TABLE IIA

Biologic Activity of Conjugates

| | Conjugate | | | Cell Line IC$_{50}$ (pM) | |
|---|---|---|---|---|---|
| Ref. | Antibody (antigen) | Dimer-linker | DAR | N87 | Hep3B |
| 1 | 6A4 (mesothelin) | IIIa-01 | 0.9-1.6 | 3-11 | — |
| 2 | 6A4 (mesothelin) | IIIb-01 | 1.9-2.6 | 46-57 | 1,400 |
| 3 | 6A4 (mesothelin) | IIIb-03 | 1 | 1,300 | — |
| 4 | 6A4 (mesothelin) | IIIc-01 | 1.1-1.2 | 2-9 | — |
| 5 | 6A4 (mesothelin) | IIIc-08 | 2.9 | 130 | — |
| 6 | 6A4 (mesothelin) | A | 1 | 30 | — |
| 7 | 4A6 (glypican 3) | IIIb-01 | 2.7 | 14,000 | 28 |
| 8 | 1F4 (CD70) | IIIa-01 | 0.6-1.5 | 2,900-3,400 | — |
| 9 | 1F4 (CD70) | IIIb-01 | 2 | 5,600 | — |
| 10 | 1F4 (CD70) | IIIb-03 | 1 | 6,700 | — |
| 11 | 1F4 (CD70) | IIIc-01 | 0.83-1.1 | 1,200 | — |
| 12 | 1F4 (CD70) | IIIc-08 | 2.3 | 1,200 | — |
| 13 | 1F4 (CD70) | A | 1.1 | 2,300 | — |

TABLE IIB

Biologic Activity of Conjugates

| | Conjugate | | | Cell Line IC$_{50}$ (nM) | |
|---|---|---|---|---|---|
| Ref. | Antibody (antigen) | Dimer-linker | DAR | N87 | 786-O |
| 14 | Anti-mesothelin | IIIa-01 | — | 0.01 | — |
| 15 | Ant-CD70 | IIIa-01 | — | — | 0.02 |
| 16 | Anti-mesothelin | IIIa-03 | — | 0.07 | — |
| 17 | Anti-mesothelin | IIIb-01 | — | 0.06 | — |
| 18 | Anti-CD70 | IIIb-01 | — | — | 0.05 |
| 19 | Anti-mesothelin | IIIb-02 | — | 0.1 | — |
| 20 | Anti-mesothelin | IIIb-03 | — | 1.23 | — |
| 21 | Anti-CD70 | IIIb-03 | — | — | 0.06 |
| 22 | Anti-mesothelin | IIIc-01 | — | 0.01 | — |
| 23 | Anti-CD70 | IIIc-01 | — | — | 0.01 |
| 24 | Anti-mesothelin | IIIc-08 | — | 0.13 | — |
| 25 | Anti-CD70 | IIIc-08 | — | — | 0.02 |

Additional results, testing against DMS 79 and H187 small-cell lung cancer cell lines, which express the antigen fucosyl GM1, are presented in Table IIC.

TABLE IIC

Biologic Activity of Conjugates

| | Conjugate | | | Cell Line: IC$_{50}$ (nM) | |
|---|---|---|---|---|---|
| Ref. | Antibody | Dimer-Linker | DAR | DMA 79 | H187 |
| 26 | Anti-fucosyl GM1 | IIIa-03 | ~2 | 0.6-1.7 | 0.5-1.0 |

Yet additional results, against N87, H226, 786-O cancer cell lines are presented in Table IID. The antibodies having an N297A substitution were conjugated using transglutaminase, as discussed above. The N297A mutation makes Q295 accessible as an amine acceptor for transglutaminase to make conjugates with a theoretical DAR of 2, although in practice conjugates with DARs in the range of 1.5 to 2 are obtained.

N87 is a stomach (gastric) cancer cell line that expresses mesothelin but not CD70 or fucosyl GM1. H226 is a lung cancer cell line that expresses mesothelin but not CD70 or fucosyl GM1. 786-O is a renal cancer cell line that expresses CD70 but not mesothelin or fucosyl GM1.

TABLE IID

Biologic Activity of Conjugates

| | Conjugate | | | Cancer | |
|---|---|---|---|---|---|
| Ref. | Antibody | Dimer-Linker | DAR | Cell Line | EC$_{50}$ (nM) |
| 27 | Anti-mesothelin* | IIIa-05 | — | N87 | 0.037 |
| 28 | Anti-fucosyl GM1* | IIIa-05 | — | N87 | 16.27 |
| 29 | Anti-mesothelin* | IIIa-06 | — | N87 | 0.028 |
| 30 | Anti-fucosyl GM1* | IIIa-06 | — | N87 | 6.9 |
| 31 | Anti-mesothelin | IIIa-03 | 3 | N87 | 0.026 |
| 32 | Anti-CD70 | IIIa-03 | 2.8 | N87 | 3.4 |
| 33 | Anti-fucosyl GM1* | IIIa-05 | — | H226 | 7.4 |
| 34 | Anti-mesothelin* | IIIa-06 | — | H226 | 0.011 |
| 35 | Anti-fucosyl GM1* | IIIa-06 | — | H226 | 4.0 |
| 36 | Anti-mesothelin* | IIIa-05 | — | H226 | 0.012 |
| 37 | Anti-mesothelin | IIIa-03 | 3 | H226 | 0.0070 |
| 38 | Anti-CD70 | IIIa-03 | 2.8 | H226 | 0.54 |
| 39 | Anti-mesothelin | IIIa-08 | 3 | 786-O | 60 |
| 40 | Anti-CD70 | IIIa-03 | 2.8 | 786-O | 0.19 |
| 41 | Anti-mesothelin* | IIIa-06 | — | 786-O | 45 |
| 42 | Anti-fucosyl GM1* | IIIa-06 | — | 786-O | 44 |

*Antibody has N297A substitution.

In one embodiment, in conjugates of this invention the antibody is an anti-mesothelin, anti-CD70, anti-glypican 3, or anti-fucosyl GM1 antibody.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Antonow et al., *J. Med. Chem.* 2010, 53, 2927.
Beau-Larvor et al., WO 2014/174111 A1 (2014).
Bose et al., *J. Am. Chem. Soc.* 1992, 114(12), 4939.
Bouchard et al., U.S. Pat. No. 8,404,678 B2 (2013).
Chari et al., WO 2013/177481 A1 (2013).
Commercon et al., U.S. Pat. No. 8,481,042 B2 (2013) [2013a].
Commercon et al., US 2013/0137659 A1 (2013) [2013b].
Fishkin et al., U.S. Pat. No. 8,765,740 B2 (2014).
Flygare et al., US 2013/0266595 A1 (2013).
Gauzy et al., U.S. Pat. No. 8,163,736 B2 (2012).
Gregson et al., *Chem. Comm.* 1999 (9), 797.
Gregson et al., *Bioorg. Med. Chem. Lett.* 2001, 11, 2859 [2001a].
Gregson et al., *J. Med. Chem.* 2001, 44, 737 [2001b].
Gregson et al., *J. Med. Chem.* 2004, 47, 1161.
Gregson et al., U.S. Pat. No. 7,612,062 B2 (2009).
Hartley, *Exp. Opinion Investigational Drugs* 2011, 20(6), 733.
Hartley et al., *Investigational New Drugs* 2012, 30, 950.
Howard, US 2014/0120118 A1 (2014) [2014a].
Howard, US 2014/0127239 A1 (2014) [2014b].
Howard, WO 2014/096365 A1 (2014) [2014c].
Howard, WO 2014/096368 A1 (2014) [2014d].
Howard, WO 2014/140174 A1 (2014) [2014e].
Howard et al., US 2007/0191349 A1 (2007).
Howard et al., U.S. Pat. No. 7,528,126 B2 (2009) [2009a].
Howard et al., U.S. Pat. No. 7,557,099 B2 (2009) [2009b].
Howard et al., U.S. Pat. No. 7,741,319 B2 (2010).
Howard et al., US 2011/0256157 A1 (2011).
Howard et al., U.S. Pat. No. 8,501,934 B2 (2013) [2013a].
Howard et al., U.S. Pat. No. 8,592,576 B2 (2013) [2013b].
Howard et al., US 2013/0028919 A1 (2013) [2013c].
Howard et al., WO 2013/041606 A1 (2013) [2013e].
Howard et al., U.S. Pat. No. 8,697,688 B2 (2014) [2014a].
Howard et al., US 2014/0120118 A1 (2014).
Howard et al. US 2014/0234346 A1 (2014) [2014b].
Howard et al., US 2014/0274907 A1 (2014) [2014c].
Howard et al., US 2014/0294868 A1 (2014).
Howard et al., WO 2014/096368 A1 (2014).
Howard et al., WO 2014/140174 A1 (2014).
Howard et al., WO 2014/140862 A2 (2014) [2014d].
Jeffrey et al., *Bioconj. Chem.* 2013, 24, 1256.
Jeffrey et al., US 2014/0286970 A1 (2014) [2014a].
Jeffrey et al., US 2014/0302066 A1 (2014) [2014b].
Kothakonda et al., *Bioorg. Med. Chem. Lett.* 2004, 14, 4371.
Li et al., U.S. Pat. No. 8,426,402 B2 (2013).
Li et al., WO 2014/031566 A1 (2014).
Liu et al., U.S. Pat. No. 7,244,724 B2 (2007).
Schrama et al., *Nature Rev. Drug Disc.* 2006, 5, 147.
Senter et al., U.S. Pat. No. 7,659,241 B2 (2010).
Thurston et al., *J. Org. Chem.* 1996, 61(23), 8141.
Thurston et al., *J. Med. Chem.* 1999, 42, 1951.
Thurston et al., U.S. Pat. No. 7,049,311 B1 (2006).
Thurston et al., U.S. Pat. No. 7,407,951 B1 (2008).
Zhao et al., WO 2014/080251 A1 (2014).

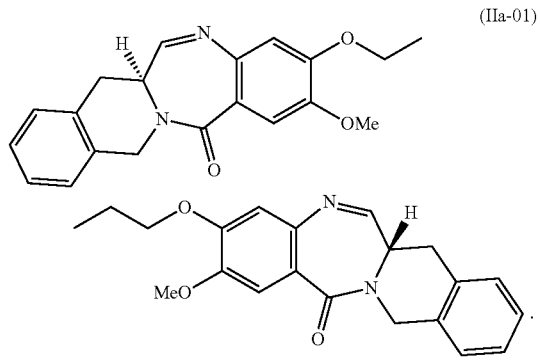

What is claimed is:

1. A compound having a structure represented by formula (IIa-01):